United States Patent
Abreu

(10) Patent No.: US 11,998,301 B2
(45) Date of Patent: Jun. 4, 2024

(54) SYSTEMS AND METHODS FOR ANALYSIS OF TEMPERATURE SIGNALS FROM AN ABREU BRAIN THERMAL TUNNEL AND TREATMENT OF HUMAN CONDITIONS VIA THE ABREU BRAIN THERMAL TUNNEL

(71) Applicant: Brain Tunnelgenix Technologies Corp., Aventura, FL (US)

(72) Inventor: Marcio Marc Abreu, Aventura, FL (US)

(73) Assignee: Brain Tunnelgenix Technologies Corp., Aventura, FL (US)

(*) Notice: Subject to any disclaimer, the term of this patent is extended or adjusted under 35 U.S.C. 154(b) by 0 days.

(21) Appl. No.: 17/963,992

(22) Filed: Oct. 11, 2022

(65) Prior Publication Data

US 2023/0032756 A1 Feb. 2, 2023

Related U.S. Application Data

(63) Continuation of application No. 15/089,198, filed on Apr. 1, 2016, now Pat. No. 11,504,008.

(Continued)

(51) Int. Cl.
| | |
|---|---|
| A61B 5/01 | (2006.01) |
| A61B 5/00 | (2006.01) |
| A61F 7/00 | (2006.01) |
| G16H 20/30 | (2018.01) |
| G16H 50/20 | (2018.01) |

(52) U.S. Cl.
CPC .............. *A61B 5/01* (2013.01); *A61B 5/0036* (2018.08); *A61B 5/4094* (2013.01); *A61B 5/6821* (2013.01); *A61B 5/7275* (2013.01); *A61B 5/746* (2013.01); *A61F 7/007* (2013.01); *G16H 20/30* (2018.01); *G16H 50/20* (2018.01); *A61B 5/6803* (2013.01); *A61F 2007/0004* (2013.01); *A61F 2007/0086* (2013.01); *A61F 2007/0096* (2013.01)

(58) Field of Classification Search
None
See application file for complete search history.

(56) References Cited

U.S. PATENT DOCUMENTS

| | | |
|---|---|---|
| 5,664,578 A | 9/1997 | Boczan |
| 5,871,526 A | 2/1999 | Gibbs et al. |

(Continued)

FOREIGN PATENT DOCUMENTS

| | | |
|---|---|---|
| WO | 2005/015163 A2 | 2/2005 |
| WO | 2015/013576 A1 | 1/2015 |

OTHER PUBLICATIONS

Notification of Transmittal of the International Search Report and the Written Opinion of the International Searching Authority; PCT/US2016/025688 dated Aug. 16, 2016.

(Continued)

*Primary Examiner* — Alex M Valvis
*Assistant Examiner* — Aurelie H Tu
(74) *Attorney, Agent, or Firm* — Studebaker & Brackett PC

(57) ABSTRACT

Systems configured to acquire temperature signals from an Abreu Brain Thermal Tunnel (ABTT), to analyze the temperatures signals, and to determine a condition of a human body from the analysis, and a method for doing the same, are described. In addition, systems for application of thermal signals to the ABTT for treatment of conditions are described.

20 Claims, 155 Drawing Sheets

Related U.S. Application Data

(60) Provisional application No. 62/141,816, filed on Apr. 1, 2015.

(56) References Cited

U.S. PATENT DOCUMENTS

| | | | |
|---|---|---|---|
| 11,504,008 B2 * | 11/2022 | Abreu | A61B 5/01 |
| 2007/0100564 A1 | 5/2007 | Fraden | |
| 2009/0105605 A1 * | 4/2009 | Abreu | A61B 5/6898 600/549 |
| 2010/0113894 A1 | 5/2010 | Padiy | |
| 2013/0030411 A1 | 1/2013 | Kreck et al. | |
| 2013/0317578 A1 | 11/2013 | Diller et al. | |

OTHER PUBLICATIONS

International Preliminary Report on Patentability dated Oct. 12, 2017, in corresponding PCT Application No. PCT/US2016/025688, 10 pp.

* cited by examiner

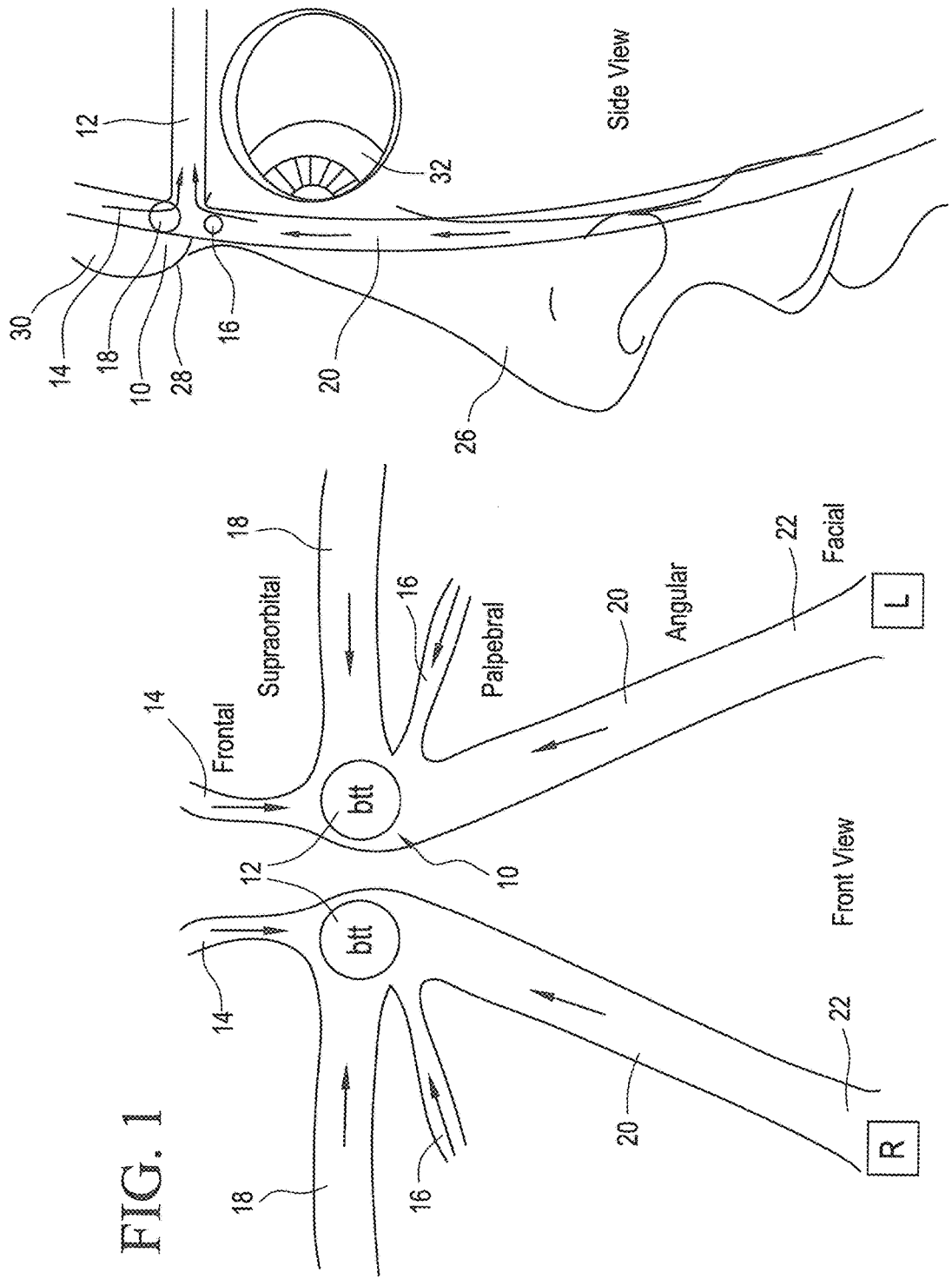

FIG. 4
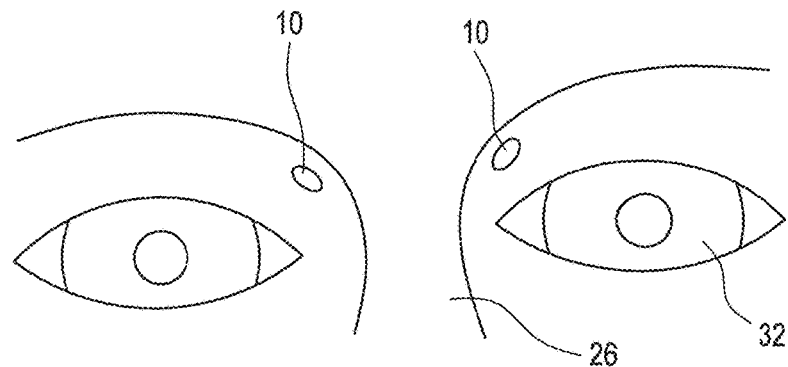
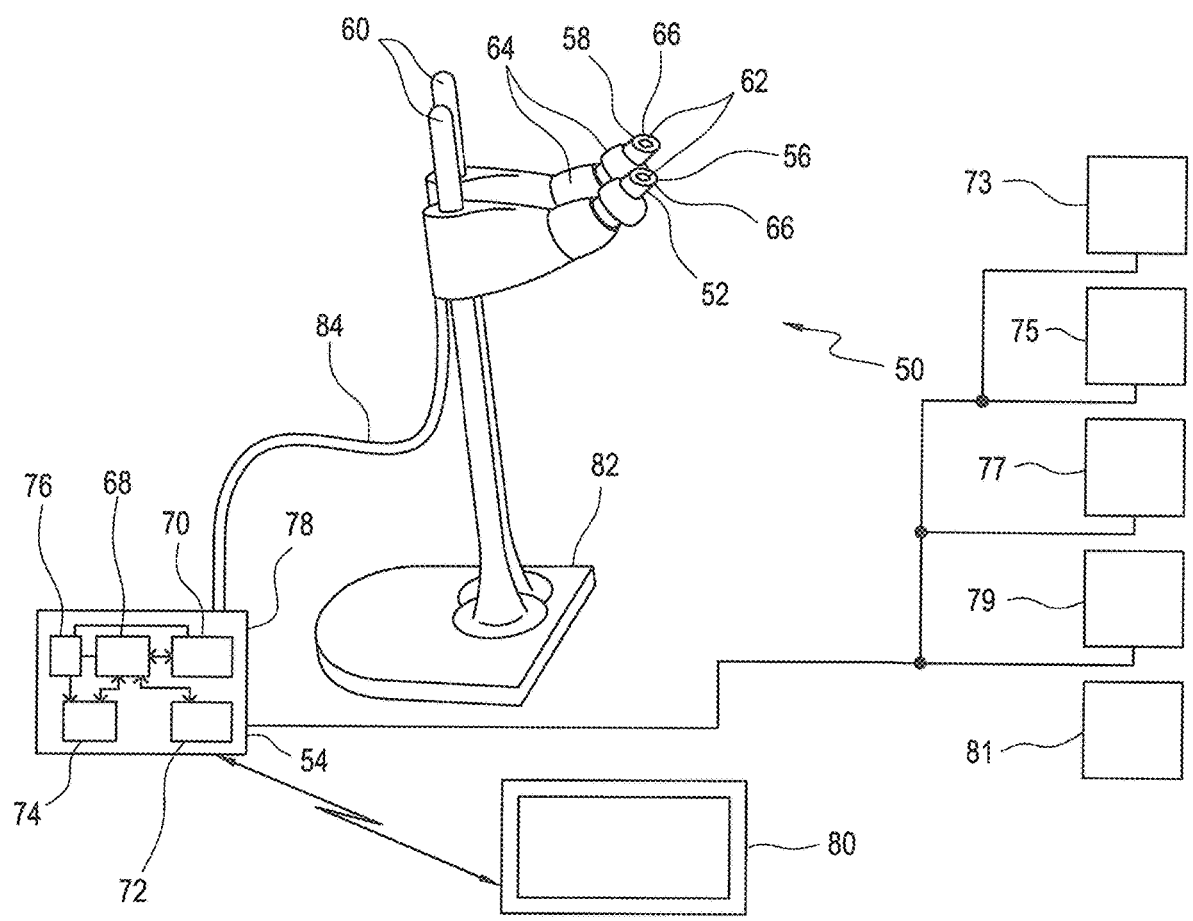
FIG. 5

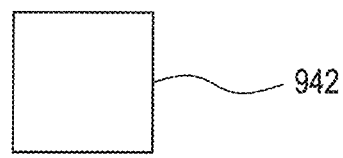
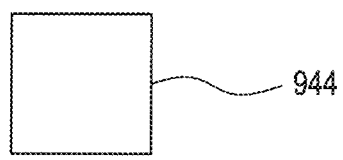
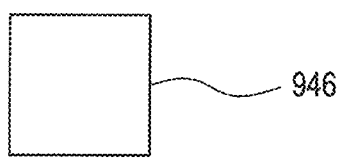
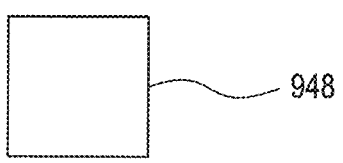
FIG. 20

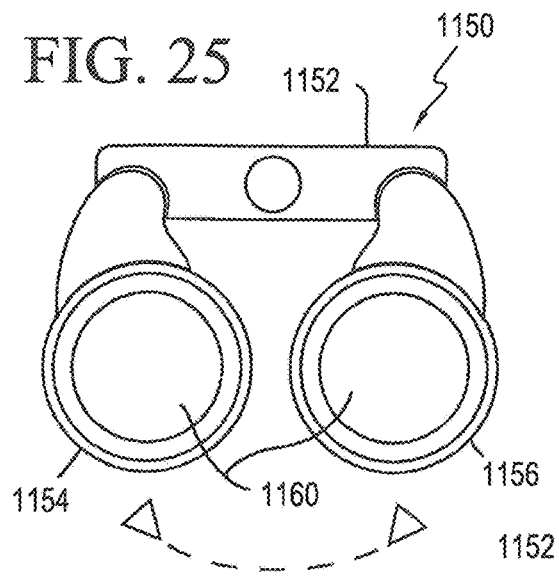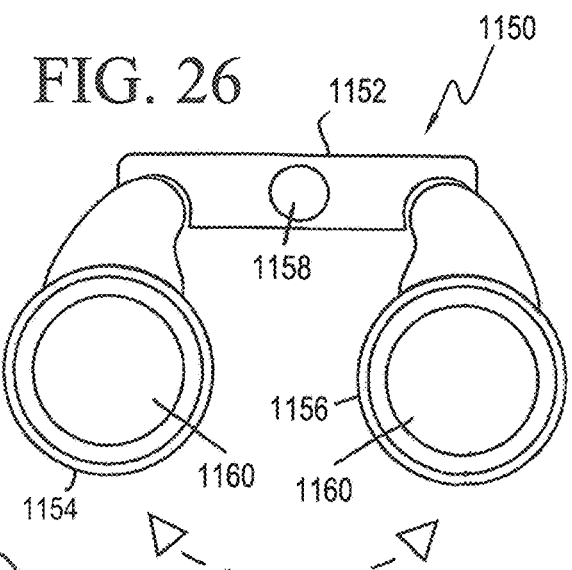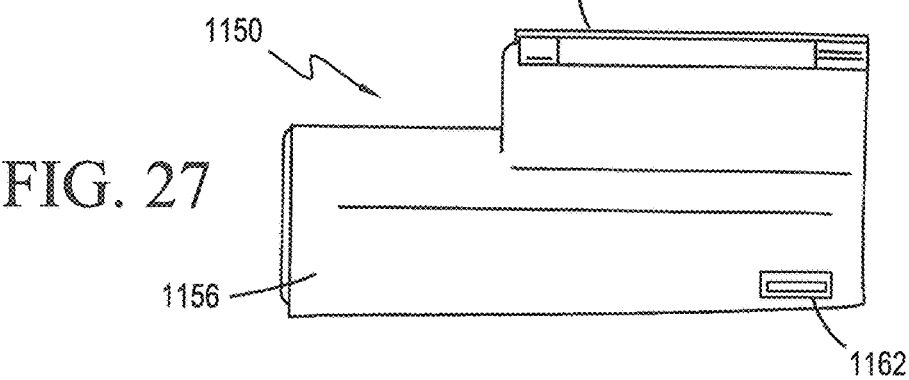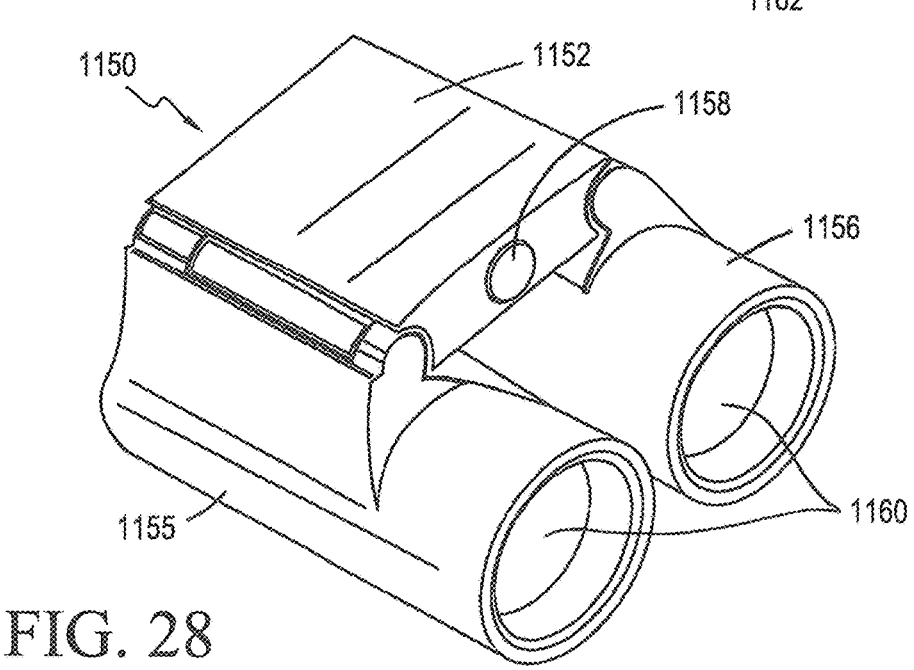

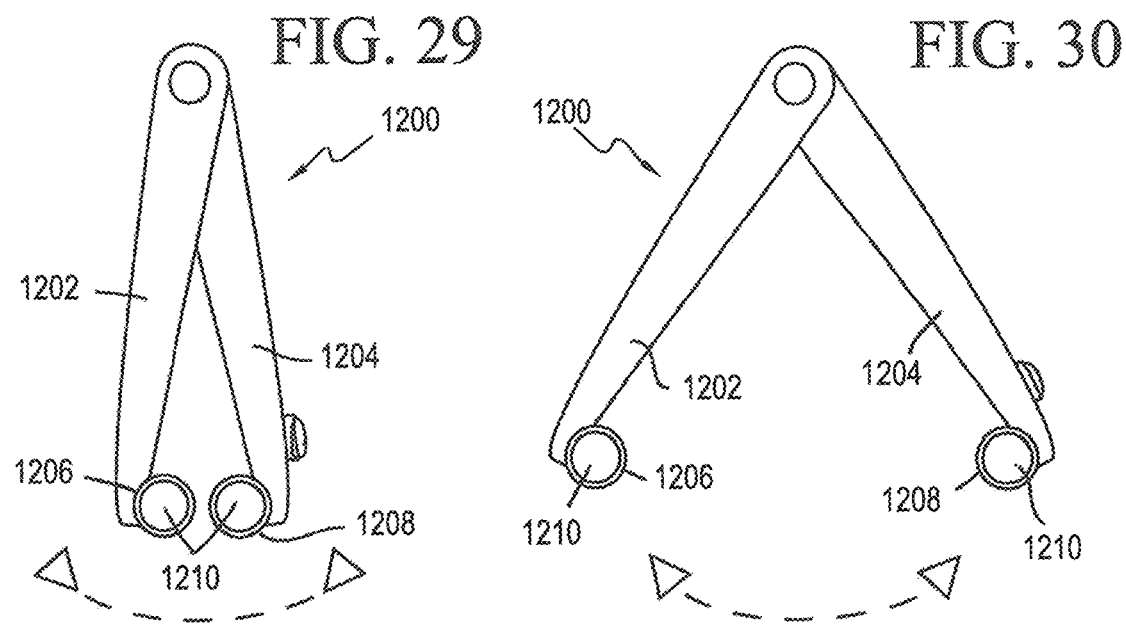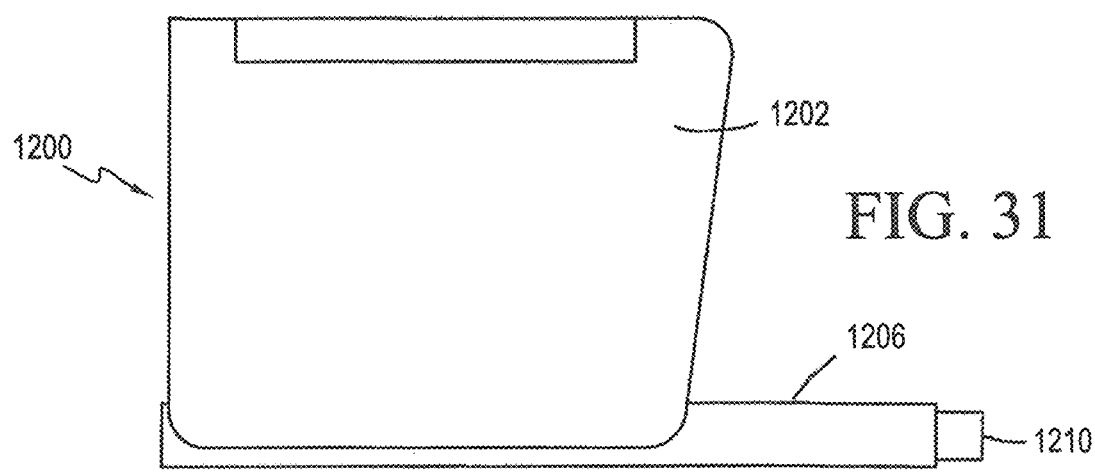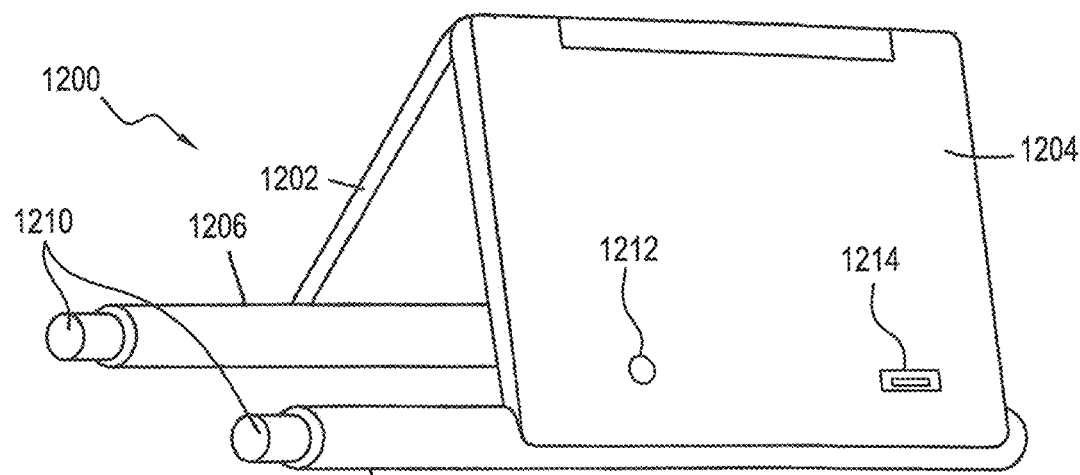

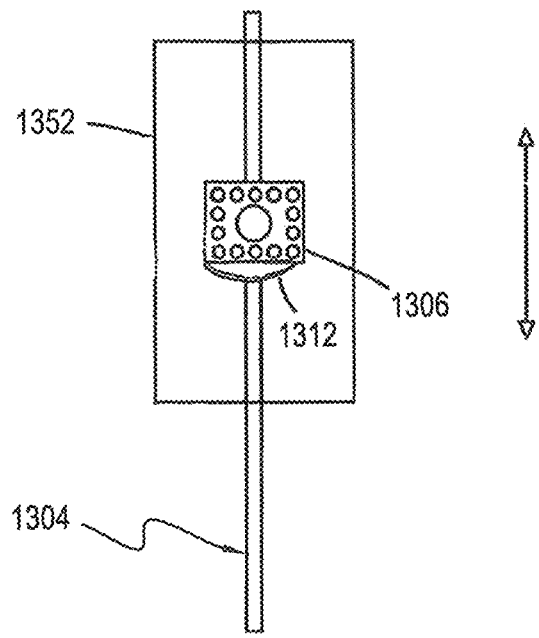
FIG. 57
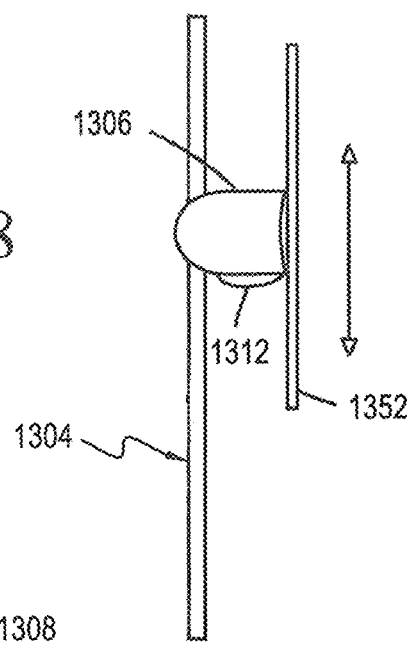
FIG. 58
FIG. 59
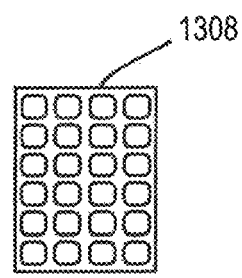

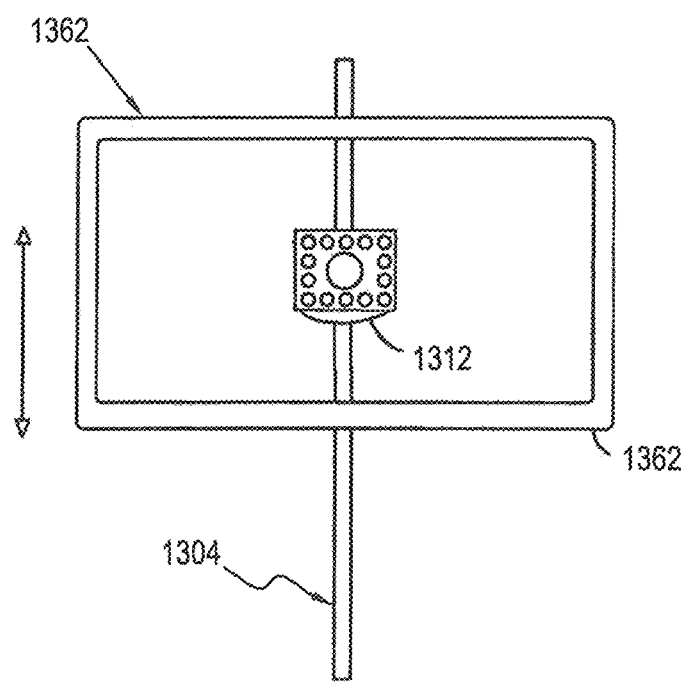
FIG. 63
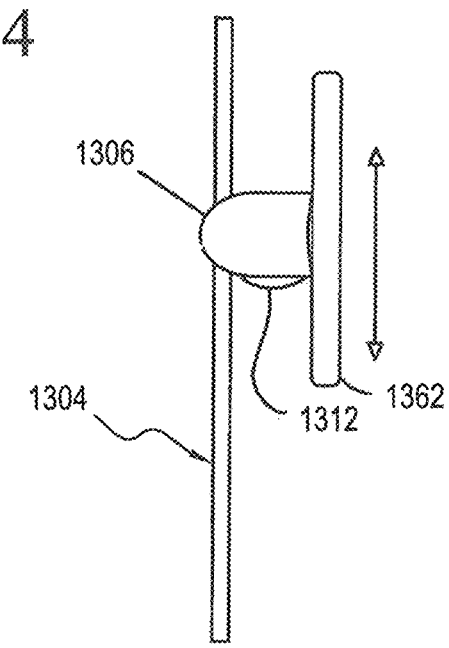
FIG. 64
FIG. 65
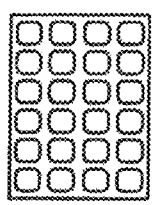

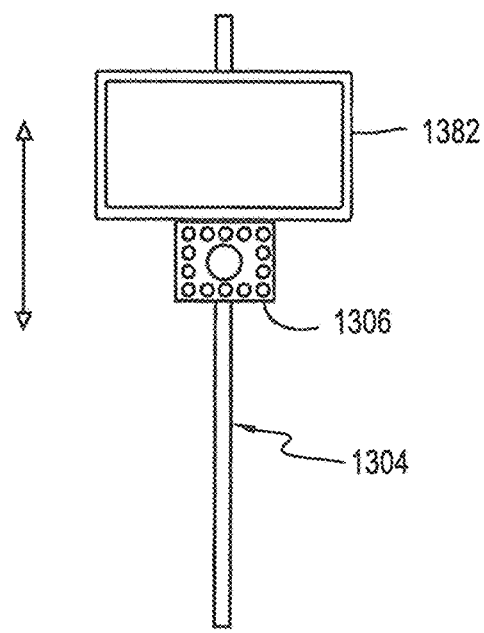
FIG. 76
FIG. 77
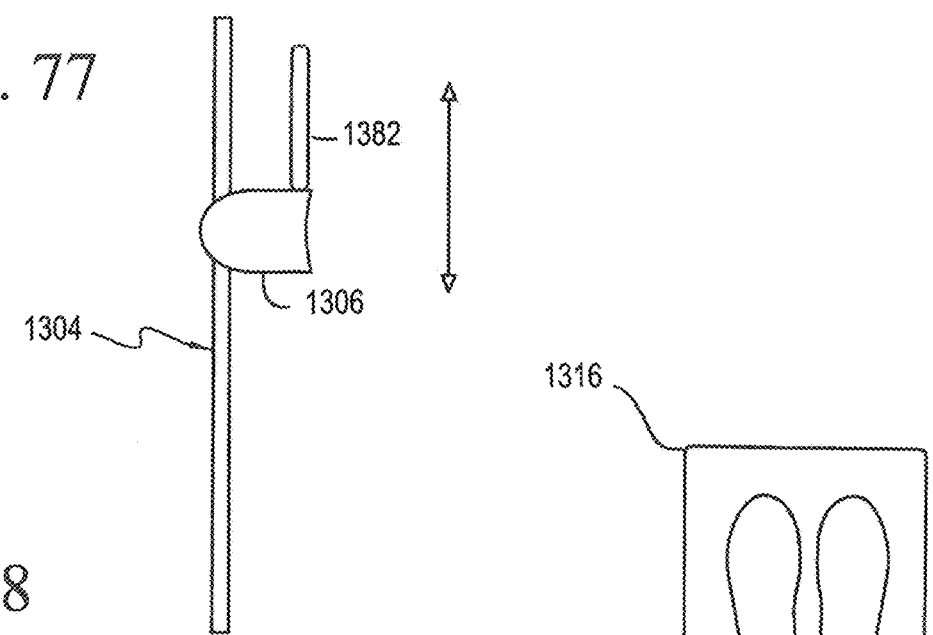
FIG. 78
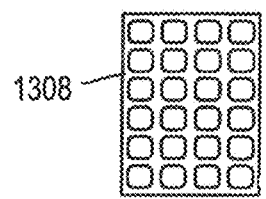
FIG. 79

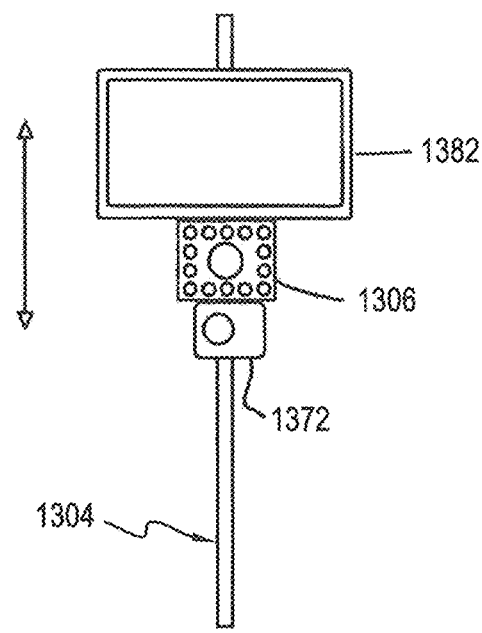
FIG. 83
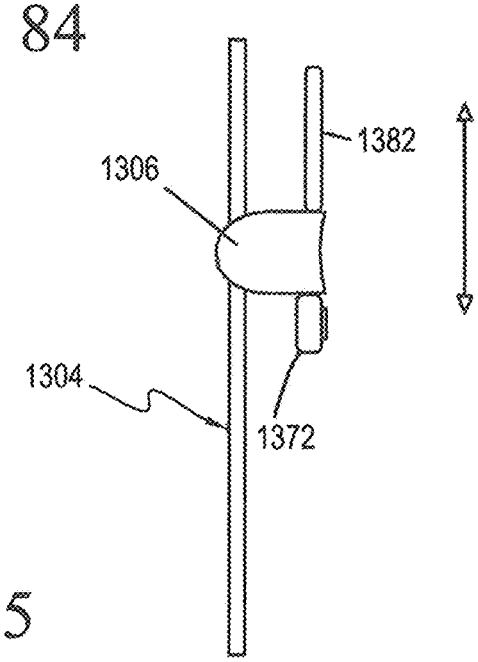
FIG. 84
FIG. 85
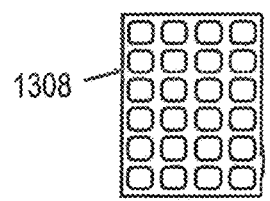
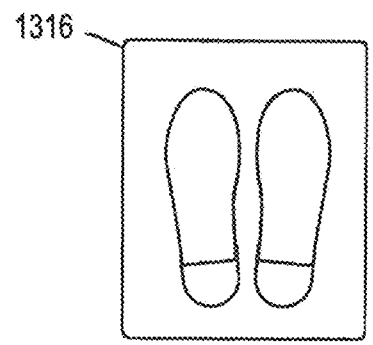
FIG. 86

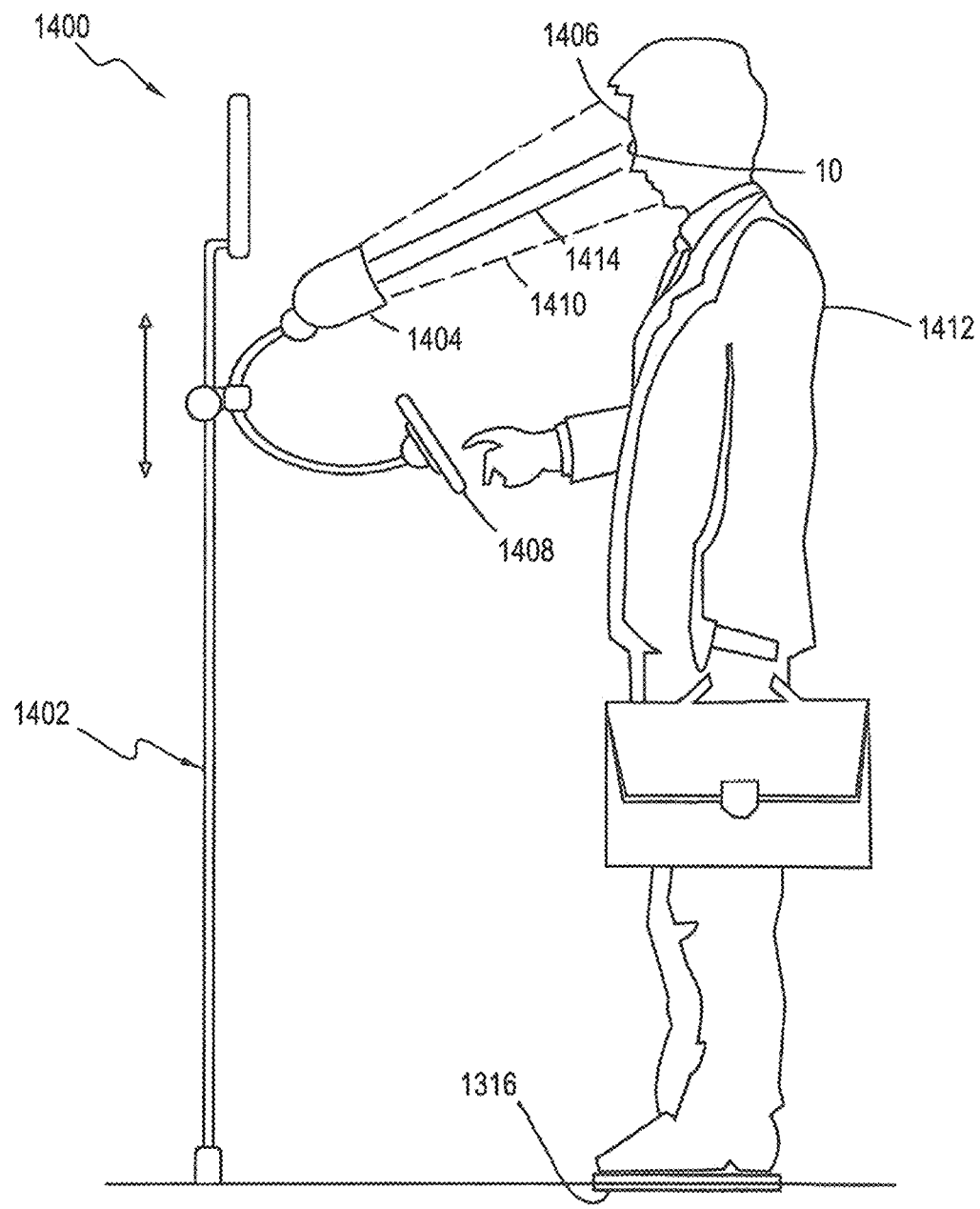
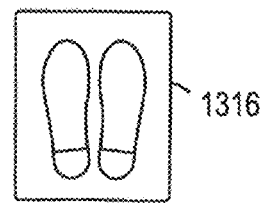
FIG. 87

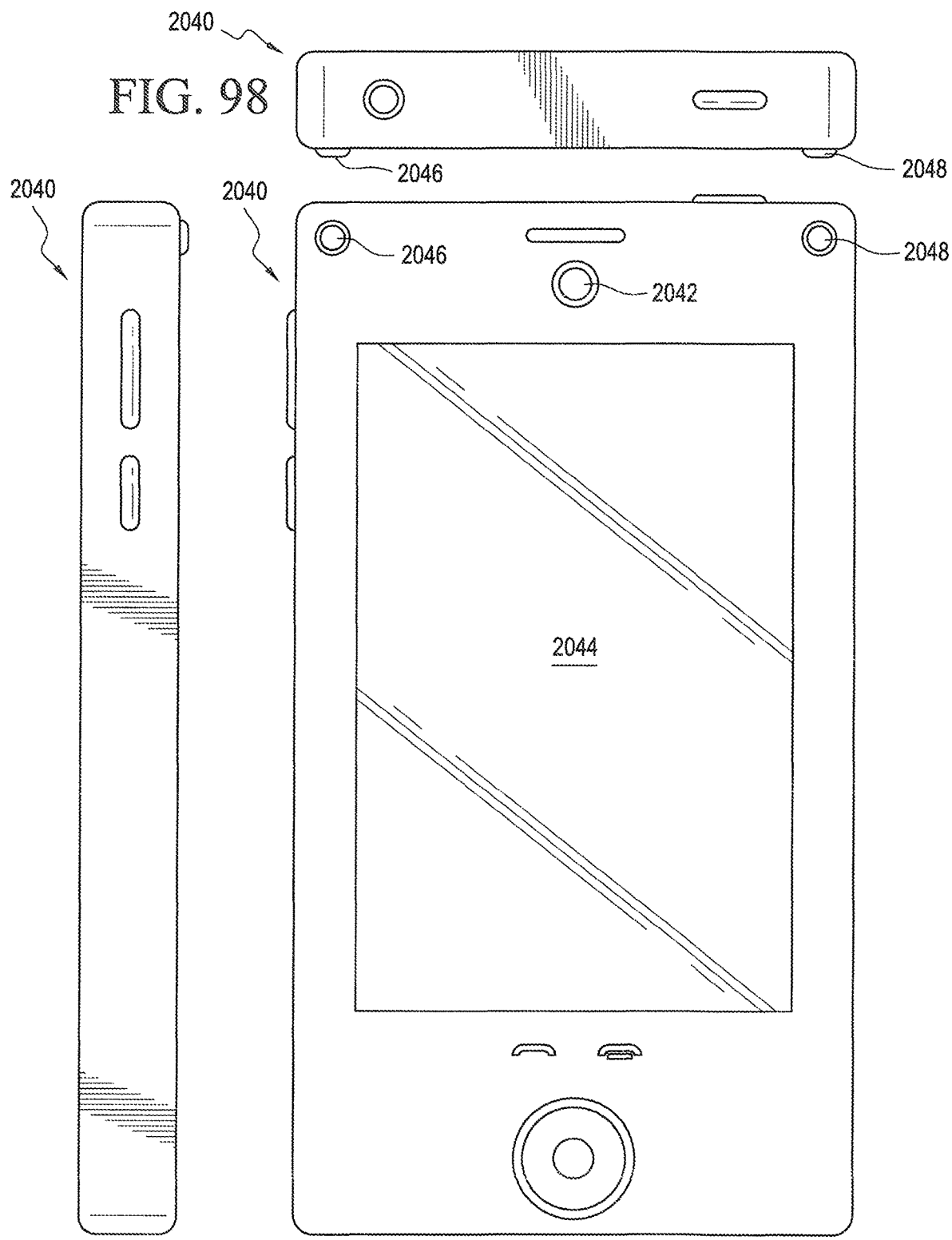

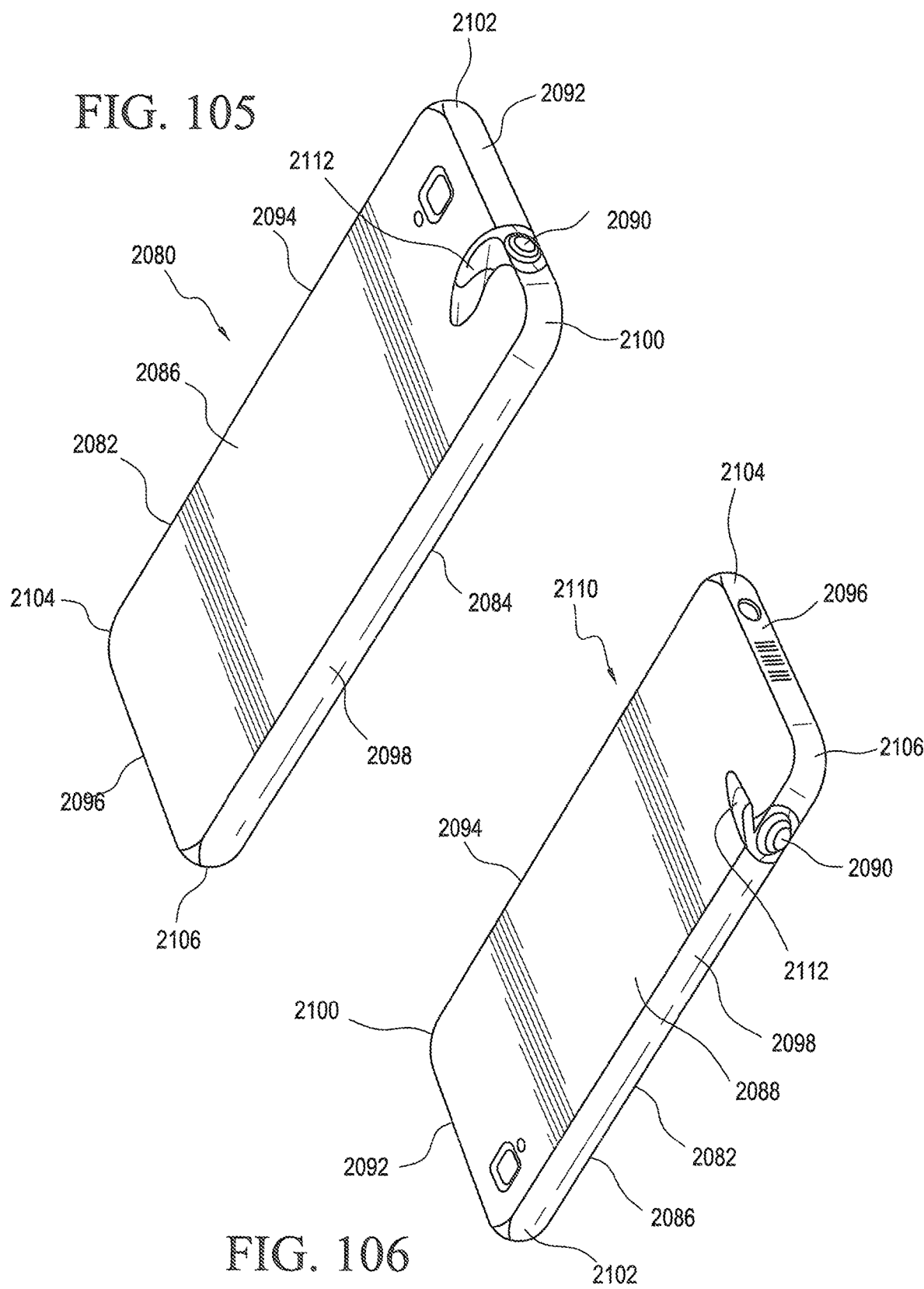

FIG. 112
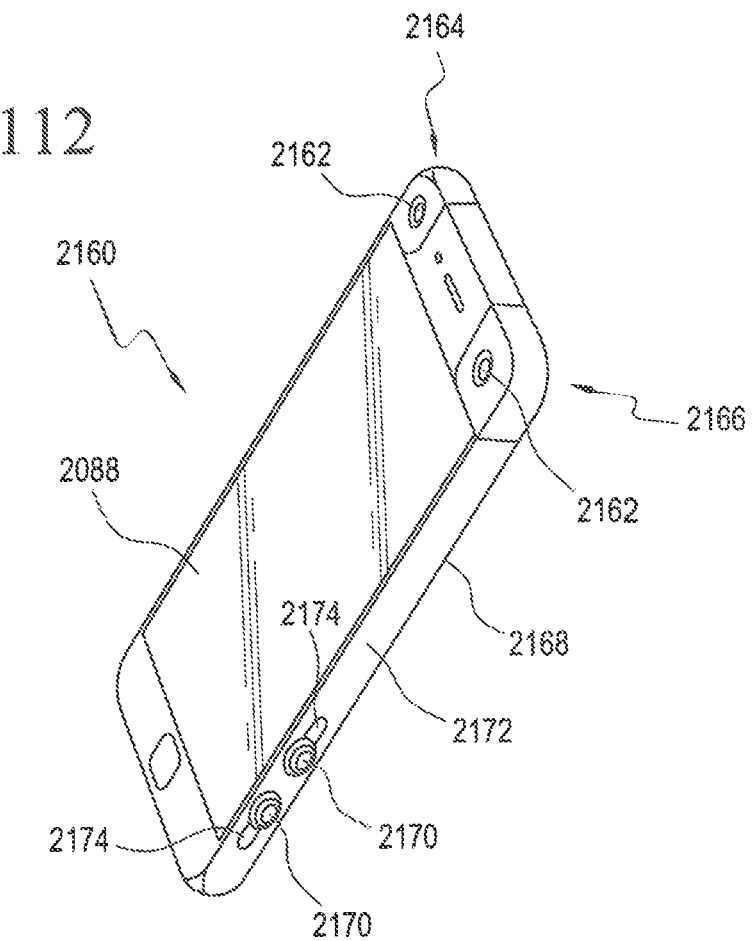
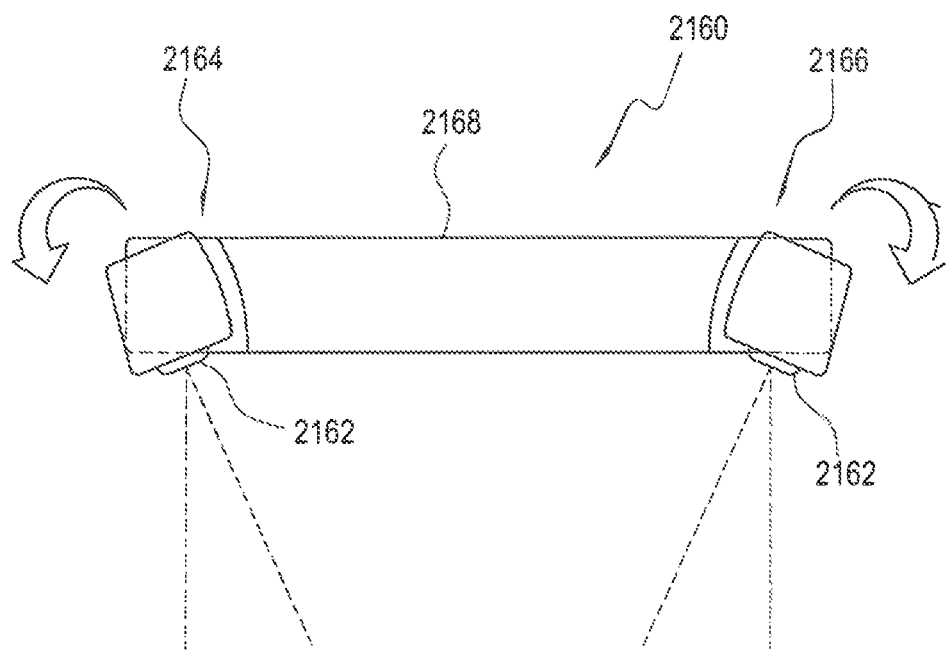
FIG. 113

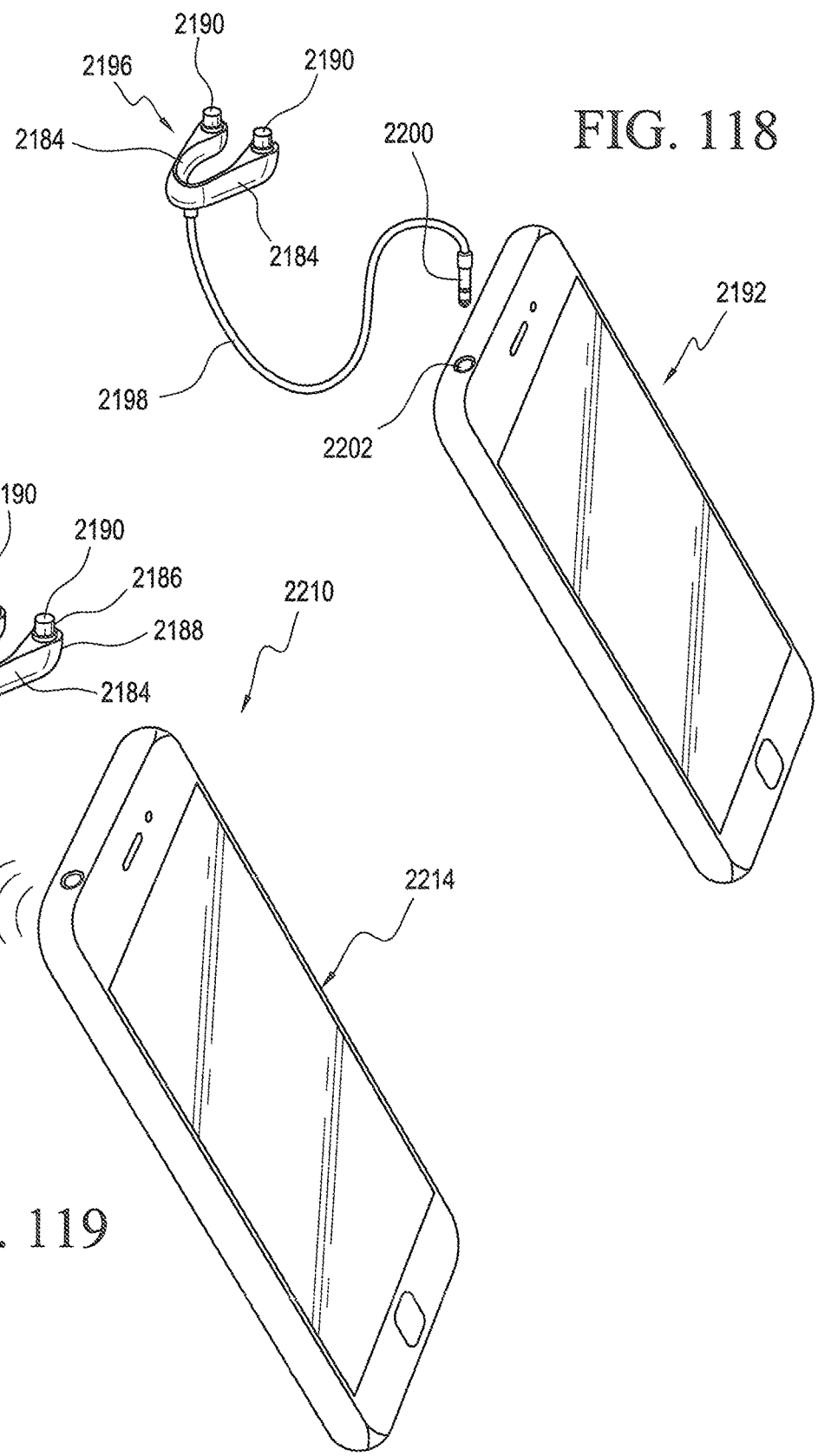

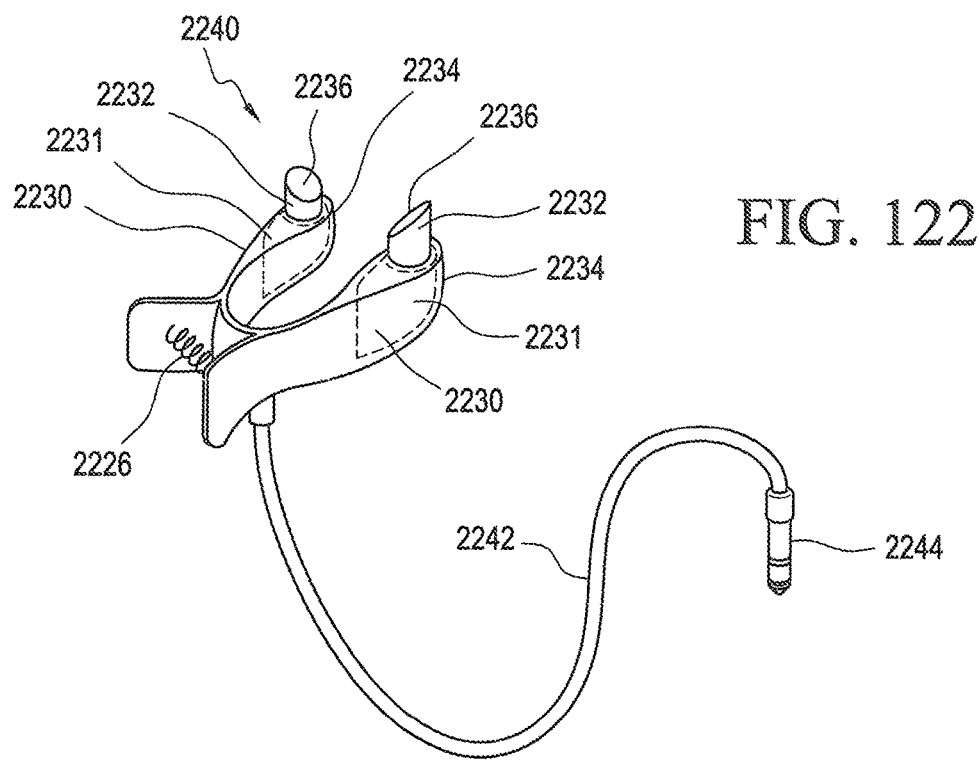
FIG. 122
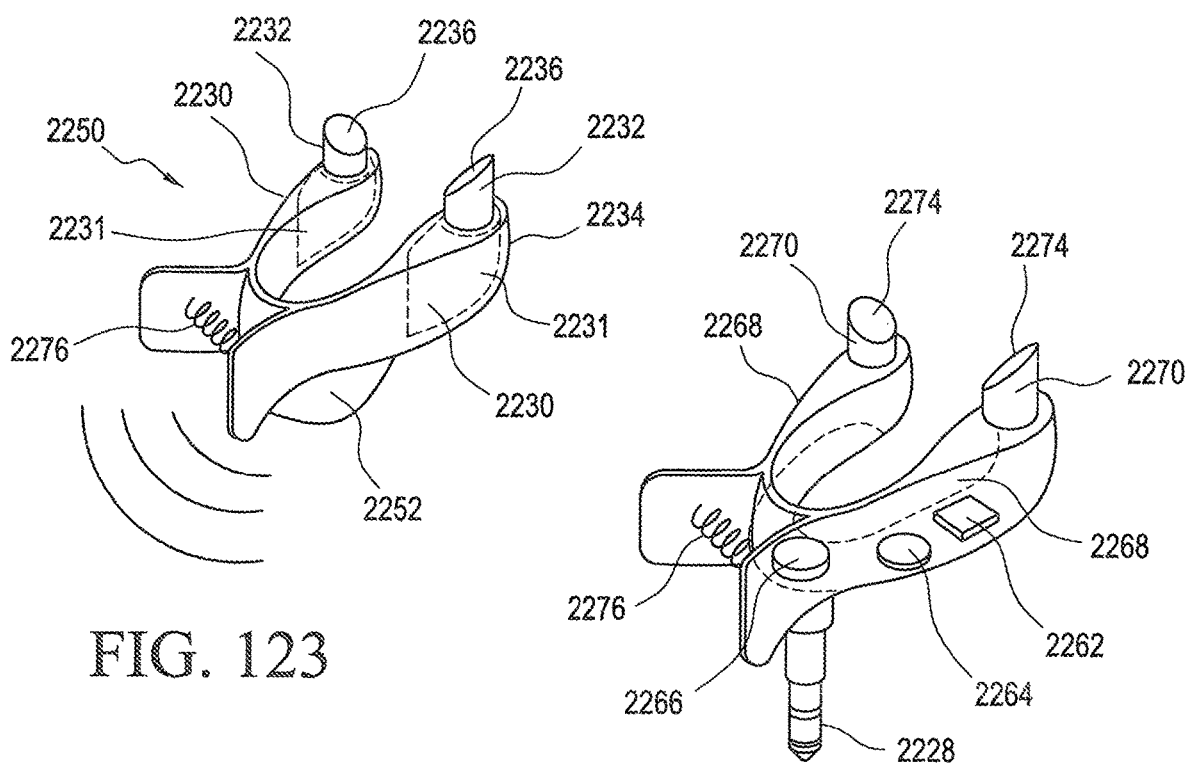
FIG. 123
FIG. 124

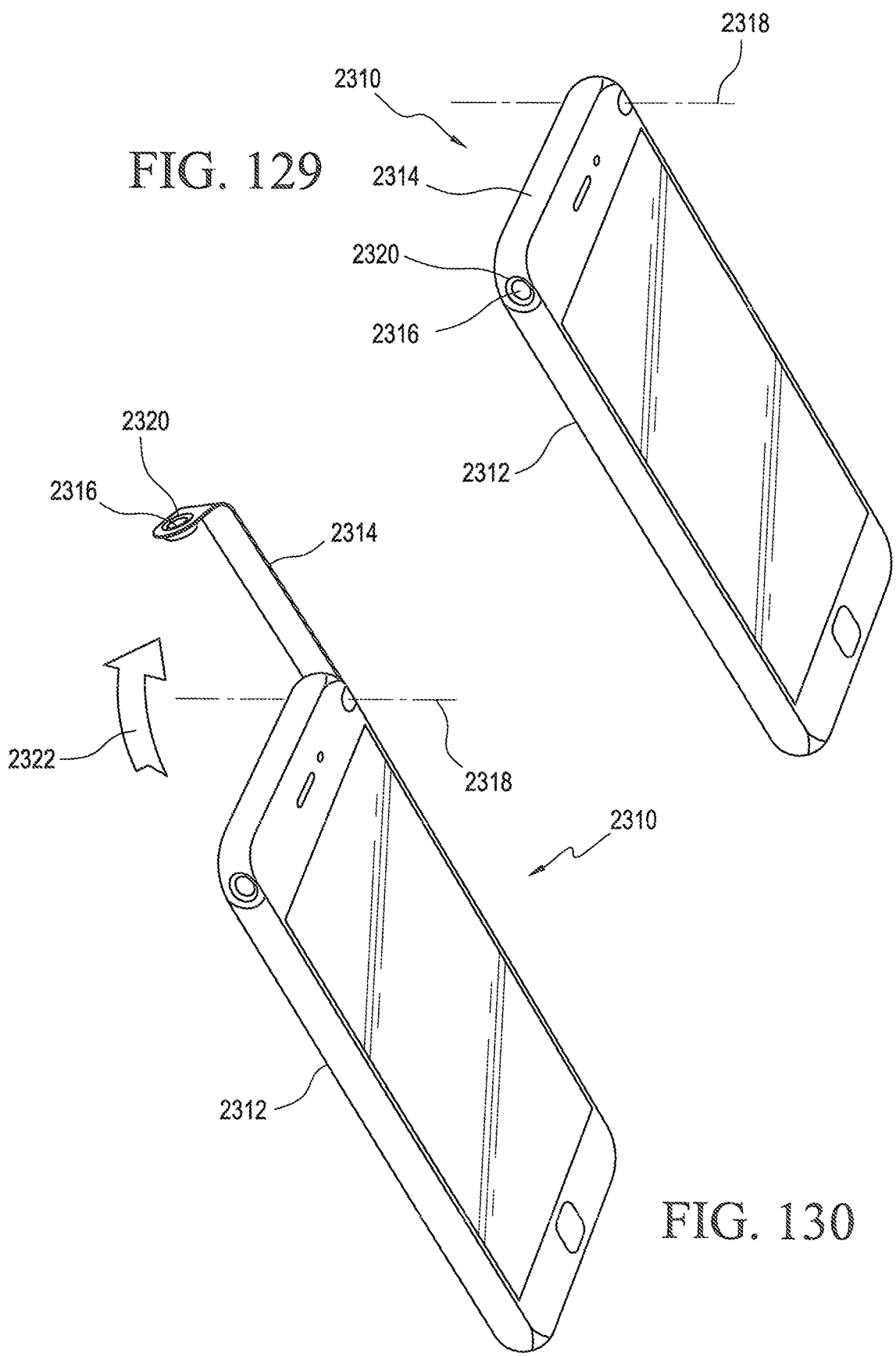

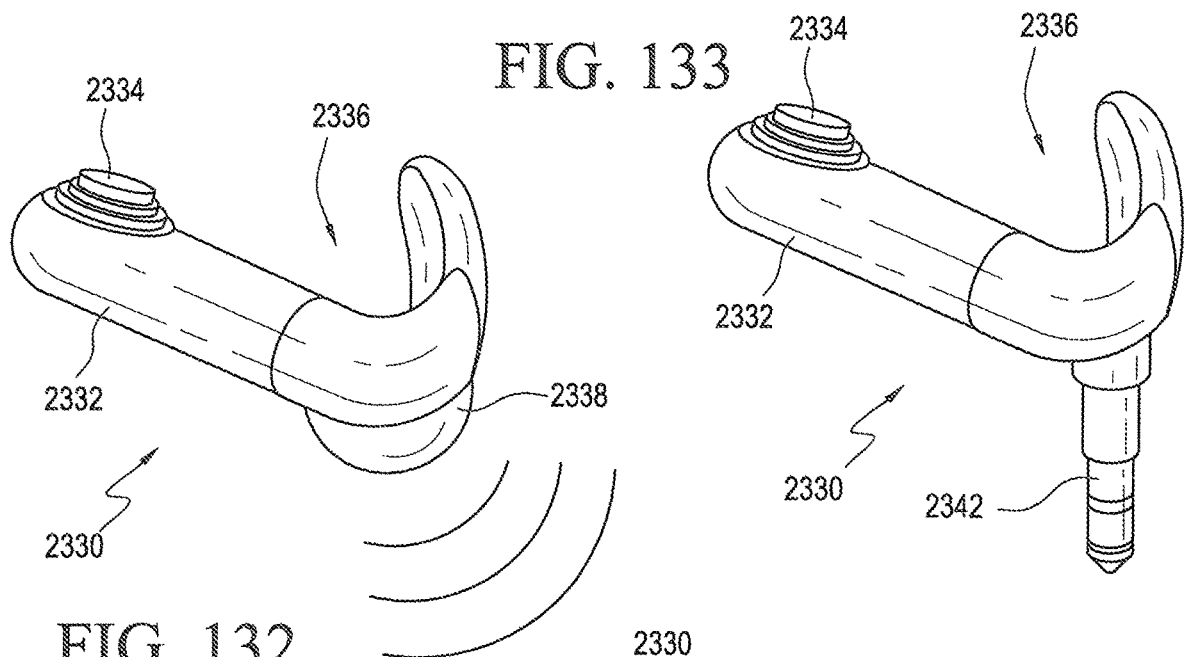
FIG. 133
FIG. 132
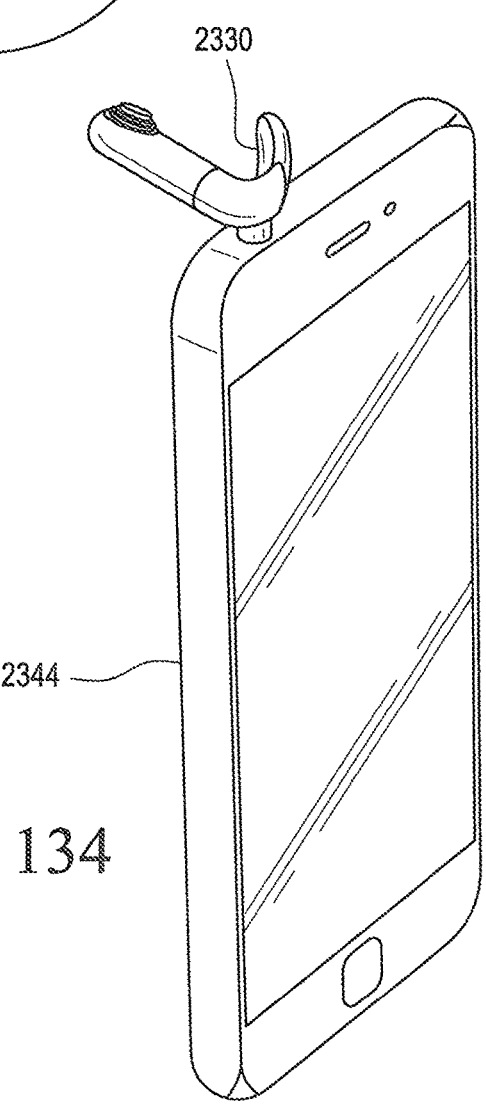
FIG. 134

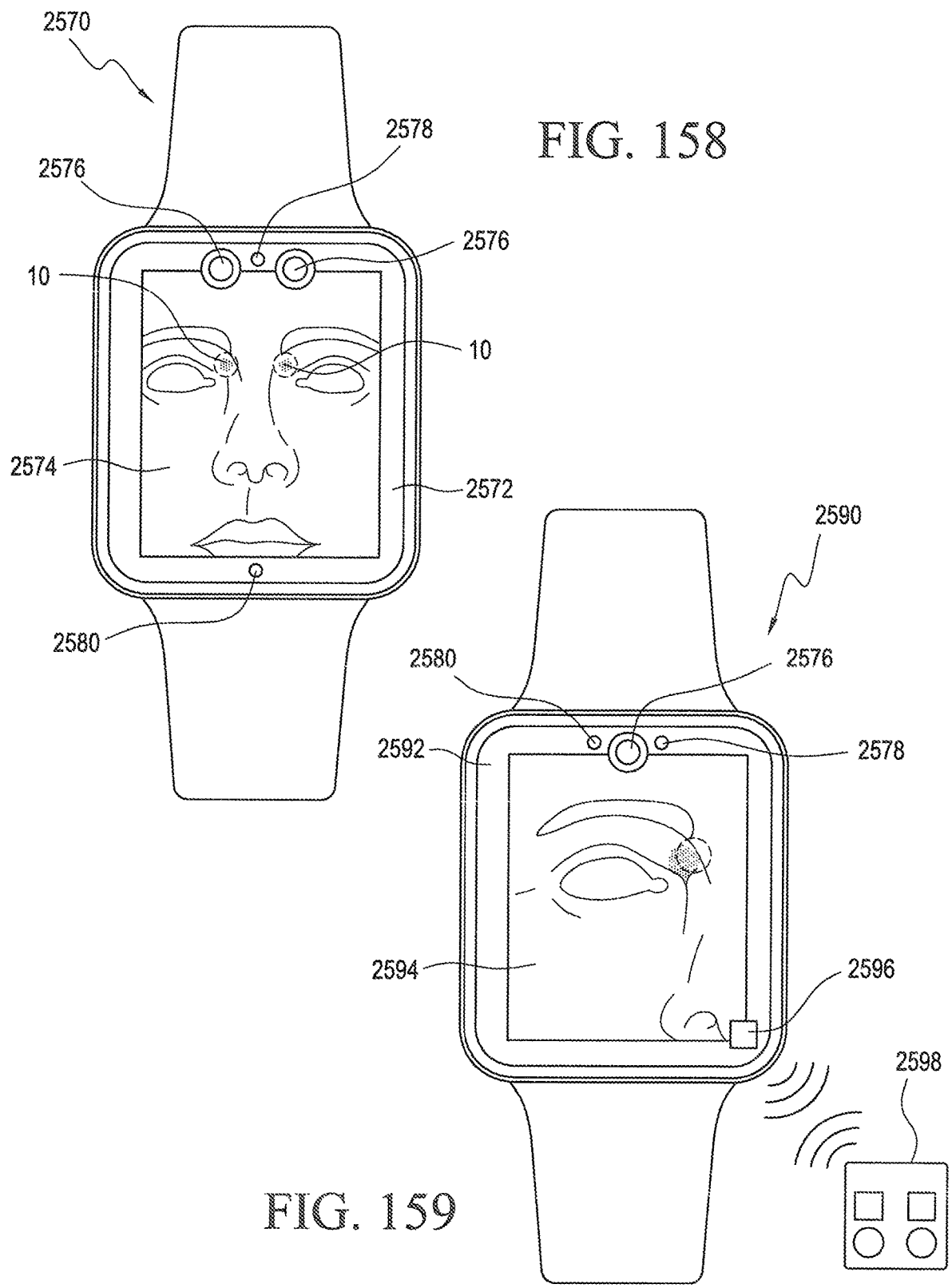

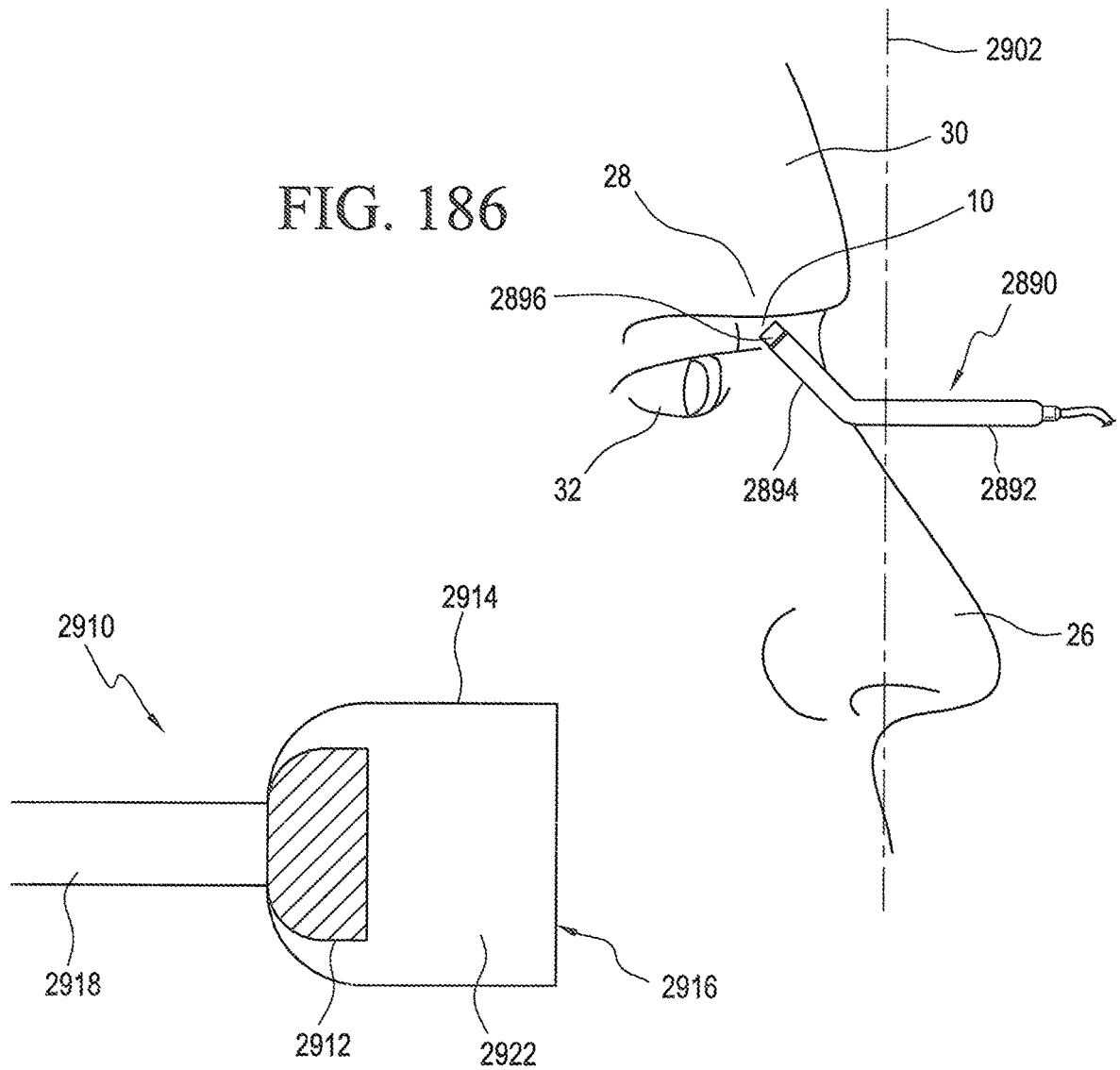
FIG. 186
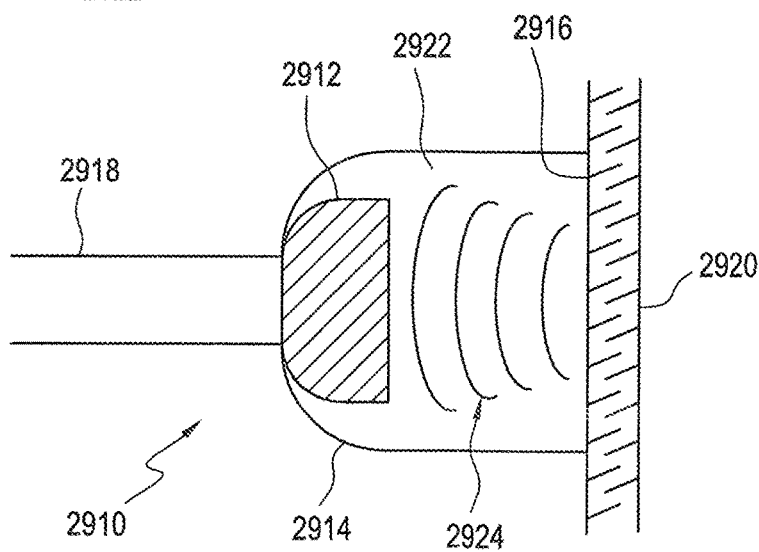
FIG. 187
FIG. 188

SYSTEMS AND METHODS FOR ANALYSIS OF TEMPERATURE SIGNALS FROM AN ABREU BRAIN THERMAL TUNNEL AND TREATMENT OF HUMAN CONDITIONS VIA THE ABREU BRAIN THERMAL TUNNEL

CROSS-REFERENCE TO RELATED APPLICATIONS

This application is a Continuation of U.S. patent application Ser. No. 15/089,198, filed Apr. 1, 2016, which claims the benefit of priority to U.S. Provisional Patent Application No. 62/141,816, filed on Apr. 1, 2015, which is hereby incorporated by reference in its entirety.

TECHNICAL FIELD

This disclosure relates to a system configured to acquire temperature signals from an Abreu Brain Thermal Tunnel (ABTT), to analyze the temperatures signals, and to determine a condition of a human body from the analysis, and a method for doing the same. In addition, this disclosure provides a system for application of thermal signals to the ABTT for treatment of conditions.

BACKGROUND

Diagnostics of human conditions, such as cancer, heart attack, seizures, stroke, and the like, are conventionally conducted using a plurality of tests that are often time consuming and expensive. Sometimes the diagnosis of a condition is based on observation, such as a seizure, where observation of a seizure is the only indication that a seizure is taking place. Furthermore, treatment of human conditions involves surgery, therapies, and drugs that frequently have catastrophic side effects.

SUMMARY

Advantages and features of the embodiments of this disclosure will become more apparent from the following detailed description of exemplary embodiments when viewed in conjunction with the accompanying drawings.

BRIEF DESCRIPTION OF THE DRAWINGS

FIG. 1 shows a simplified view of the ABTT and facial veins associated with the ABTT.

FIG. 2 shows a simplified partial cross-sectional view through a human skull in a vertical direction, showing the Abreu brain thermal tunnel and certain other facial features.

FIG. 4 shows a view of a portion of a face that shows the approximate location of the ABTT terminus.

FIG. 5 shows a view of a first system in accordance with an exemplary embodiment of the present disclosure.

FIG. 20 shows additional measuring devices that can acquire or measure data, information, or characteristics present at the ABTT terminus.

FIG. 25 shows a view of yet another device configured to locate at least one ABTT terminus and then to measure the temperature of the at least one ABTT terminus, with the device in a first configuration, in accordance with an exemplary embodiment of the present disclosure.

FIG. 26 shows another view of the device of FIG. 25, with the device in a second configuration.

FIG. 27 shows a side view of the device of FIG. 25.

FIG. 28 shows a perspective view of the device of FIG. 25.

FIG. 29 shows a view of a device configured to measure the temperature of at least one ABTT terminus, with the device in a first position, in accordance with an exemplary embodiment of the present disclosure.

FIG. 30 shows another view of the device of FIG. 29, with the device in a second position.

FIG. 31 shows a side view of the device of FIG. 29.

FIG. 32 shows a perspective view of the device of FIG. 29.

FIG. 57 shows a view of a support structure for the system of FIG. 55, in accordance with an exemplary embodiment of the present disclosure.

FIG. 58 shows a side view of the support structure of FIG. 57.

FIG. 59 shows a view of a device to control a camera position of the system of FIG. 55.

FIG. 63 shows a view of a support structure for the system of FIG. 60, in accordance with an exemplary embodiment of the present disclosure.

FIG. 64 shows a side view of the support structure of FIG. 63.

FIG. 65 shows a view of a device to control a camera position of the system of FIG. 60.

FIG. 76 shows a view of a support structure for the system of FIG. 73, in accordance with an exemplary embodiment of the present disclosure.

FIG. 77 shows a side view of the support structure of FIG. 76.

FIG. 78 shows a view of a device to control a camera position of the system of FIG. 73.

FIG. 79 shows a view of an activation device of the system of FIG. 73.

FIG. 83 shows a view of a support structure for the system of FIG. 80, in accordance with an exemplary embodiment of the present disclosure.

FIG. 84 shows a side view of the support structure of FIG. 83.

FIG. 85 shows a view of a device to control a camera position of the system of FIG. 80.

FIG. 86 shows a view of an activation device of the system of FIG. 80.

FIG. 87O shows a view of a further sensor device in accordance with an exemplary embodiment of the present disclosure.

FIG. 87P shows a view of an even further sensor device in accordance with an exemplary embodiment of the present disclosure.

FIG. 87Q shows a view of the system of FIG. 87L with modified features.

FIG. 88 shows an ABTT acquisition process in accordance with an exemplary embodiment of the present disclosure.

FIG. 89 shows a graph of ABTT temperatures showing a risk of aneurysm.

FIG. 90 shows a graph of ABTT temperatures showing a risk of cancer.

FIG. 91 shows a graph of ABTT temperatures showing a risk of seizures.

FIG. 92 shows a graph of ABTT temperatures showing a progression of infection.

FIG. 93 shows a graph of ABTT temperatures indicating Alzheimer's disease or spread of Alzheimer's disease beyond the hippocampus.

FIG. 94 shows a graph of ABTT temperatures indicating a risk of abscess.

FIG. 95 shows a numerical display of ABTT temperatures indicating a risk of stroke.

FIG. 96 shows a view of an electronic apparatus configured with a measurement device in accordance with an exemplary embodiment of the present disclosure.

FIG. 97 shows a side view of the electronic apparatus of FIG. 96.

FIG. 98 shows an end view of the electronic apparatus of FIG. 96.

Figure 99:
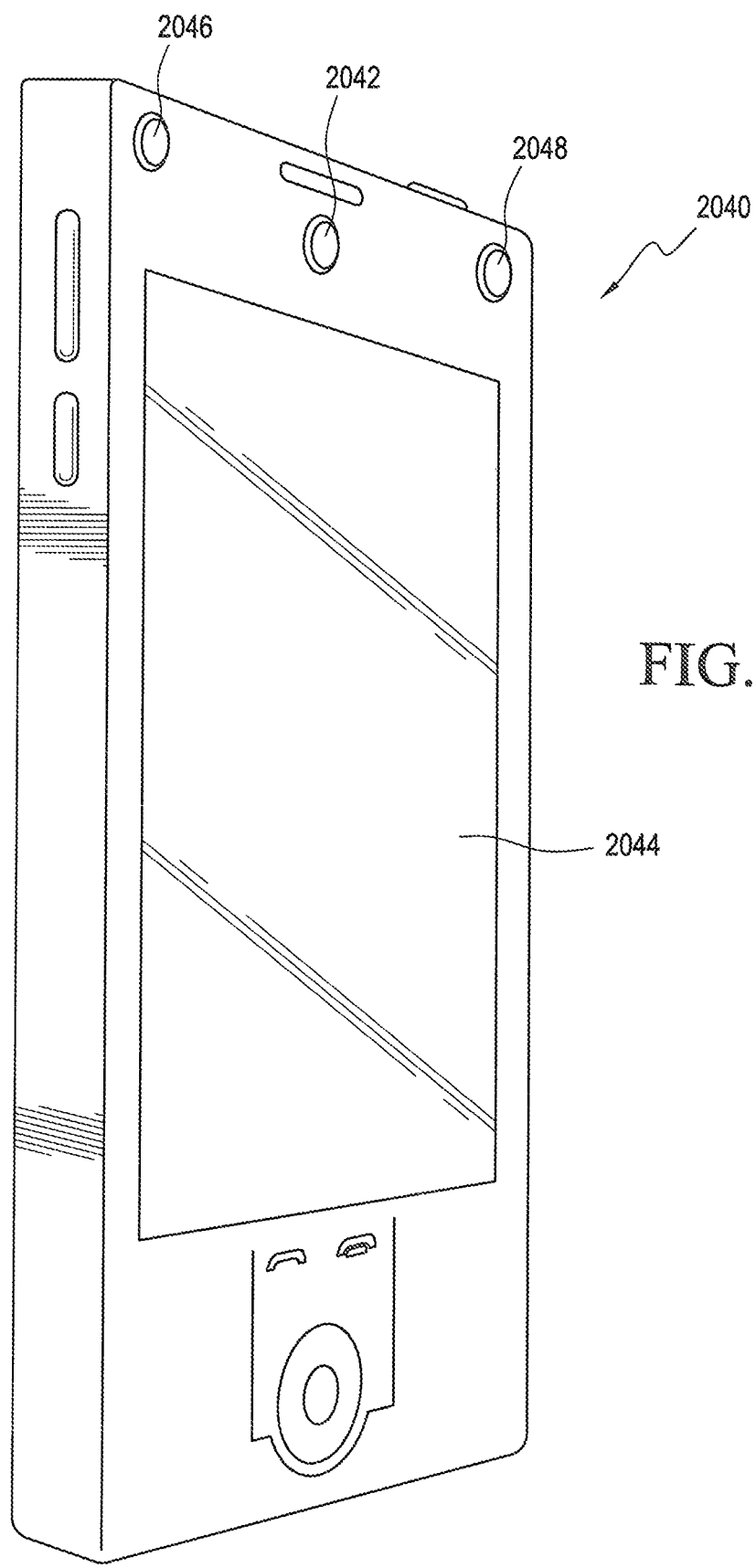

FIG. 99 shows a perspective view of the electronic apparatus of FIG. 96.

Figure 100:
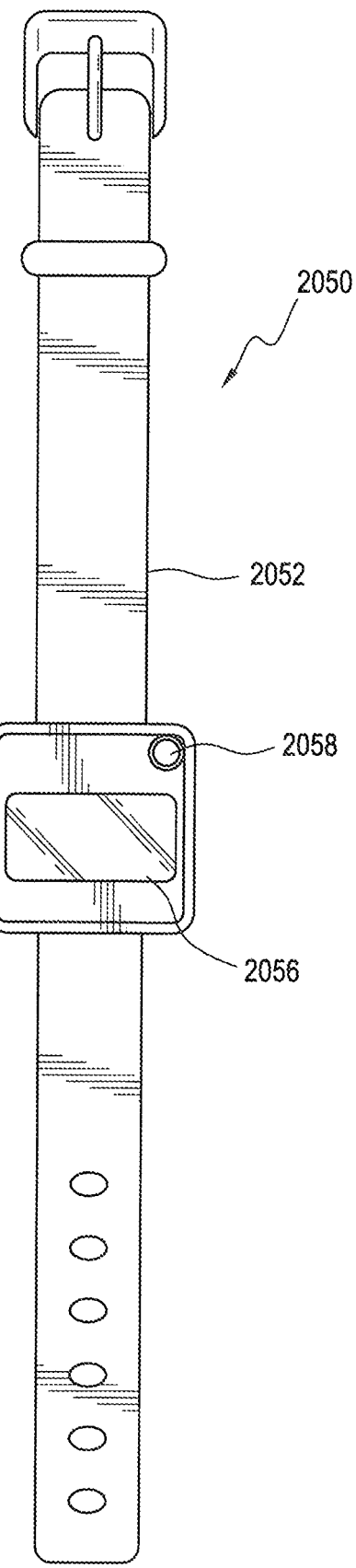

FIG. 100 shows a plan view of another electronic apparatus configured with a measurement device in accordance with an exemplary embodiment of the present disclosure.

Figure 101:
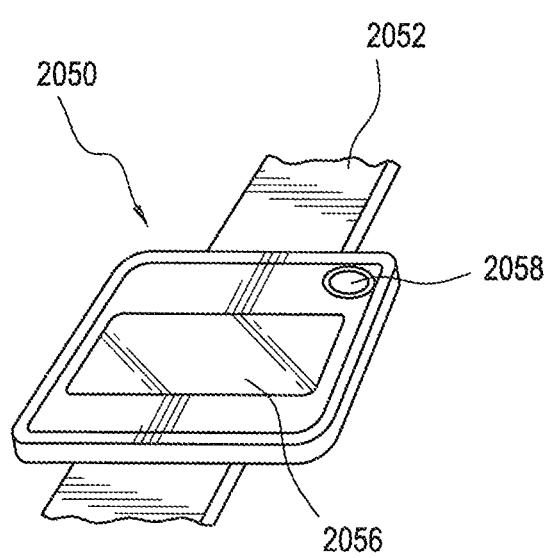

FIG. 101 shows a perspective view of the device of FIG. 100.

Figure 102:
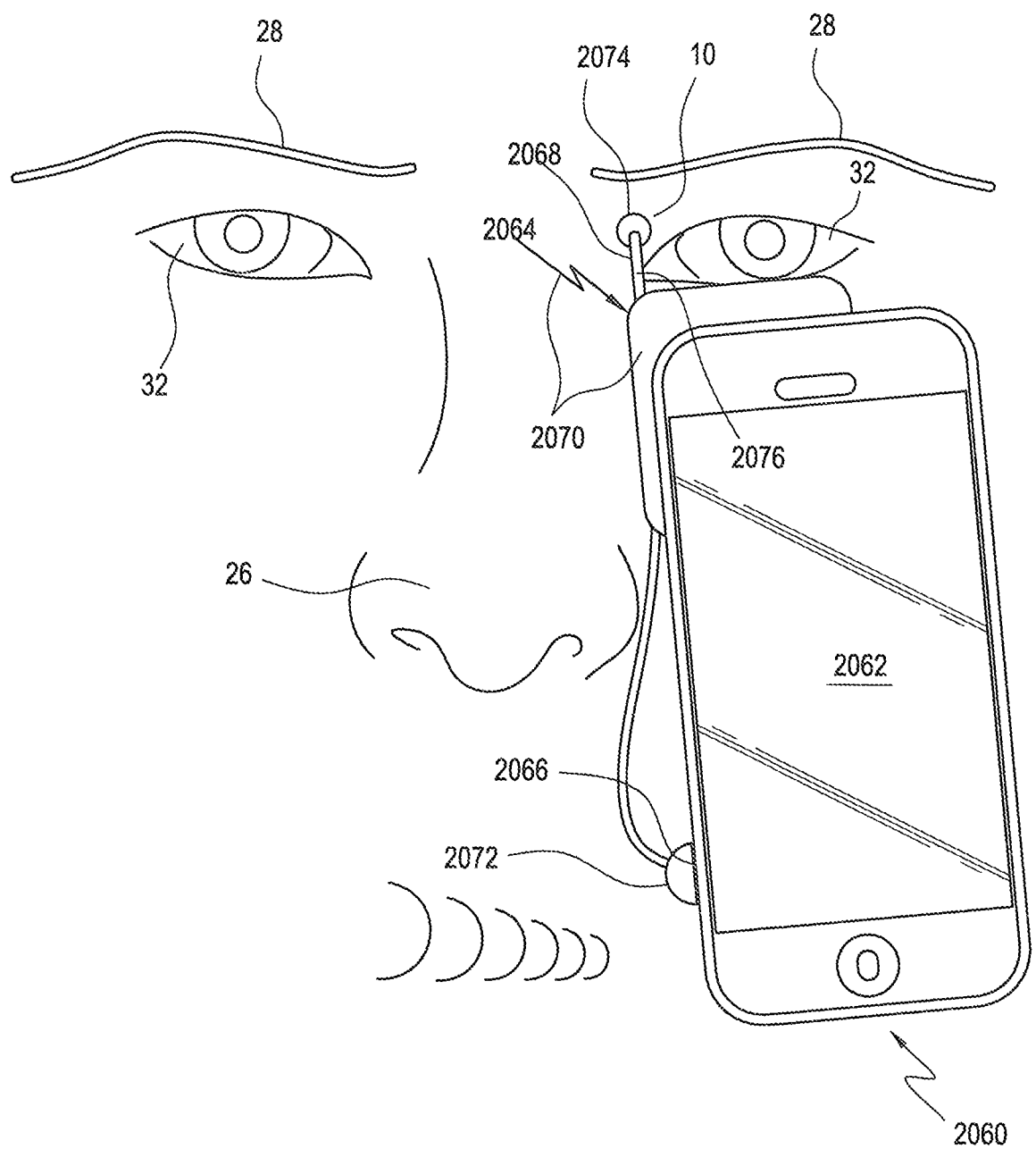

FIG. 102 shows a view of yet another electronic apparatus configured with a measurement device in accordance with an exemplary embodiment of the present disclosure.

Figure 103:
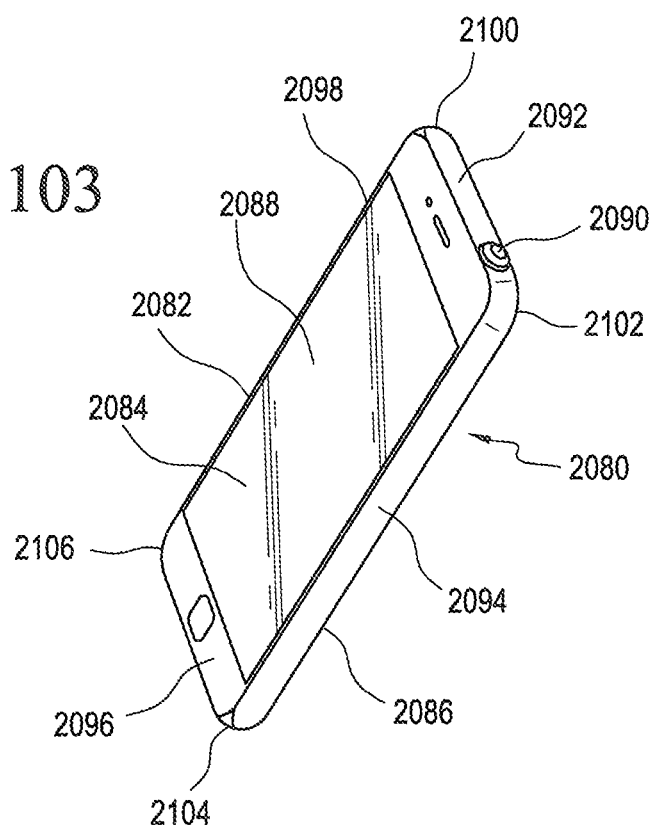

FIG. 103 shows a perspective view of a further electronic apparatus configured with a measurement device in accordance with an exemplary embodiment of the present disclosure.

Figure 104:
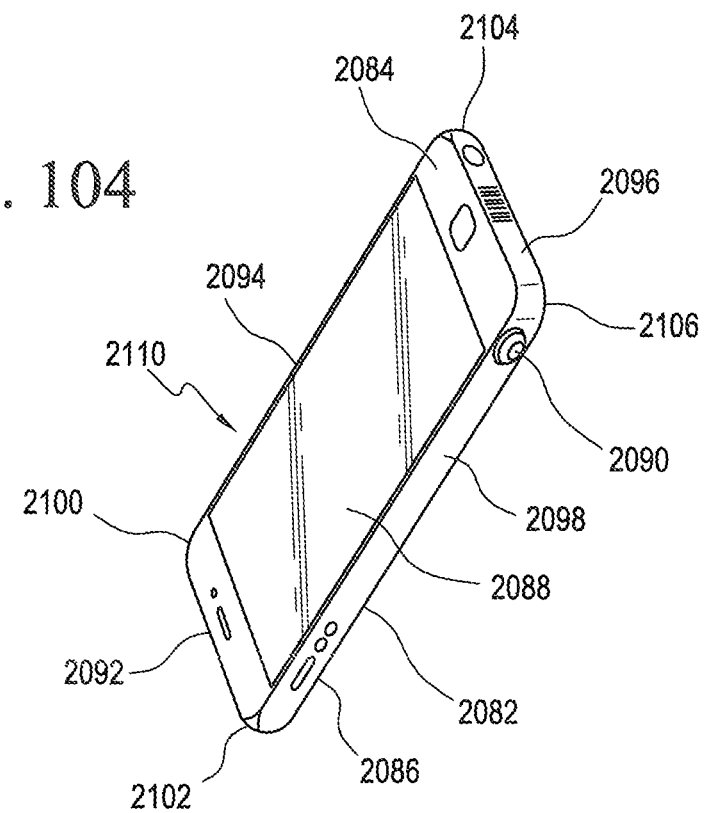

FIG. 104 shows a perspective view of a yet further electronic apparatus configured with a measurement device in accordance with an exemplary embodiment of the present disclosure.

FIG. 105 shows a perspective view the electronic apparatus of FIG. 103 with a nose piece positioned around a sensor in accordance with an exemplary embodiment of the present disclosure.

FIG. 106 shows a perspective view the electronic apparatus of FIG. 104 with a nose piece positioned around a sensor in accordance with an exemplary embodiment of the present disclosure.

Figure 107:
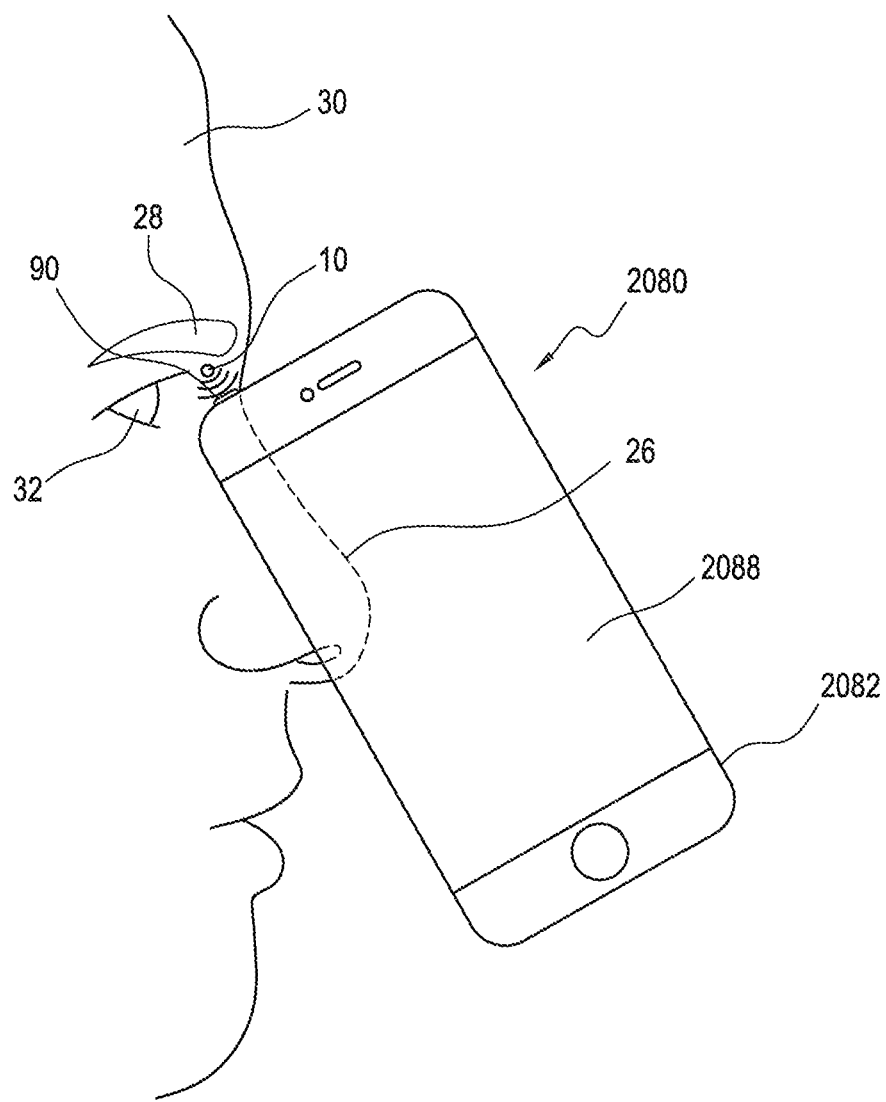

FIG. 107 shows a view of the device of FIG. 103 in use.

Figure 108:
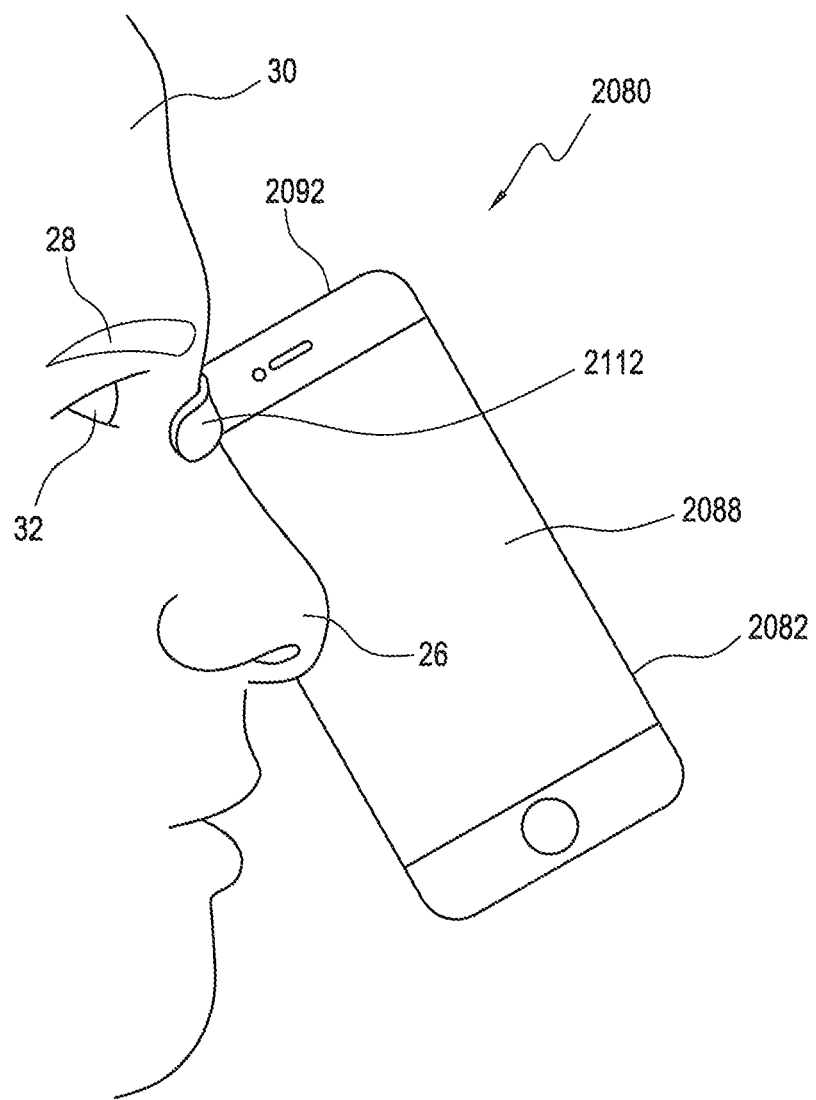

FIG. 108 shows a view of the device of FIG. 103 in use with a nose piece.

Figure 109:
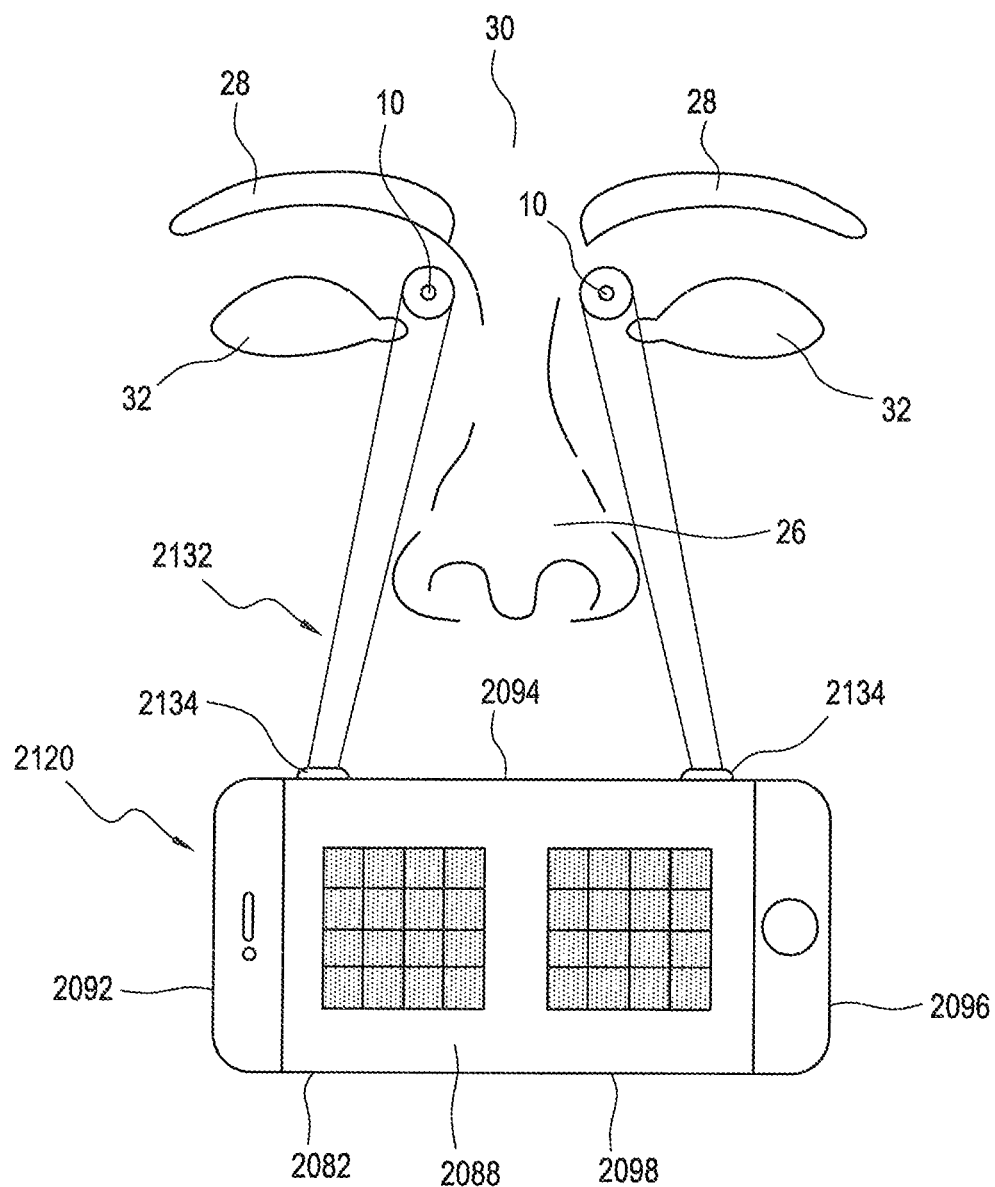

FIG. 109 shows a view of an electronic apparatus configured with a measurement device in accordance with an exemplary embodiment of the present disclosure.

Figure 110:
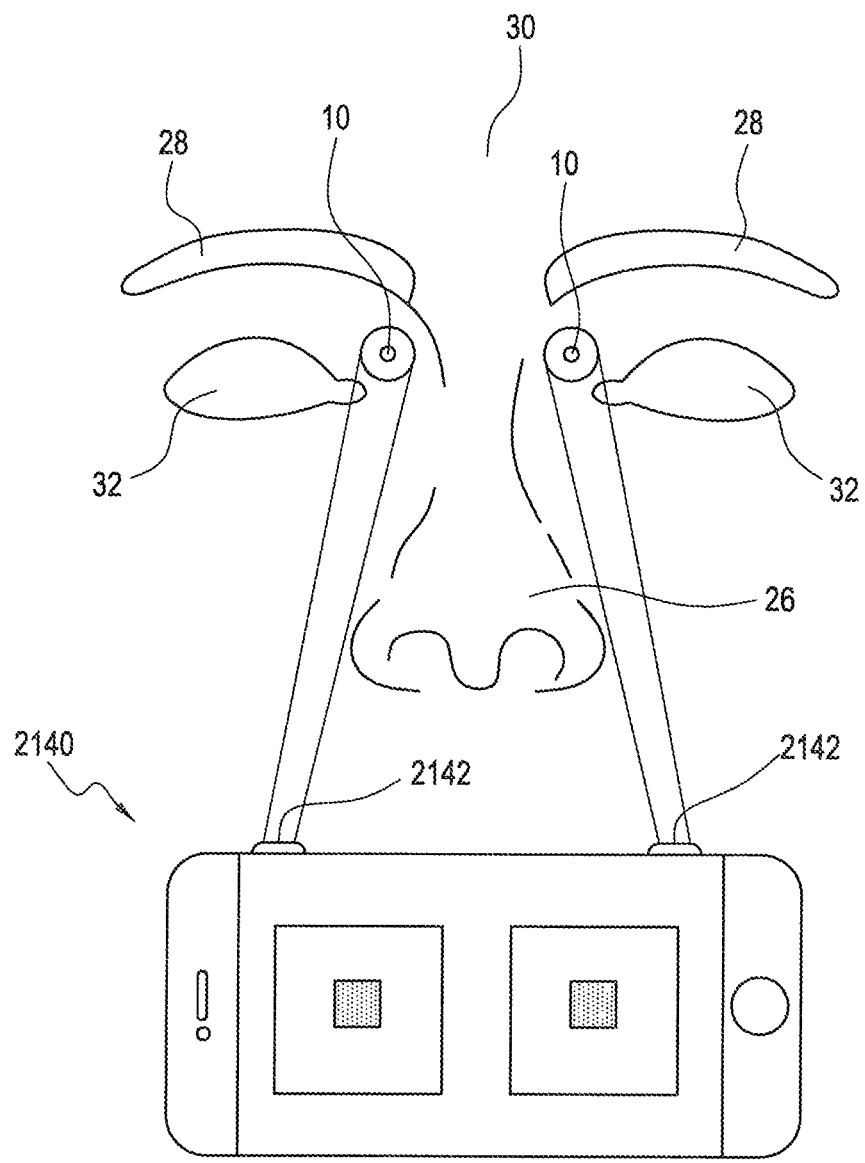

FIG. 110 shows a view of an electronic apparatus configured with a measurement device in accordance with another exemplary embodiment of the present disclosure.

Figure 111:
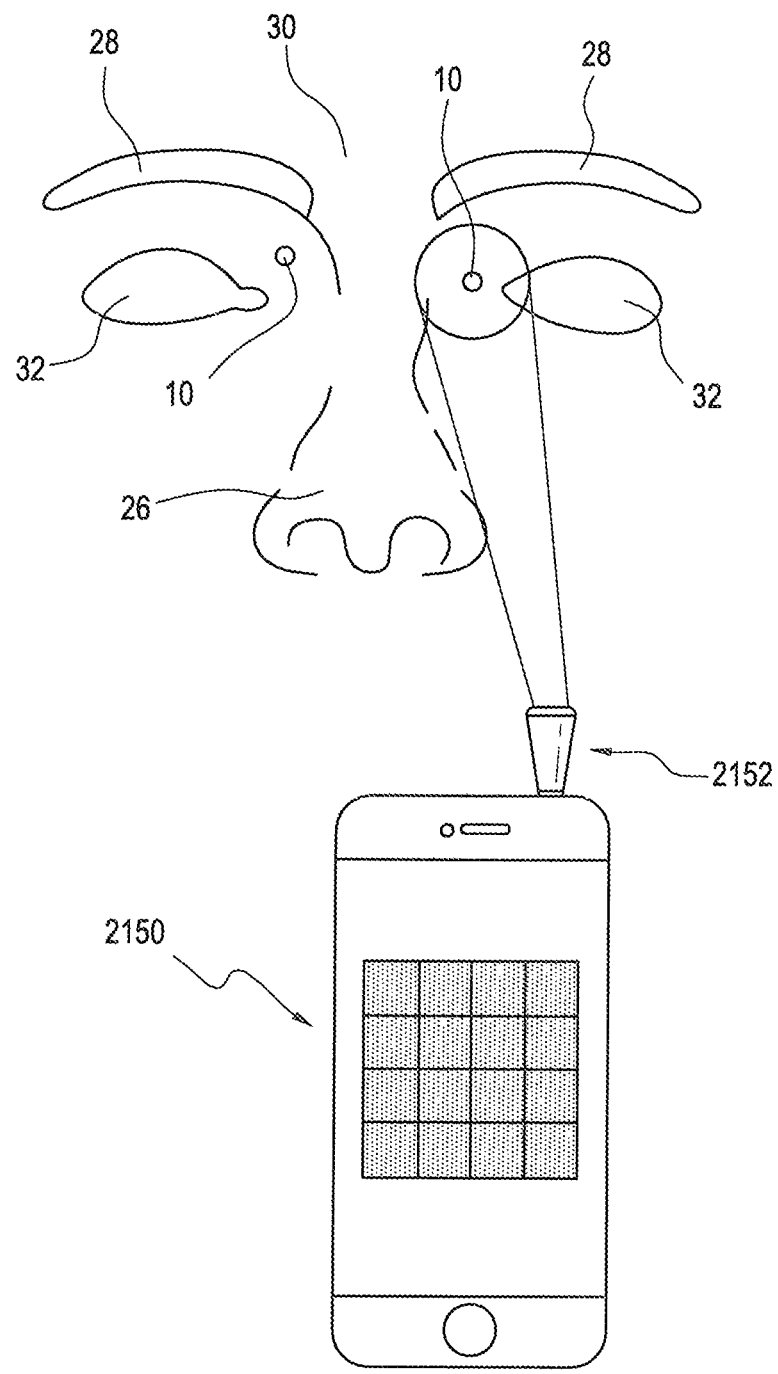

FIG. 111 shows a view of an electronic apparatus configured with a measurement device in accordance with yet another exemplary embodiment of the present disclosure.

FIG. 112 shows a perspective view of an electronic apparatus configured with a measurement device in accordance with a further exemplary embodiment of the present disclosure.

FIG. 113 shows a view of an end of the electronic apparatus of FIG. 112.

Figure 114:
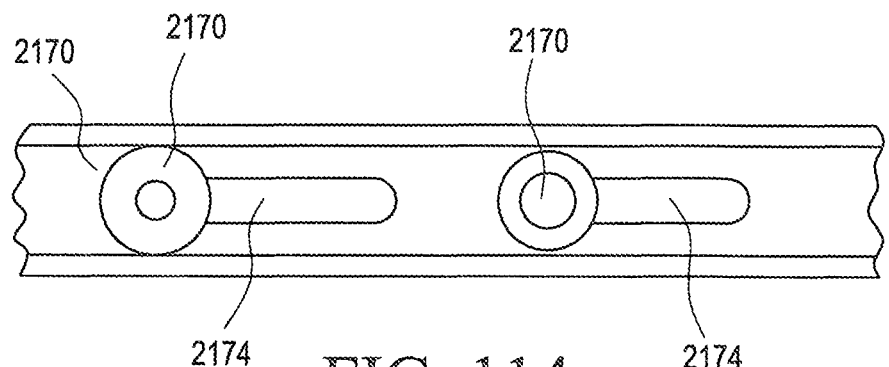

FIG. 114 shows a view of a side of the electronic apparatus of FIG. 112.

Figure 115:
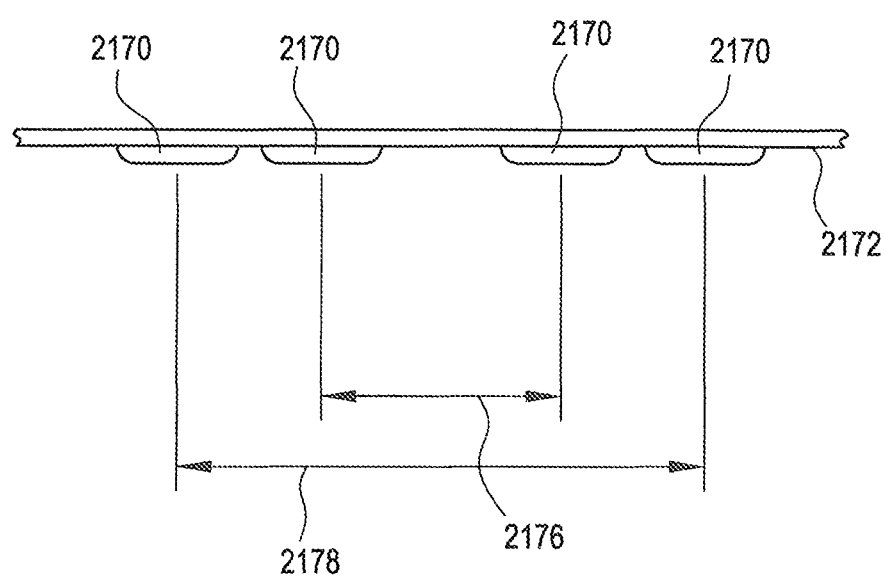

FIG. 115 shows another view of the electronic apparatus of FIG. 112 showing available positions for measurement devices of the electronic apparatus.

Figure 116:
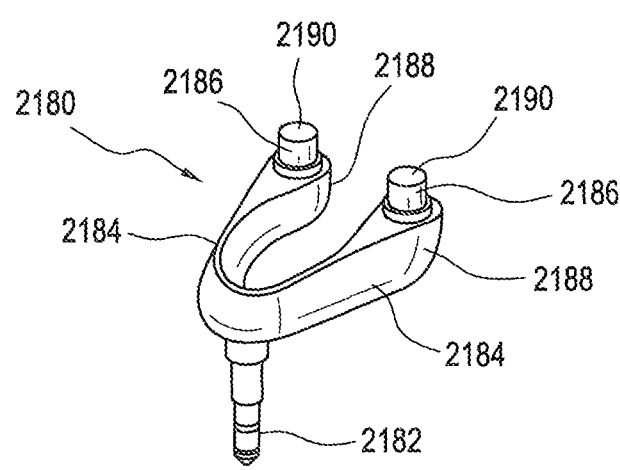

FIG. 116 shows a perspective view of a separable sensor device in accordance with an exemplary embodiment of the present disclosure.

Figure 117:
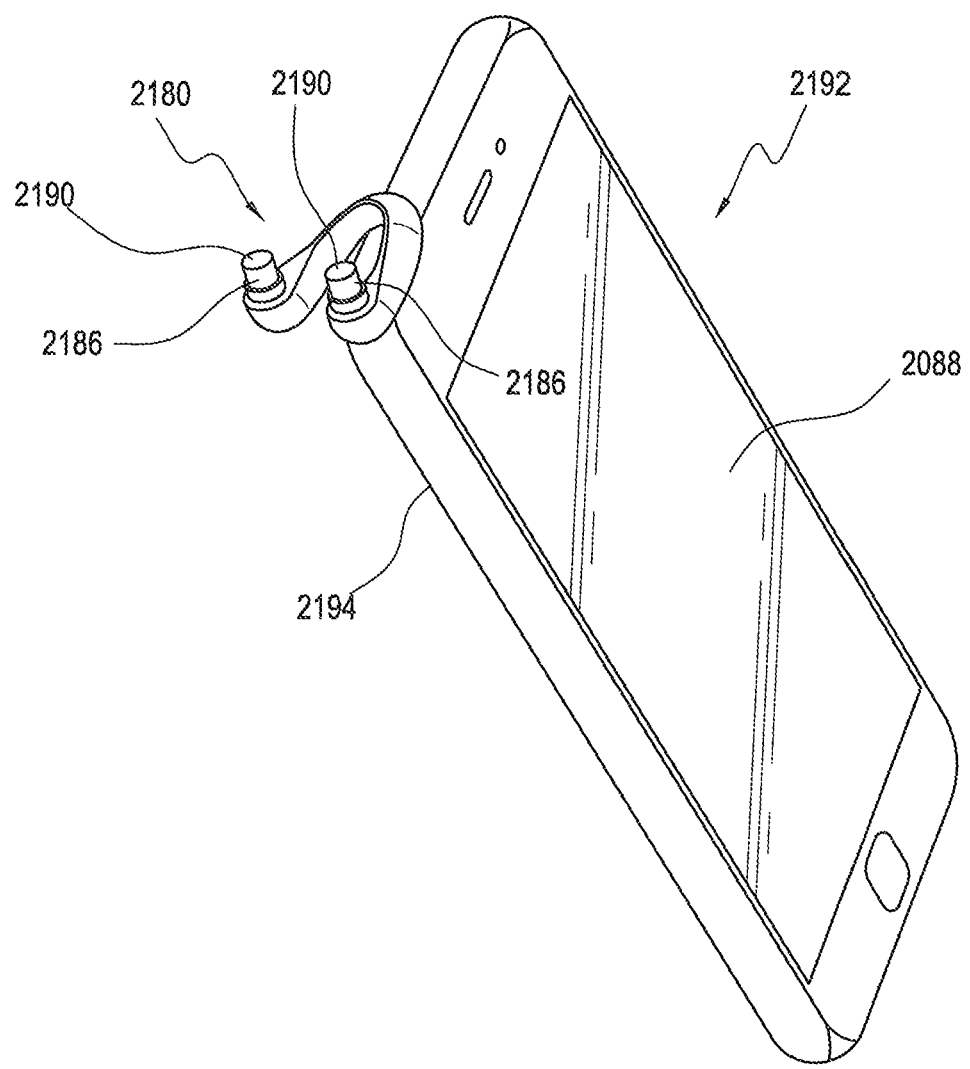

FIG. 117 shows a perspective view of an electronic apparatus incorporating the separable sensor device of FIG. 116 in accordance with another exemplary embodiment of the present disclosure.

FIG. 118 shows a perspective view of a separable sensor device and an electronic apparatus in accordance with yet another exemplary embodiment of the present disclosure.

FIG. 119 shows a perspective view of a sensor system in accordance with a further exemplary embodiment of the present disclosure.

Figures 120, 121:
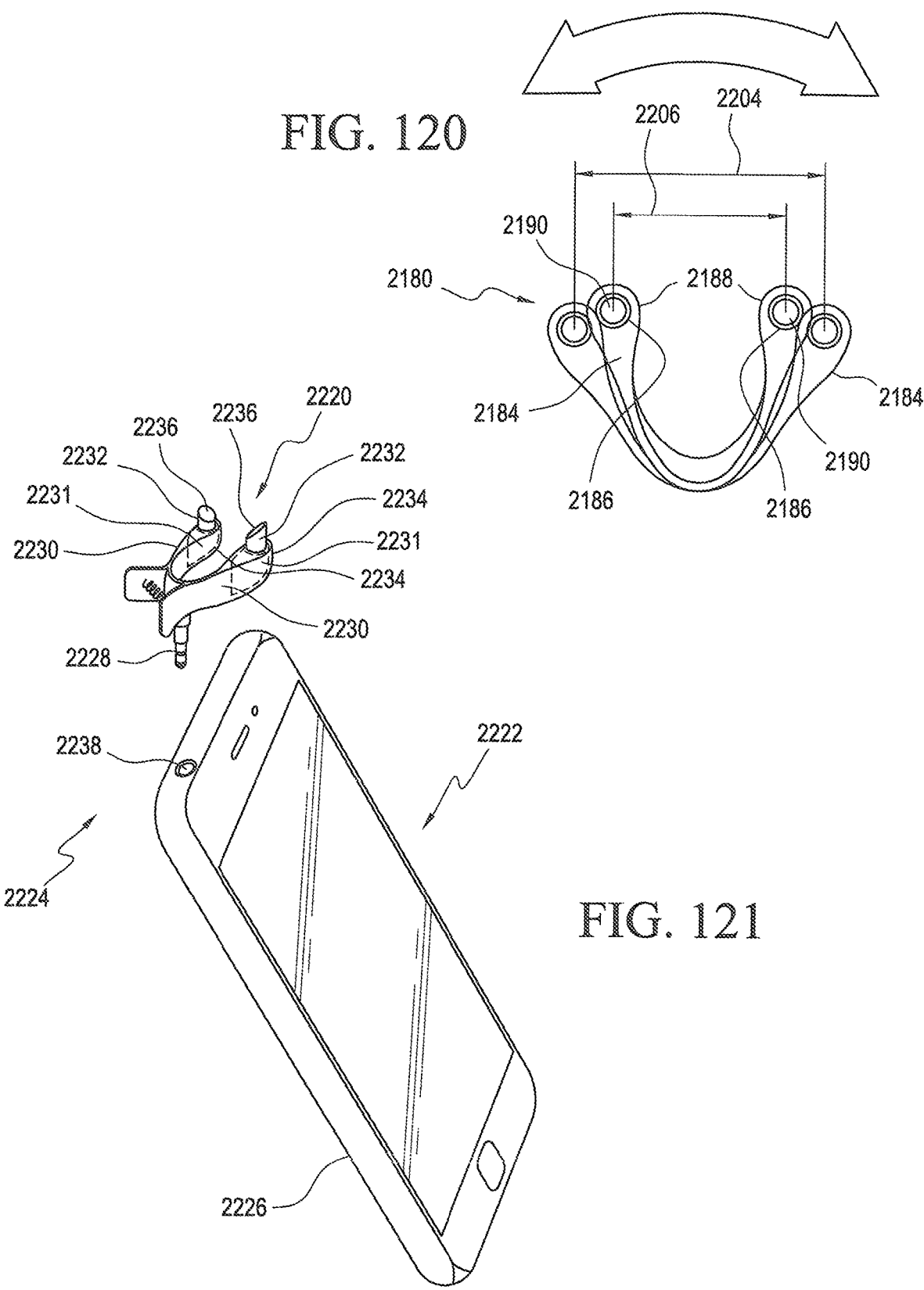

FIG. 120 shows a view of the separable sensor device of FIG. 116.

FIG. 121 shows a view of a temperature modification device and an electronic apparatus in accordance with an exemplary embodiment of the present disclosure.

FIG. 122 shows a view of a temperature modification device in accordance with another exemplary embodiment of the present disclosure.

FIG. 123 shows a view of a temperature modification device in accordance with yet another exemplary embodiment of the present disclosure.

FIG. 124 shows a view of a temperature modification device in accordance with still yet another exemplary embodiment of the present disclosure.

Figure 125:
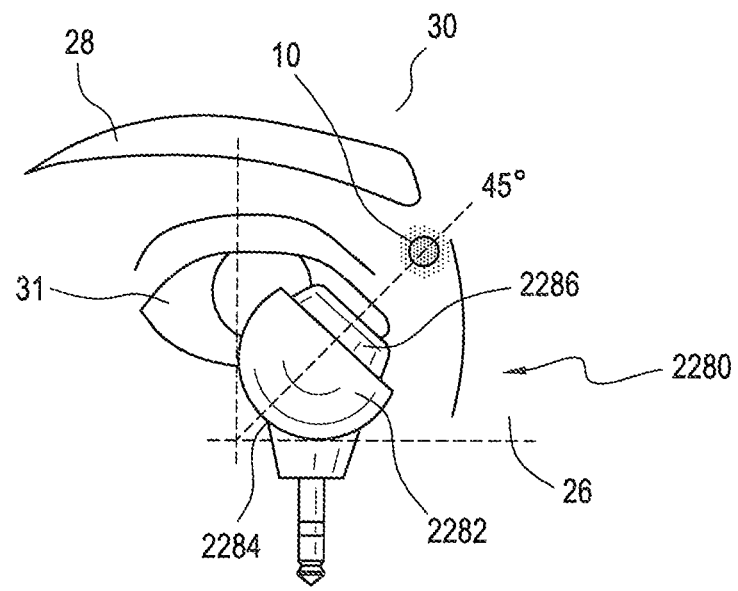

FIG. 125 shows a view of a separable sensor device in accordance with an exemplary embodiment of the present disclosure.

Figure 126:
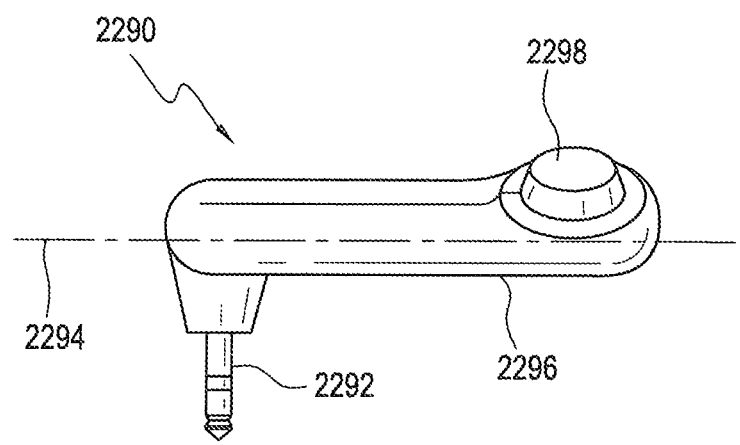

FIG. 126 shows a view of a separable sensor device in accordance with another exemplary embodiment of the present disclosure.

Figure 127:
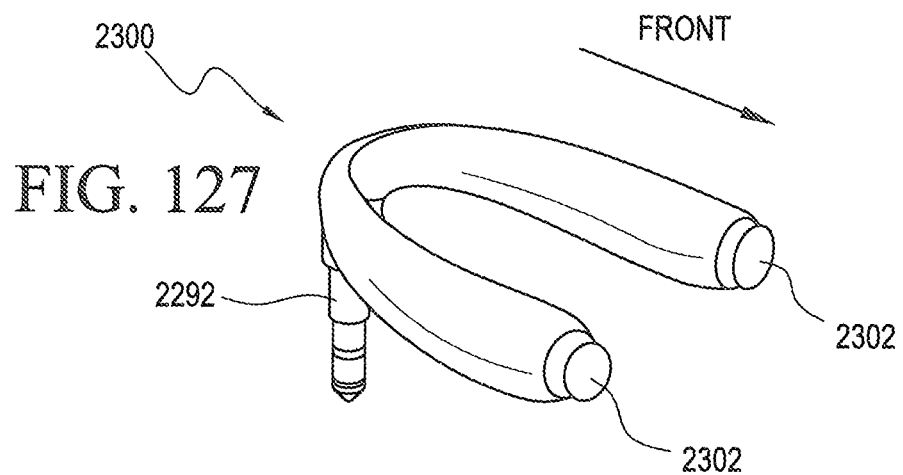

FIG. 127 shows a perspective view of another separable sensor device in accordance with an exemplary embodiment of the present disclosure.

Figure 128:
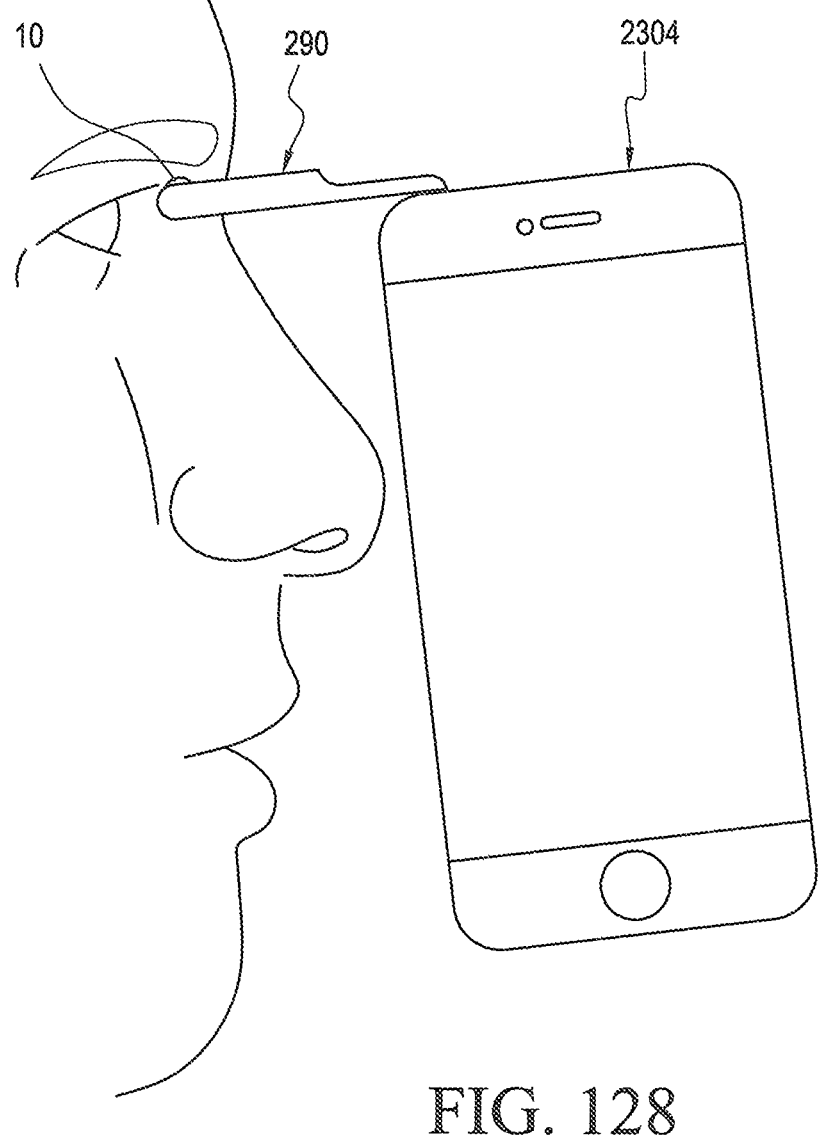

FIG. 128 shows a view of the separable sensor device of FIG. 126 inserted into an electronic apparatus in accordance with an exemplary embodiment of the present disclosure.

FIG. 129 shows a view of an electronic apparatus configured with a measurement device in accordance with an exemplary embodiment of the present disclosure.

FIG. 130 shows another view of the electronic apparatus of FIG. 129.

Figure 131:
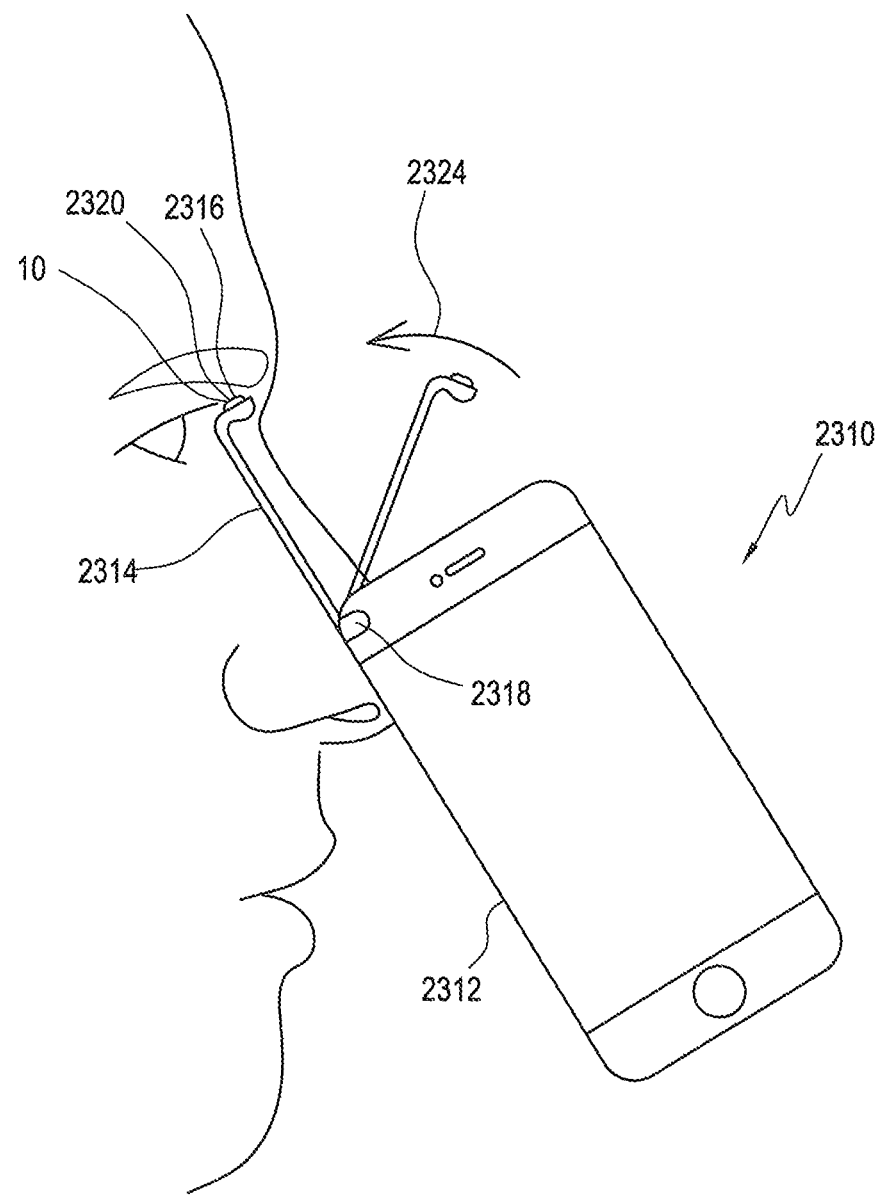

FIG. 131 shows yet another view of the electronic apparatus of FIG. 129.

FIG. 132 shows a view of a separable sensor device in accordance with an exemplary embodiment of the present disclosure.

FIG. 133 shows a view of another separable sensor device in accordance with an exemplary embodiment of the present disclosure.

FIG. 134 shows a perspective view of an electronic apparatus with the separable sensor device of FIG. 133 positioned thereon in accordance with an exemplary embodiment of the present disclosure.

Figure 135:
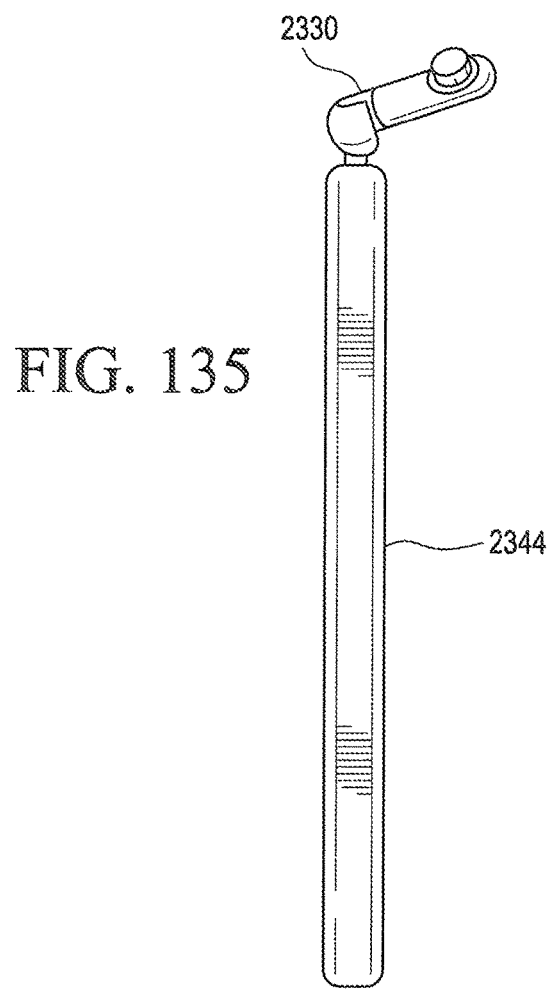

FIG. 135 shows a further view of the separable sensor device and the electronic apparatus of FIGS. 133 and 134.

Figure 136:
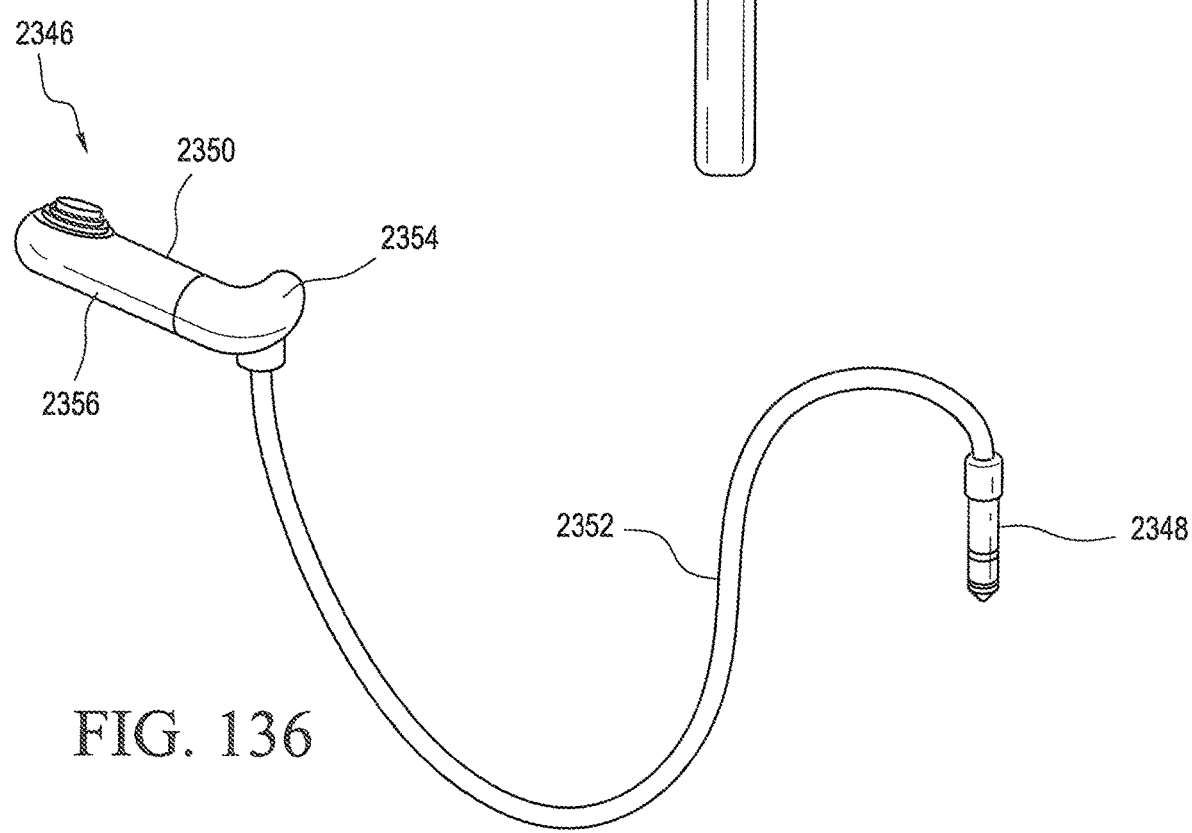

FIG. 136 shows a view of a yet even further separable sensor device in accordance with an exemplary embodiment of the present disclosure.

Figure 137:
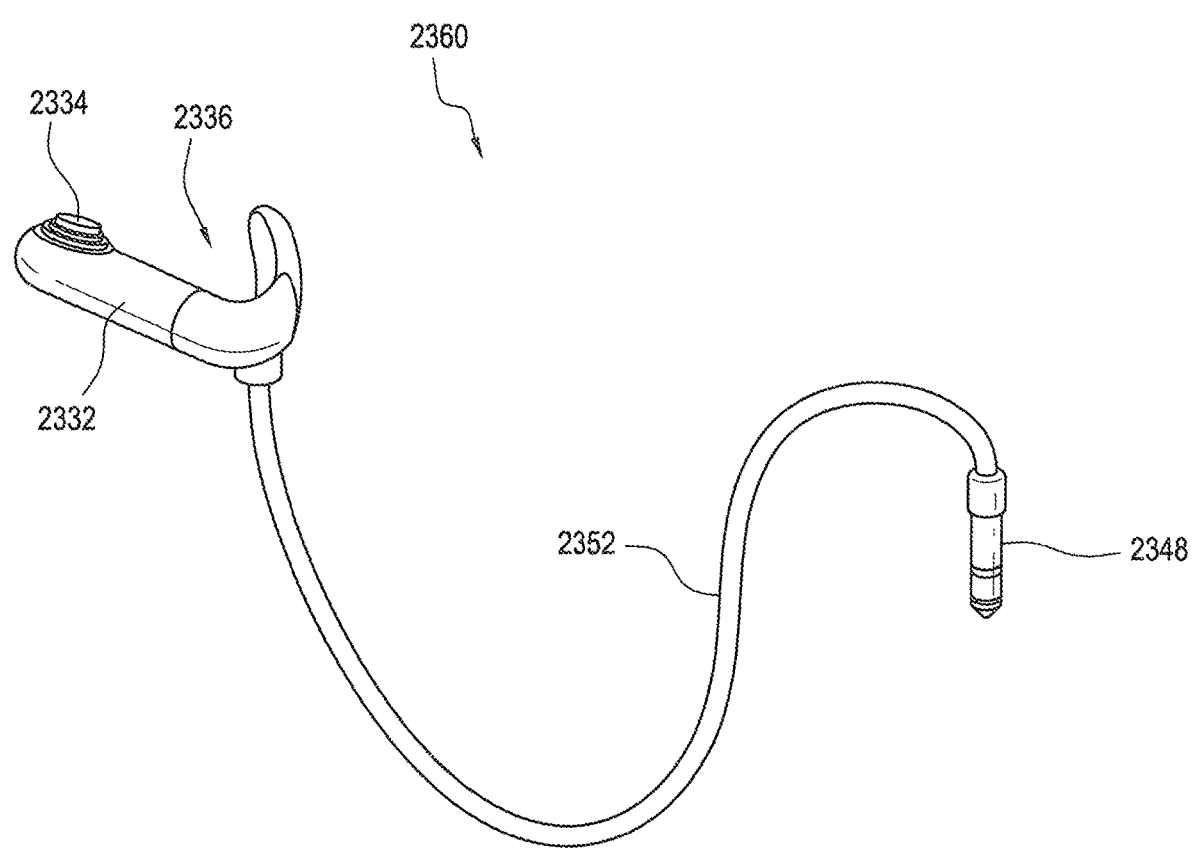

FIG. 137 shows a view of a still further separable sensor device in accordance with an exemplary embodiment of the present disclosure.

Figure 138:
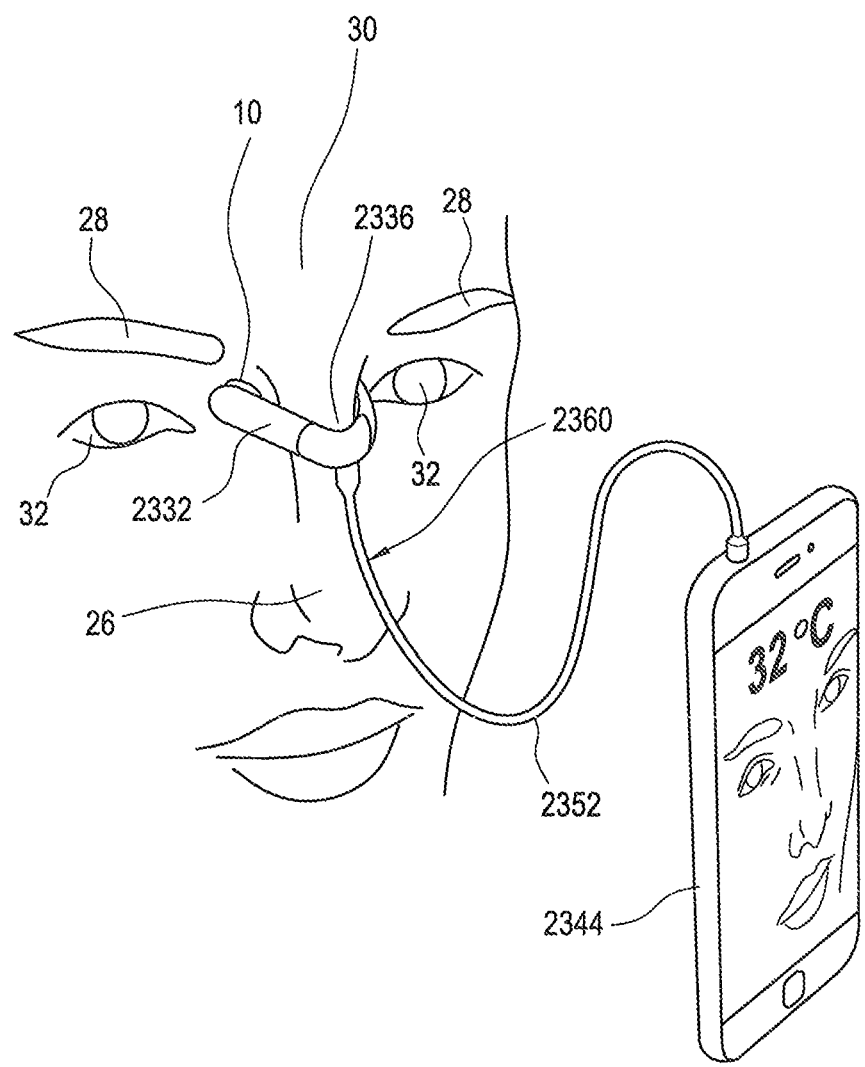

FIG. 138 shows a perspective view of the separable sensor device of FIG. 137 attached to an electronic apparatus with the separable sensor device positioned on a nose of a user in accordance with an exemplary embodiment of the present disclosure.

Figure 139:
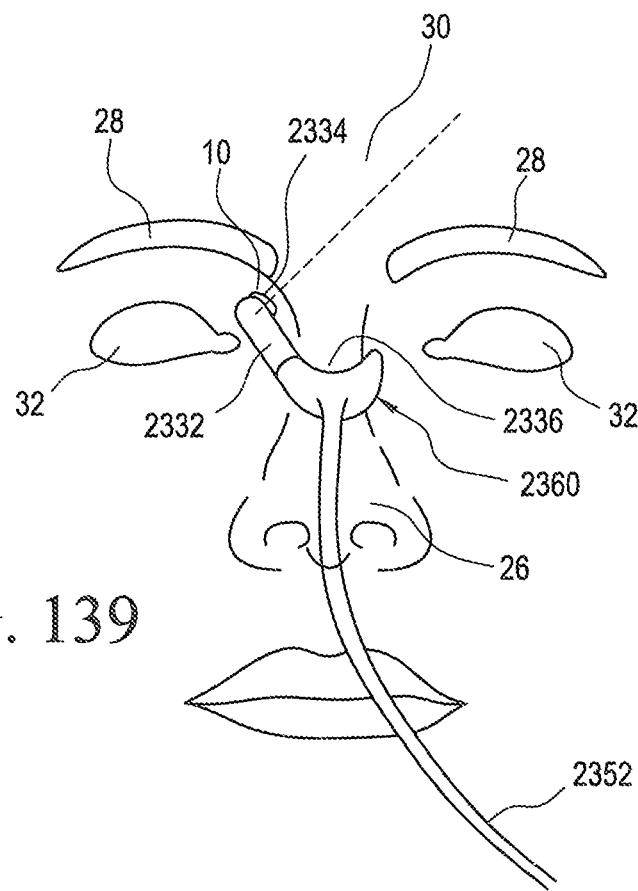

FIG. 139 shows a further view of the separable sensor device of FIG. 137 positioned on the nose of a user.

Figure 140:
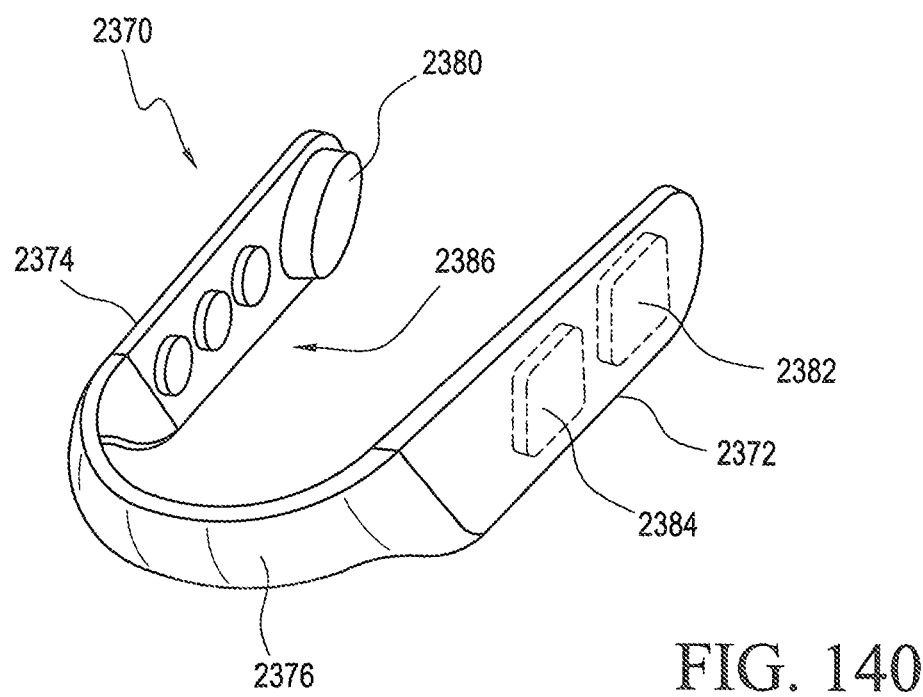

FIG. 140 shows a perspective view of another separable sensor device in accordance with an exemplary embodiment of the present disclosure.

Figure 141:
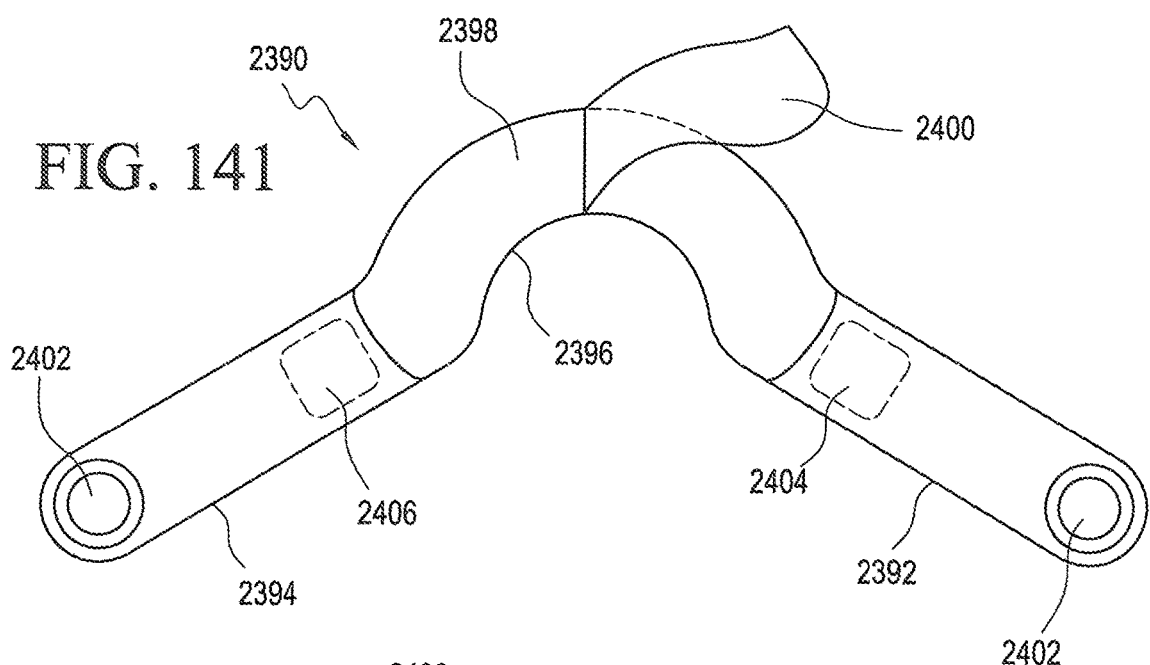

FIG. 141 shows a view of yet another separable sensor device in accordance with an exemplary embodiment of the present disclosure.

Figure 142:
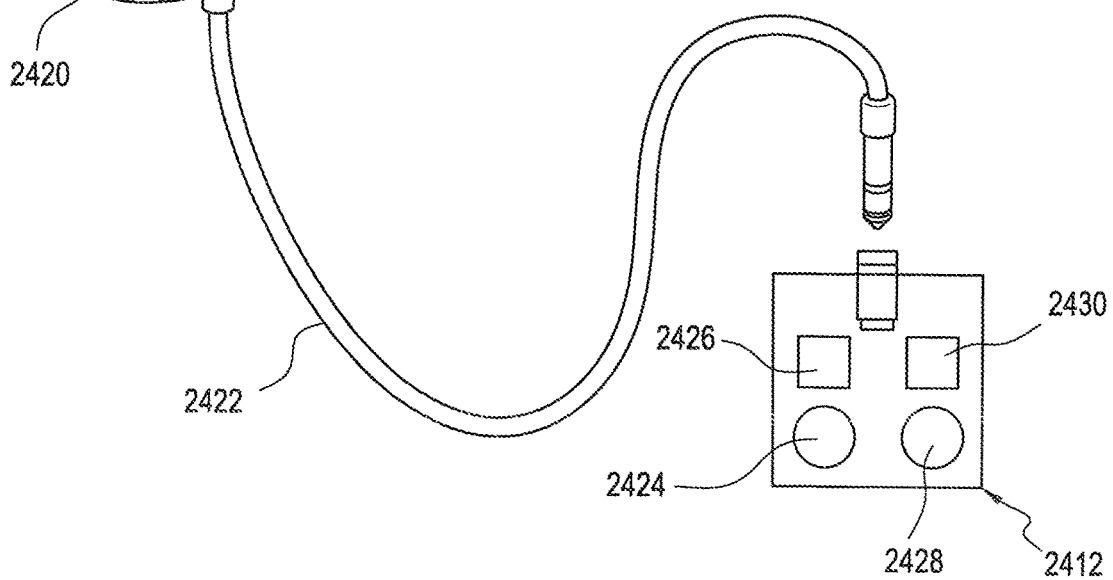

FIG. 142 shows a perspective view of a further separable sensor device and an electronic apparatus in accordance with an exemplary embodiment of the present disclosure.

Figure 143:
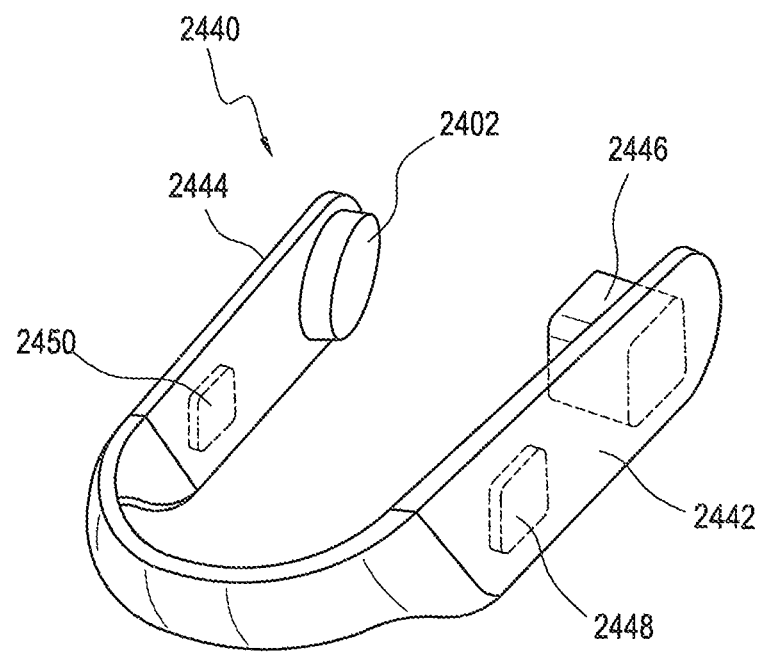

FIG. 143 shows a perspective view of a still further separable sensor device in accordance with an exemplary embodiment of the present disclosure.

Figure 144:
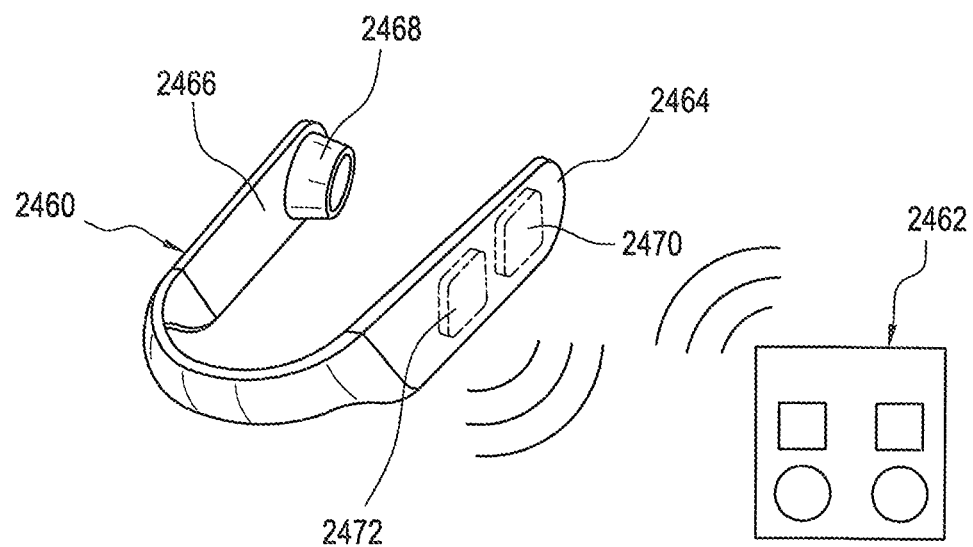

FIG. 144 shows a perspective view of a separable temperature modification device and an electronic apparatus in accordance with an exemplary embodiment of the present disclosure.

Figure 145:
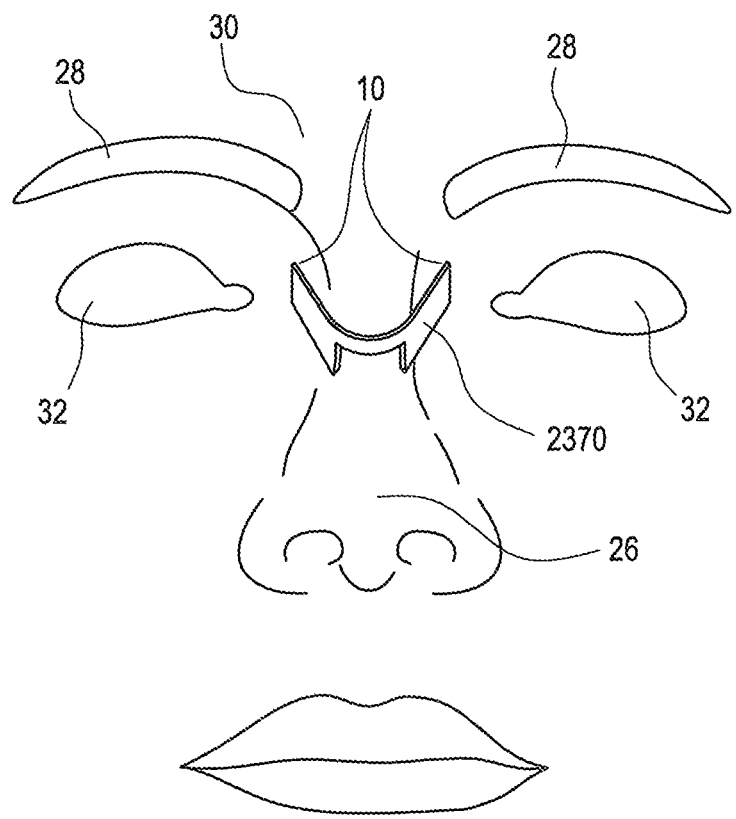

FIG. 145 shows a view of the separable sensor device of FIG. 140 positioned on the nose of a user.

Figure 146:
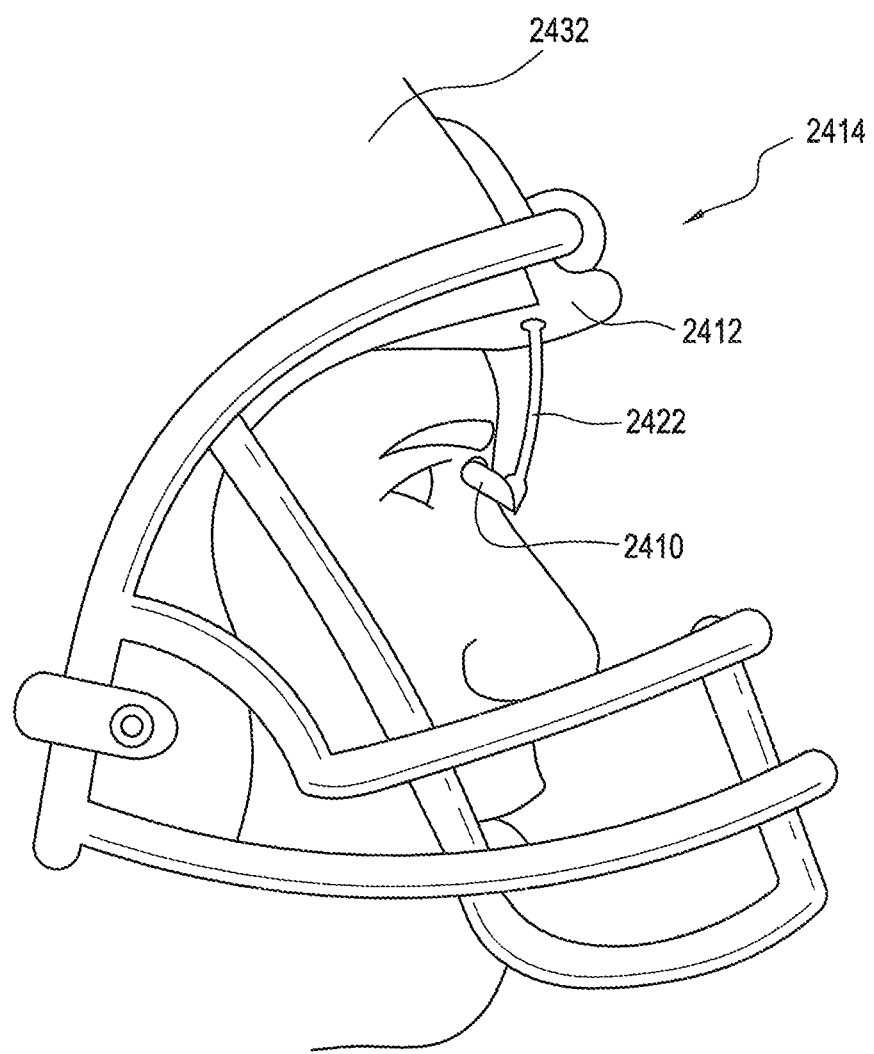

FIG. 146 shows a view of the separable sensor device of FIG. 142 positioned on the nose of a user and supported by a sport helmet in accordance with an exemplary embodiment of the present disclosure.

Figure 147:
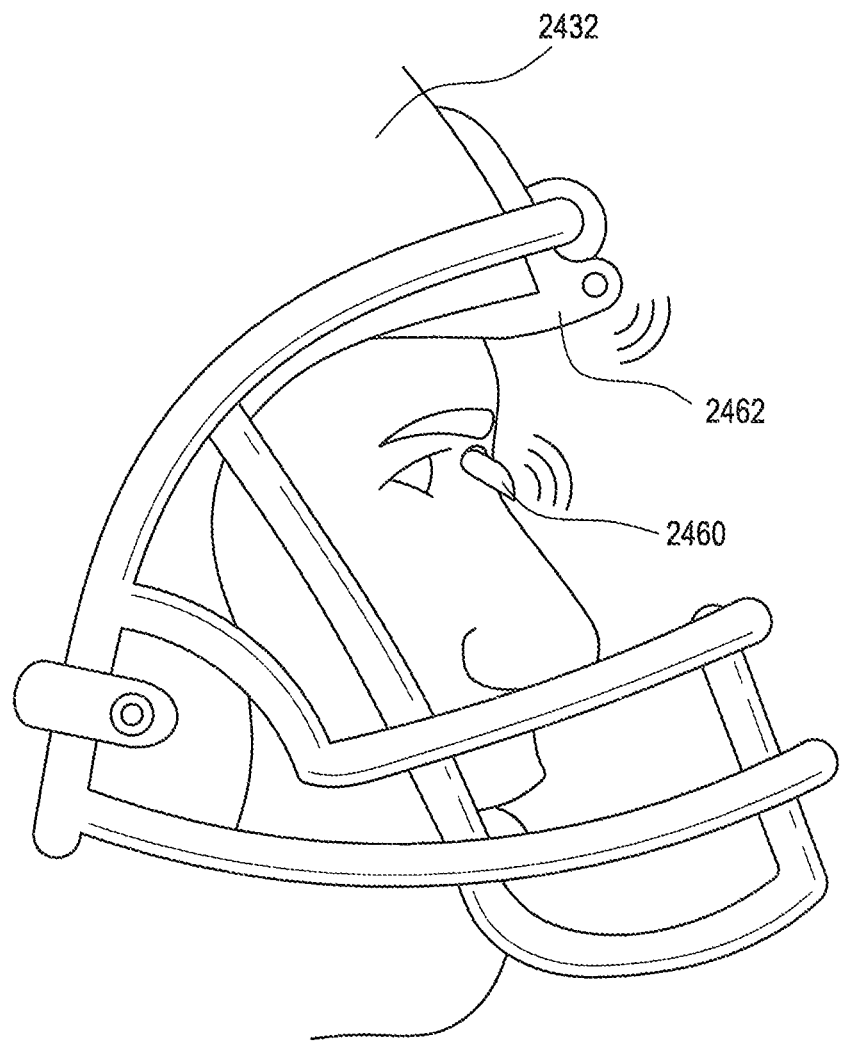

FIG. 147 shows a view of the separable sensor device of FIG. 144 positioned on the nose of a user and the electronic apparatus of FIG. 144 supported by a sport helmet in accordance with an exemplary embodiment of the present disclosure.

Figure 148:
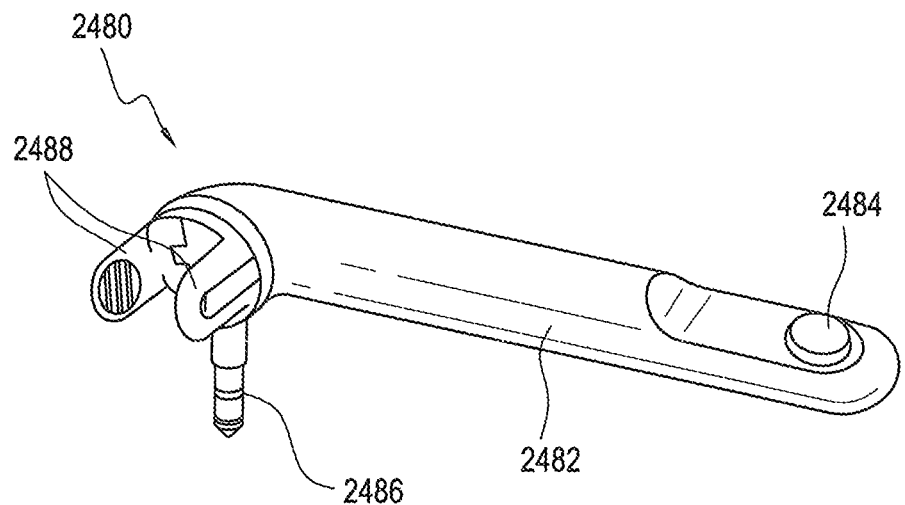

FIG. 148 shows a perspective view of a separable sensor device in accordance with an exemplary embodiment of the present disclosure.

Figure 149:
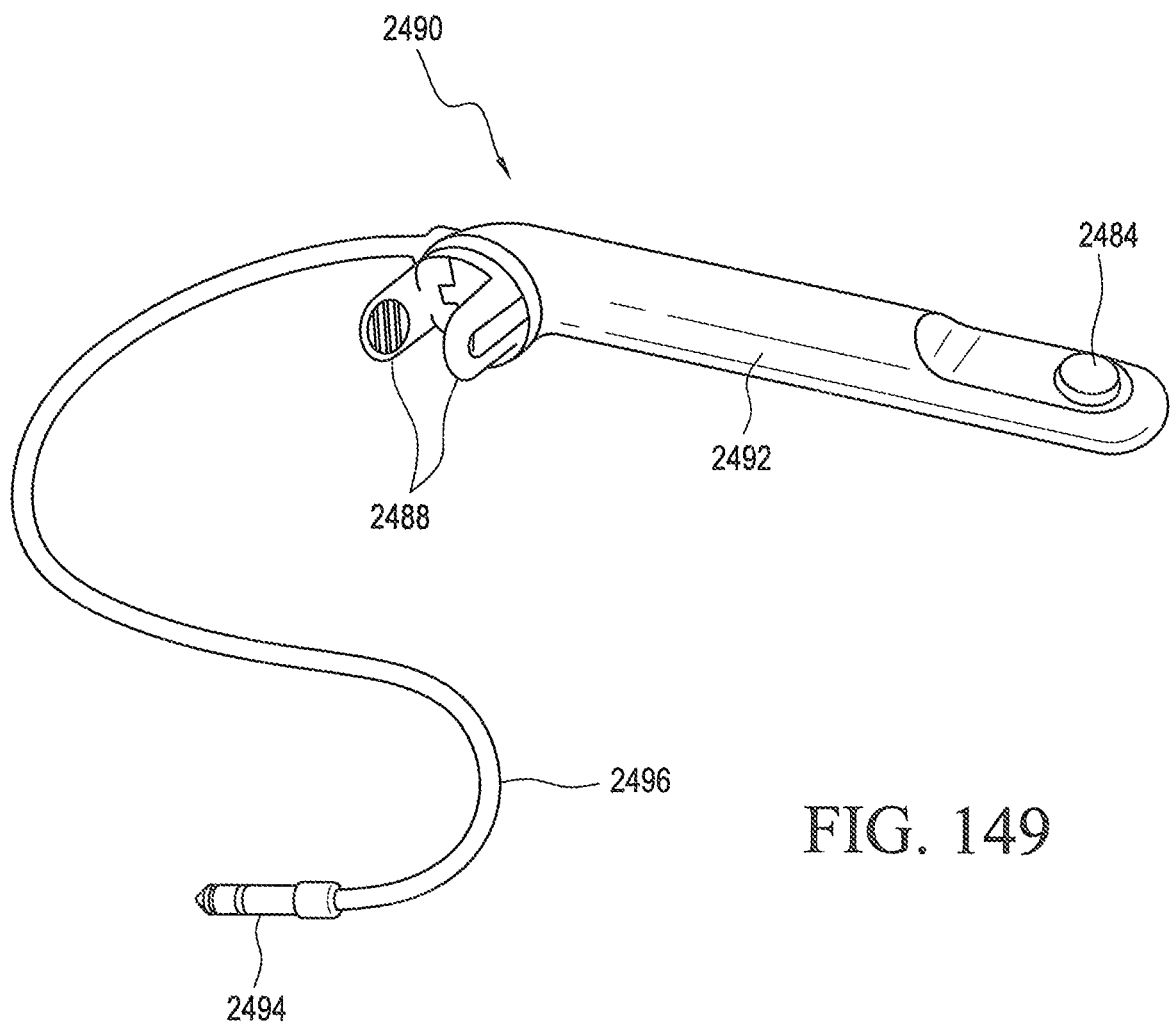

FIG. 149 shows a perspective view of another separable sensor device in accordance with an exemplary embodiment of the present disclosure.

Figure 150:
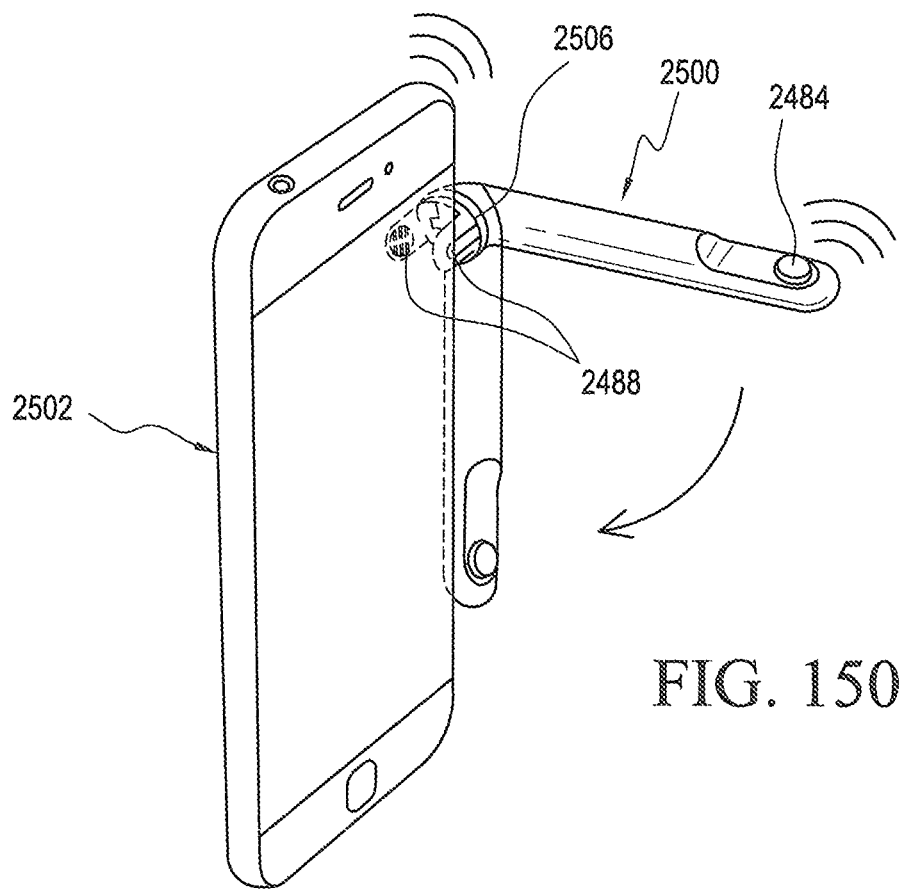

FIG. 150 shows a perspective view of a separable sensor device attached to an electronic apparatus in accordance with an exemplary embodiment of the present disclosure.

Figure 151:
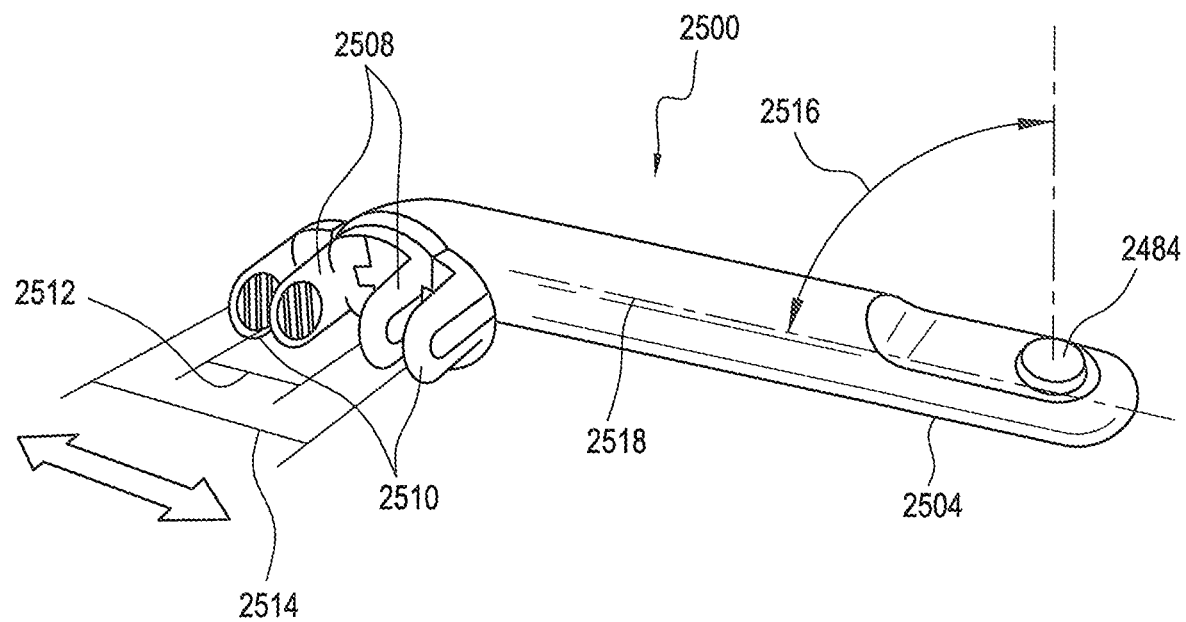

FIG. 151 shows a perspective view of a further separable sensor device in accordance with an exemplary embodiment of the present disclosure.

Figure 152:
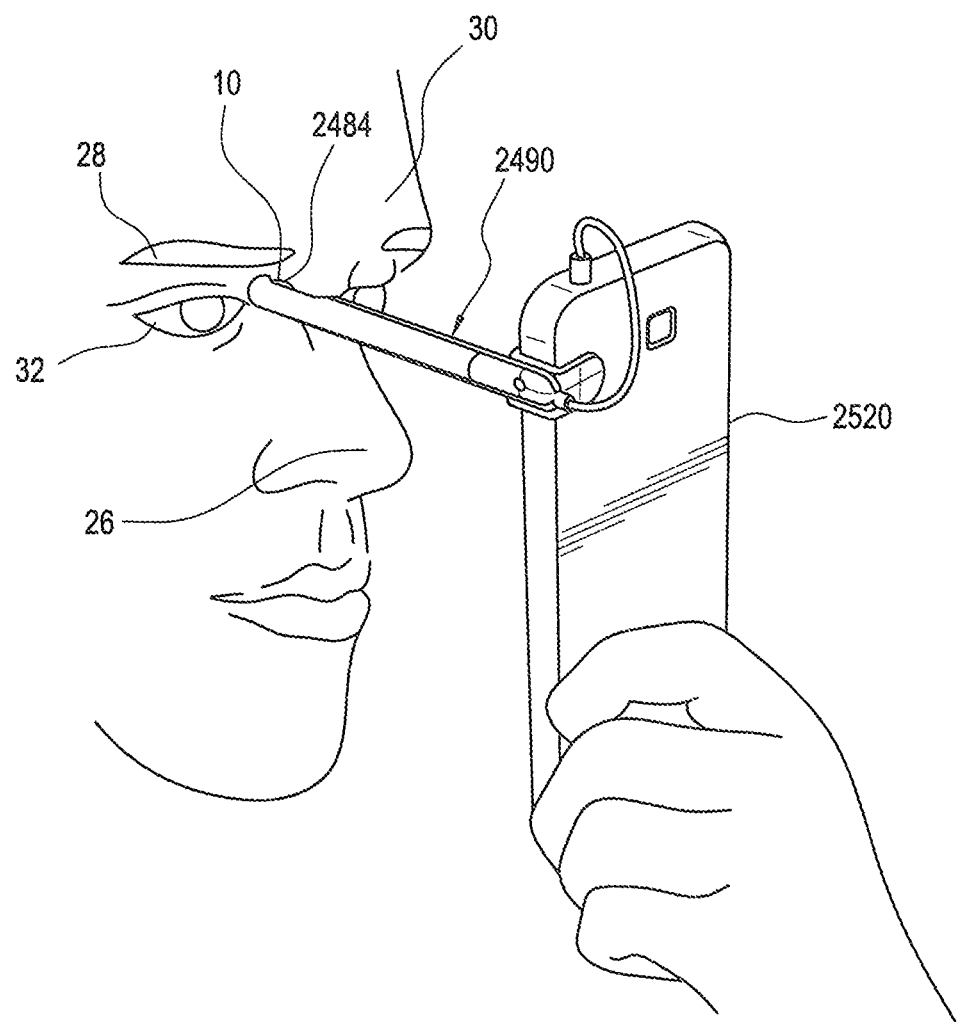

FIG. 152 shows a perspective view of the separable sensor device of FIG. 149 attached to an electronic apparatus and being used by a user to make a measurement of an emission from the ABTT.

Figure 153:
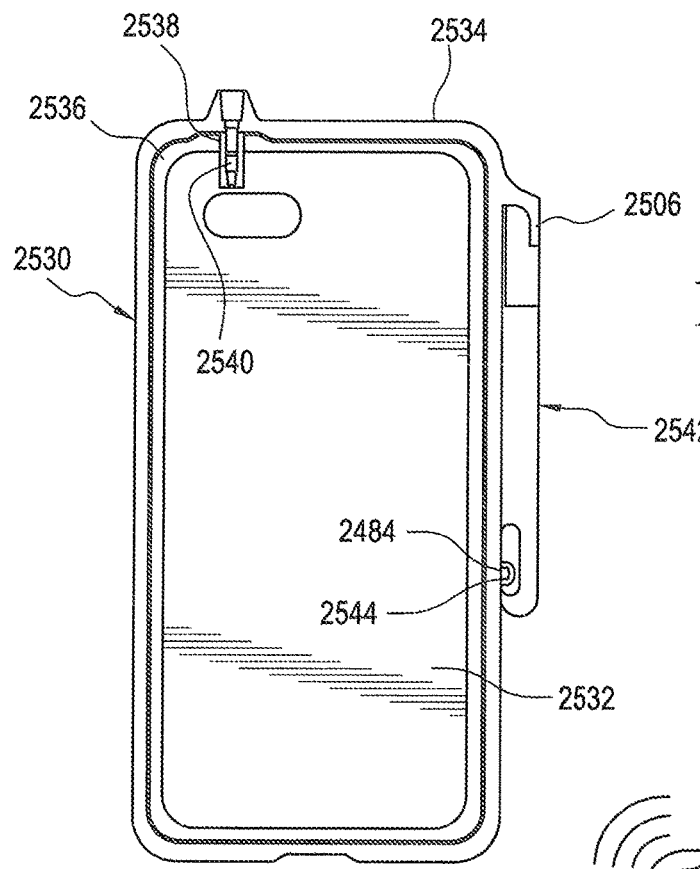

FIG. 153 shows a view of yet another separable sensor device positioned on an electronic apparatus in accordance with an exemplary embodiment of the present disclosure.

Figure 154:
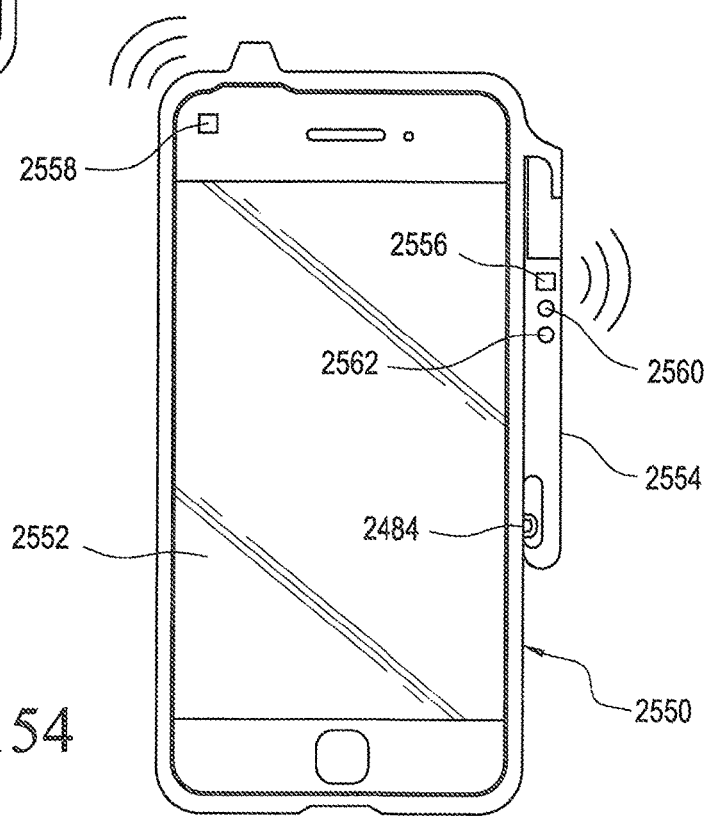

FIG. 154 shows a view of still yet another separable sensor device positioned on an electronic apparatus in accordance with an exemplary embodiment of the present disclosure.

Figure 155:
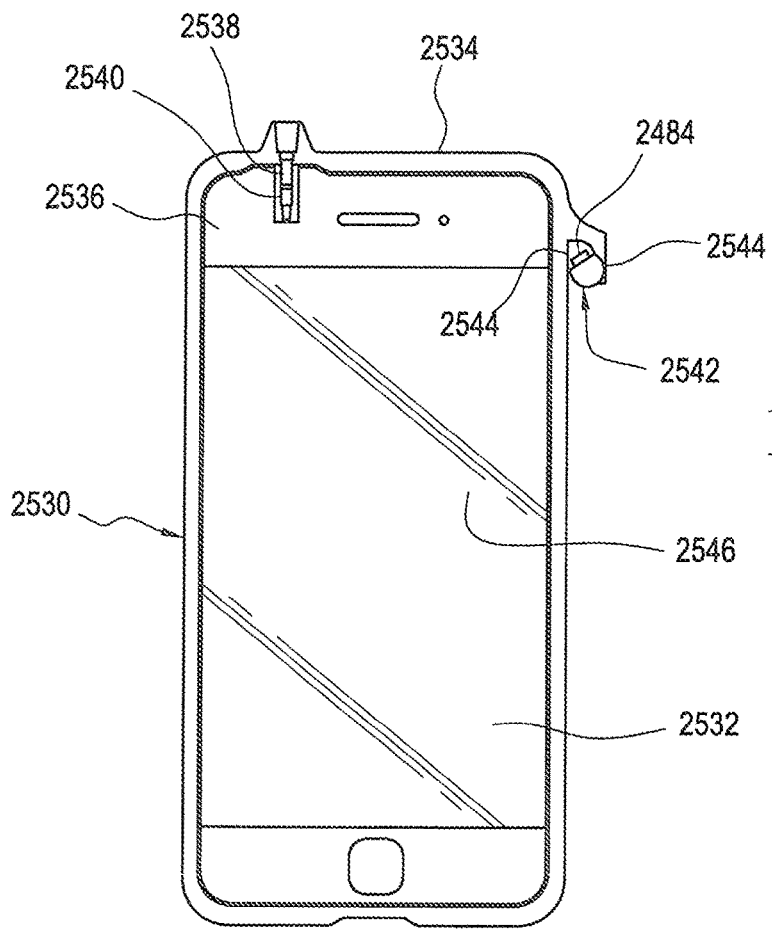

FIG. 155 shows a view of the separable sensor device and electronic apparatus of FIG. 153 with a portion of the separable sensor device pivoted to a position to measure an emission from the ABTT.

Figure 156:
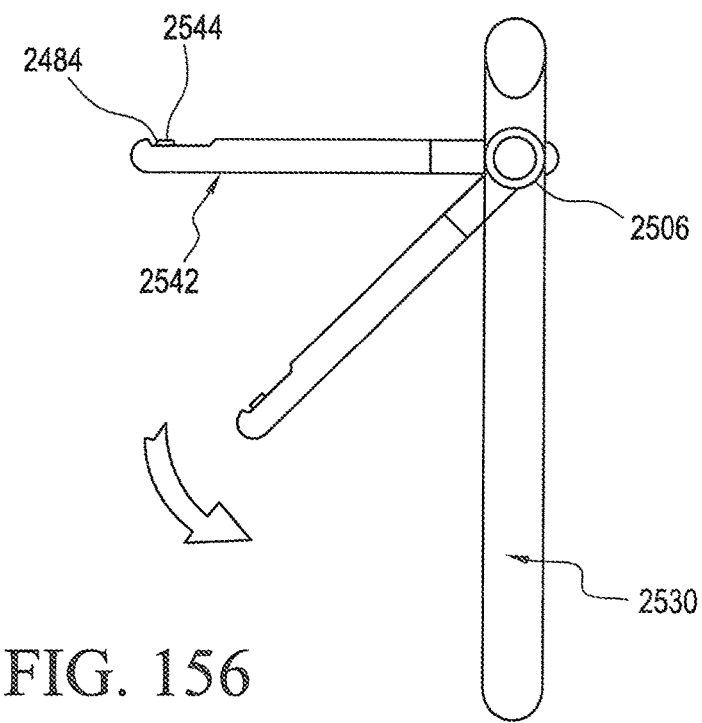

FIG. 156 shows another view of the separable sensor device and electronic apparatus of FIGS. 153 and 155.

Figure 157:
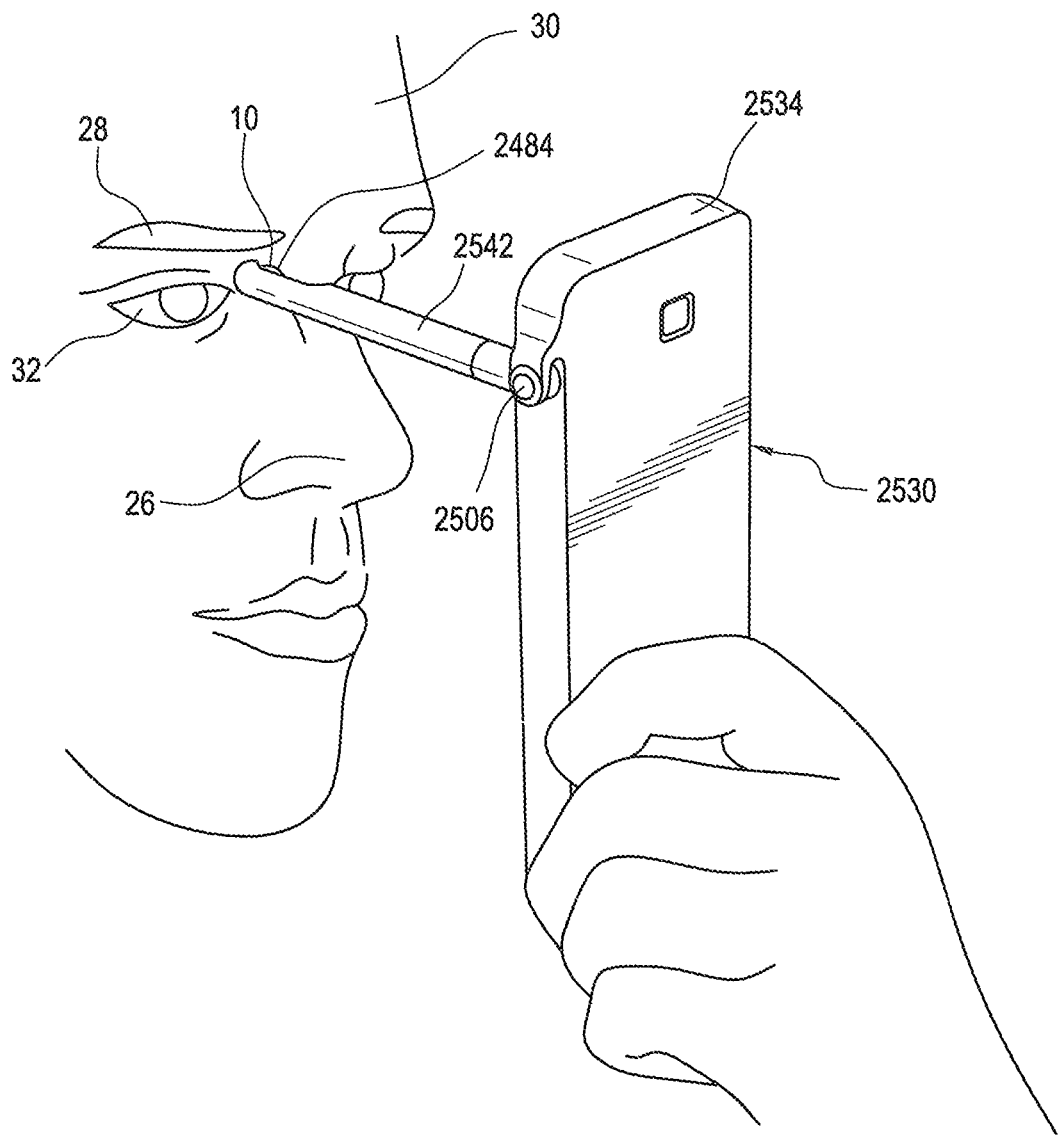

FIG. 157 shows a perspective view of the separable sensor device and electronic apparatus of FIG. 154 being operated by a user to read an emission from the ABTT.

FIG. 158 shows a view of a watch including a measurement device in accordance with an exemplary embodiment of the present disclosure.

FIG. 159 shows a view of a watch including a measurement device in accordance with another exemplary embodiment of the present disclosure.

Figure 160:
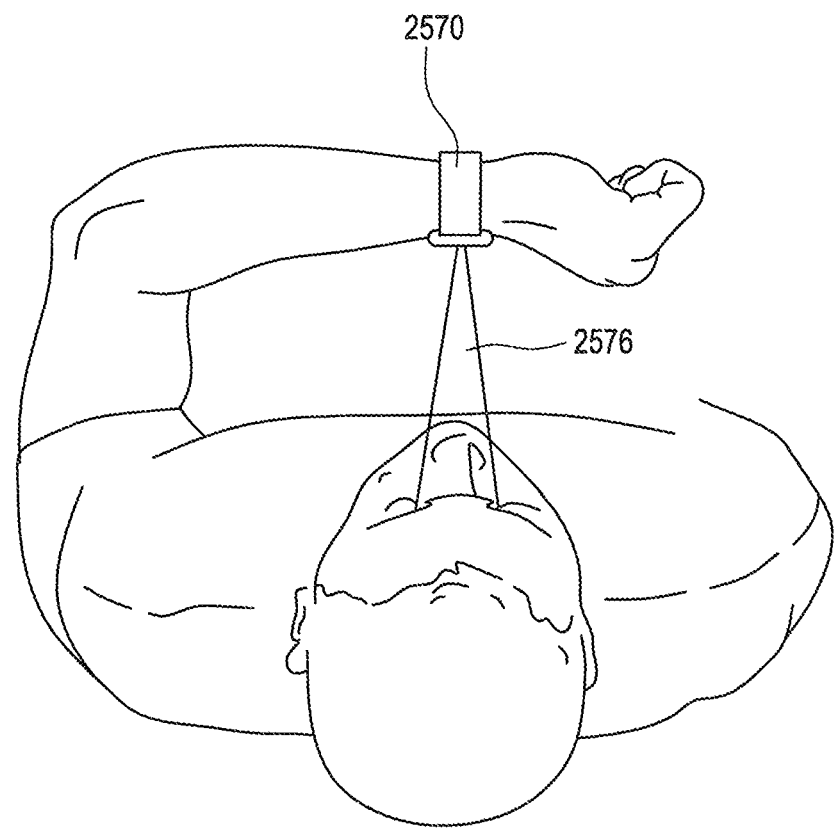

FIG. 160 shows a view of a user operating the watch of FIG. 158 to read an emission from the ABTT.

Figure 161:
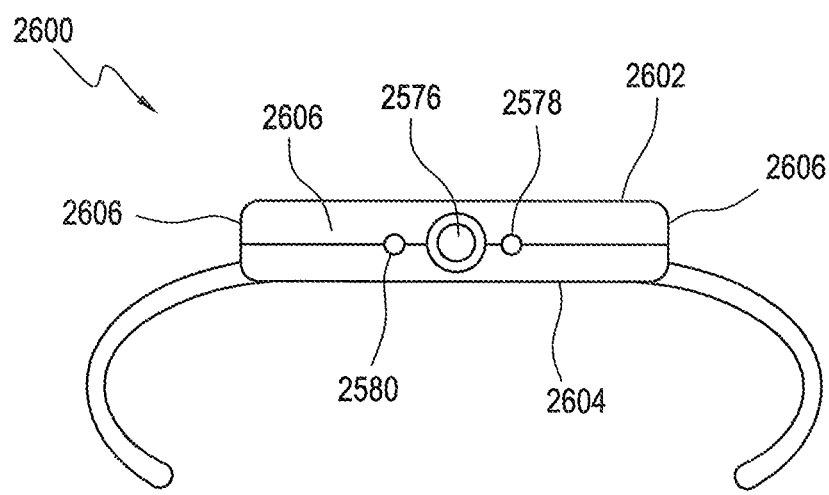

FIG. 161 shows a view a watch including a measurement device in accordance with yet another exemplary embodiment of the present disclosure.

Figure 162:
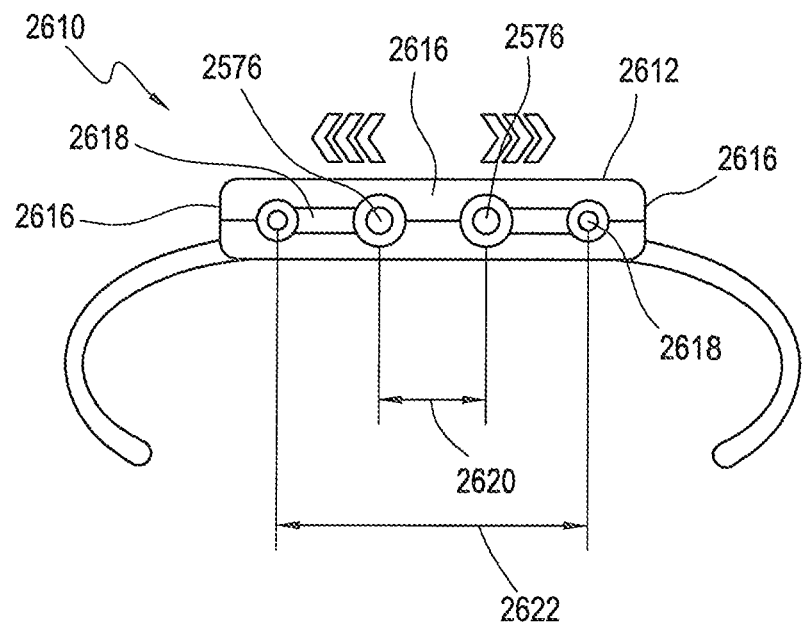

FIG. 162 shows a view of a watch including a measurement device in accordance with still another exemplary embodiment of the present disclosure.

Figure 163:
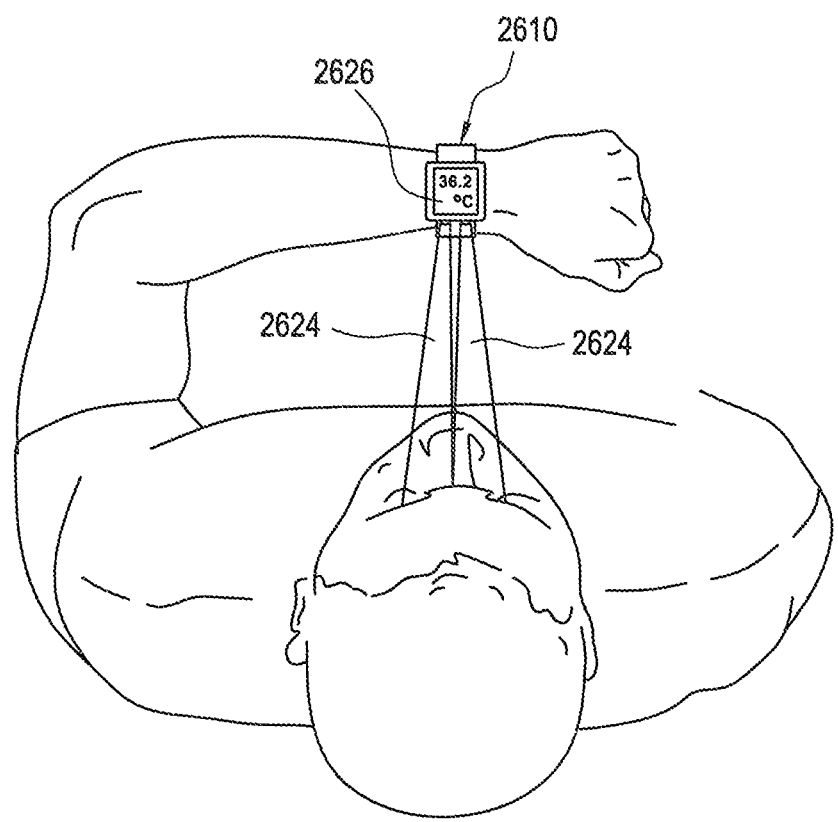

FIG. 163 shows a view of a user operating the watch of FIG. 163 to read an emission from the ABTT.

Figure 164:
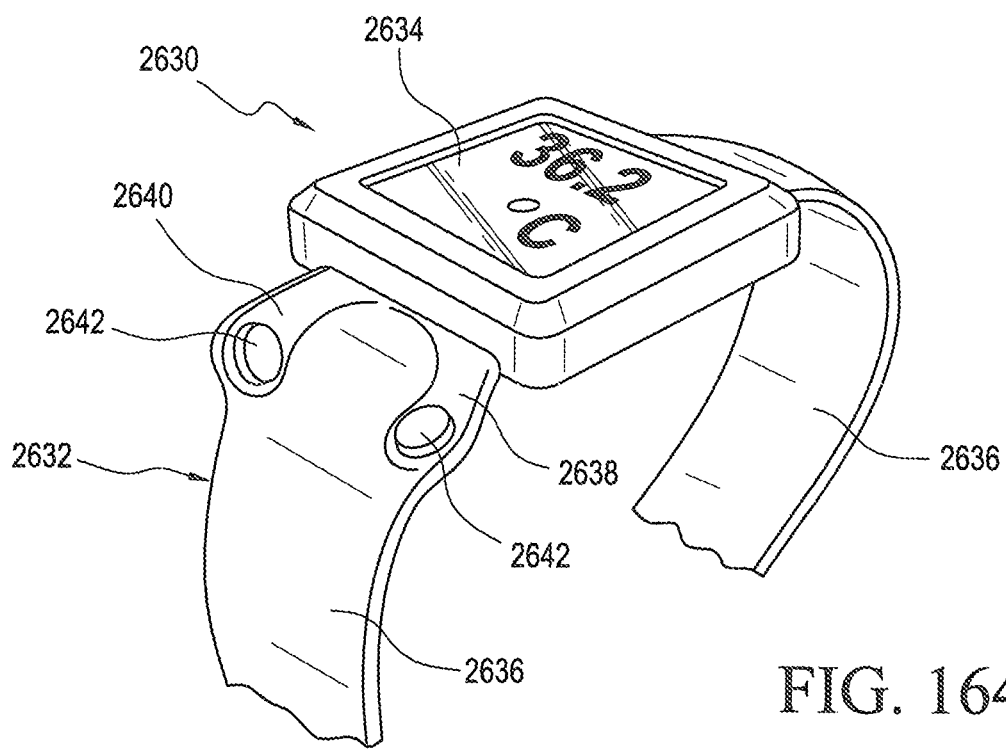

FIG. 164 shows a view of a watch including a measurement device in accordance with an even further exemplary embodiment of the present disclosure.

Figure 165:
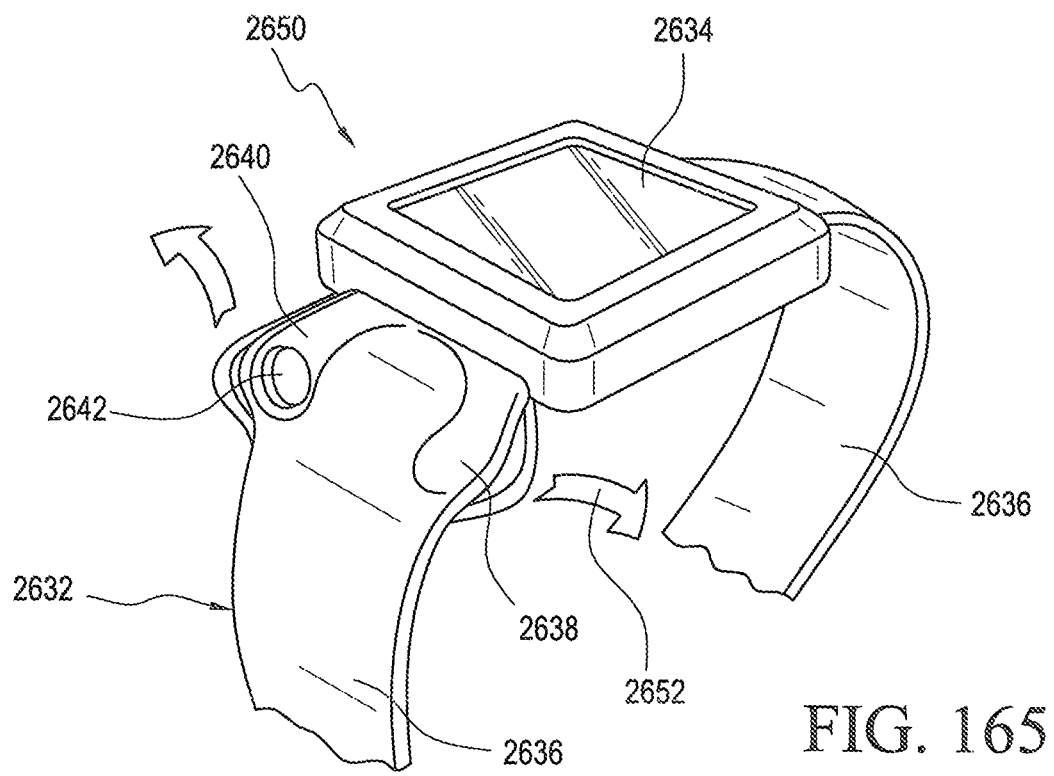

FIG. 165 shows a view of a watch including a measurement device in accordance with an even yet further exemplary embodiment of the present disclosure.

Figure 166:
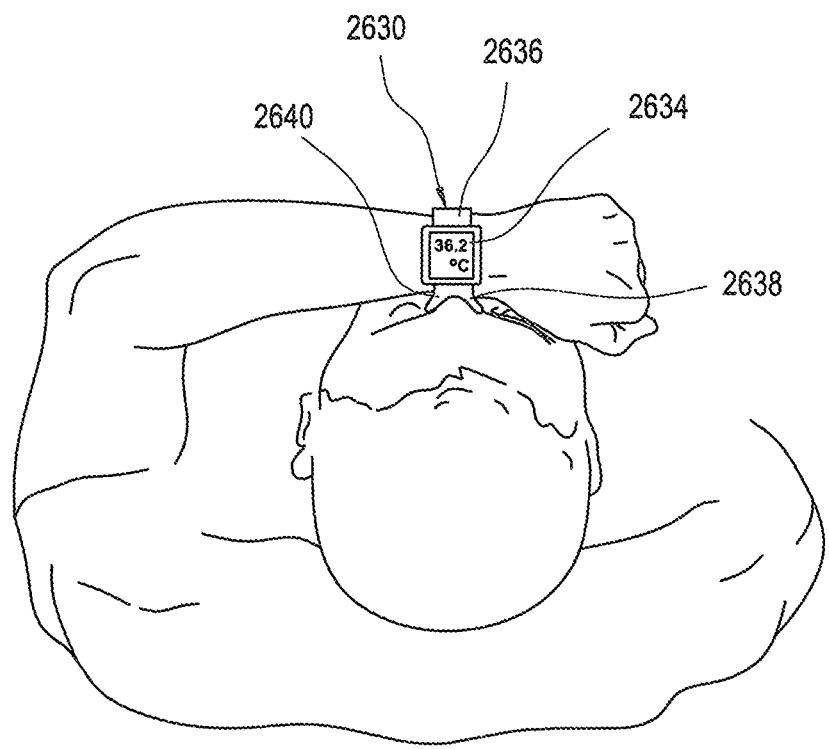

FIG. 166 shows a view of a user operating the watch of FIG. 164 to read an emission from the ABTT.

Figure 167:
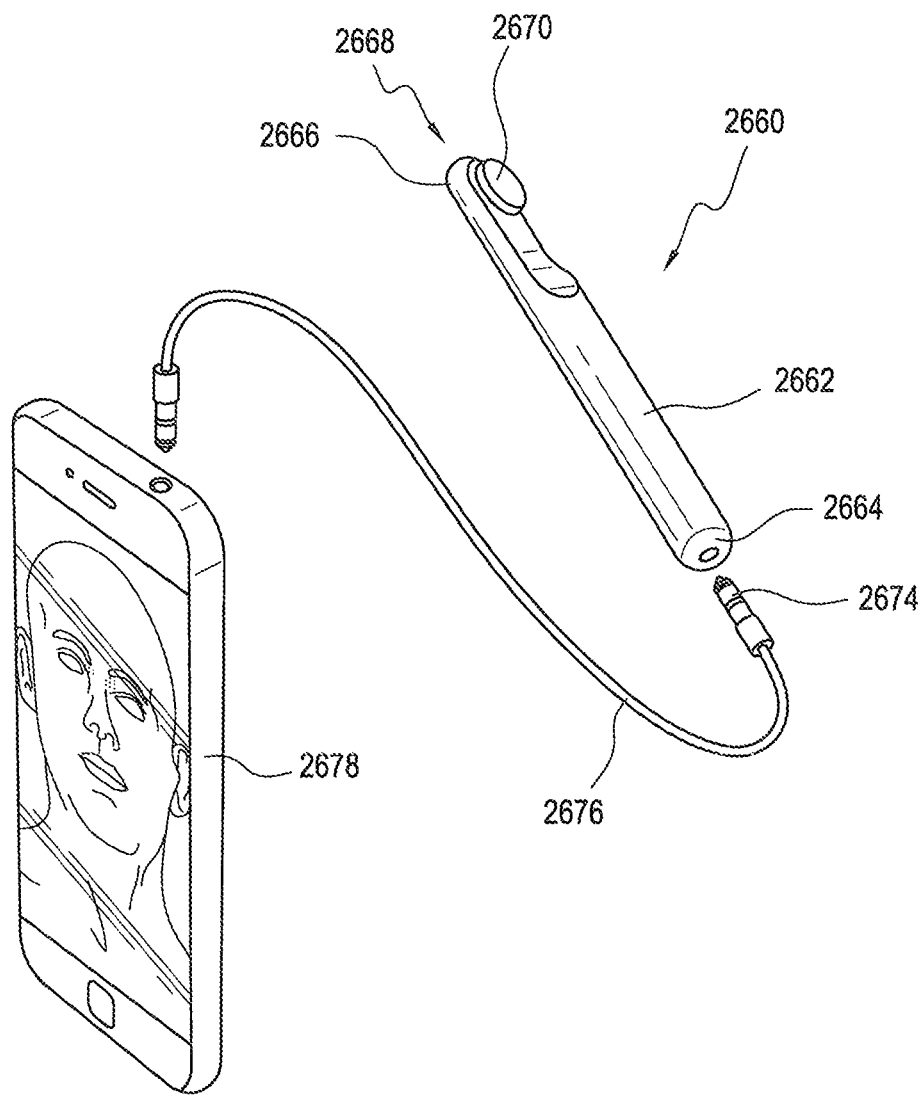

FIG. 167 shows a view of a sensor device in accordance with an exemplary embodiment of the present disclosure.

Figure 168:
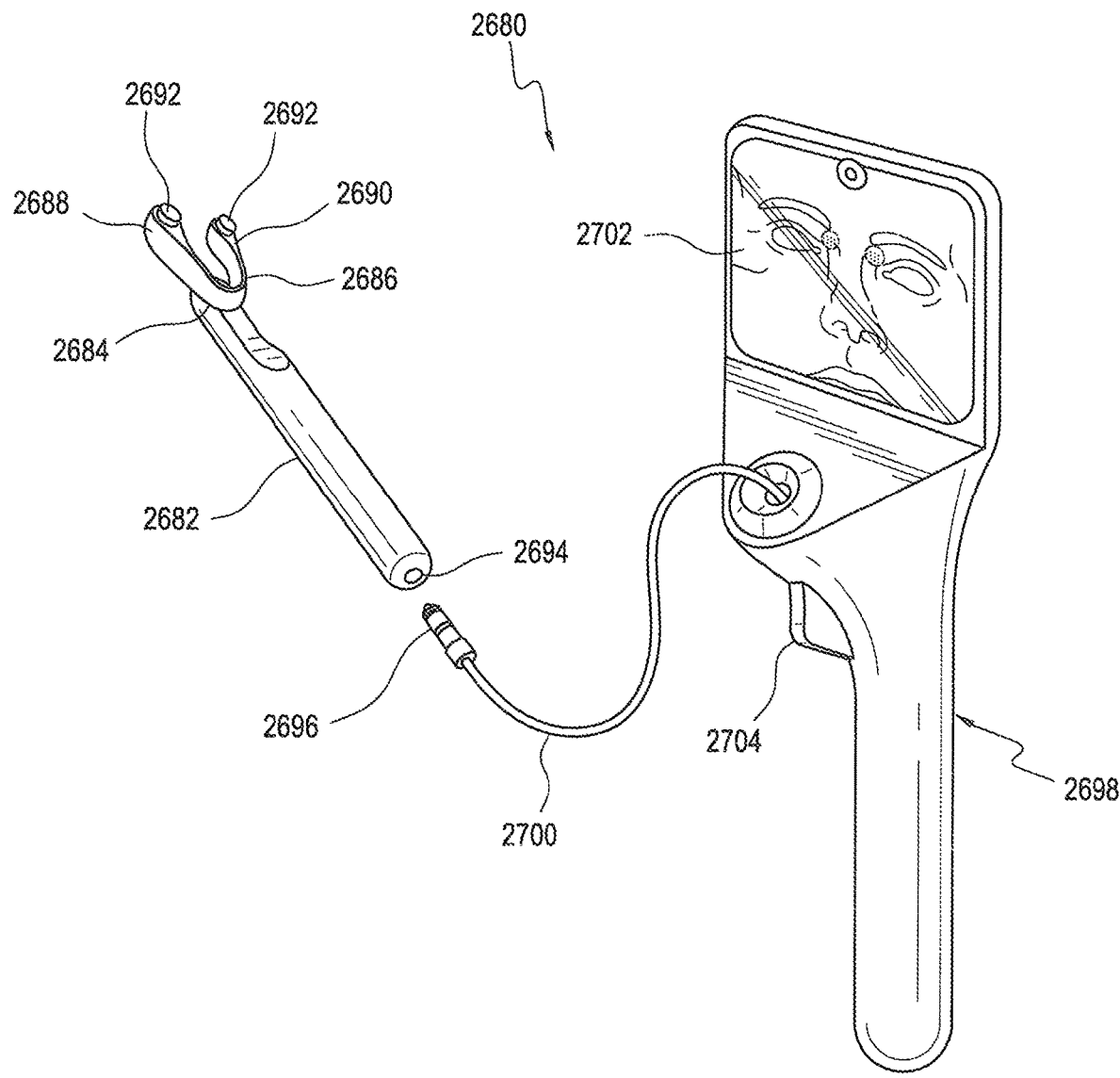

FIG. 168 shows a view of another sensor device in accordance with an exemplary embodiment of the present disclosure.

Figure 169:
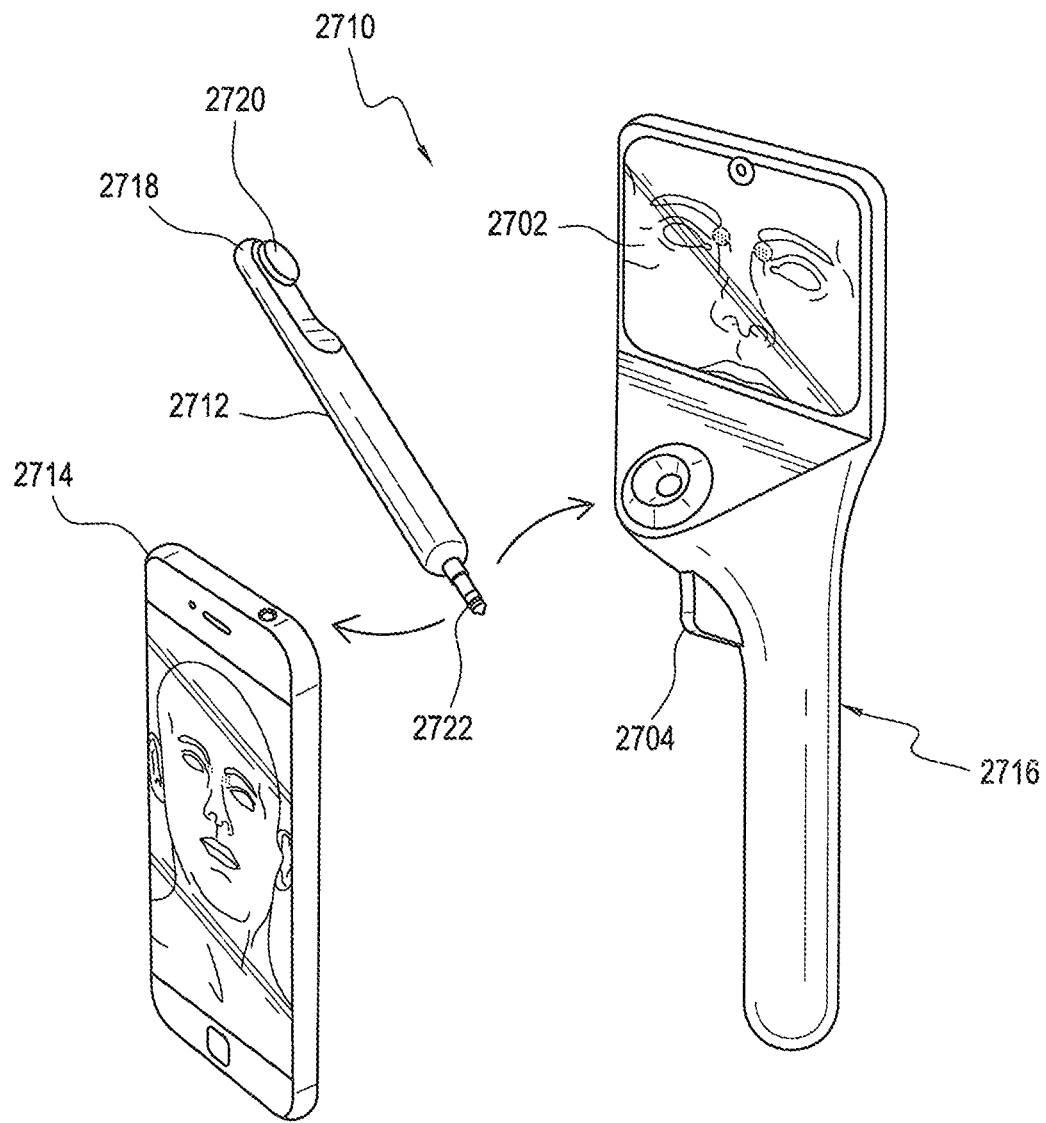

FIG. 169 shows a view of yet another sensor device in accordance with an exemplary embodiment of the present disclosure.

Figure 170:
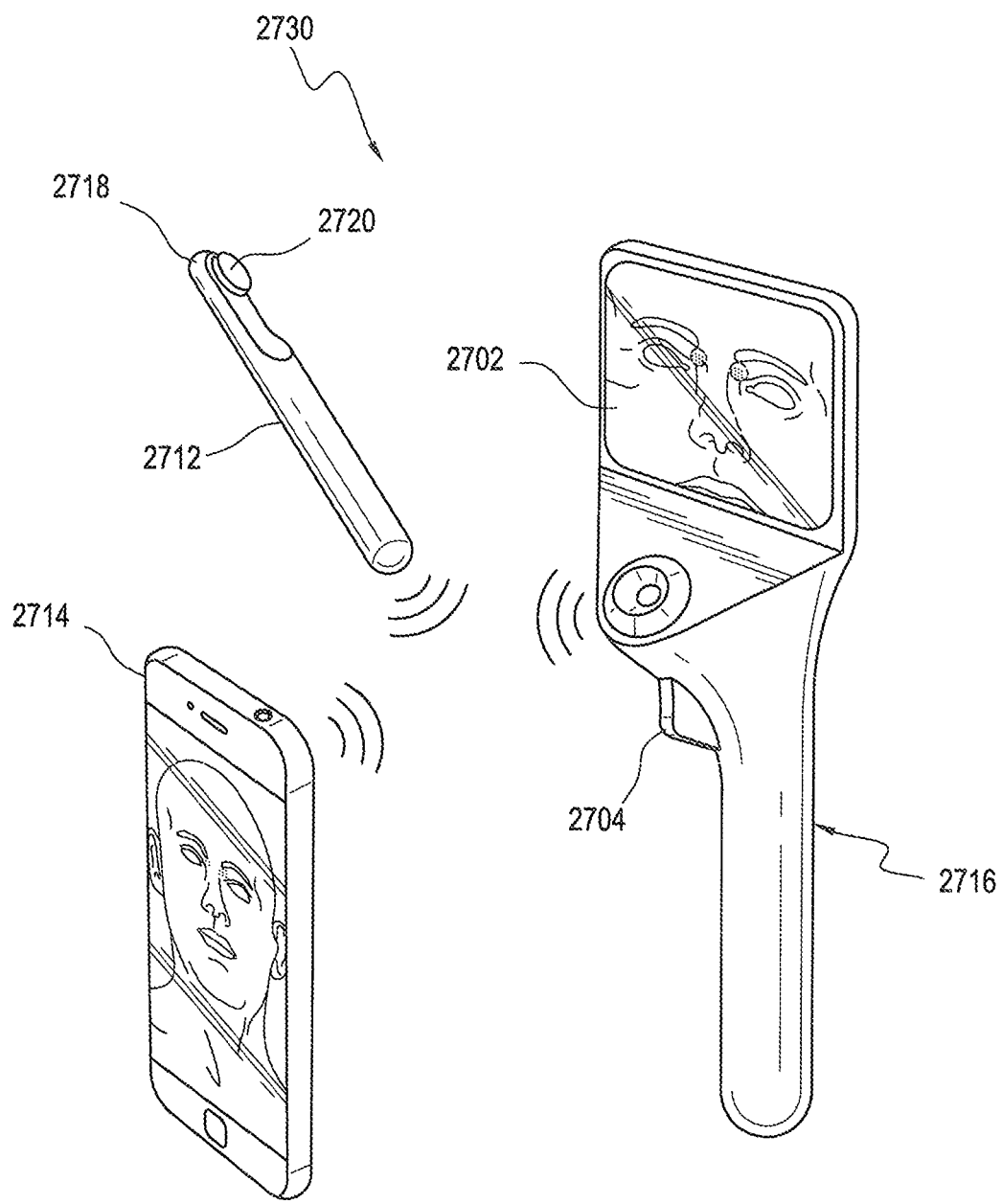

FIG. 170 shows a view of a further sensor device in accordance with an exemplary embodiment of the present disclosure.

Figure 171:
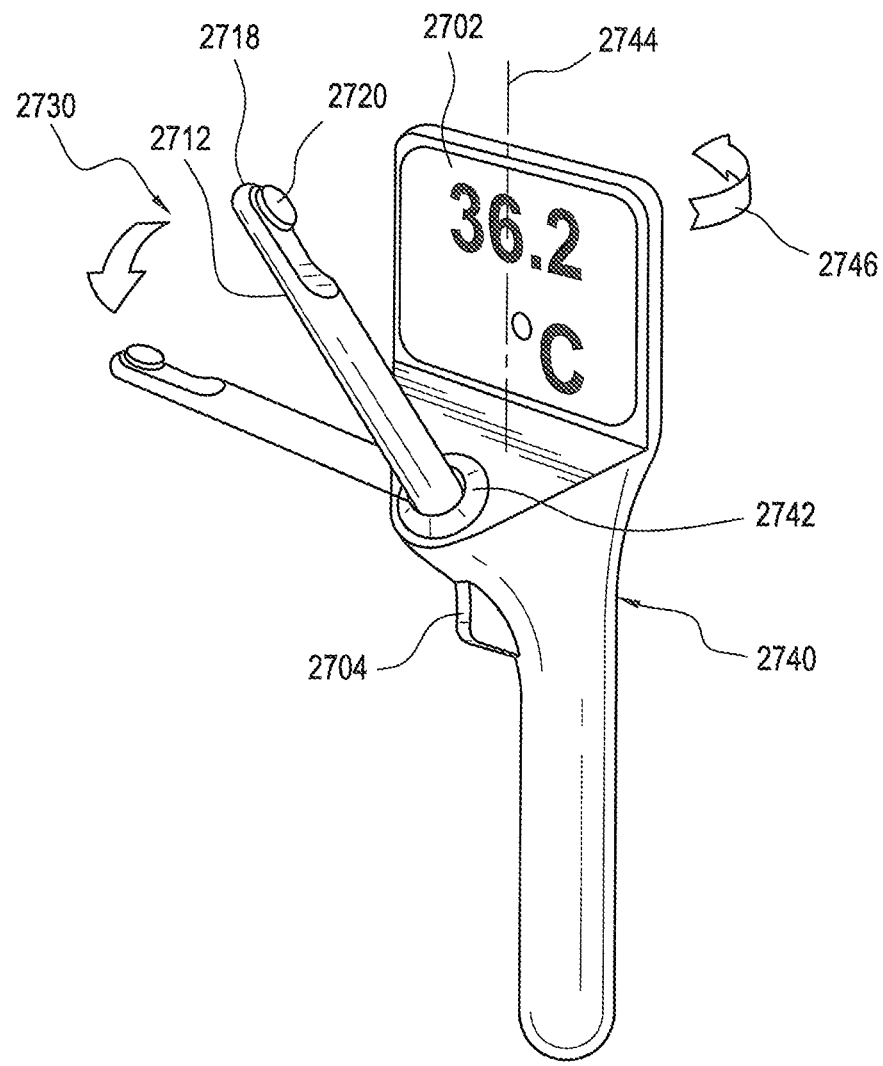

FIG. 171 shows the sensor device of FIG. 169 connected to an electronic apparatus in accordance with an exemplary embodiment of the present disclosure.

Figure 172:
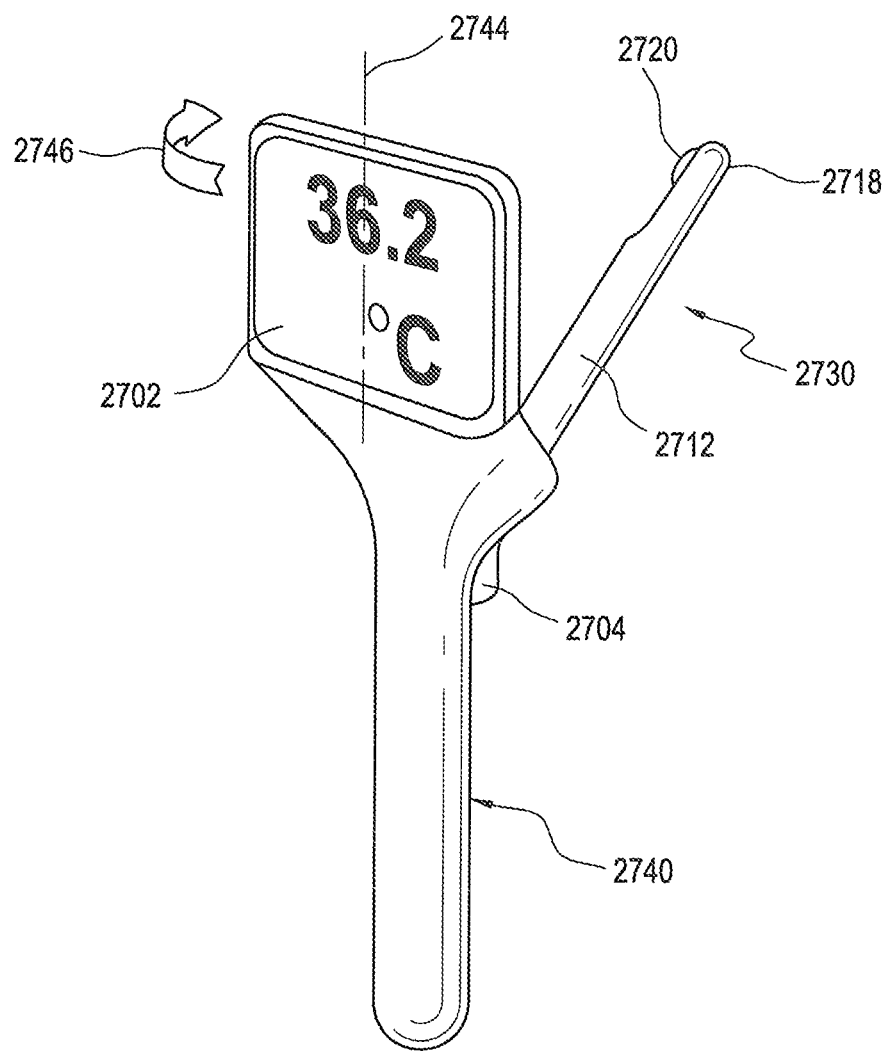

FIG. 172 shows a view of a view of a rotating mechanism of a display compatible with the sensor devices of FIGS. 168-171 in accordance with an exemplary embodiment of the present disclosure.

Figures 173, 174:
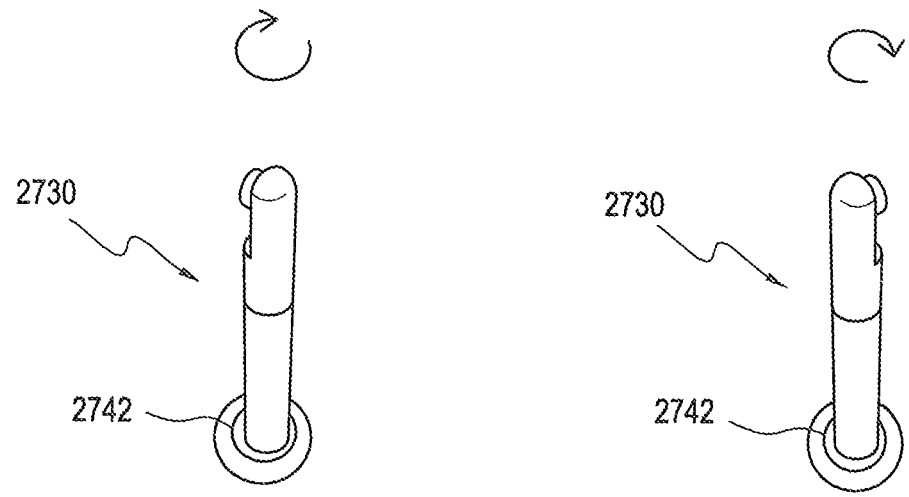

FIG. 173 shows a first view of a rotating mechanism of the device of FIG. 171.

FIG. 174 shows a second view of a rotating mechanism of the device of FIG. 79.

Figures 175, 176:
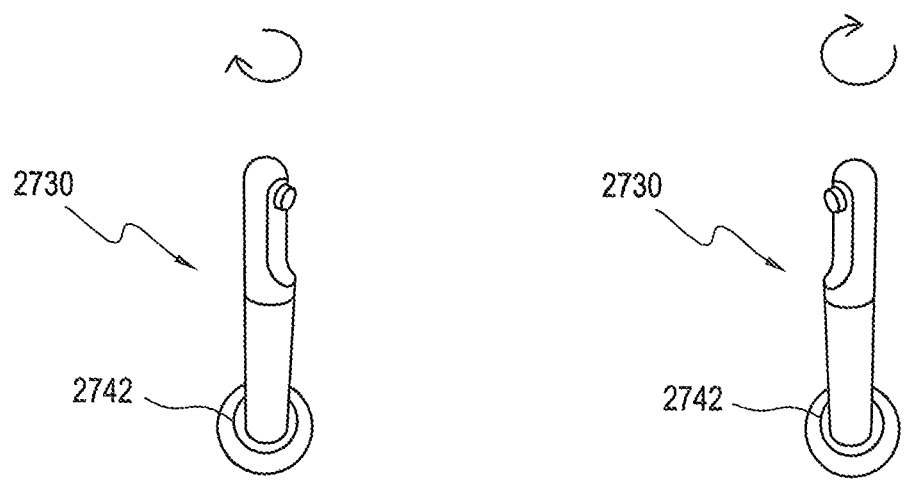

FIG. 175 shows a third view of a rotating mechanism of the device of FIG. 171.

FIG. 176 shows a fourth view of a rotating mechanism of the device of FIG. 171.

Figure 177:
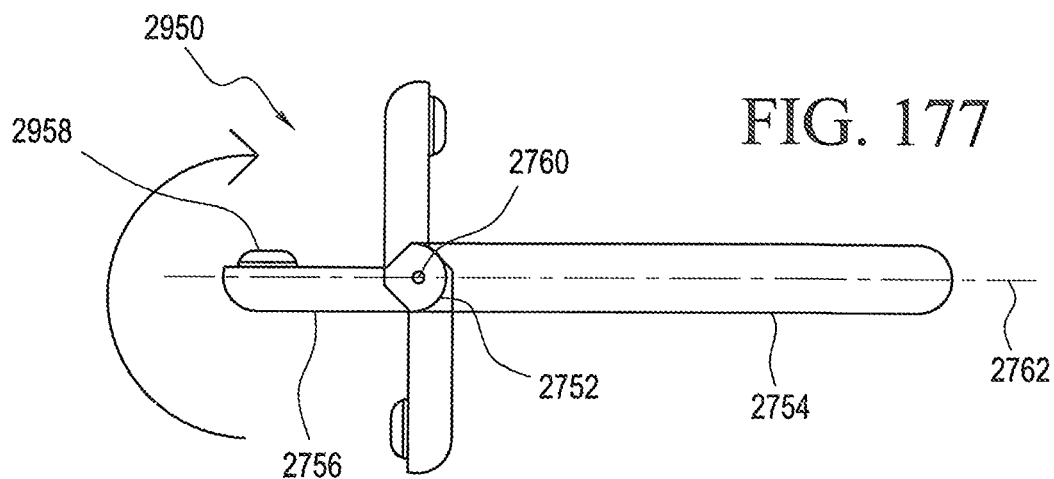

FIG. 177 shows a view of a rotating mechanism of a sensor device in accordance with an exemplary embodiment of the present disclosure.

Figure 178:
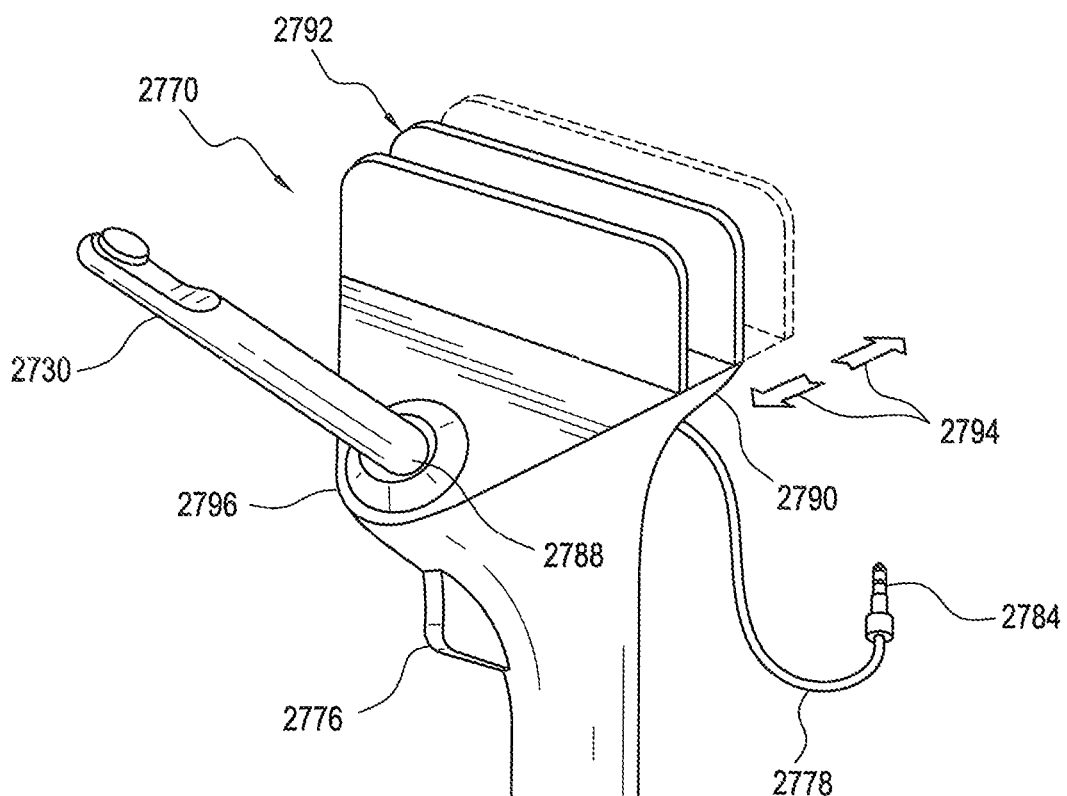

FIG. 178 shows a view of a support structure in accordance with an exemplary embodiment of the present disclosure.

Figure 179:
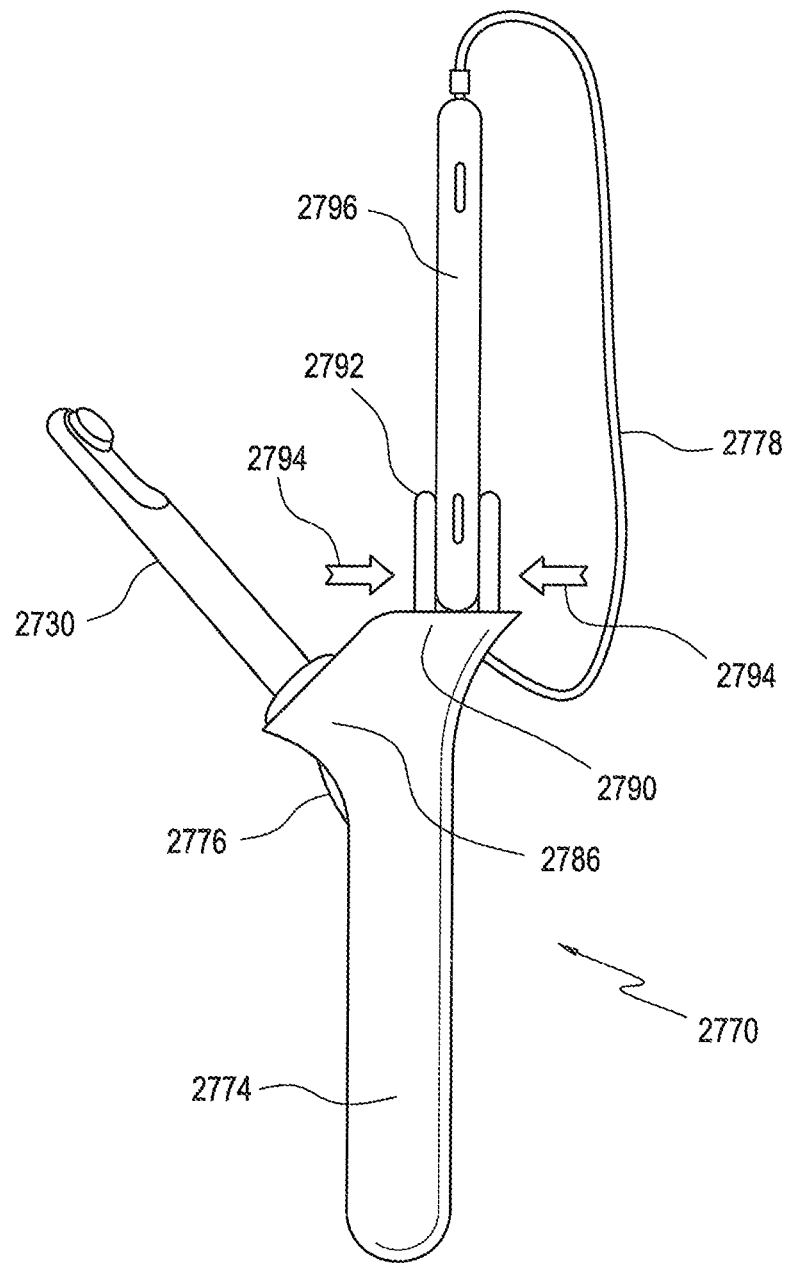

FIG. 179 shows another view of the support structure of FIG. 178.

Figure 180:
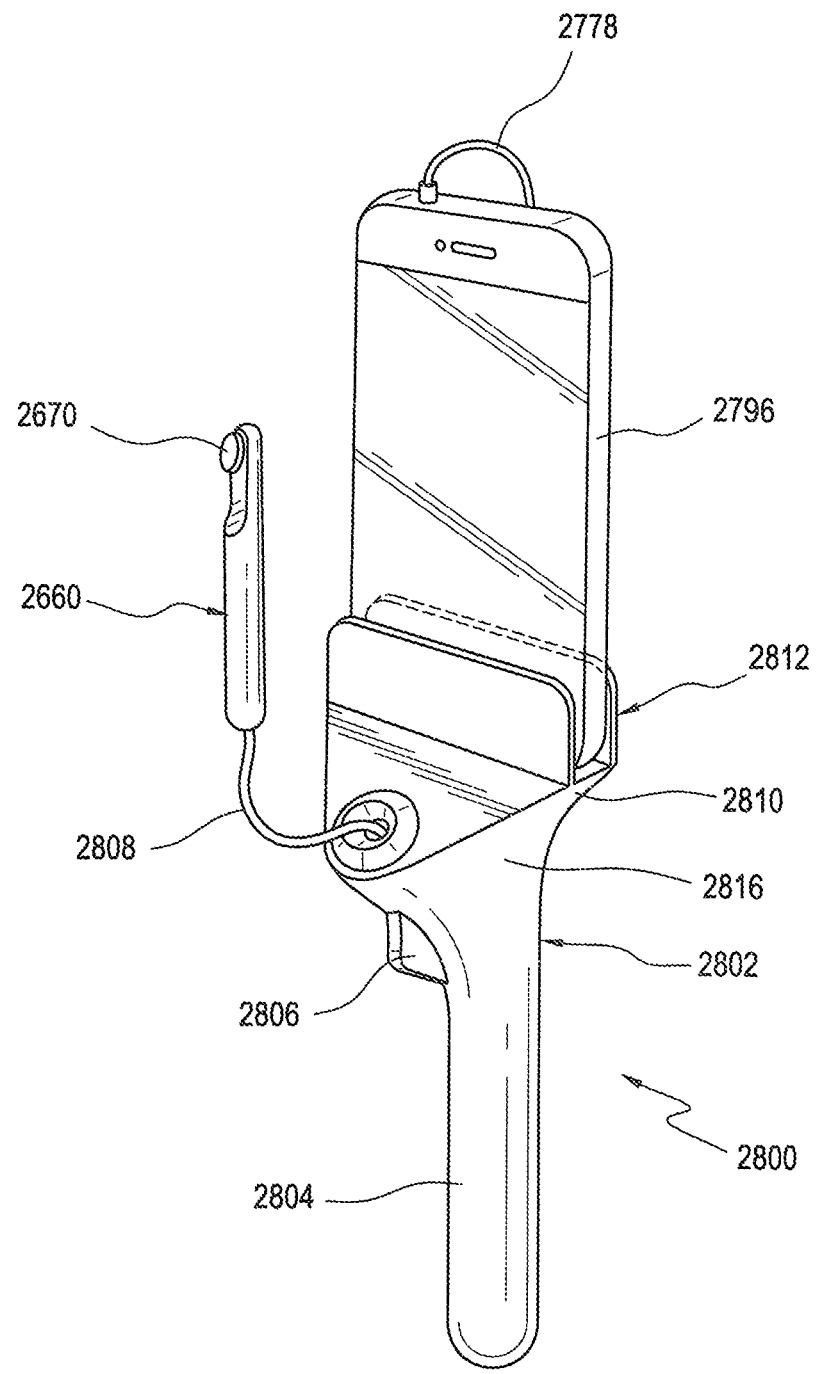

FIG. 180 shows a view of another support structure in accordance with an exemplary embodiment of the present disclosure.

Figure 181:
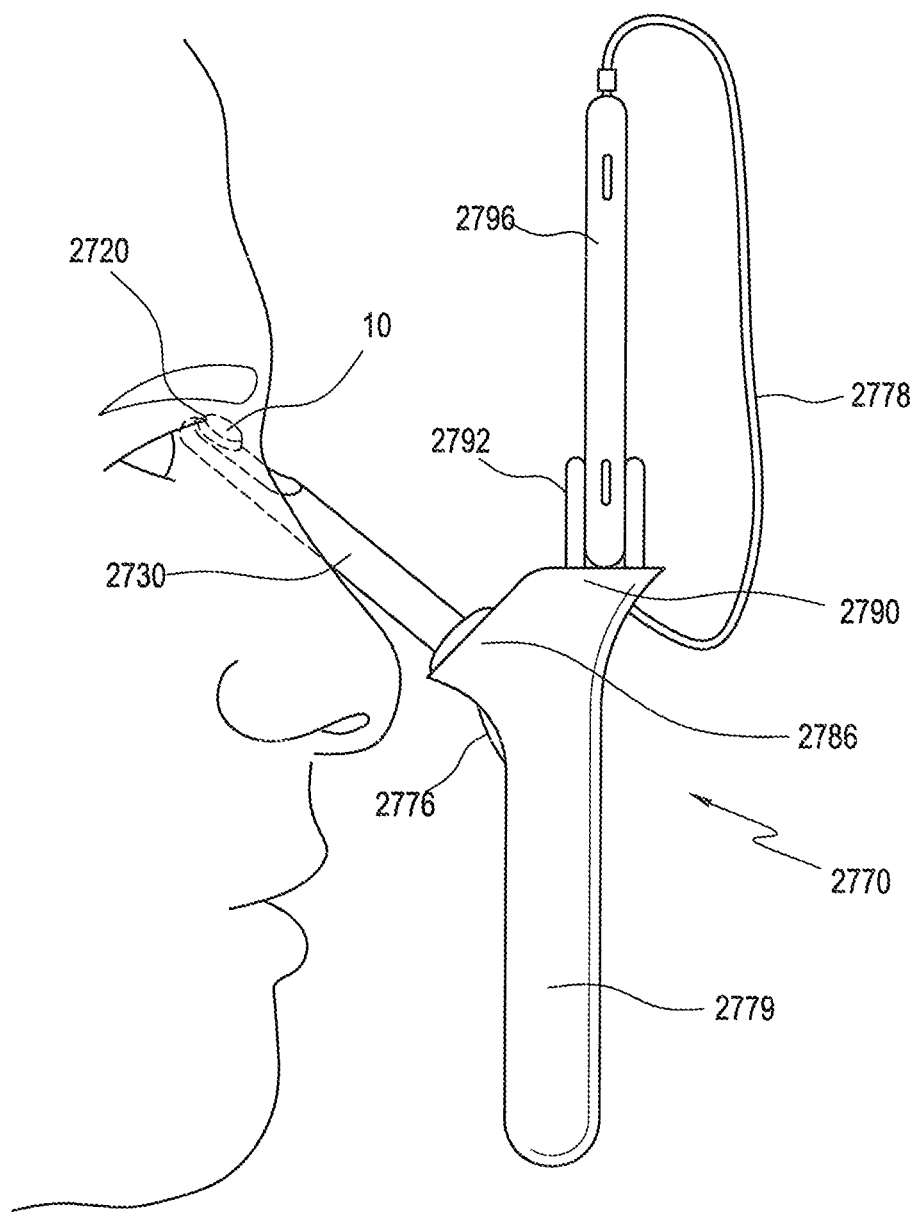

FIG. 181 shows another view of the support structure of FIGS. 178 and 179.

Figure 182:
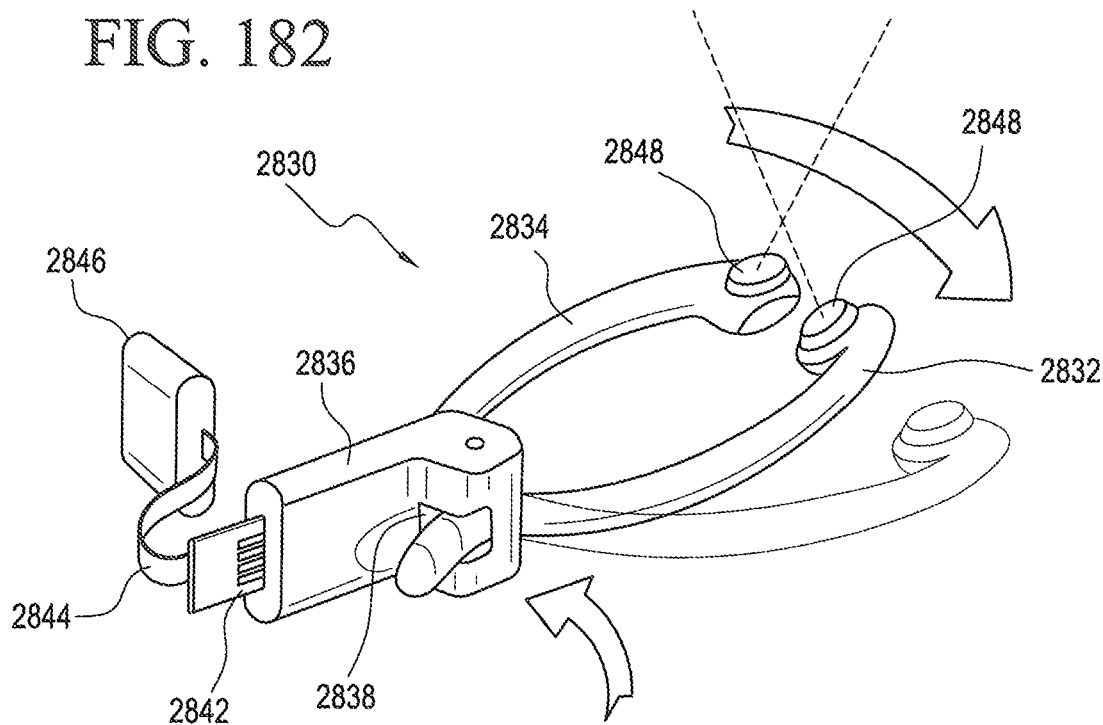

FIG. 182 shows a view of a sensor clip assembly in accordance with an exemplary embodiment of the present disclosure.

Figure 183:
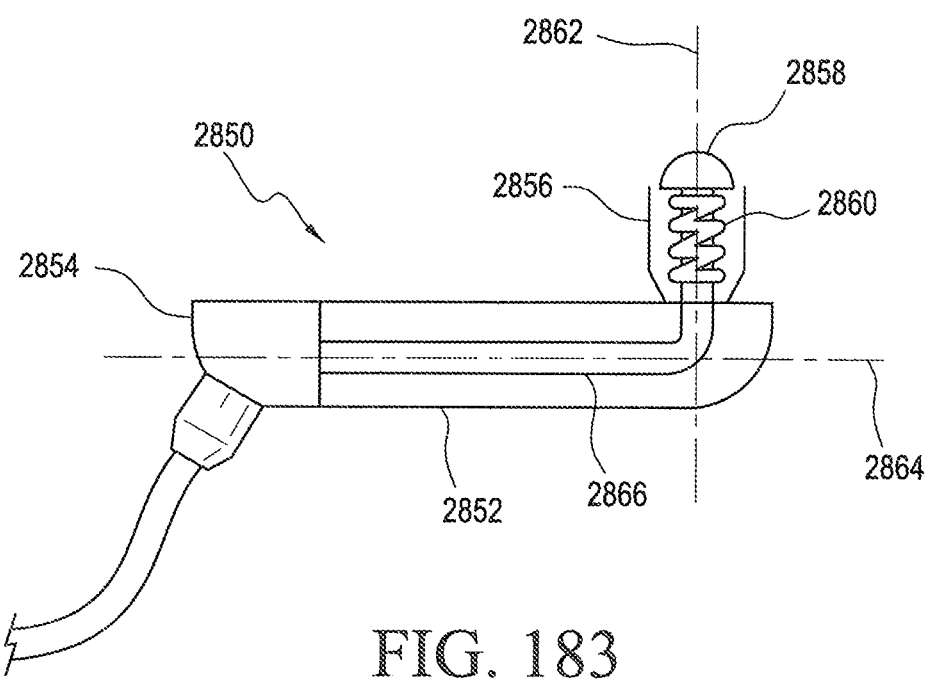

FIG. 183 shows a view of a sensor head in accordance with an exemplary embodiment of the present disclosure.

Figure 184:
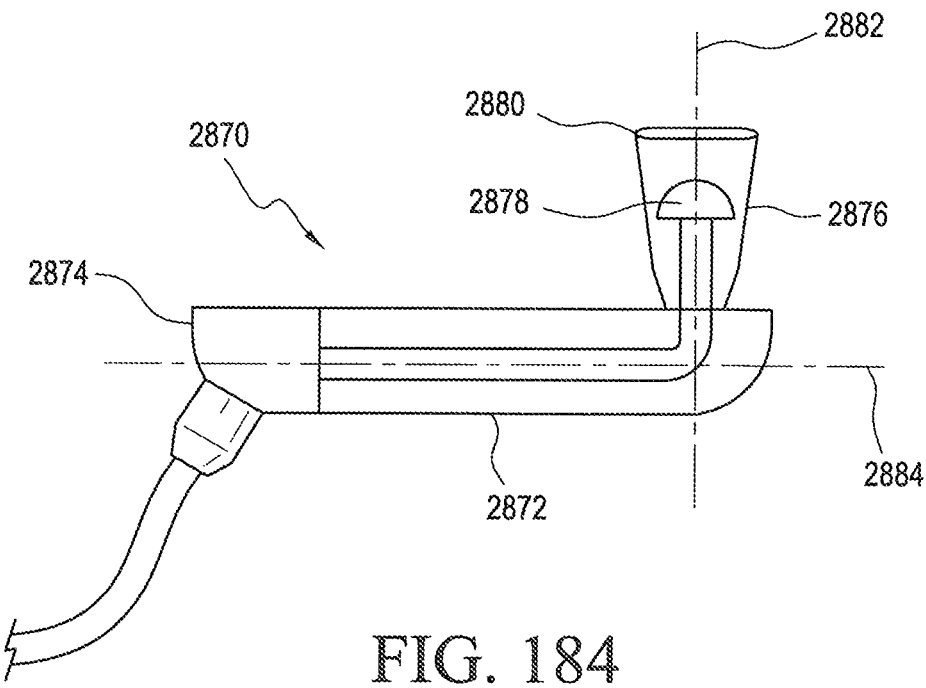

FIG. 184 shows a view of sensor head in accordance with another exemplary embodiment of the present disclosure.

Figure 185:
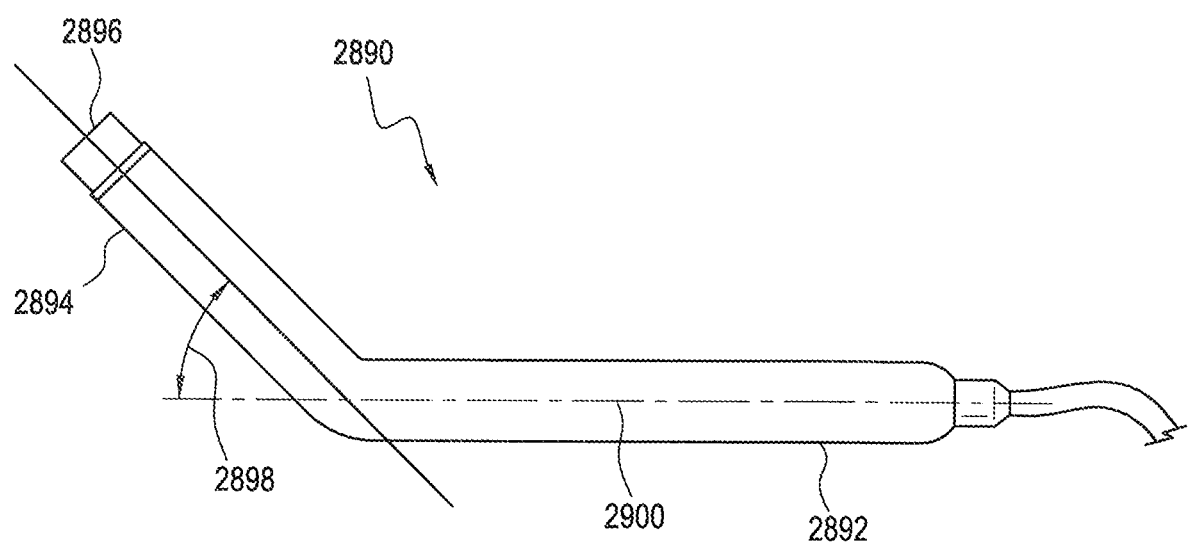

FIG. 185 shows a view of a thermometer in accordance with an exemplary embodiment of the present disclosure.

FIG. 186 shows another view of the thermometer of FIG. 185.

FIG. 187 shows a sensor head in accordance with an exemplary embodiment of the present disclosure.

FIG. 188 shows another view of the sensor head of FIG. 187.

Figure 189:
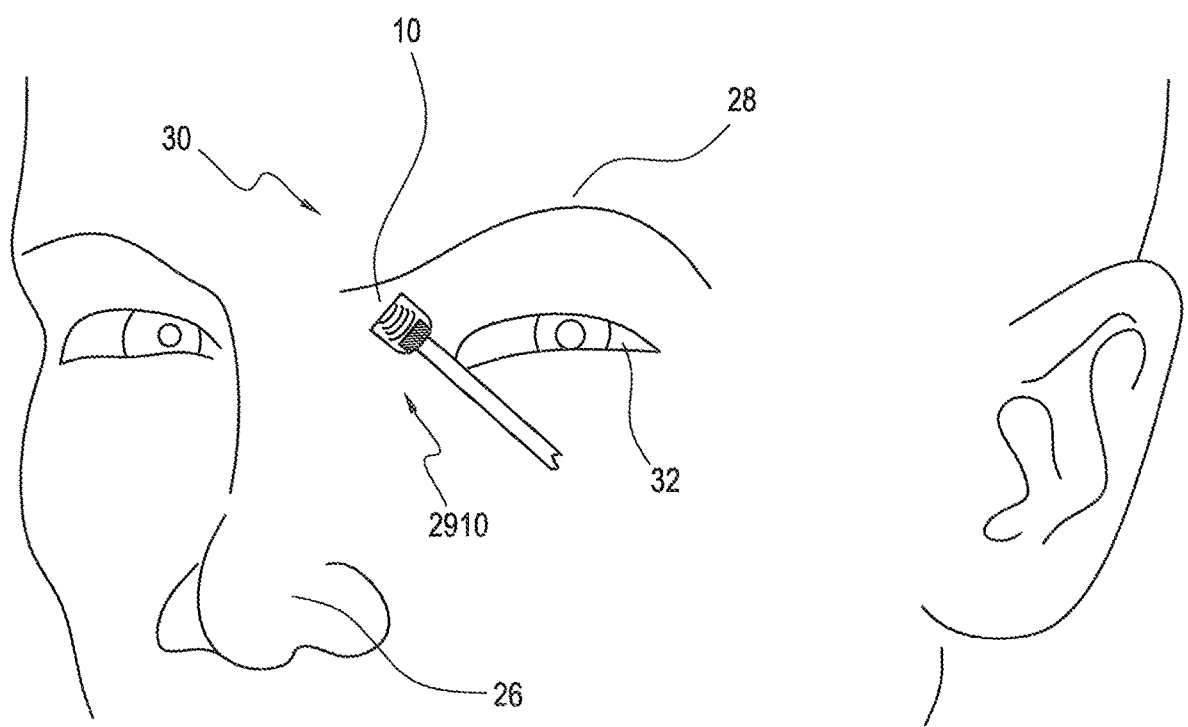

FIG. 189 shows a further view of the sensor head of FIG. 187.

Figure 190:
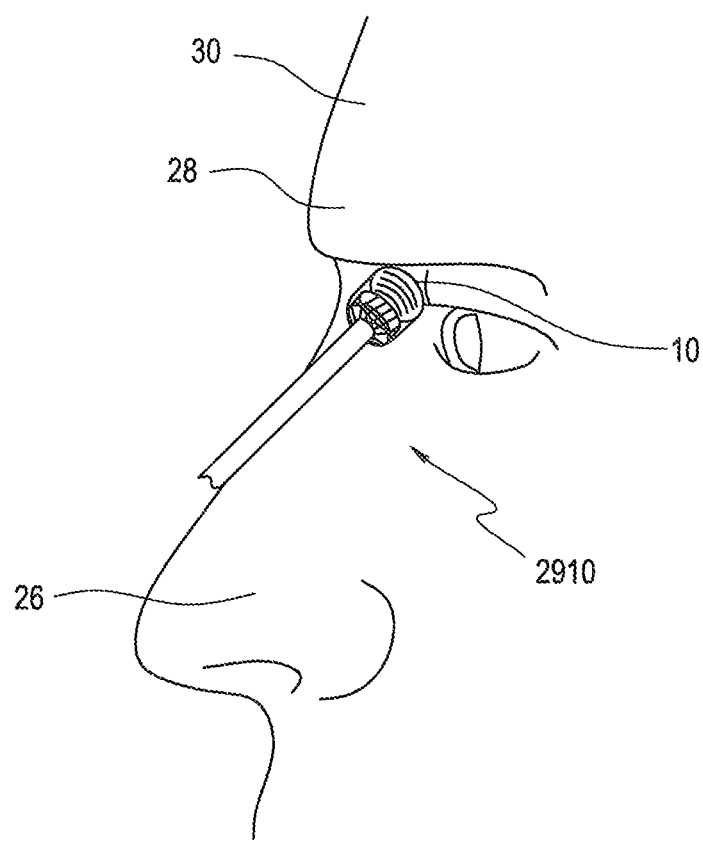

FIG. 190 shows an even further view of the sensor head of FIG. 187.

Figure 191:
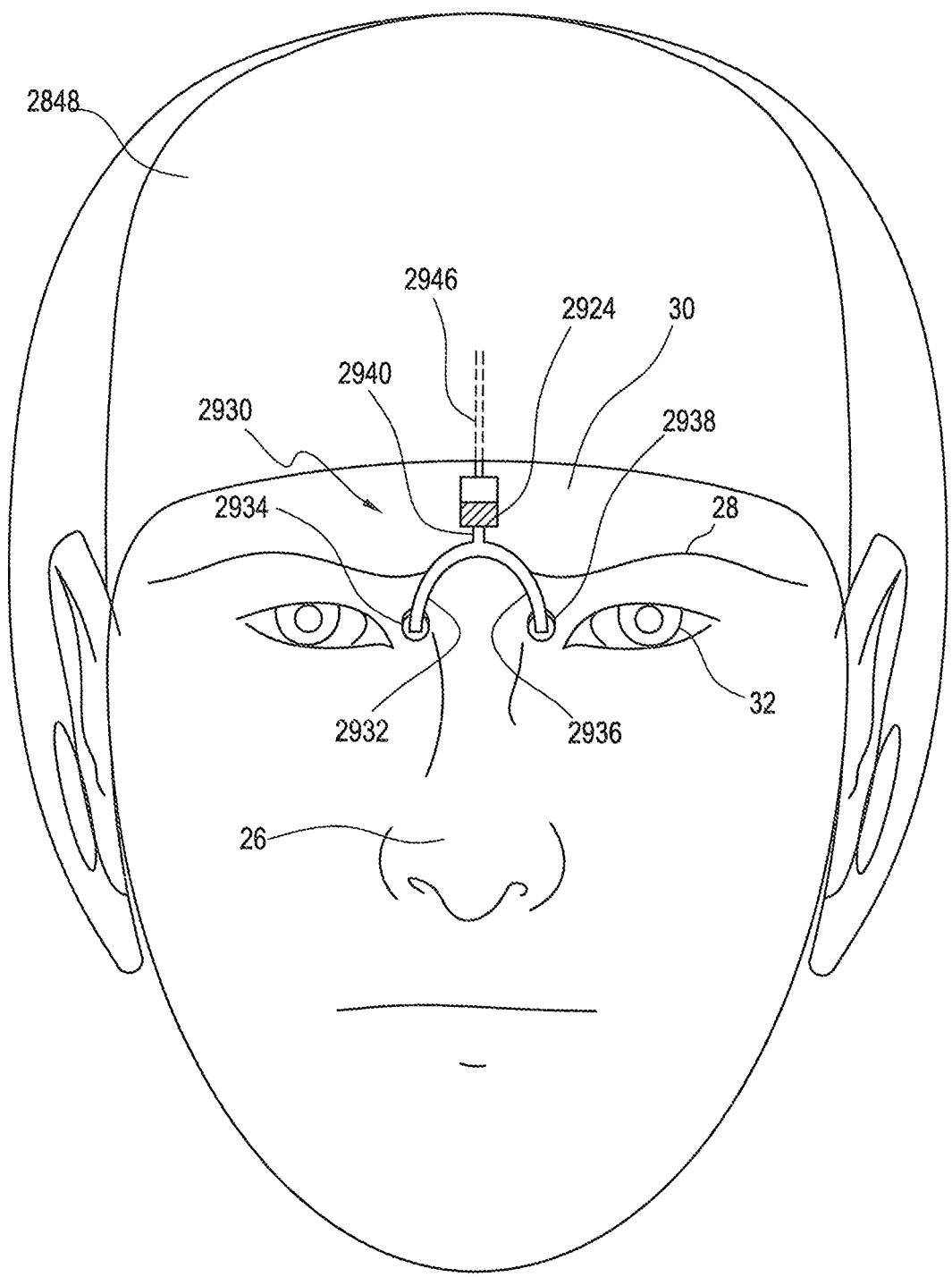

FIG. 191 shows a sensor device in accordance with an exemplary embodiment of the present disclosure.

Figure 192:
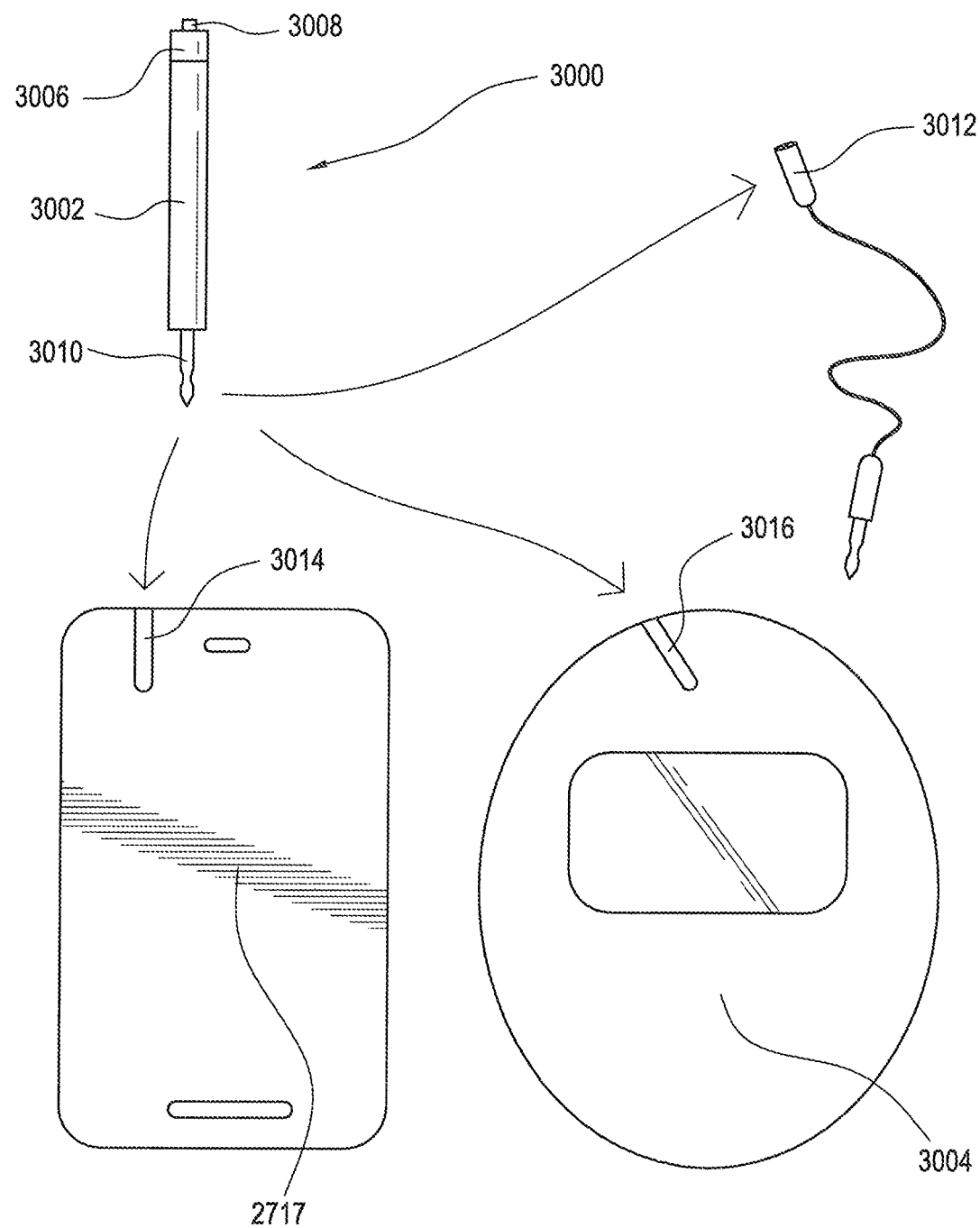

FIG. 192 shows another sensor device in accordance with an exemplary embodiment of the present disclosure.

Figure 193:
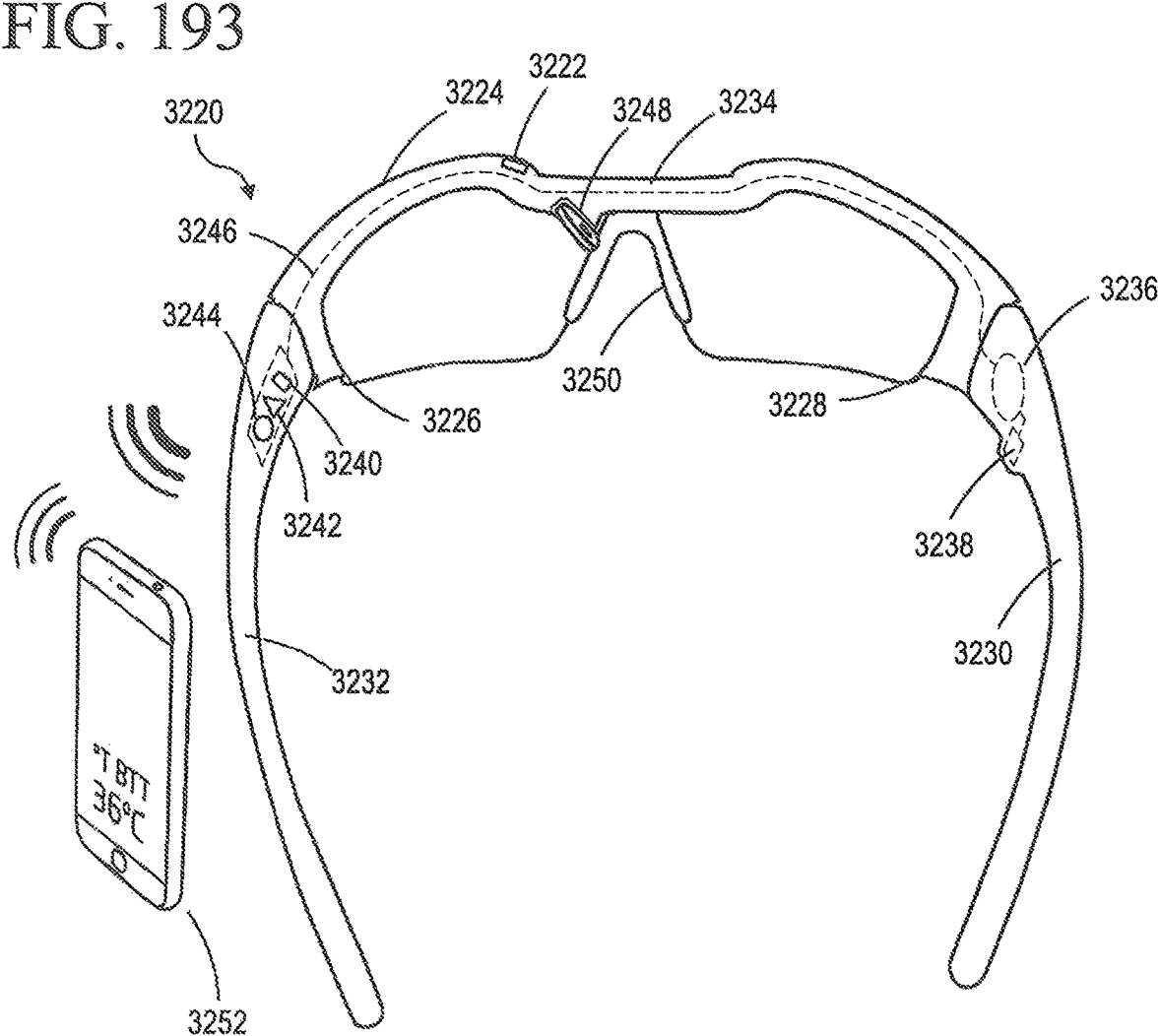

FIG. 193 shows a view of another electronic apparatus in accordance with an exemplary embodiment of the present disclosure.

Figure 194:
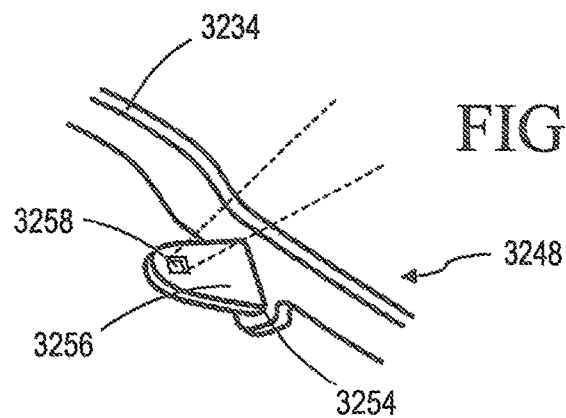

FIG. 194 shows a view of a portion of the electronics apparatus of FIG. 193.

FIG. 195 shows a view of yet another apparatus in accordance with an exemplary embodiment of the present disclosure.

Figure 196:
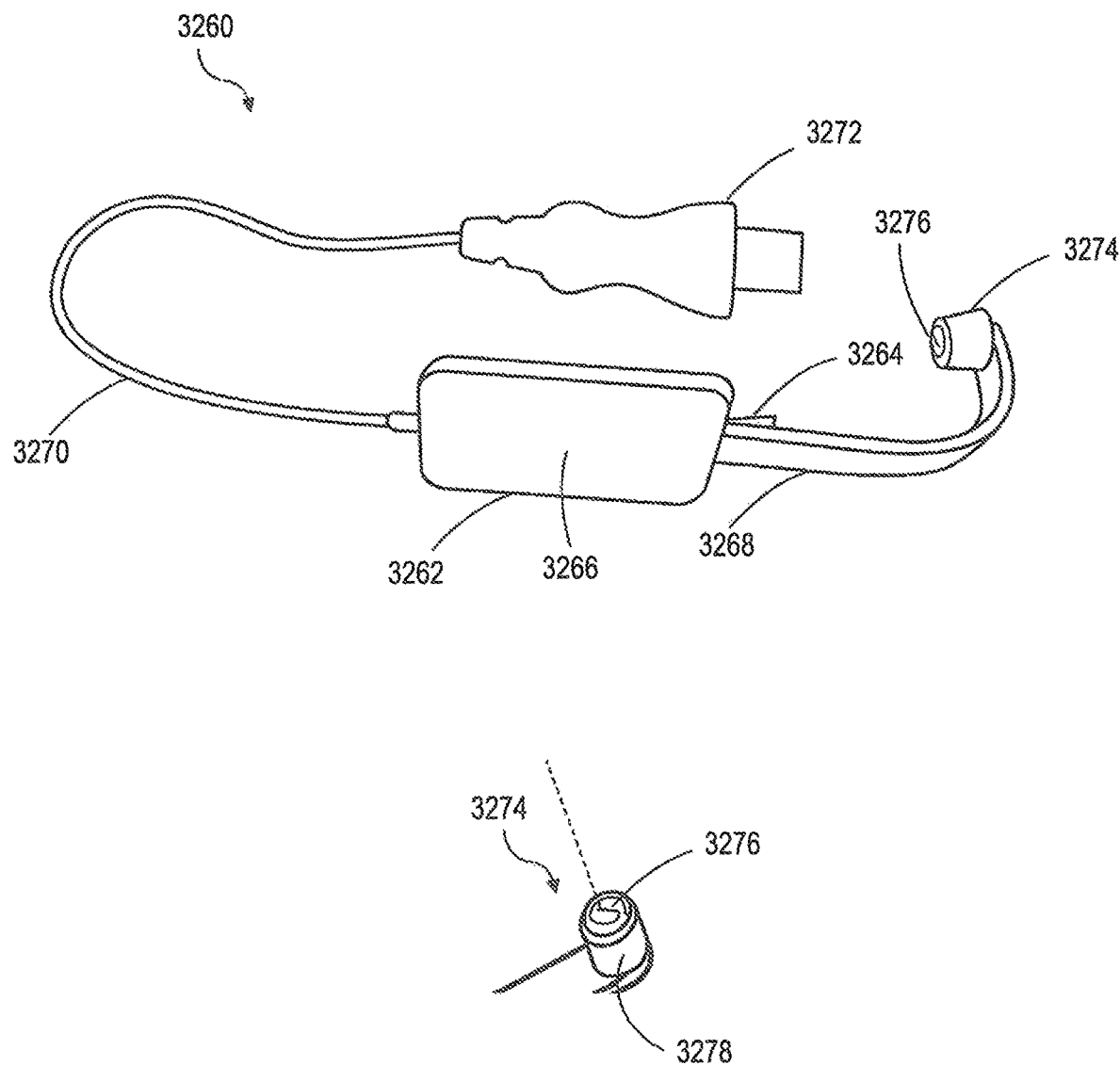

FIG. 196 shows another view of the apparatus of FIG. 195.

Figure 197:
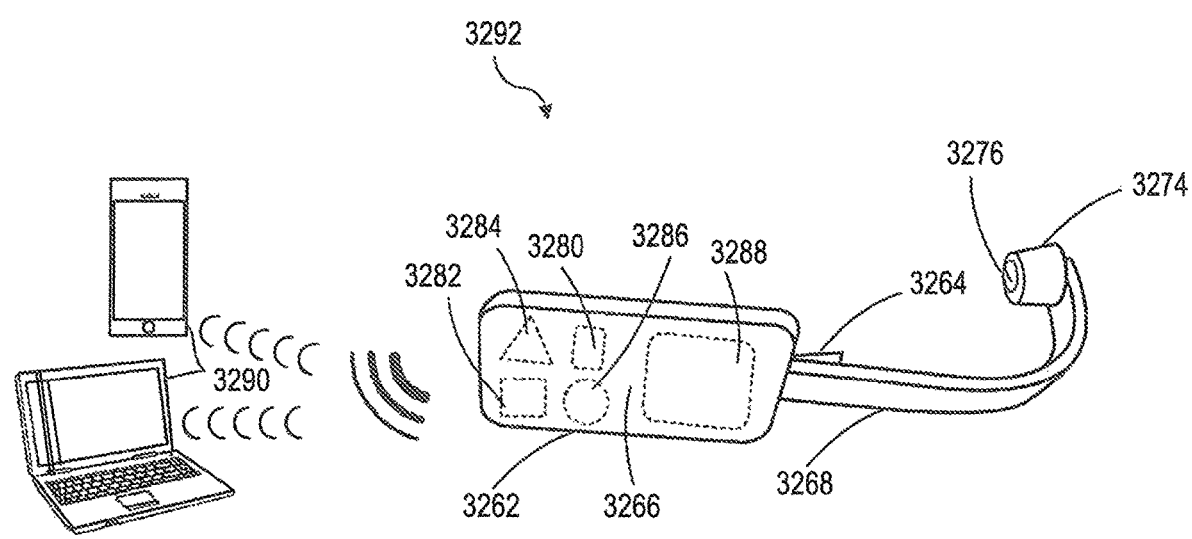

FIG. 197 shows a view of a further apparatus in accordance with an exemplary embodiment of the present disclosure.

DETAILED DESCRIPTION

Diagnosis and treatment of human conditions, such as cancer, heart attack, seizures, stroke, and the like, are conventionally conducted using a plurality of tests and treatments that are often time consuming and expensive. Sometimes the diagnosis of a condition is based on observation, such as a seizure, where observation of a seizure is the only indication that a seizure is taking place. Similarly, treatment can be time consuming and often fails to focus on the root cause of a condition. Even worse, treatment is often the cause of additional problems due to the invasive nature of some treatments or the side effects of some treatments.

The present disclosure arises from the discovery that an Abreu brain thermal tunnel, or ABTT, provides the first known structure for brain-surface thermodynamic communication and thermal connection directly with the center of the brain. Anatomically and physiologically speaking, and as shown in FIGS. 1-4, ABTT 12 includes a continuous, direct, and undisturbed connection between a brain core 24 at the control center of the brain and the skin of ABTT terminus 10. The skin of ABTT terminus 10 is unique in that it is the thinnest skin with the fewest layers, it is absent a fat layer, and it has the highest thermal conductivity of any skin on the human body.

The physical and physiological events at one end of the tunnel are reproduced at the opposite end. Thus, ABTT 12 enables the direct transfer of temperature signals from brain core 24 to ABTT terminus 10 without significant barriers, as described in co-pending U.S. patent application Ser. No. 14/512,421, filed on Oct. 11, 2014, incorporated by reference herein in its entirety. Furthermore, modification of temperature at ABTT terminus 10, including application of heat and removal of heat, directly affects brain core 24, and ultimately, the entire body of the patient or subject. Accordingly, the present disclosure describes systems and methods for acquiring temperature signals from ABTT terminus 10, analyzing those signals, and determining a human condition from those signals, as well as treating specific conditions by the application or removal of heat from ABTT terminus 10. It should be clearly understood that the systems and methods of the present disclosure are predictive of conditions as well as being diagnostic of presently existing conditions. While "predictive" diagnostics currently exist from the perspective that such diagnostics can determine, for example, a pre-diabetic condition, or a high blood cholesterol level, these diagnostics are only indicators that a future condition might occur. In contrast, the systems and method of the present disclosure are able to determine that an actual medical condition is in the early stages of occurrence, which is beneficial in taking preemptive action to prevent the condition from turning catastrophic. Such preemptive action can include the application or removal of heat to ABTT terminus 10.

Anatomy shows the convergence of four veins at ABTT target area 10: frontal 14, superior palpebral 16, supraorbital 18, and angular 20. As angular vein 20 extends further from ABTT 12, it transitions into facial vein 22. Having converged, there is a direct, valve-free connection from ABTT target area 10 between an eye 32 and the eyebrow 28 into the center of the brain 24, which is the temperature center present in the hypothalamus or thermal storage area of the body present in the cavernous sinus.

FIGS. 1 and 2 show the approximate location of these veins in relation to other facial features. Angular/facial vein 20/22 runs up alongside nose 26, superior palpebral vein 16 runs along eyebrow 28, and frontal vein 14 and supraorbital vein 18 run through forehead 30. For the purposes of disclosure, terminology referring to relevant facial areas or veins herein will be described as one or more of the above-referenced veins and ABTT target area 10.

As described herein, veins 14, 16, 18, 20, and 22 converge in the superomedial orbit in the region of the upper eyelid and adjacent to the bridge of the nose, and flow directly, without inhibition, to the center of the brain. The skin in this area, as shown in co-pending U.S. patent application Ser. No. 14/512,421 by Applicant, incorporated by reference in its entirety, is the thinnest skin in the body and free of fat, providing an unexpectedly rapid communication of temperature from the brain core 24 to the skin of ABTT terminus 10. These vessels lack valves, which are typically an important barrier to blood flow and direct and rapid transmission of temperature signals along the vessels. Without valves, these blood vessels truly provide a direct, uninhibited passage for transporting temperature signals directly to and from the hypothalamic region of the brain. Moreover, ABTT 12 includes a superior ophthalmic vein (SOV) 23, which connects the skin surface of ABTT terminus 10 to the brain and corresponds to the central portion of the tunnel (ABTT 12), is valveless and has bidirectional blood flow. The SOV lies directly underneath the skin of the superomedial orbit, i.e., ABTT terminus 10, between eye 32 and eyebrow 28, and is a direct conduit from the surface of the skin of ABTT terminus 10, to the brain, and to the hypothalamus. The hypothalamic region of the brain is the link between the central nervous system and the endocrine system and, as such, acts as the center of control for many basic bodily functions such as, for example, hunger, thirst, body temperature, fatigue, blood pressure, immune responses, circadian cycles, hormone production and secretion, and many others.

The facial end of ABTT 12, herein referred to as a target area, or terminus 10 on the skin on, over, or adjacent to ABTT 12, measures about 11 mm in diameter measured from the medial corner of eye 32 at the medial canthal tendon and extends superiorly for about an additional 6 or 7 mm in an ABTT superior projection 11, and then extends into an upper eyelid in a horn-like projection for another 22 mm. Fat is absent in ABTT terminus 10 and in ABTT horn-like projections near to ABTT terminus 10, with a fat layer present in areas a spaced distance away from ABTT terminus 10.

Many aspects of the disclosure are described in terms of sequences of actions to be performed by elements of a computer system or other hardware capable of executing programmed instructions, for example, a general-purpose computer, special purpose computer, workstation, or other programmable data process apparatus. It will be recognized that in each of the embodiments, the various actions could be performed by specialized circuits (e.g., discrete logic gates interconnected to perform a specialized function), by program instructions (software), such as program modules, being executed by one or more processors (e.g., one or more microprocessors, a central processing unit (CPU), and/or application specific integrated circuit), or by a combination of both. For example, embodiments can be implemented in hardware, software, firmware, microcode, or any combination thereof. The instructions can be program code or code segments that perform necessary tasks and can be stored in a non-transitory machine-readable medium such as a storage medium or other storage(s). A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents.

The non-transitory machine-readable medium can additionally be considered to be embodied within any tangible form of computer readable carrier, such as solid-state memory, magnetic disk, and optical disk containing an appropriate set of computer instructions, such as program modules, and data structures that would cause a processor to carry out the techniques described herein. A computer-readable medium may include the following: an electrical connection having one or more wires, magnetic disk storage, magnetic cassettes, magnetic tape or other magnetic storage devices, a portable computer diskette, a random access memory (RAM), a read-only memory (ROM), an erasable programmable read-only memory (e.g., EPROM, EEPROM, or Flash memory), or any other tangible medium capable of storing information. It should be noted that the system of the present disclosure is illustrated and discussed herein as having various modules and units that perform particular functions.

It should be understood that these modules and units are merely described based on their function for clarity purposes, and do not necessarily represent specific hardware or software. In this regard, these modules, units and other components may be hardware and/or software implemented to substantially perform their particular functions explained herein. The various functions of the different components can be combined or segregated as hardware and/or software modules in any manner, and can be useful separately or in combination. Input/output or I/O devices or user interfaces including, but not limited to, keyboards, displays, pointing devices, and the like can be coupled to the system either directly or through intervening I/O controllers. Thus, the various aspects of the disclosure may be embodied in many different forms, and all such forms are contemplated to be within the scope of the disclosure.

FIG. 5 shows a view of a first system in accordance with an exemplary embodiment of the present disclosure, indicated generally at 50. System 50 is configured to include an ABTT terminus interface 52 and a control unit 54. ABTT terminus interface 52 is configured to include a first interface module 56 and a second interface module 58. Each interface module 56 and 58 is positioned to be movable at least vertically on a post 60, which is also configured to permit each interface module 56 and 58 to swivel rotationally about post 60. Each post 60 is configured to be supported on a base 82, which can be floor mounted, table mounted, bed mounted, rack mounted, etc. It should be understood that there are a plurality of configurations for first interface module 56 and second interface module 58, including a plate having two rods or protrusions configured to fit on, over, or adjacent to ABTT terminuses 10, and configured with the adjustability of first interface module 56 and second interface module 58 to change the spacing of first interface module 56 and second interface module 58 for various size faces. Such adjustability may be manual, electronic, or electrical by, for example, motors, and can be automatic by analysis of temperature inputs from first interface module 56 and second interface module 58. It should further be understand that the plate may only have one rod or protrusion. It should further be understood that dual sensor rods or protrusions can be configured as part of a computer screen, cell phone device, television, mirror, watch, any screen, such as a credit card machine, and any device that a user or subject usually watches or sees, and the like. It should further be understood that dual sensors can include contact sensors and/or non-contact sensors.

Each interface module 56 and 58 is configured to include a temperature or thermal sensor 62 and at least one temperature modification device 64. Thus, system 50 is configured as a standalone unit that includes a dual sensor or pair of sensors configuration, which is thus configured to measure ABTT terminuses 10 bilaterally and simultaneously. It should be understood that system 50 can be a standalone unit that includes one sensor or one detector configuration, which is thus configured to measure ABTT terminus 10 unilaterally, and after measurement in one side, device 50 is adjusted to measure ABTT terminus 10 on the contra-lateral side. It should be understood that system 50 can be include one sensor, and no temperature modification device, and thereby function as a diagnostic or monitoring device. It should be understood that system 50 can include one temperature modification device, and no sensor, and thereby function as a treatment device. It should be understood that system 50 can include as a standalone unit that includes one sensor or one detector configuration, which is thus configured to measure ABTT terminus 10 unilaterally, and after measurement in one side, device 50 is adapted to treat ABTT terminus 10 on the contra-lateral side. It should be understood that system 50 can be a standalone unit that includes one temperature modification device configuration, which is thus configured to treat ABTT terminus 10 unilaterally, and after treatment is done in one side, device 50 is adapted to treat ABTT terminus 10 on the contra-lateral side. Temperature or thermal sensor 62 can be for example, a contact or non-contact sensor such as a thermopile, thermistor, thermocouple, infrared (IR), and the like, or a combination of contact and non-contact sensors. Sensor configurations can further include arrays, including imaging and non-imaging arrays. A non-contact sensor can be configured as a plate that on which is positioned an array of thermopiles or other thermal sensors configured or adapted to create a thermal map of a face, including ABTT terminus 10. Such a contact or non-contact sensor is configured to measure ABTT terminus 10 temperature as a single measurement or over time. The array of thermopiles can be included as a part of a computer screen, a cell phone device, a television, a mirror, a watch, any screen, such as a screen of a credit card machine, and any device that forces a user or subject to look at the device, and the like.

Temperature modification devices 64 can be, for example, a thermoelectric device, a resistive heater, and the like, that permit increasing or decreasing the temperature of interface module 56 and 58. Each temperature module 56 and 58 is further configured to include a protrusion that terminates in an ABTT interface surface 66, which can be a contact surface or a non-contact surface that is positioned on, over, near, or adjacent to a respective ABTT terminus 10. Of course, for treatment of conditions, described further herein, it is anticipated that the most effective configuration for treatment is for ABTT interface surface 66 to be in contact with ABTT terminus 10.

Control unit 54 is configured to include at least a processor 68, a non-transitory memory 70, a transceiver 72 for bidirectional communication with an external electronic device 80, such as a cell phone, watch, television, laptop, eyewear, etc., a display 74, a power supply or power source 76, all of which are positioned within a housing 78. It should be apparent that power source 76 can include a conventional wall outlet, batteries, a solar array, a generator, etc. Control unit 54 can be connected to ABTT terminus interface 52 by a wire or cable 84, or can be connected wirelessly. Input to control unit 54 can be via display 74, a separate keyboard that can be connected by wire or wirelessly to control unit 54, and by other apparatuses, including another electronic apparatus remotely located, such as a cell phone or other wireless device. The functioning of systems such as system 50, which is configured to gather temperature signals from at least one ABTT terminus 10 and to provide treatment to at least one ABTT terminus 10, is described in more detail herein. System 50 can further be configured to include an input apparatus or device configured to permit a medical practitioner to enter symptoms, medical history, medications taken, surgeries, or any health information that are acquired while providing a diagnosis or condition evaluation.

It should understood that the systems, devices and methods of the present disclosure include a combination of measuring devices and heat delivering or heat removing devices, the heat delivering devices and heat removing devices acting on the skin of ABTT terminus(es) 10, and the measuring devices measuring temperature at ABTT terminus(es) 10, or alternatively having devices measuring temperature on the surface of the body and/or devices measuring temperature inside the body. For example, and as shown in FIG. 5, devices measuring temperature at locations inside the body, such as an oral temperature sensor 73, a tympanic temperature sensor 75, an esophageal temperature sensor 77, a bladder temperature sensor 79, a rectum or rectal temperature sensor 81, and the like, can be alternatively used when both ABTT terminuses 10, right and left, are being used for applying or removing heat. Such temperature measuring devices can be connected by a wire or cable 83 to control unit 54 or can be connected wirelessly to control unit 54. It is further understood that the present invention also includes a device adapted to fit the ABTT that has a temperature measuring portion and a heat delivery portion.

Figure 6:
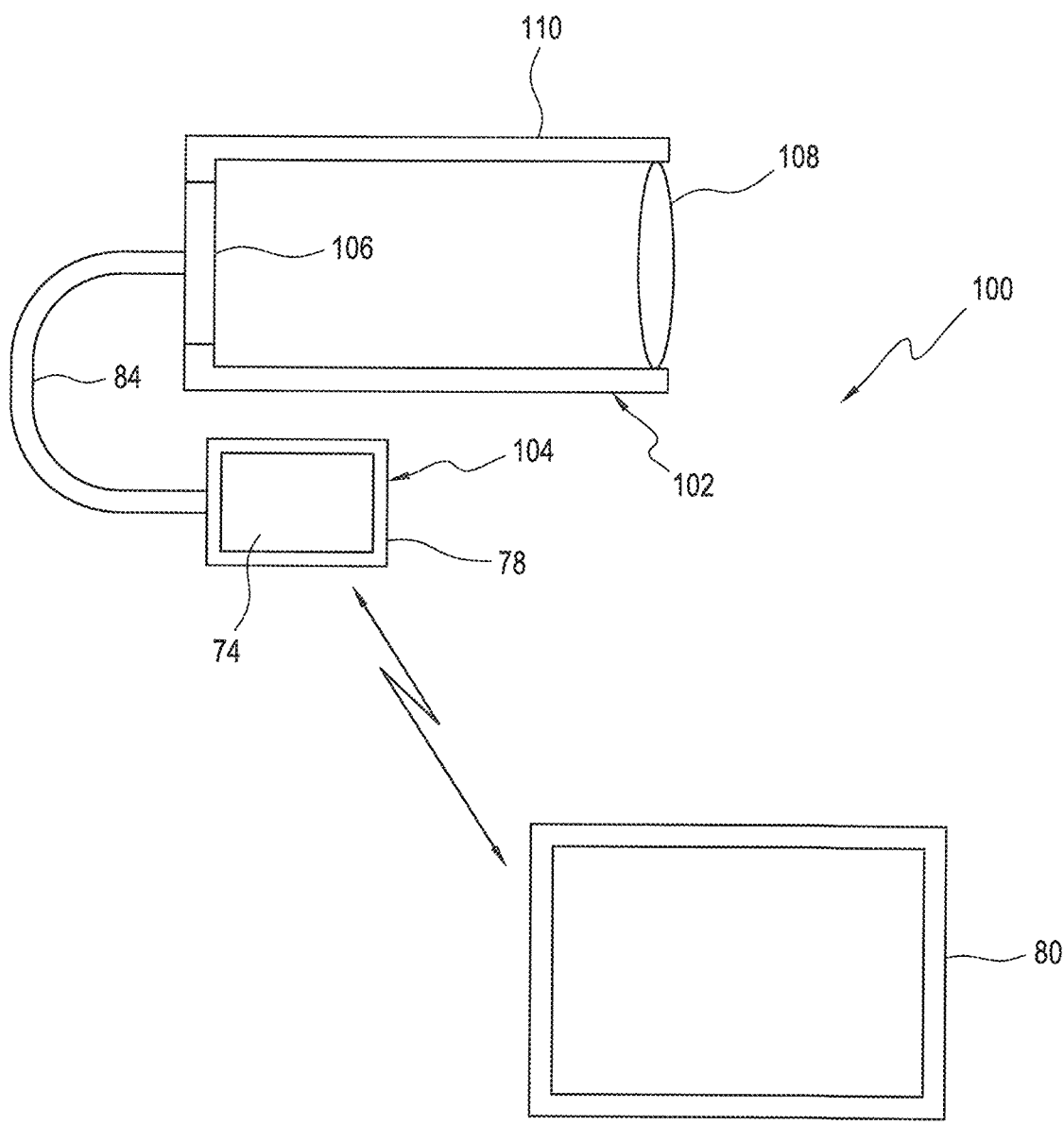
FIG. 6 shows a view of a second system in accordance with an exemplary embodiment of the present disclosure.

FIG. 6 shows a view of a second system in accordance with an exemplary embodiment of the present disclosure, indicated generally at 100. System 100 is configured as a diagnostic temperature measurement device rather than including the capability to provide or remove heat from ABTT terminus 10. System 100 is configured to include an optical assembly 102 and an electronic assembly 104. Optical assembly 102 is configured to include an IR imaging array 106, and can be configured to include a lens assembly 108, both of which are positioned in a housing 110. IR imaging array 106 is configured to capture a temperature profile, map or image of at least one ABTT terminus 10 and area surrounding ABTT terminus 10, and can be configured to capture the temperature profiles of both ABTT terminuses 10 simultaneously. Electronic assembly 104 can be configured to include the features of control unit 54, including processor 68, non-transitory memory 70, transceiver 72 for bidirectional communication with external electronic device 80, display 74, power supply 76, all of which are positioned within housing 78. Control unit 54 can be connected to ABTT terminus interface 52 by wire or cable 84, or can be connected wirelessly.

Figure 7:
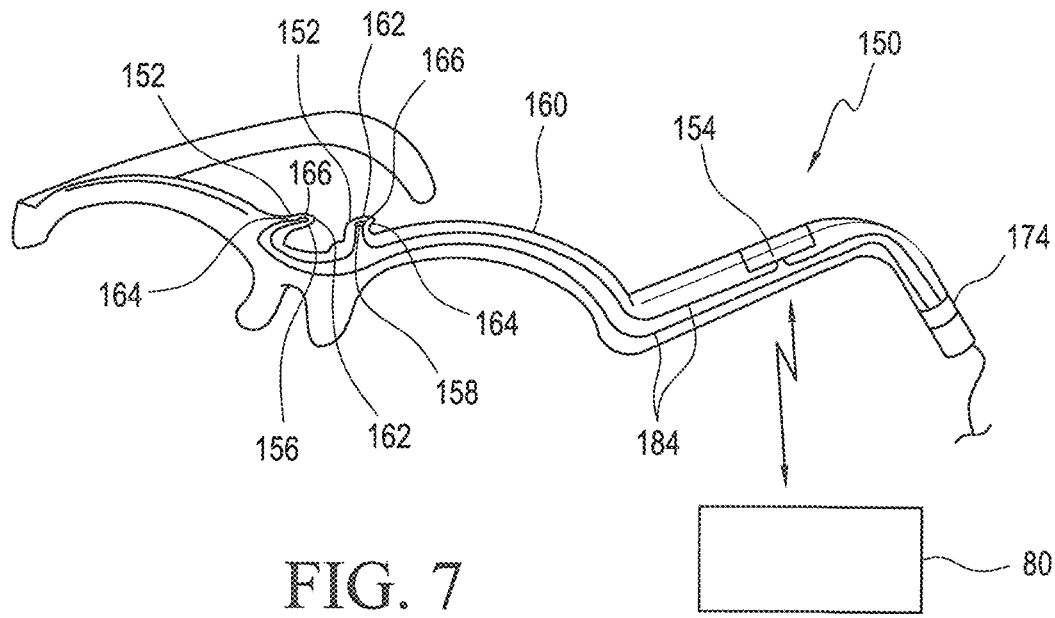
FIG. 7 shows a view of a third system in accordance with an exemplary embodiment of the present disclosure.

FIG. 7 shows a view of a third system in accordance with an exemplary embodiment of the present disclosure, indicated generally at 150. System 150 is configured to include an ABTT terminus interface 152 and a control unit 154, both of which are positioned or supported on a support frame 160. Support frame 160 is configured in a manner similar to eyeglass frames, though the presence of lenses is not required. ABTT terminus interface 152 is configured to include a first interface module 156 and a second interface module 158. Each interface module 156 and 158 is positioned to be flexibly movable on and with respect to support frame 160. Each interface module 156 and 158 is configured to include a temperature sensor 162 and at least one temperature modification device 164. Temperature modification devices 164 can be, for example, a thermoelectric device, a resistive heater, and the like, that permit increasing or decreasing the temperature of interface modules 156 and 158. Each temperature module 156 and 158 is further configured to include an ABTT interface surface 166, which can be a contact surface or a non-contact surface. Of course, for treatment of conditions, described further herein, it is anticipated that the most effective configuration for treatment is for ABTT interface surface 166 to be in contact with ABTT terminus 10.

Control unit 154 is configured to include at least processor 68, non-transitory memory 70, transceiver 72 for bidirectional communication with an external electronic device 80, such as a cell phone, watch, television, laptop, mirror, credit card device, etc., and a power supply 176, all of which are positioned on support frame 160. Control unit 154 can be connected to ABTT terminus interface 152 by one or more wires or a cable 184, or can be connected wirelessly. Input to control unit 154 can be via separate electronic device 80, or can be via a connector 174 positioned on support frame 160 that is configured to provide a wired connection to a remote control device, a separate keyboard, and by other apparatuses, including another electronic apparatus remotely located, such as a cell phone or other wireless device. The functioning of systems such as system 150, which is configured to gather temperature signals from at least one ABTT terminus 10 and to provide treatment to at least one ABTT terminus 10, is described in more detail herein.

Figure 8:
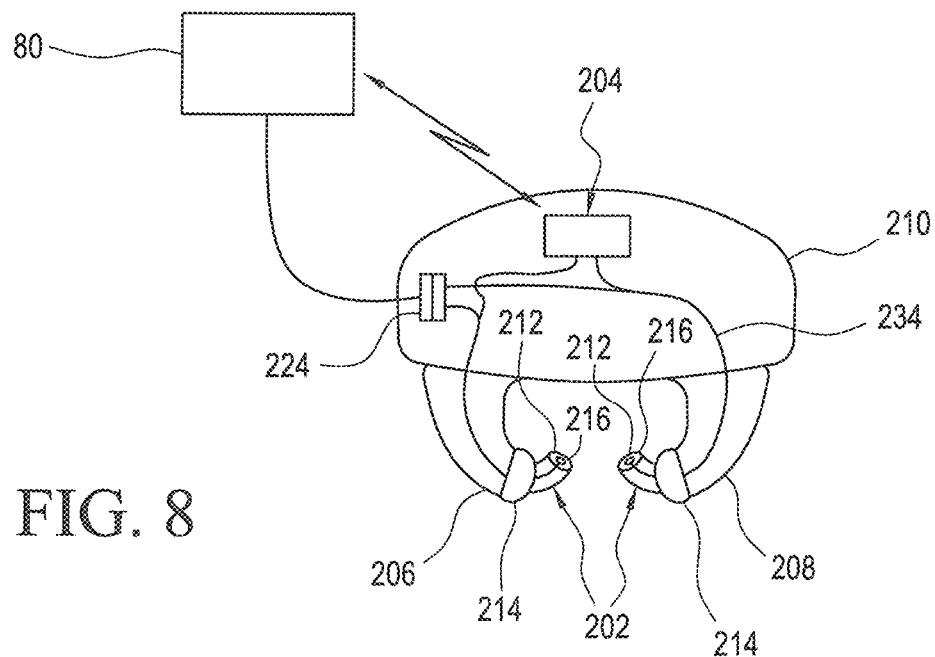
FIG. 8 shows a view of a fourth system in accordance with an exemplary embodiment of the present disclosure.

FIG. 8 shows a view of a fourth system in accordance with an exemplary embodiment of the present disclosure, indicated generally at 200. System 200 is configured to include an ABTT terminus interface 202 and a control unit 204, both of which are positioned or supported on a wearable support 210. Wearable support 210 can be configured as a nose clip, hat, a cap, a headband, a head appliance, and other head-supported and heat-mounted configurations, particularly in the manner of a wearable article. ABTT terminus interface 202 is configured to include a first interface module 206 and a second interface module 208. Each interface module 206 and 208 is positioned to be flexibly movable on and with respect to wearable support 210. Each interface module 206 and 208 is configured to include a temperature sensor 212 and at least one temperature modification device 214. Temperature modification devices 214 can be, for example, a thermoelectric device, a resistive heater, and the like, that permit increasing or decreasing the temperature of interface module 206 and 208. Each temperature module 206 and 208 is further configured to include an ABTT interface surface 216, which can be a contact surface or a non-contact surface. Of course, for treatment of conditions, described further herein, it is anticipated that the most effective configuration for treatment is for ABTT interface surface 216 to be in contact with ABTT terminus 10.

Control unit 204 is configured to include at least processor 68, non-transitory memory 70, transceiver 72 for bidirectional communication with an external electronic device 80, such as a cell phone, watch, television, laptop, etc., and a power supply 76, all of which are positioned on wearable support 210. Control unit 204 can be connected to ABTT terminus interface 202 by one or more wires or a cable 234, or can be connected wirelessly. Input to control unit 204 can be via separate electronic device 80, or can be via a connector 224 positioned on wearable support 210 that is configured to provide a wired connection to a remote control device, a separate keyboard, and by other apparatuses, including another electronic apparatus remotely located, such as a cell phone or other wireless device. The functioning of systems such as system 200, which is configured to gather temperature signals from at least one ABTT terminus 10 and to provide treatment to at least one ABTT terminus 10, is described in more detail herein.

It should be understood that the systems described hereinabove are exemplary only. The systems can be configured to provide diagnosis only, treatment only, or a combination of diagnosis and treatment. Furthermore, in systems that include only one ABTT interface or temperature sensor, rather than the dual ABTT interfaces and temperature sensors described herein that are configured to measure both ABTT terminuses 10 bilaterally and simultaneously, measurement can be made of one ABTT terminus 10, followed by the other ABTT terminus 10, to accomplish the comparisons described herein. In other words, the systems described herein are merely exemplary descriptions of systems that are implemented using the processes described herein.

The processes described hereinbelow take advantage of hitherto unknown characteristics of the human body. More specifically, the brain has a middle cerebral vein that Applicant recognized through experiments has thermodynamic properties, by carrying thermal information from the brain to ABTT terminus 10. Hence, a variety of brain conditions can be detected, as described in the present disclosure, by identifying changes, oscillations, or gradients that occur at ABTT terminus 10. Bilateral measurements can predict the onset of seizure or can be used to diagnose seizure, wherein there is a gradient between two ABTT terminuses 10 of a patient or subject, with an increase greater than or equal to 0.25 degrees Celsius on the affected side as compared to the opposite, non-affected or "good" side.

Bilateral measurements predict the onset of stroke or diagnose of stroke, wherein there is a gradient between two ABTT terminuses 10 of a patient or subject, with a decrease greater than or equal to 0.2 degrees Celsius on the affected side as compared to the opposite good or non-affected side.

The brain has an aberration in which an artery (internal carotid) with high pressure is contained in a pool of venous blood (cavernous sinus) with low pressure, which may lead to serious complications and rupture. Applicant recognized through experiments that this dissimilar blood vessel pressure and artery-vein combination with high Reynolds number has thermodynamic properties, by carrying thermal information from heart to the cavernous sinus and to the brain, which information is present at ABTT terminus 10. Hence, a variety of ailments, physiologic conditions, and heart conditions can be detected by the apparatus and methods of the present disclosure by identifying changes or gradients that occur at ABTT terminus 10.

For example, bilateral measurement of ABTT terminuses 10 predicts the onset of a heart attack, heart disease, or diagnoses heart attack or heart disease, when there is a bilateral decrease in ABTT terminus 10 temperature greater than or equal to 0.2 degrees Celsius that occurs, without change in ambient temperature, in a period less than or equal to 120 minutes, and prior to 2300 hours or 11 PM. Note that such systems are configured to include ambient temperature sensing, humidity sensing, and time interval monitoring, such as by a clock. Since there is a natural decline in brain temperature during sleep, as shown by Applicant, detection of a bilateral decrease that occurs after 2200 hours or 10 PM is preferably compared by processor 68 to a normal or typical baseline for that individual stored in memory, such as non-transitory memory 70. If there is typically a decrease in temperature of 0.3 degrees Celsius during sleep, or after 2200 hours, and the device identifies at that time, or during sleep, a decline that is greater than or equal to 0.4 degrees bilaterally, then a heart abnormality is indicated. If there is typically a decrease in temperature of 0.4 degrees Celsius during sleep, or after 2200 hours, and the device identifies at that time, or during sleep, a decline that is greater than or equal to 0.5 degrees bilaterally, then a heart abnormality is indicated. If there is typically a decrease in temperature of "x" degrees Celsius during sleep, or after 2200 hours, and the device identifies at that time, or during sleep, a decline that is greater than "x" by 0.2 degrees bilaterally, then a heart abnormality is indicated, independent of the absolute value of "x." If there is typically a decrease in temperature of "x" degrees Celsius during sleep, or after 2200 hours, and the device identifies at that time, or during sleep, a decline that is greater than "x" by 0.4 degrees bilaterally, then a severe heart abnormality is indicated, independent of the absolute value of "x."

In mild heart conditions, the left side has lower temperature due to the thermodynamics of the heart-brain connection identified by the Applicant. When there is a moderate heart condition, the temperature of both ABTT terminuses 10 decreases, reduces, or suffers approximately equally. A processor, such as processor 68, is also configured to identify whether there is a greater temperature change at left ABTT terminus 10 as compared to right ABTT terminus 10. If there is a decrease in temperature of any value, but preferably a decrease greater than or equal to 0.1 degrees Celsius, at left ABTT terminus 10 as compared to right ABTT terminus 10, then the diagnosis of impeding or evolving heart condition, such as heart ischemia, myocardial infarction, or arrhythmia, is confirmed, the larger the gradient between left and right the more serious the condition, from the more severe, which is myocardial infarction to the less severe which is myocardial ischemia. Likewise, high response atrial fibrillation (severe arrhythmia) has a greater thermal gradient between right and left as compared to a mild arrhythmia, such as low ventricular response atrial fibrillation.

Applicant also recognized and tested that right or left dominance, often informally described as left or right handedness, influences the temperature of ABTT 12 and ABTT terminus 10. For a right-handed person, left ABTT terminus 10 is higher than the temperature of right ABTT terminus 10. For a left-handed person, right ABTT terminus 10 has a higher temperature than left ABTT terminus 10. The systems and methods of the present disclosure are configured to permit a user, subject, or patient to be able to enter which side is dominant, and/or testing to identify dominance, such as writing on a tablet to detect the use of the left or right hand, and a system in accordance with such an embodiment is configured to include an electronic pad or the like to determine dominance. Applicant also recognized and tested that right or left dominance, often informally described as left or right handedness, by using thermal image or thermal mapping using noncontact thermopiles and thermistors, and further recognized that dominance influences the size of the heat island (isotherm) having the highest temperature of ABTT 12 and ABTT terminus 10. For a right-handed person, the size of the image with high temperature of the left ABTT terminus 10 is higher than the size of the image with high temperature of right ABTT terminus 10. For a left-handed person, right ABTT terminus 10 has a larger high temperature zone in thermal image than left ABTT terminus 10.

Dominance can be accounted or considered in the diagnosis of any condition described herein to determine severity or to predict a condition far in advance of manifestation of the condition. For example, an increase in ABTT terminus 10 temperature on one side that is greater than or equal to 0.2 degrees Celsius indicates the onset of seizure in that side in a person with history of seizures or with a family history of seizures. It should be understood that an increase in ABTT terminus 10 temperature on one side that is greater than or equal to 0.3 degrees Celsius indicates the onset of moderate seizure in that side in a person with history of seizures or with a family history of seizures. It should be understood that an increase in ABTT terminus 10 temperature on one side that is greater than or equal to 0.4 degrees Celsius indicates the onset of severe seizure in that side in a person with history of seizures or with a family history of seizures. It should be understood that an increase in ABTT terminus 10 temperature on one side that is greater than or equal to 0.1 degrees Celsius indicates the onset of mild seizure in that side in a person with history of seizures or with a family history of seizures. If the baseline temperature has value of "y" and if there is an increase in temperature between greater than 0.1 degrees Celsius and lower than 0.25 degrees Celsius above "y" temperature level in one side as compared to the contra-lateral side, then a mild seizure is indicated, independent of the absolute value of "y." If the baseline temperature has value of "y" and if there is an increase in temperature equal to or greater than 0.25 degrees Celsius above "y" temperature level in one side as compared to the contra-lateral side, then a seizure is indicated, independent of the absolute value of "y."

In this embodiment, dominance is taken into consideration. A reversal of temperature dominance between left ABTT terminus 10 and right ABTT terminus 10 indicates a more serious or more imminent condition. Reversal of temperature is defined as ABTT terminus 10 of the non-dominant side, which normally has lower temperature, obtains a higher temperature than ABTT terminus 10 of the dominant side. By way of example, a right-handed person normally will have a higher temperature at left ABTT terminus 10, as identified by the Applicant. Hence, if the systems and methods of the present disclosure determine that ABTT terminus 10 on the non-dominant side has a temperature higher than ABTT terminus 10 on the dominant side, such as a higher temperature at right ABTT terminus 10 than the temperature at left ABTT terminus 10 in a right-handed person, such condition indicates a temperature reversal and a more serious problem, or more severe seizure.

A temperature decrease greater than or equal to 0.2 degrees Celsius at one ABTT terminus 10 only indicates the onset of stroke on that side in a person with history of vascular abnormalities or with family history of stroke. It should be understood that a temperature decrease in ABTT terminus 10 on one side that is greater than or equal to 0.3 degrees Celsius indicates the onset of moderate stroke in that side in a person with history of hypertension and/or diabetes or with a family history of stroke. It should be understood that a temperature decrease in ABTT terminus 10 on one side that is greater than or equal to 0.4 degrees Celsius indicates the onset of severe stroke in that side in a person with history of stroke or with a family history of stroke. It should be understood that a temperature decrease in ABTT terminus 10 on one side that is greater than or equal to 0.1 degrees Celsius indicates the onset of mild stroke in that side in a person with history of stroke or with a family history of stroke. If the baseline temperature has value of "z" and if there is a decrease in temperature between greater than 0.1 degrees Celsius and lower than 0.25 degrees Celsius in relation to "z" temperature level in one side as compared to the contra-lateral side, then a mild stroke or brain ischemia is indicated, independent of the absolute value of "z." If the baseline temperature has value of "z" and if there is a decrease in temperature equal to or greater than 0.25 degrees Celsius in relation to "z" temperature level in one side as compared to the contra-lateral side, then a stroke is indicated, independent of the absolute value of "z." In this embodiment, dominance is taken into consideration. Hence, if there is a reversal of temperature dominance, as described hereinabove, a more serious or more imminent condition is indicated. By way of example, a right-handed person normally will have a higher temperature at left ABTT terminus 10, as identified by Applicant. Hence, if the systems and method of the present disclosure detect a relatively higher temperature in the non-dominant side, such as a higher temperature at right ABTT terminus 10 in a right-handed person, the risk of a severe stroke in the left side of the individual is indicated. If, on the other hand, the stroke is occurring in the right side of a right-handed person, the gradient between right and left ABTT terminuses 10 will be much larger than normal since the right side normally has a lower temperature that is further decreased by the stroke, causing the difference between right and left ABTT terminus 10 to be greater. Thus, a greater temperature difference between right and left ABTT terminuses 10 corresponds to the diagnosis of stroke in the non-dominant side.

As previously described hereinabove, bilateral measurement predicts the onset of a heart attack, heart disease, or diagnosis of a heart attack or heart disease, when there is a bilateral decrease greater than or equal to 0.2 degrees Celsius. Considering that a temperature decrease at left ABTT terminus 10 is indicative of a heart condition, and further considering that the dominant hemisphere of the brain has a higher temperature, then a system of the present disclosure is configured to account for the temperature of each ABTT terminus 10 side being measured. Accordingly, the systems and methods of the present disclosure are configured to identify the sensors associated with left ABTT terminus 10 and right ABTT terminus 10. Hence, if a right-handed person, who is expected to have a higher temperature at left ABTT terminus 10 because of its dominance, has a lower temperature than right ABTT terminus 10, a heart condition is indicated. In mild heart conditions, the temperature at left ABTT terminus 10 has a lower temperature due to the thermodynamics of the heart-brain as identified by Applicant. When there is a moderate condition, both ABTT terminuses 10 experience a temperature reduction or suffer equally. It should be understood that a temperature decrease in ABTT terminus 10 on both sides that is greater than or equal to 0.3 degrees Celsius indicates the onset of moderate heart attack in a person with history of hypertension or with a family history of heart disease. It should be understood that a temperature decrease in ABTT terminus 10 on both sides that is greater than or equal to 0.4 degrees Celsius indicates the onset of severe heart attack in a person with history of hypertension or with a family history of heart disease. It should be understood that a temperature decrease in ABTT terminus 10 that is greater than or equal to 0.1 degrees Celsius indicates the onset of heart ischemia in a person with history of hypertension or with a family history of heart disease. If the baseline temperature has value of "w" and if there is a decrease in temperature between greater than 0.1 degrees Celsius and lower than 0.20 degrees Celsius in relation to "w" temperature, then a heart ischemia is indicated, independent of the absolute value of "w." If the baseline temperature has value of "w" and if there is a decrease in temperature equal to or greater than 0.20 degrees Celsius in relation to "w" temperature level, then a heart attack is indicated, independent of the absolute value of "w."

A temperature decrease greater than or equal to 0.25 degrees Celsius at one ABTT terminus 10 only indicates mild neck artery thrombosis (e.g., carotid artery thrombosis) on that side in a person with history of vascular abnormalities or atherosclerosis. It should be understood that a temperature decrease in ABTT terminus 10 on one side that is greater than or equal to 0.35 degrees Celsius indicates moderate neck artery thrombosis (e.g., carotid artery thrombosis) on that side in a person with history of vascular abnormalities or atherosclerosis. It should be understood that a temperature decrease in ABTT terminus 10 on one side that is greater than or equal to 0.5 degrees Celsius indicates severe neck artery thrombosis (e.g., carotid artery thrombosis) on that side in a person with history of vascular abnormalities or atherosclerosis. It should be understood that a temperature decrease in ABTT terminus 10 on one side that is greater than or equal to 0.1 degrees Celsius indicates incipient neck artery thrombosis (e.g., carotid artery thrombosis) on that side in a person with history of vascular abnormalities or atherosclerosis. If the baseline temperature has value of "p" and if there is a decrease in temperature between greater than 0.2 degrees Celsius and lower than 0.3 degrees Celsius in relation to "p" temperature level in one side as compared to the contra-lateral side, then neck artery thrombosis (e.g., carotid artery thrombosis) is indicated, independent of the absolute value of "p." If the baseline temperature has value of "p" and if there is a decrease in temperature equal to or greater than 0.3 degrees Celsius in relation to "p" temperature level in one side as compared to the contra-lateral side, then severe neck artery thrombosis (e.g., carotid artery thrombosis) is indicated, independent of the absolute value of "p." In this embodiment, dominance is taken into consideration. Hence, if there is a reversal of temperature dominance, as described hereinabove, a more serious or more imminent condition is indicated. By way of example, a right-handed person normally will have a higher temperature at left ABTT terminus 10, as identified by Applicant. Hence, if the systems and method of the present disclosure detect a relatively higher temperature in the non-dominant side, such as a higher temperature at right ABTT terminus 10 in a right-handed person, the risk of a severe neck artery thrombosis (e.g., carotid artery thrombosis) in the left side of the individual is indicated. If, on the other hand, the neck artery thrombosis (e.g., carotid artery thrombosis) is occurring in the right side of a right-handed person, the gradient between right and left ABTT terminuses 10 will be much larger than normal since the right side normally has a lower temperature that is further decreased by the thrombosis, causing the difference between right and left ABTT terminus 10 to be greater. Thus, a greater temperature difference between right and left ABTT terminuses 10 corresponds to the diagnosis of neck artery thrombosis (e.g., carotid artery thrombosis) in the non-dominant side.

A temperature increase greater than or equal to 0.15 degrees Celsius at one ABTT terminus 10 only indicates mild neck vein thrombosis (e.g., jugular vein thrombosis) on that side in a person with history of vascular abnormalities or atherosclerosis. It should be understood that a temperature increase in ABTT terminus 10 on one side that is greater than or equal to 0.25 degrees Celsius indicates moderate neck vein thrombosis (e.g., jugular vein thrombosis) on that side in a person with history of vascular abnormalities or atherosclerosis. It should be understood that a temperature increase in ABTT terminus 10 on one side that is greater than or equal to 0.35 degrees Celsius indicates severe neck vein thrombosis (e.g., jugular vein thrombosis) on that side in a person with history of vascular abnormalities or atherosclerosis. It should be understood that a temperature increase in ABTT terminus 10 on one side that is greater than or equal to 0.1 degrees Celsius indicates incipient neck vein thrombosis (e.g., jugular vein thrombosis) on that side in a person with history of vascular abnormalities or atherosclerosis. If the baseline temperature has value of "q" and if there is an increase in temperature between greater than 0.15 degrees Celsius and lower than 0.3 degrees Celsius in relation to "q" temperature level in one side as compared to the contra-lateral side, then neck vein thrombosis (e.g., jugular vein thrombosis) is indicated, independent of the absolute value of "q." If the baseline temperature has value of "q" and if there is an increase in temperature equal to or greater than 0.3 degrees Celsius in relation to "q" temperature level in one side as compared to the contra-lateral side, then severe neck vein thrombosis (e.g., jugular vein thrombosis) is indicated, independent of the absolute value of "p."

As exemplary examples, in a person who is would normally considered right handed or right dominant, with a temperature X at left ABTT terminus 10 and temperature Y at right ABTT terminus 10, the typical temperature relationships are X>Y. If a right-handed or right dominant person has a heart condition, the temperature at left ABTT terminus 10 will be X minus 0.2 degrees Celsius, and the temperature at right ABTT terminus 10 will be Y minus 0.1 degrees Celsius. While the temperature of both ABTT terminuses 10 decreases, the left ABTT terminus 10 temperature decreases more in the left side. Hence, temperatures tend to equalize in a heart condition that is mild, with right and left ABTT having about the same temperature. In a more serious condition both sides will reduce equally, hence the left ABTT remains higher than the right ABTT, in a right-handed person.

For a left-handed or left dominant person, conditions are reversed from that of a right-handed person. Thus, the typical temperature relationships are X<Y. If a left handed or left dominant person has a heart condition, the temperature at left ABTT terminus will still be X minus 0.2 degrees Celsius and the temperature at right ABTT terminus will still be Y minus 0.1 degrees Celsius, but the temperature of left ABTT terminus 10 will be much lower than the decreased temperature of left ABTT terminus 10 for a right-handed person, since the temperature of left ABTT terminus 10 is already lower than the temperature of right ABTT terminus 10 for a left-handed person. Hence, there is a larger difference between right and left ABTT terminus 10 temperature when there is a mild heart condition for a left-handed person. In a more serious condition, the temperature of both ABTT terminuses 10 will reduce equally, hence the difference between right and left ABTT terminuses 10 remains stable in this situation.

The end of ABTT terminus 10 internally connects with the central portion of the brain called the hypothalamus and the hypothalamic-hypophyseal axis, which consists of a neuroendocrine connection, meaning a connection of the nervous system to the location where the hormones are generated by the brain or the pituitary gland. Applicant recognized that ABTT 12 connects with this axis and the pituitary gland, and Applicant recognized and tested the axis via ABTT terminus 10, observing that it is possible to act on the axis and pituitary gland using a specialized device and method, such as those that are disclosed herein. The device is configured to include a temperature modification device, which can include thermally retentive materials, thermoelectric devices or Peltier devices, infrared heat-generating non-contact devices, and the like, which apply a certain amount of heat to ABTT terminus 10, the amount of heat preferably reaching a value greater than or equal to 37.5 degrees Celsius, preferably for a period greater than or equal to 10 minutes. It should be understood that the amount of heat and duration of exposure to heat vary and are dependent on stage of the disease and type of disease. This thermal effect is carried via ABTT 10, which acts as a heat pipe, to the hypothalamic-hypophyseal axis and pituitary gland, indicating the need to reduce production of thermogenesis, or reduce production of hormones associated with thermogenesis. A main hormone associated with thermogenesis is the thyroid hormone, and thus through this device and method reduction of production of the thyroid hormone can be achieved. Heat via ABTT 12 causes a reduction in production of thyroid release hormone, thereby reducing production of thyroid hormones. Conversely, removal of heat from ABTT terminus 10 causes an increase in the production of thyroid release hormone. For example, in an exemplary embodiment, a system for applying heat to ABTT terminus 10 can increase the temperature at ABTT terminus 10 by an amount greater than or equal to 0.3 degrees Celsius as compared to a baseline temperature to decrease production of hormones. Similarly, a system for removing heat from ABTT terminus 10 can decrease the temperature at ABTT terminus 10 by an amount greater than or equal to 0.3 degrees Celsius as compared to a baseline temperature to increase production of hormones. Hence, the devices and methods of the present disclosure can be used for treating hyperthyroidism or any increase in thyroid hormone. Moreover, commonly thyroid cancer is associated with growth of a tumor via the presence of thyroid hormones stimulating the cancerous tissue. Hence, a reduction of the thyroid hormone as provided by the teachings of the present disclosure can be used for treatment of thyroid cancer. Further, though specific treatment embodiments are described herein, it should be understood that increasing and decreasing the temperature at ABTT terminus 10 can be used for treating other disorders. By way of example, the present disclosure also provides a device and method for treating Alzheimer's disease, by a device delivering heat, the amount of heat preferably reaching a value greater than or equal to 37.0 degrees Celsius, preferably for a period great than or equal to than 5 minutes. The present disclosure also provides a device and method for preventing Alzheimer's disease, by a device delivering heat, the amount of heat preferably reaching a value greater than or equal to 37.0 degrees Celsius, preferably for a period greater than or equal to 10 minutes. It should be understood that the amount of heat and duration of exposure to heat vary in Alzheimer's disease and are dependent on the stage of the disease.

Another embodiment for increasing production of thyroid hormones and treating a variety of disorders includes a device that is configured to include a temperature modification device, such as thermally retentive materials, thermoelectric or Peltier devices, infrared non-contact devices, and the like, which remove a certain amount of heat from ABTT terminus 10, the amount of heat being removed preferably by a device having a temperature value less than or equal to 35 degrees Celsius, preferably for a period greater than or equal to 3 minutes. The present disclosure also provides a device and method for treating multiple sclerosis, by a device removing heat, the amount of heat preferably reaching a value less than or equal to 34.5 degrees Celsius, preferably for a period greater than or equal to 5 minutes.

Another embodiment for increasing production of thyroid hormones and treating a variety of disorders includes a device that is configured to include a temperature modification device, such as thermally retentive materials, thermoelectric or Peltier devices, and the like, which remove heat from ABTT terminus 10, the amount of heat being removed preferably being removed by a device having a temperature value that is lower than a baseline temperature by an amount that is greater than or equal to 0.2 degrees Celsius, preferably for a period greater than or equal to 5 minutes, the device configured to include a processor that is configured to identify a baseline value and to activate the temperature modification device by transmitting temperature control signals to the temperature modification device to achieve a temperature that is lower than a baseline temperature by an amount that is greater than or equal to 0.2 degrees Celsius.

Another embodiment for reducing production of thyroid hormones and treating a variety of disorders includes a device that is configured to include a temperature modification device, such as thermally retentive materials, thermoelectric or Peltier devices, infrared non-contact devices, and the like, which apply a certain amount of heat to ABTT terminus 10, the amount of heat being applied is applied preferably by a temperature modification device having a temperature value that is higher than a baseline temperature by an amount that is greater than or equal to 0.2 degrees Celsius, preferably for a period that is greater than or equal to 10 minutes, the device configured to include a processor that is configured to identify the baseline value and to activate the temperature modification device to achieve a temperature that is higher than the baseline temperature by an amount that is greater than or equal to 0.2 degrees Celsius.

Is should be understood that other hormones can be activated, i.e., increasing production or reducing production of hormones, in accordance with the devices and methods of the present disclosure. It should also be understood that that other hypothalamic centers, such as hunger, pleasure, pain, sleep, thermal, and the suprachiasmatic nucleus can be stimulated or inhibited in accordance with the devices and methods of the present disclosure. The present disclosure also provides a device and method for treating obesity and/or for inhibition of hunger center, by a device removing heat, the amount of heat preferably reaching a value less than or equal to 34 degrees Celsius, preferably for a period greater than or equal to 20 minutes. The present disclosure also provides a device and method for treating pain and/or for inhibition of the pain center, by a device removing heat, the amount of heat preferably reaching a value less than or equal to 34 degrees Celsius, preferably for a period greater than or equal to 15 minutes.

Heart rate, blood pressure, blood flow, oxygen levels and oxygen saturation, and body chemistry such as glucose level, and the like, besides carbon dioxide and other gases. Altered thermodynamics with brain temperature being out of the optimal brain thermal zone can cause cardiovascular changes and identify neoplasia and/or neural conditions. In another embodiment, the dual sensing system of the present disclosure includes a bilateral heart beat detection system detecting a heart rate at one or more ABTT terminuses 10, wherein a difference in heart beat detected at one site as compared to the contralateral side is indicative of abnormal thermodynamics and/or of a thrombo-embolic process. By way of example, when a thrombo-embolic process is occurring in the right cardiovascular or cerebral network the heart rate at right ABTT terminus 10 differs from left ABTT terminus 10 by an amount of 1 beat or more per 60 seconds. In another embodiment, the dual sensing system of the present invention includes bilateral blood pressure detection system detecting blood pressure at ABTT terminus 10, wherein a difference in blood pressure detected at one site as compared to the contralateral side is indicative of abnormal thermodynamics and/or of neoplasia and/or thrombo-embolic process. By way of example, when a neoplasia or thrombotic process is occurring in the right cerebral network, the blood pressure at right ABTT terminus 10 differs from the blood pressure at left ABTT terminus 10 by an amount greater than or equal to 5 mm Hg for either systolic or diastolic blood pressure. In another embodiment, the dual sensing system of the present invention includes bilateral oxygen detection system detecting oxygen level or oxygen saturation at ABTT terminus 10, wherein a difference in oxygen level or oxygen saturation detected at one site as compared to the contralateral side is indicative of abnormal thermodynamics and/or of neoplasia, and/or neural dysfunction and/or vascular process. By way of example, when a traumatic brain injury is occurring in the right cerebral network, the oxygen at right ABTT terminus 10 differs from left ABTT terminus 10, right ABTT terminus 10 having an oxygen saturation equal to or lower than 94% while left ABTT terminus 10 has oxygen saturation between 95% and 100%. When a severe traumatic brain injury or stroke is occurring in the right cerebral network, the oxygen at right ABTT terminus 10 differs from left ABTT terminus 10, right ABTT terminus 10 having an oxygen saturation equal to or lower than 91% while left ABTT terminus 10 has oxygen saturation between 95% and 100%. When a severe stroke is occurring in the right cerebral network, the oxygen at right ABTT terminus 10 differs from left ABTT terminus 10, right ABTT terminus 10 having an oxygen saturation less than or equal to 86% while left ABTT terminus 10 has oxygen saturation between 95% and 100%. In another embodiment, the dual sensing system of the present invention includes bilateral glucose detection system detecting glucose level at ABTT terminus 10, wherein a difference in glucose level detected at one site as compared to the contralateral side is indicative of abnormal thermodynamics and/or of neoplasia, and/or neurologic conditions and/or vascular process. By way of example, when neoplasia is occurring in the right brain, the glucose level at right ABTT terminus 10 differs from left ABTT terminus 10, right ABTT terminus 10 having a glucose level greater than or equal to 3 mg/dl as compared to glucose levels at left ABTT terminus 10. FIG. 20 shows exemplary measuring devices that can be coupled to ABTT terminus 10, including a spectrometer 942 for measuring glucose, a light source and photodetector 944 for measuring oxygenation, a pressure plate 946 for measuring blood pressure and pulse rate, and a piezoelectric sensor 948, also for measuring blood pressure and pulse rate. Of course, such devices are exemplary, and can be combined with a temperature sensor or with each other to obtain a plurality of simultaneous measurements from ABTT terminus.

A temperature increase greater than or equal to 0.15 degrees Celsius at one ABTT terminus 10 only indicates mild traumatic brain injury on that side in a person with history of brain injury or concussion. It should be understood that a temperature increase in ABTT terminus 10 on one side that is greater than or equal to 0.25 degrees Celsius indicates moderate traumatic brain injury on that side in a person with history of brain injury or concussion. It should be understood that a temperature increase in ABTT terminus 10 on one side that is greater than or equal to 0.35 degrees Celsius indicates severe traumatic brain injury on that side in a person with history of brain injury or concussion. It should be understood that a temperature increase in ABTT terminus 10 on one side that is greater than or equal to 0.1 degrees Celsius indicates incipient traumatic brain injury on that side in a person with history of vascular abnormalities or atherosclerosis. If the baseline temperature has value of "b" and if there is an increase in temperature between greater than 0.15 degrees Celsius and lower than 0.25 degrees Celsius in relation to "b" temperature level in one side as compared to the contra-lateral side, then traumatic brain injury on that side in a person with history of brain injury or concussion is indicated, independent of the absolute value of "b." If the baseline temperature has value of "b" and if there is an increase in temperature equal to or greater than 0.25 degrees Celsius in relation to "b" temperature level in one side as compared to the contra-lateral side, then severe traumatic brain injury on that side in a person with history of brain injury or concussion is indicated, independent of the absolute value of "p."

FIG. 20 shows additional measuring devices that can acquire or measure data, information, or characteristics present at the ABTT terminus or other body regions, including a spectrometer 942 for measuring glucose, a light source and photodetector 944 for measuring oxygenation, a pressure plate 946 for measuring blood pressure and pulse rate, and a piezoelectric sensor 948, also for measuring blood pressure and pulse rate.

Figure 9:
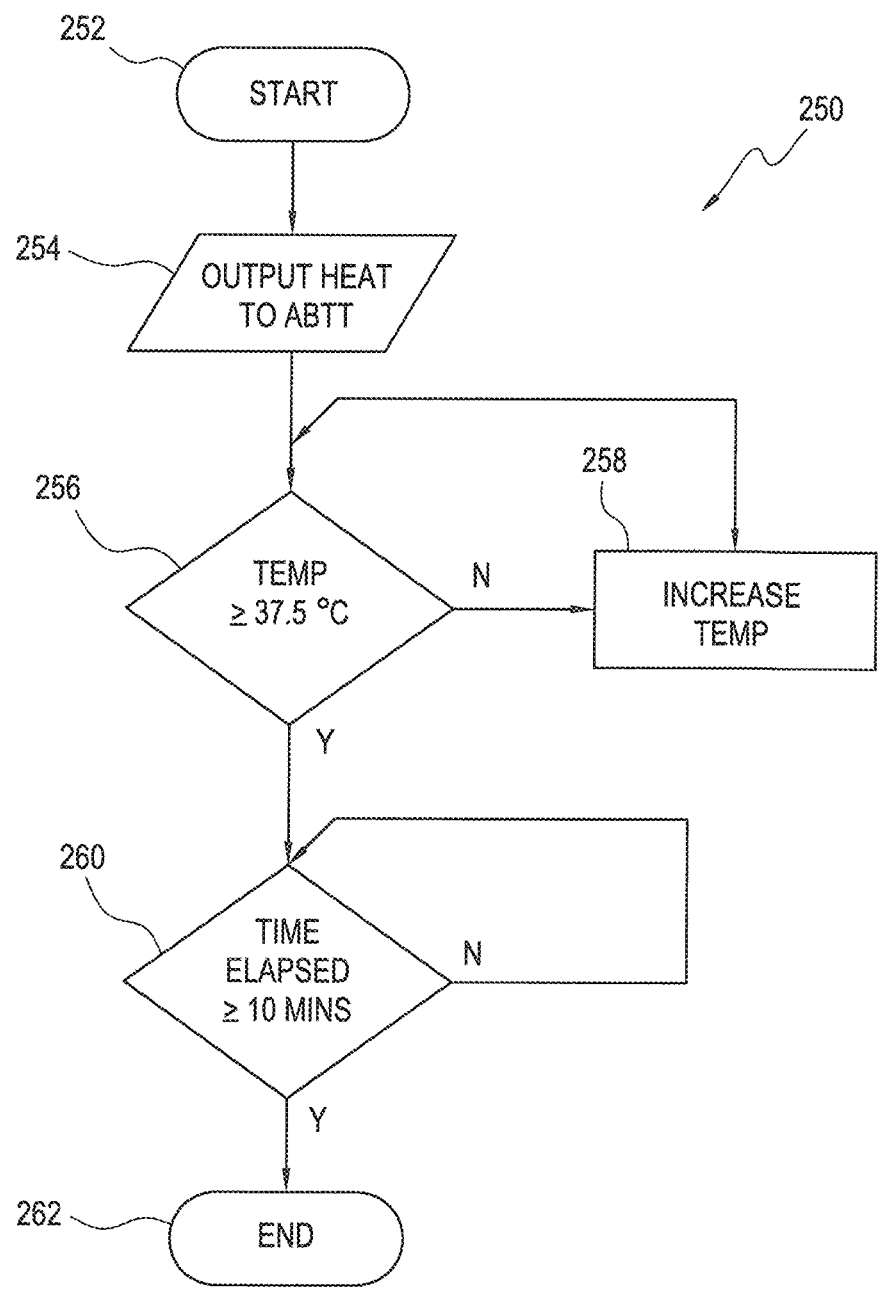
FIG. 9 shows a first treatment process for thyroid and other disorders in accordance with an exemplary embodiment of the present disclosure.

FIG. 9 shows a first treatment process for thyroid and other disorders in accordance with an exemplary embodiment of the present disclosure, indicated generally at 250. The end of ABTT 12 internally connects with the central portion of the brain called the hypothalamus and the hypothalamic-hypophyseal axis, which consists of a neuro-endocrine connection, meaning a connection of the nervous system to the location where the hormones are generated by the brain (or pituitary gland). Applicant recognized that ABTT 12 connects with this axis and the pituitary gland, and Applicant recognized and tested the axis via ABTT, and observed that it is possible to act on the axis and pituitary gland using a specialized device, such as those disclosed herein configured to provide heat to ABTT terminus 10. The device includes thermal input, including thermally retentive materials, thermoelectric devices, Peltier devices, infrared heat-generating non-contact devices, and the like that apply a certain amount of heat to ABTT 12, the amount of heat preferably reaching a value that is greater than or equal to 37.5 degrees Celsius, preferably for a period greater than or equal to 10 minutes. This thermal effect is carried via ABTT 12 heat pipe to the axis and pituitary gland, indicating the need to reduce production of thermogenesis, or reduce production of hormones associated with thermogenesis. A main hormone associated with thermogenesis is a thyroid hormone, and thus through this device and the method of process 250, reduction of production of thyroid hormone can be achieved. Heat via ABTT 12 causes a reduction in production of a thyroid release hormone, reducing thereby production of thyroid hormones. Hence, the method of process 250 and associated device can be used for treating hyperthyroidism or any increase in thyroid hormone. Moreover, commonly thyroid cancer is associated with growth of tumor via the presence of thyroid hormones stimulating the cancerous tissue. Hence, a reduction of thyroid hormone as provided by the present disclosure can be used for treatment of thyroid cancer.

Process 250 begins with a start process 252, which can include initializing a control device, temperature sensors, and other electronic elements of a system, loading a program and predetermined values for comparison from non-transitory memory, and the like. Once start process 252 is completed, control passes from start process 252 to a heat output process 254.

In heat output process 254, one or more temperature modification devices, such as temperature modification devices 64, are actuated or powered to provide heat to at least one ABTT interface surface 66. The initial temperature can be a predetermined value, such as 37.5 degrees Celsius. As heat is being generated, a temperature sensor, such as temperature sensor 62, can be simultaneously measuring the temperature of at least one ABTT terminus 10. Although ABTT terminus 10 is the ideal location for a temperature sensor location, and although other locations in the body will not have the same precision and accuracy as ABTT terminus 10, it should be understood that temperature sensors located elsewhere on the surface of the body or inside the body can be used to monitor the changes in temperature from applying heat to ABTT terminus(es) 10 or removing heat from ABTT terminus(es) 10, and the surface sensors or internal sensors can be applied to any embodiment of the present disclosure. Moreover, sensors located in other parts the body, both on the surface of the body and inside the body, are within the scope of the present disclosure and provide information on decoupling of the brain and skin surface, and decoupling between the brain and the internal part of the body. Once heat output process 254 is complete, control passes from process 254 to a predetermined temperature decision process 256.

In predetermined temperature decision process 256, a determination is made as to whether the temperature of an associated ABTT terminus 10 has reached a predetermined temperature, which in the exemplary embodiment of FIG. 9 is 37.5 degrees Celsius. If the temperature of ABTT terminus 10 is not greater than or equal to the predetermined temperature, control passes from decision process 256 to an increase output temperature process 258. If the temperature of ABTT terminus 10 is greater than or equal to the predetermined temperature, control passes from decision process 256 to an elapsed time decision process 260.

In elapsed time decision process 260, a determination of whether a predetermined time has passed is made. If the predetermined time has passed, which is 10 minutes in the embodiment of FIG. 9, then control passes from elapsed time decision process 260 to an end process 262, where notification can be provided to a user or operator that process 250 is complete. Such notification can be via, for example, a display, vibration, or audible sound. If the predetermined time has yet to pass, control remains with elapsed time decision process 260 via a loop back to elapsed time decision process 260 until the elapsed time is greater than or equal to the predetermined time interval.

Figure 10:
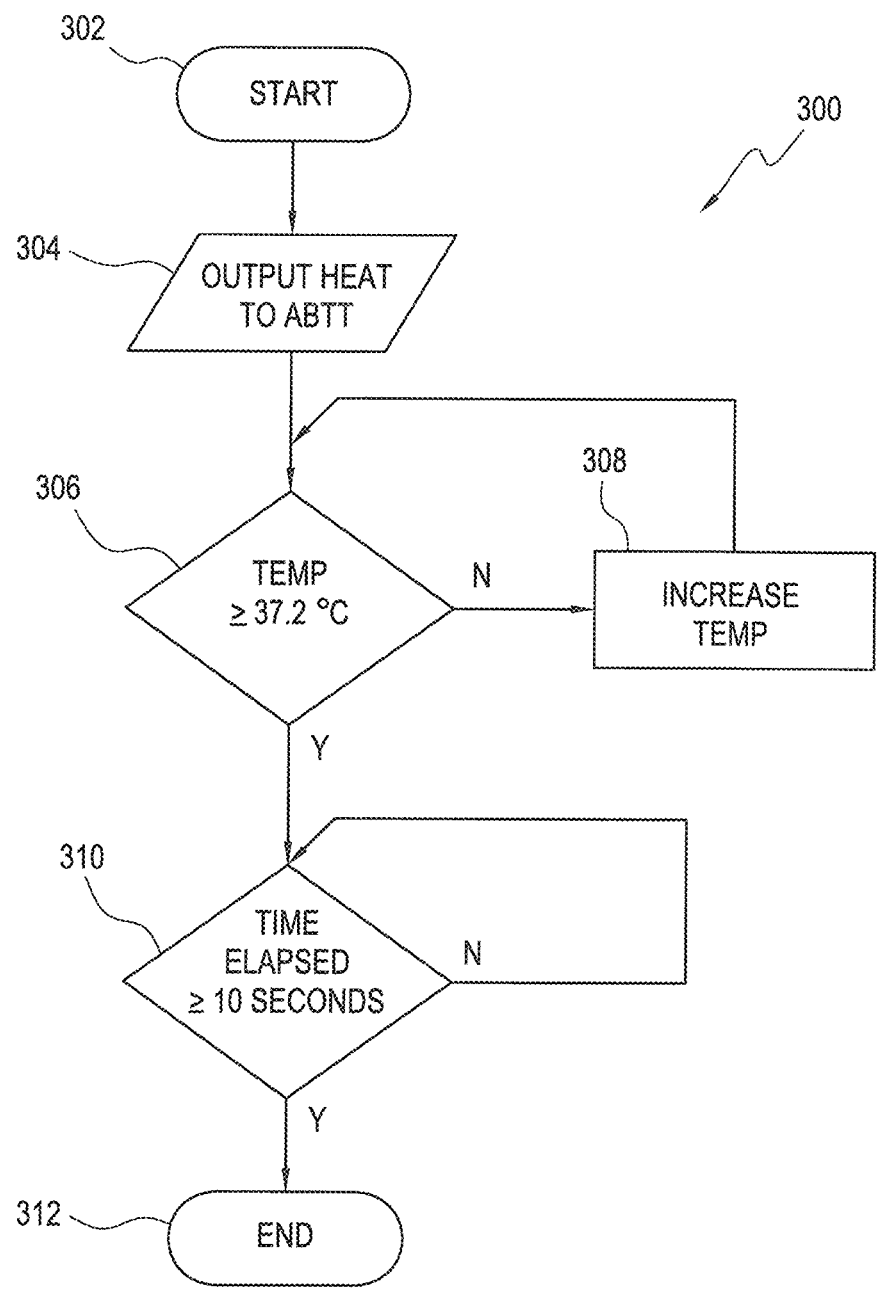
FIG. 10 shows a second treatment process for thyroid and other disorders in accordance with an exemplary embodiment of the present disclosure.

FIG. 10 shows a second treatment process for thyroid and other disorders in accordance with an exemplary embodiment of the present disclosure, indicated generally at 300. This embodiment for acting on the hypothalamus or for decreasing production of thyroid hormones includes a device that further includes a thermal input device, apparatus, or mechanism, such as thermally retentive materials, thermoelectric devices, Peltier devices, infrared non-contact devices, and the like, which provide a certain amount of heat to ABTT terminus 10, the amount of heat being added preferably being added by a device having a temperature value greater than or equal to 37.2 degrees Celsius, preferably for a period greater than or equal to 10 seconds, the device having a controller that activates the temperature modification device to achieve a temperature greater than or equal to 37.2 degrees Celsius.

Process 300 begins with a start process 302, which can include initializing a control device, temperature sensors, and other electronic elements of a system, loading a program and predetermined values for comparison from non-transitory memory, and the like. Once start process 302 is completed, control passes from start process 302 to a heat output decision process 304.

In heat output decision process 304, one or more temperature modification devices, such as temperature modification devices 64, are actuated or powered to provide heat to at least one ABTT interface surface 66. The initial temperature can be a predetermined value, such as 37.2 degrees Celsius. As heat is being generated, a temperature sensor, such as temperature sensor 62, can be simultaneously measuring the temperature of at least one ABTT terminus 10. Once heat output decision process 304 is complete, control passes from decision process 304 to a predetermined temperature process 306.

In predetermined temperature process 306, a determination is made as to whether the temperature of an associated ABTT terminus 10 has reached a predetermined temperature, which in the exemplary embodiment of FIG. 10 is 37.2 degrees Celsius. If the temperature of ABTT terminus 10 is not greater than or equal to the predetermined temperature, control passes from process 306 to an increase output temperature process 308. If the temperature of ABTT terminus 10 is greater than or equal to the predetermined temperature, control passes from process 306 to an elapsed time decision process 310.

In elapsed time decision process 310, a determination of whether a predetermined time has passed is made. If the predetermined time has passed, which is 10 seconds in the embodiment of FIG. 10, then control passes from elapsed time decision process 310 to an end process 312, where notification can be provided to a user or operator that process 300 is complete. Such notification can be via, for example, a display, vibration, or audible sound. If the predetermined time has yet to pass, control remains with elapsed time decision process 310 via a loop back to elapsed time decision process 310 until the elapsed time is greater than or equal to the predetermined time interval.

Figure 11:
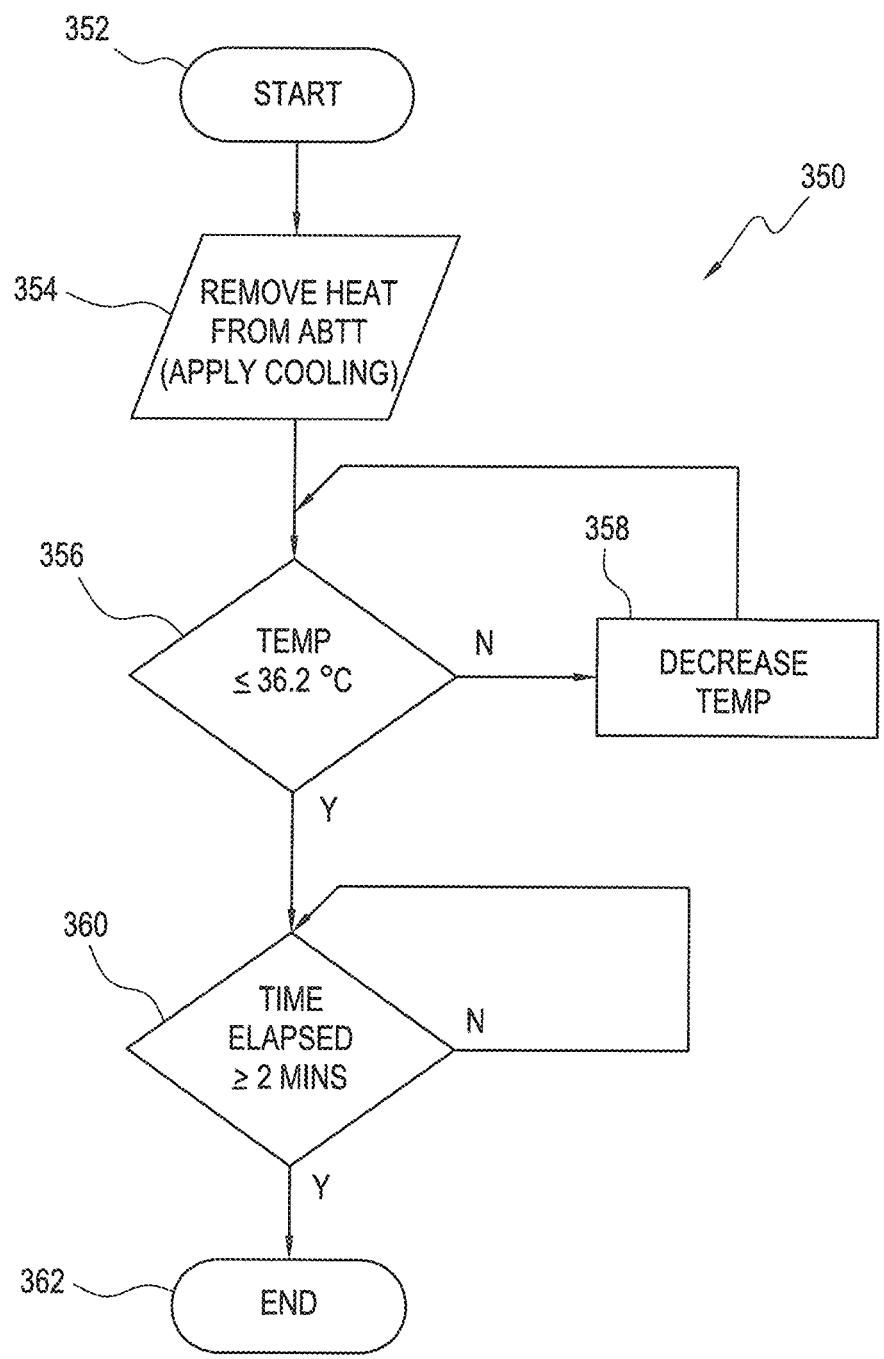
FIG. 11 shows a third treatment process for thyroid and other disorders in accordance with an exemplary embodiment of the present disclosure.

FIG. 11 shows a third treatment process for thyroid and other disorders in accordance with an exemplary embodiment of the present disclosure, indicated generally at 350. This embodiment for increasing production of thyroid hormones includes a device that further includes a device that is able to remove heat from ABTT terminus 10, such as thermally retentive materials that are cooled, thermoelectric or Peltier devices, and the like that remove a certain amount of heat from ABTT terminus 10, the heat being removed preferably by a device having temperature value greater than or equal to 36.2 degrees Celsius, preferably for a period greater than or equal to 2 minutes.

Process 350 begins with a start process 352, which can include initializing a control device, temperature sensors, and other electronic elements of a system, loading a program and predetermined values for comparison from non-transitory memory, and the like. Once start process 352 is completed, control passes from start process 352 to a heat removal process 354.

In heat removal process 354, one or more temperature modification devices, such as temperature modification devices 64, are actuated or powered to remove heat from at least one ABTT interface surface 66. The initial temperature of ABTT interface surface 66 can be a predetermined value, such as 36.2 degrees Celsius. As heat is being removed, a temperature sensor, such as temperature sensor 62, can be simultaneously measuring the temperature of at least one ABTT terminus 10. Once heat removal process 354 is complete, control passes from process 354 to a predetermined temperature decision process 356.

In predetermined temperature decision process 356, a determination is made as to whether the temperature of an associated ABTT terminus 10 has reached a predetermined temperature, which in the exemplary embodiment of FIG. 11 is 36.2 degrees Celsius. If the temperature of ABTT terminus 10 is not less than or equal to the predetermined temperature, control passes from decision process 356 to a decrease output temperature process 358. If the temperature of ABTT terminus 10 is less than or equal to the predetermined temperature, control passes from decision process 356 to an elapsed time decision process 360.

In elapsed time decision process 360, a determination of whether a predetermined time has passed is made. If the predetermined time has passed, which is 2 minutes in the embodiment of FIG. 11, then control passes from elapsed time decision process 360 to an end process 362, where notification can be provided to a user or operator that process 350 is complete. Such notification can be via, for example, a display, vibration, or audible sound. If the predetermined time has yet to pass, control remains with elapsed time decision process 360 via a loop back to elapsed time decision process 360 until the elapsed time is greater than or equal to the predetermined time interval.

Figure 12:
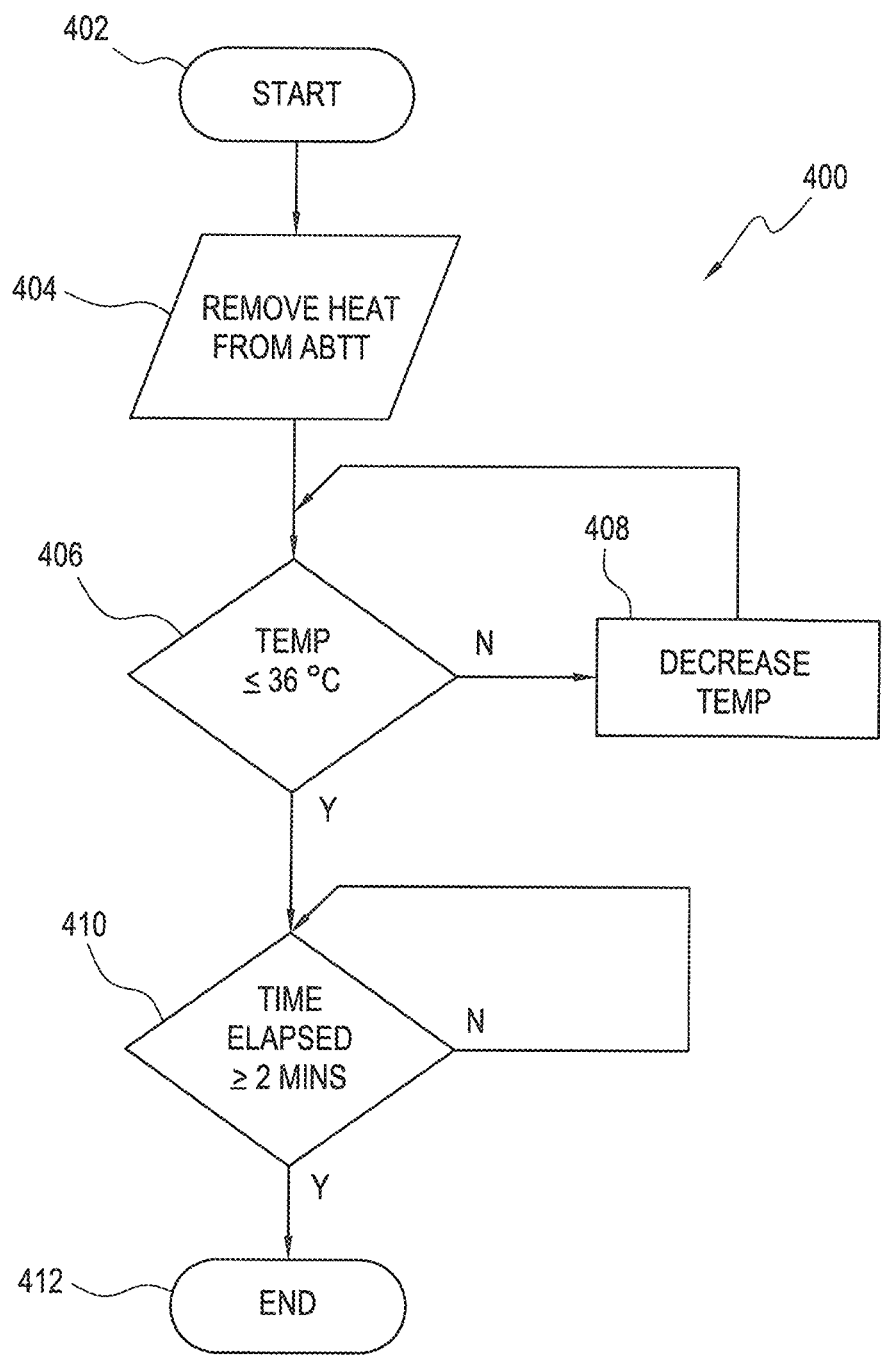
FIG. 12 shows a fourth treatment process for thyroid and other disorders in accordance with an exemplary embodiment of the present disclosure.

FIG. 12 shows a fourth treatment process for thyroid and other disorders in accordance with an exemplary embodiment of the present disclosure, indicated generally at 400. This embodiment for increasing production of thyroid hormones includes a device that further includes a device that is able to remove heat from ABTT terminus 10, such as thermally retentive materials that are cooled, thermoelectric or Peltier devices, and the like that remove a certain amount of heat from ABTT terminus 10, the heat being removed preferably by a device having temperature value less than or equal to 36.0 degrees Celsius, preferably for a period greater than or equal to 2 minutes.

Process 400 begins with a start process 402, which can include initializing a control device, temperature sensors, and other electronic elements of a system, loading a program and predetermined values for comparison from non-transitory memory, and the like. Once start process 402 is completed, control passes from start process 402 to a heat removal process 404.

In heat removal process 404, one or more temperature modification devices, such as temperature modification devices 64, are actuated or powered to remove heat from at least one ABTT interface surface 66. The initial temperature of ABTT interface surface 66 can be a predetermined value, such as 36.0 degrees Celsius. As heat is being removed, a temperature sensor, such as temperature sensor 62, can be simultaneously measuring the temperature of at least one ABTT terminus 10. Once heat removal process 404 is complete, control passes from process 404 to a predetermined temperature decision process 406.

In predetermined temperature decision process 406, a determination is made as to whether the temperature of an associated ABTT terminus 10 has reached a predetermined temperature, which in the exemplary embodiment of FIG. 12 is 36.0 degrees Celsius. If the temperature of ABTT terminus 10 is not less than or equal to the predetermined temperature, control passes from decision process 406 to a decrease output temperature process 408. If the temperature of ABTT terminus 10 is less than or equal to the predetermined temperature, control passes from decision process 406 to an elapsed time decision process 410.

In elapsed time decision process 410, a determination of whether a predetermined time has passed is made. If the predetermined time has passed, which is 2 minutes in the embodiment of FIG. 12, then control passes from elapsed time decision process 410 to an end process 412, where notification can be provided to a user or operator that process 400 is complete. Such notification can be via, for example, a display, vibration, or audible sound. If the predetermined time has yet to pass, control remains with elapsed time decision process 410 via a loop back to elapsed time decision process 410 until the elapsed time is greater than or equal to the predetermined time interval.

Figure 13:
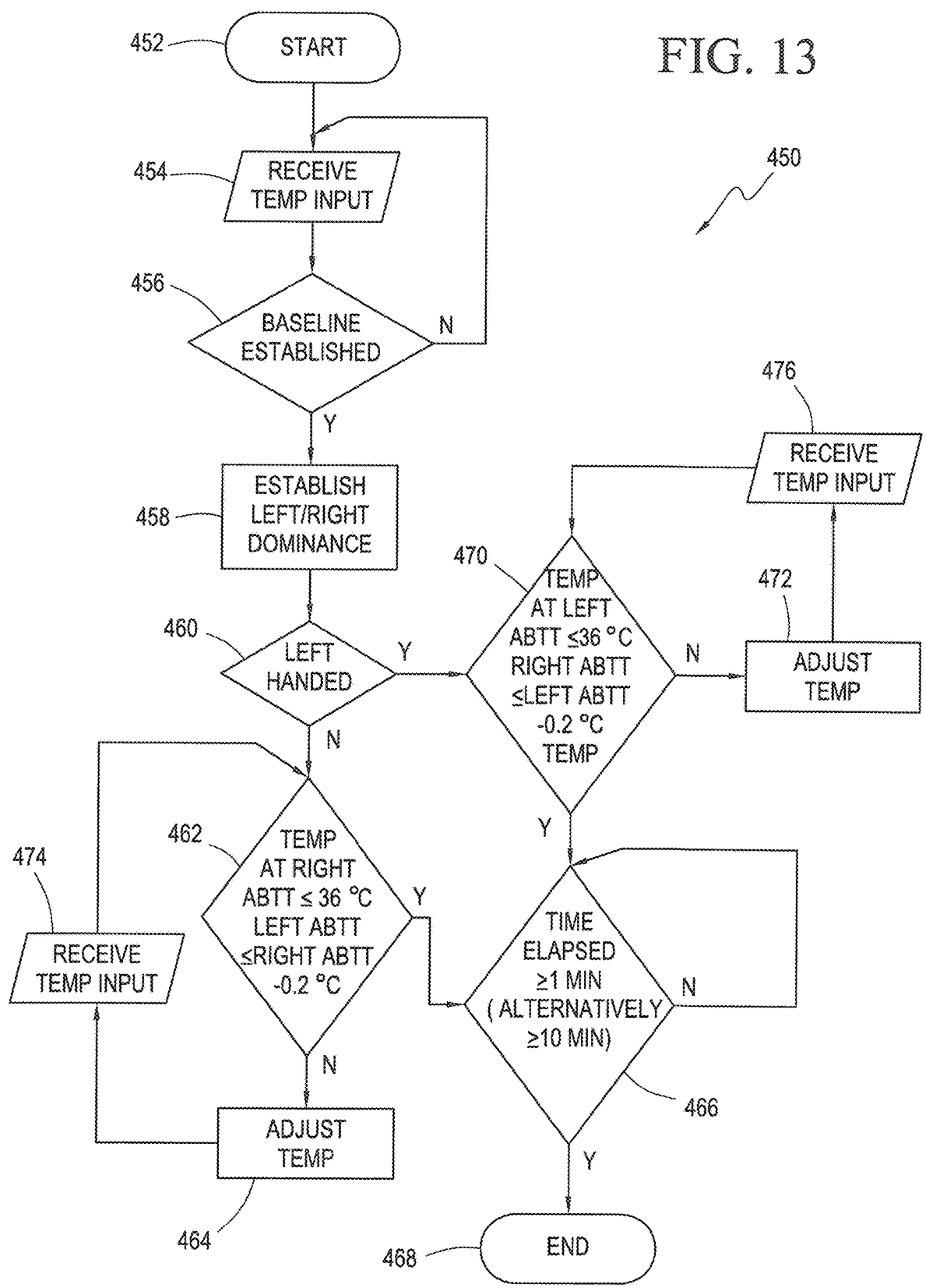
FIG. 13 shows a fifth treatment process for thyroid and other disorders in accordance with an exemplary embodiment of the present disclosure.

FIG. 13 shows a fifth treatment process for thyroid and other disorders in accordance with an exemplary embodiment of the present disclosure, indicated generally at 450. This embodiment for increasing production of thyroid hormones includes a device that further includes a device for the removal of heat from ABTT terminus 10, such as thermally retentive materials that can be cooled, thermoelectric or Peltier devices, and the like that are able remove heat from ABTT terminus 10, the heat being preferably removed by a device having temperature value less than or equal to 0.2 degrees Celsius as compared to a baseline temperature, preferably for a period greater than or equal to 1 minute, the device having a controller that identifies the baseline value and activates the heat removal device or apparatus to achieve a temperature less than or equal to 0.2 degrees Celsius as compared to the baseline temperature. In alternative embodiments, the period can be longer, such as greater than or equal to 3 minutes, or greater than or equal to 10 minutes, as described herein.

Process 450 begins with a start process 452, which can include initializing a control device, temperature sensors, and other electronic elements of a system, loading a program and predetermined values for comparison from non-transitory memory, and the like. Once start process 452 is completed, control passes from start process 452 to a receive temperature input process 454.

In temperature input process 454, temperature signals from one or more temperature sensors, such as temperature sensors 62, is received. As described herein, such signals, which represent the temperature of ABTT terminus 10, can be from one ABTT terminus 10 or from two ABTT terminuses 10. Once temperature signals have been received, control passes from temperature input process 454 to an establish baseline decision process 456.

In establish baseline decision process 456, a processor, such as processor 68, determines whether sufficient temperature information has been received to establish a baseline temperature. If sufficient information has yet to be received, control passes from establish baseline decision process 456 to receiving temperature input process 454. If sufficient temperature information has been received to establish a baseline temperature, which should be considered an average temperature over an interval, such as at least two minutes, control passes from establish baseline decision process 456 to an establish left/right dominance process 458.

Applicant recognized and tested that right or left dominance influences the temperature of ABTT terminus 10. For a right-handed person, left ABTT terminus 10 has a higher temperature than right ABTT terminus 10. For a left-handed person, right ABTT terminus 10 has a higher temperature than left ABTT terminus 10. The systems of the present disclosure can be configured to include an input apparatus to enter information regarding the dominant side, the system processor can analyze received temperature information to determine the dominant side, or other testing techniques, such as determining the dominant side in writing, can be used to determine dominance. Thus, process 450 can be implemented on a system that is configured to include electronic pad or the like to enable a written input to determine dominance. Such dominance is established in process 458, by analysis, testing, or input. Once dominance is established, control passes from establish left/right dominance process 458 to a left-handed decision process 460.

In left handed decision process 460, if the subject or patient is not left handed, control passes to a temperature decision process 462. If the subject or patient is left handed, control passes to a temperature decision process 470.

In temperature decision process 462, process 450 determines whether the temperature at right ABTT terminus 10 is less than or equal to 36.0 degrees Celsius, and whether the temperature of left ABTT terminus 10 is less than or equal to the temperature of right ABTT terminus 10 minus 0.2 degrees Celsius. If the conditions of decision process 462 are not met, control passes to an adjust temperature process 464, where the temperature of temperature modification devices, such as devices 64, is decreased. Control then passes to a receive temperature input process 474.

In receive temperature input process 474, temperature signals are received from, for example, one or more temperature sensors 62. Once, the temperature signals are received, control passes to temperature decision process 462, which functions as previously described herein.

Once the conditions of temperature decision process 462 are met, control passes from process 462 to a time elapsed process 466. In time elapsed process 466, a determination of whether a predetermined interval has passed is determined. In an exemplary embodiment, the predetermined interval is at least 1 minute. In another exemplary embodiment, the predetermined interval is at least 10 minutes. If the predetermined interval has passed, control passes from time elapsed process 466 to an end process 468, where notification can be provided to a user or operator that process 450 is complete. Such notification can be via, for example, a display, vibration, or audible sound. If the predetermined time has yet to pass, control remains with elapsed time decision process 466 via a loop back to elapsed time decision process 466 until the elapsed time is greater than or equal to the predetermined time interval.

Returning to temperature decision process 470, process 450 determines whether the temperature at left ABTT terminus 10 is less than or equal to 36.0 degrees Celsius, and whether the temperature of right ABTT terminus 10 is less than or equal to the temperature of left ABTT terminus 10 minus 0.2 degrees Celsius. If the conditions of decision process 470 are not met, control passes to an adjust temperature process 472, where the temperature of temperature modification devices, such as devices 64, is decreased. Control then passes to a receive temperature input process 476.

In receive temperature input process 476, temperature signals are received from, for example, one or more temperature sensors 62. Once, the temperature signals are received, control passes to temperature decision process 470. Once the conditions of temperature decision process 470 are met, control passes from process 470 to elapsed time decision process 466, which functions as described hereinabove.

Figure 14:
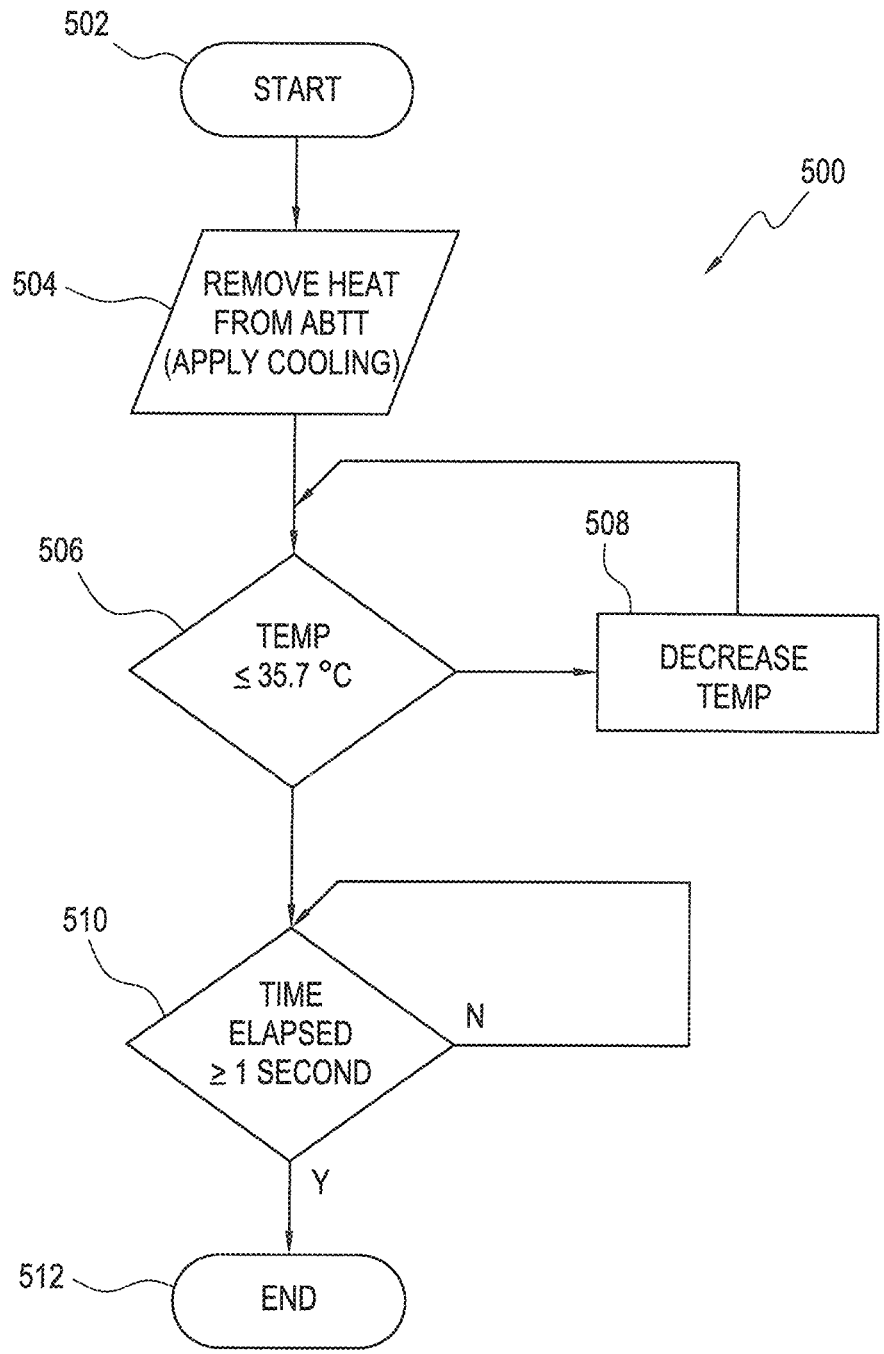
FIG. 14 shows a sixth treatment process for thyroid and other disorders in accordance with an exemplary embodiment of the present disclosure.

FIG. 14 shows a sixth treatment process for thyroid and other disorders in accordance with an exemplary embodiment of the present disclosure, indicated generally at 500. This embodiment for acting on the hypothalamus or increasing production of thyroid hormones includes a device that further includes a device that is able to remove heat from ABTT terminus 10, such as thermally retentive materials that are cooled, thermoelectric or Peltier devices, and the like that remove a certain amount of heat from ABTT terminus 10, the heat being removed preferably by a device having a temperature value less than or equal to 35.7 degrees Celsius, preferably for a period great than or equal to 1 second, the device including a processor, such as processor 68, which identifies the baseline value and activates the thermal removal device or apparatus to achieve a temperature less than or equal to 35.7 degrees Celsius.

Process 500 begins with a start process 502, which can include initializing a control device, temperature sensors, and other electronic elements of a system, loading a program and predetermined values for comparison from non-transitory memory, and the like. Once start process 502 is completed, control passes from start process 502 to a heat removal process 504.

In heat removal process 504, one or more temperature modification devices, such as temperature modification devices 64, are actuated or powered to remove heat from at least one ABTT interface surface 66. The initial temperature of ABTT interface surface 66 can be a predetermined value, such as 30.0 degrees Celsius. As heat is being removed, a temperature sensor, such as temperature sensor 62, can be simultaneously measuring the temperature of at least one ABTT terminus 10. Once heat removal process 504 is complete, control passes from process 504 to a predetermined temperature decision process 506.

In predetermined temperature decision process 506, a determination is made as to whether the temperature of an associated ABTT terminus 10 has reached a predetermined temperature, which in the exemplary embodiment of FIG. 14 is less than or equal to 35.7 degrees Celsius. If the temperature of ABTT terminus 10 is not less than or equal to the predetermined temperature, control passes from decision process 506 to a decrease output temperature process 508. If the temperature of ABTT terminus 10 is less than or equal to the predetermined temperature, control passes from decision process 506 to an elapsed time decision process 510. In elapsed time decision process 510, a determination of whether a predetermined time has passed is made. If the predetermined time has passed, which is 1 second in the embodiment of FIG. 14, then control passes from elapsed time decision process 510 to an end process 512, where notification can be provided to a user or operator that process 500 is complete. Such notification can be via, for example, a display, vibration, or audible sound. If the predetermined time has yet to pass, control remains with elapsed time decision process 510 via a loop back to elapsed time decision process 510 until the elapsed time is greater than or equal to the predetermined time interval.

Figure 15:
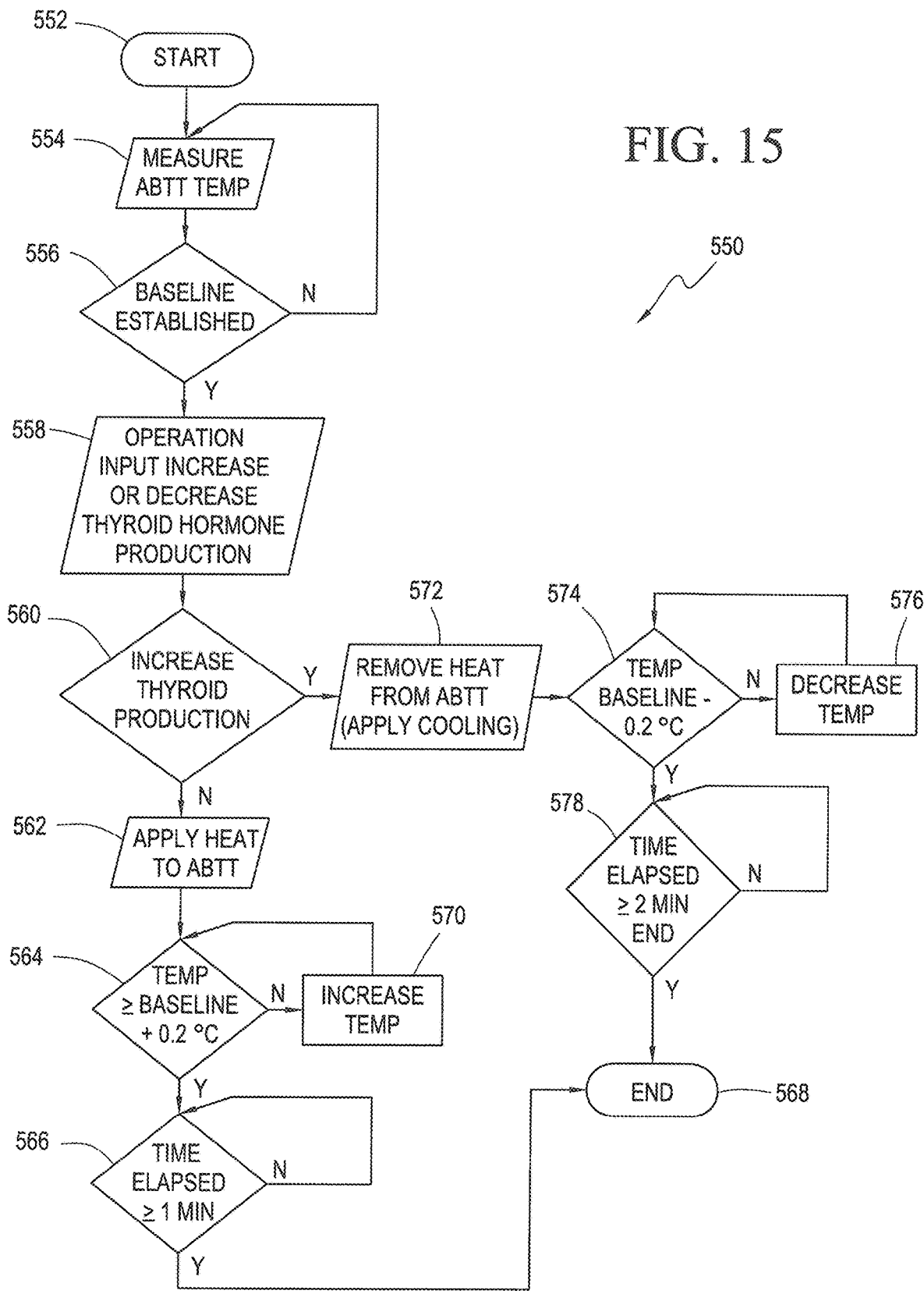
FIG. 15 shows a seventh treatment process for thyroid and other disorders in accordance with an exemplary embodiment of the present disclosure.

FIG. 15 shows a seventh treatment process for thyroid and other disorders in accordance with an exemplary embodiment of the present disclosure, indicated generally at 550, which is similar to the embodiment of FIG. 13 in some respects. This embodiment for increasing or decreasing production of thyroid hormones includes a device that can add or remove heat from ABTT terminus 10, such as a thermoelectric or Peltier device, that is able to add or remove heat from ABTT terminus 10, as described herein.

The embodiment of FIG. 15 is configured to prevent or treat Alzheimer's disease and to prevent or treat high fever, by increasing the temperature at ABTT terminus 10 by an amount that is higher than a baseline temperature by an amount that is greater than or equal to 0.2 degrees Celsius.

Further, the embodiment of FIG. 15 is configured to prevent or treat Parkinson's disease, to prevent or treat traumatic brain injury, and to prevent or treat sudden infant death syndrome (SIDS) by decreasing the temperature at ABTT terminus 10 by an amount that is lower than a baseline temperature by an amount that is greater than or equal to 0.2 degrees Celsius.

Process 550 begins with a start process 552, which can include initializing a control device, temperature sensors, and other electronic elements of a system, loading a program and predetermined values for comparison from non-transitory memory, and the like. Once start process 552 is completed, control passes from start process 552 to a receive temperature input process 554.

In temperature input process 554, temperature signals from one or more temperature sensors, such as temperature sensors 62, is received. As described herein, such signals can be from one ABTT terminus 10 or from two ABTT terminuses 10. Once temperature signals have been received, control passes from temperature input process 554 to an establish baseline decision process 556.

In establish baseline decision process 556, a processor, such as processor 68, determines whether sufficient temperature information has been received to establish a baseline temperature. If sufficient information has yet to be received, control passes from establish baseline decision process 556 to receiving temperature input process 554. If sufficient temperature information has been received to establish a baseline temperature, which should be considered an average temperature over an interval, such as at least two minutes, control passes from establish baseline decision process 556 to an operator input process 558.

In operator input process 558, an operator or other user inputs whether a system needs to increase or decrease hormone production. Once operator input process 558 is complete, control passes from operator input process 558 to an increase thyroid production decision process 560.

In increase thyroid product decision process 560, if hormone production is to be increased, control passes to remove heat process 572. If hormone production is to be decreased, control passes from decision process 560 to an apply heat process 562.

In apply heat process 562, the temperature of one or more temperature modification devices, such as devices 64, is increased to apply heat to one or more ABTT terminuses 10. Control then passes from apply heat process 562 to a temperature decision process 564.

In temperature decision process 564, it is determined whether the temperature of each ABTT terminus 10 is greater than or equal to the baseline temperature plus 0.2 degrees Celsius. If the temperature is less than this value, control passes to an increase temperature process 570. If the temperature is greater than or equal to this value, control passes from decision process 564 to a time elapsed decision process 566.

In time elapsed decision process 566, it is determined whether the elapsed time of heat application has reached greater than or equal to a predetermined period, such as 1 minute. If the predetermined elapsed time has been reached, control passes to an end process 568, where process 550 is terminated. If the elapsed time is less than the predetermined period, control loops back to time elapsed decision process 566 until the predetermined interval is reached.

Returning to increase temperature process 570, the temperature of the temperature modification device is increased by a predetermined amount, such as 0.1 degrees Celsius. Control then passes from increase temperature process 570 to temperature decision process 564, which functions as previously described hereinabove.

Returning now to remove heat process 572, the temperature modification device is actuated to remove heat from ABTT terminus 10 to increase hormone production. The initial temperature of the temperature modification device can be the baseline temperature, or the baseline temperature minus 0.2 degrees Celsius, or another value. Once remove heat process 572 is complete, control passes to a temperature decision process 574.

In temperature decision process 574, it is determined whether the temperature of each ABTT terminus 10 is less than or equal to the baseline temperature minus 0.2 degrees Celsius. If the temperature is greater than this value, control passes to a decrease temperature process 576. If the temperature is less than or equal to this value, control passes from decision process 574 to a time elapsed decision process 578.

In time elapsed decision process 578, it is determined whether the elapsed time of heat removal has reached greater than or equal to a predetermined period, such as 2 minutes. If the predetermined elapsed time has been reached, control passes to end process 568, described hereinabove. If the elapsed time is less than the predetermined period, control loops back to time elapsed decision process 578 until the predetermined interval is reached.

Returning to decrease temperature process 576, the temperature of the temperature modification device is decreased by a predetermined amount, such as 0.1 degrees Celsius. Control then passes from decrease temperature process 576 to temperature decision process 574, which functions as previously described hereinabove.

FIGS. 16A-G show a diagnostic process in accordance with an exemplary embodiment of the present disclosure, indicated generally at 600. Process 600 is configured to detect a plurality of conditions, as will be seen from the following description. It should be understood from the description provided herein that the disclosure envisions detecting and identifying conditions by various combinations of measurements and periods using the devices, apparatuses, and systems disclosed herein. Accordingly, is should be understood that FIGS. 16A-G are representative of a portion of the combinations disclosed elsewhere herein. Process 600 begins with a start process 602, which can include initializing a control device, temperature sensors, and other electronic elements of a system, loading a program and predetermined values for comparison from non-transitory memory, and the like. Once start process 602 is completed, control passes from start process 602 to a receive temperature input process 604.

In receive temperature input process 604, temperature signals are received from a temperature sensor such as sensor 62. Once temperature data has been received, control passes from receive temperature input process 604 to a receive ambient temperature process 606.

In ambient temperature process 606, temperature regarding the ambient temperature of a patient or subject is received from a conventional temperature sensor (not shown). Once the ambient temperature is received, control is passed to a receive time information process 608.

In time information process 608, current time data is received. Such data may come from an external source, processor 68, or from another source. Once time information has been received, control passes from time information process 608 to a baseline established decision process 610.

In baseline established decision process 610, process 600 determines whether sufficient temperature information has been acquired to establish a baseline temperature for ABTT terminuses 10. If sufficient information is available, control passes from baseline established decision process 610 to an establish left/right dominance process 612. If insufficient information is available, control passes from process 610 to receive temperature sensor input process 604, which functions as described hereinabove.

In establish left/right dominance process 612, process 600 uses the temperature information previously acquired to determine which ABTT terminus 10 is the dominant ABTT terminus 10. Such information can also be acquired via user or operator input or by testing, described hereinabove. Once left/right dominance is determined, control passes from establish left/right dominance process 612 to a predetermined temperature increase decision process 624.

In temperature increase decision process 624, it is determined whether the temperature of either ABTT terminus has increased by an amount greater than or equal to 0.2 degrees Celsius. If the temperature has increased by this predetermined amount, control passes from temperature increase decision process 624 to an elapsed time decision process 626. If the temperature of only one ABTT terminus 10 has not increased by greater than or equal to 0.2 degrees Celsius, control passes from temperature increase process 624 to a temperature decrease decision process 632.

In elapsed time decision process 626, process 600 determines whether the total elapsed time of temperature measurements has occurred in an interval greater than or equal to 120 hours. If the increase has occurred in a shorter interval, control passes to connector 628, which connects to another portion of process 600 described further hereinbelow. If the increase has occurred at greater than or equal to 120 hours, control passes to connector 630, which connects to another portion of process 600 described further hereinbelow. It should be noted that a consistent gradual increase in temperature that occurs in a period that is greater than 120 hours is indicative of cancer.

Returning to temperature decrease decision process 632, if the temperature of one ABTT terminus 10 has decreased by an amount greater than or equal to 0.2 degrees Celsius, control passes to ambient temperature decision process 634. Otherwise, control passes to connector 648.

Returning to ambient temperature decision process 634, it is determined whether an ambient temperature change has occurred that would account for the decrease in ABTT terminus 10. If ambient temperature appears to account for the decrease, control passes to connector 648. Otherwise, control passes to an elapsed time decision process 636.

In elapsed time decision process 636, it is determined whether the elapsed time of the temperature decrease is in an interval of less than 12 hours. If the interval is less than 12 hours, control passes to connector 638, described further hereinbelow. Otherwise, control passes to temperature decrease on one side decision process 640.

In temperature decrease on one side decision process 640, it is determined whether the temperature decrease of one ABTT 10 is greater than or equal to 0.6 degrees Celsius. If this condition is met, control passes from one side decision process 640 to an elapsed time decision process 644. Otherwise, control passes from one side decision process 640 to connector 642, described further hereinbelow.

In elapsed time decision process 644, it is determined whether the elapsed time is less than or equal to 120 hours. If this condition is met, control is passed to connector 638, described further hereinbelow. Otherwise, control passes to connector 642.

Figure 16A:
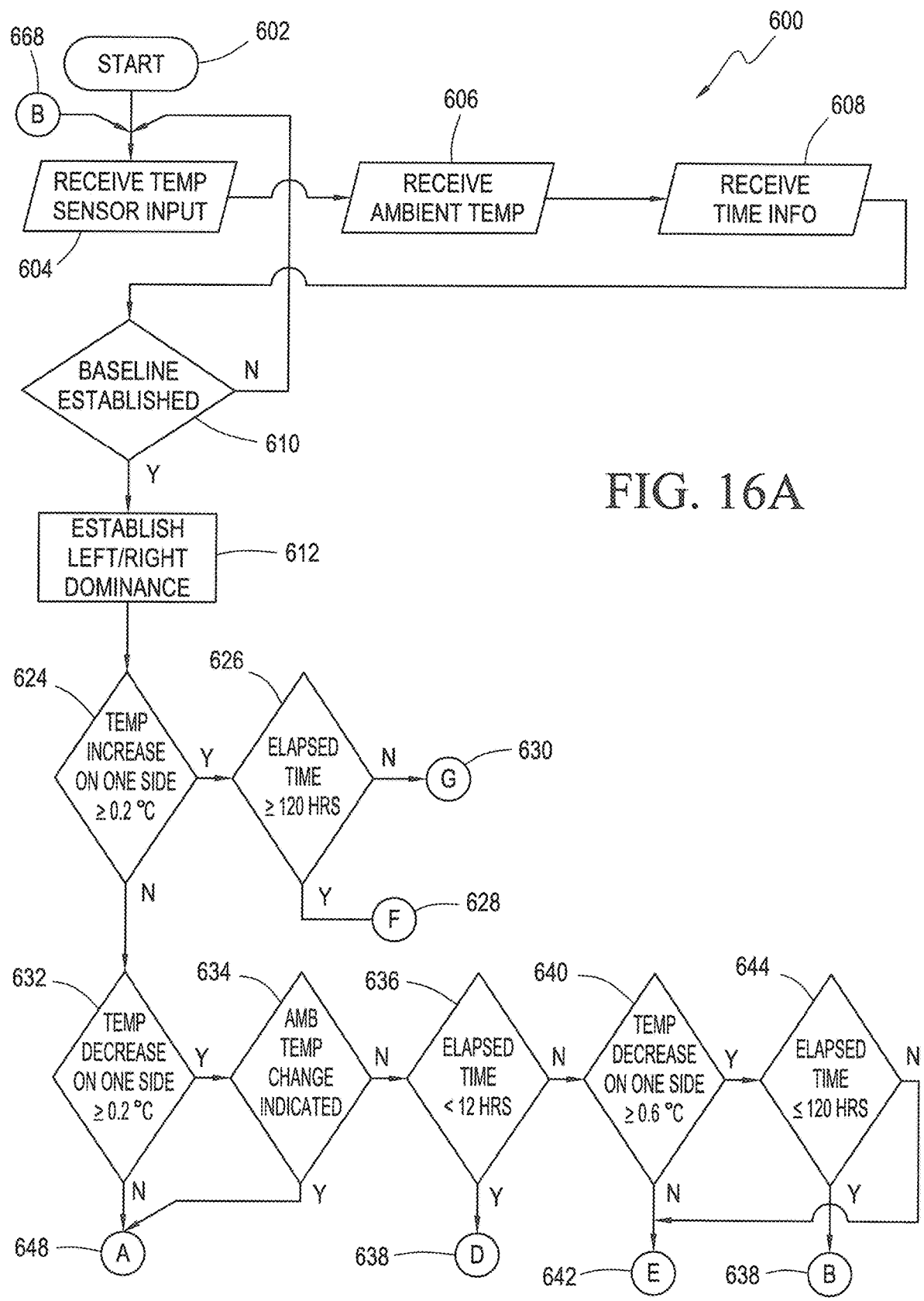
FIGS. 16A-G show a diagnostic process in accordance with an exemplary embodiment of the present disclosure.
Figure 16B:
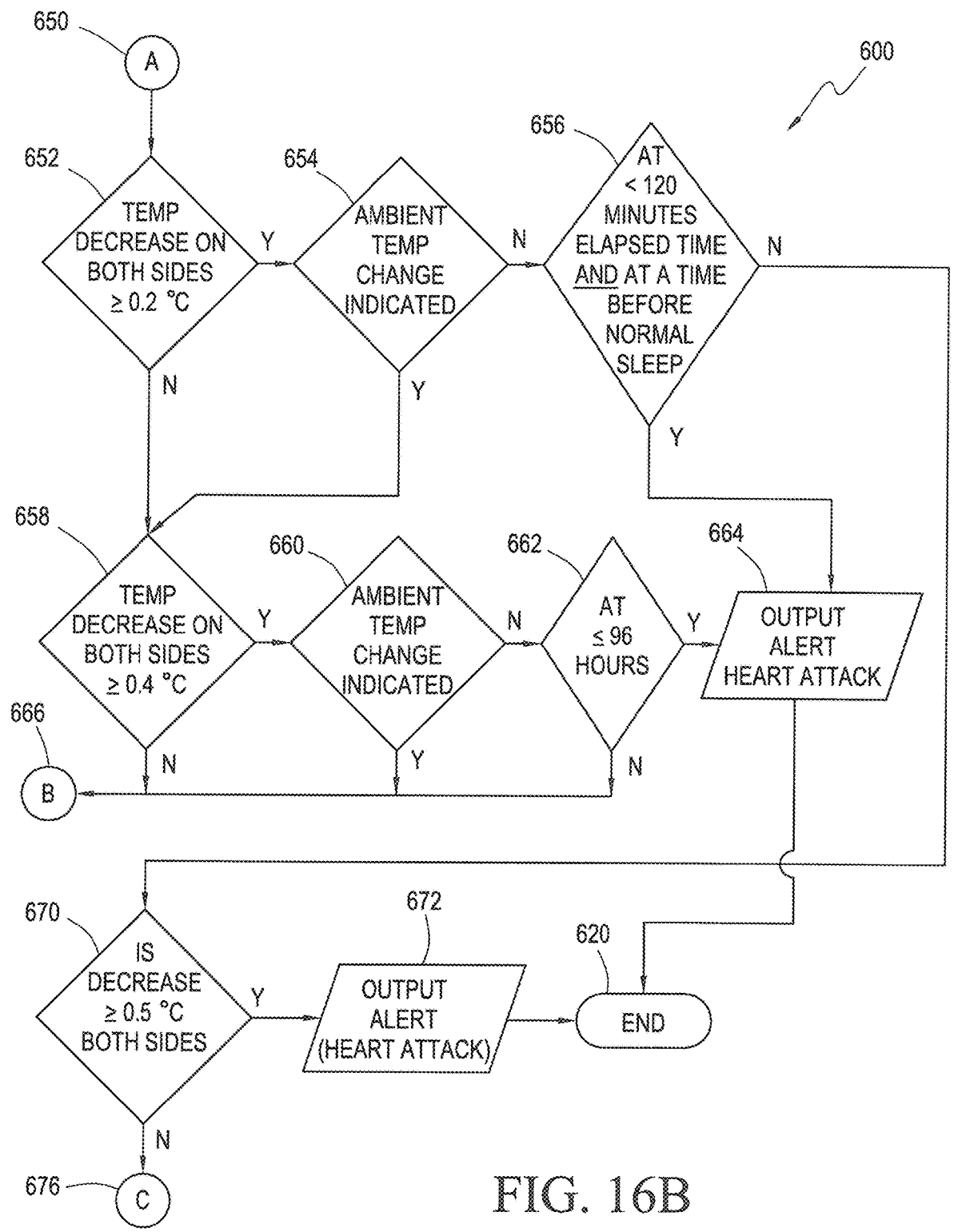
Figure 16C:
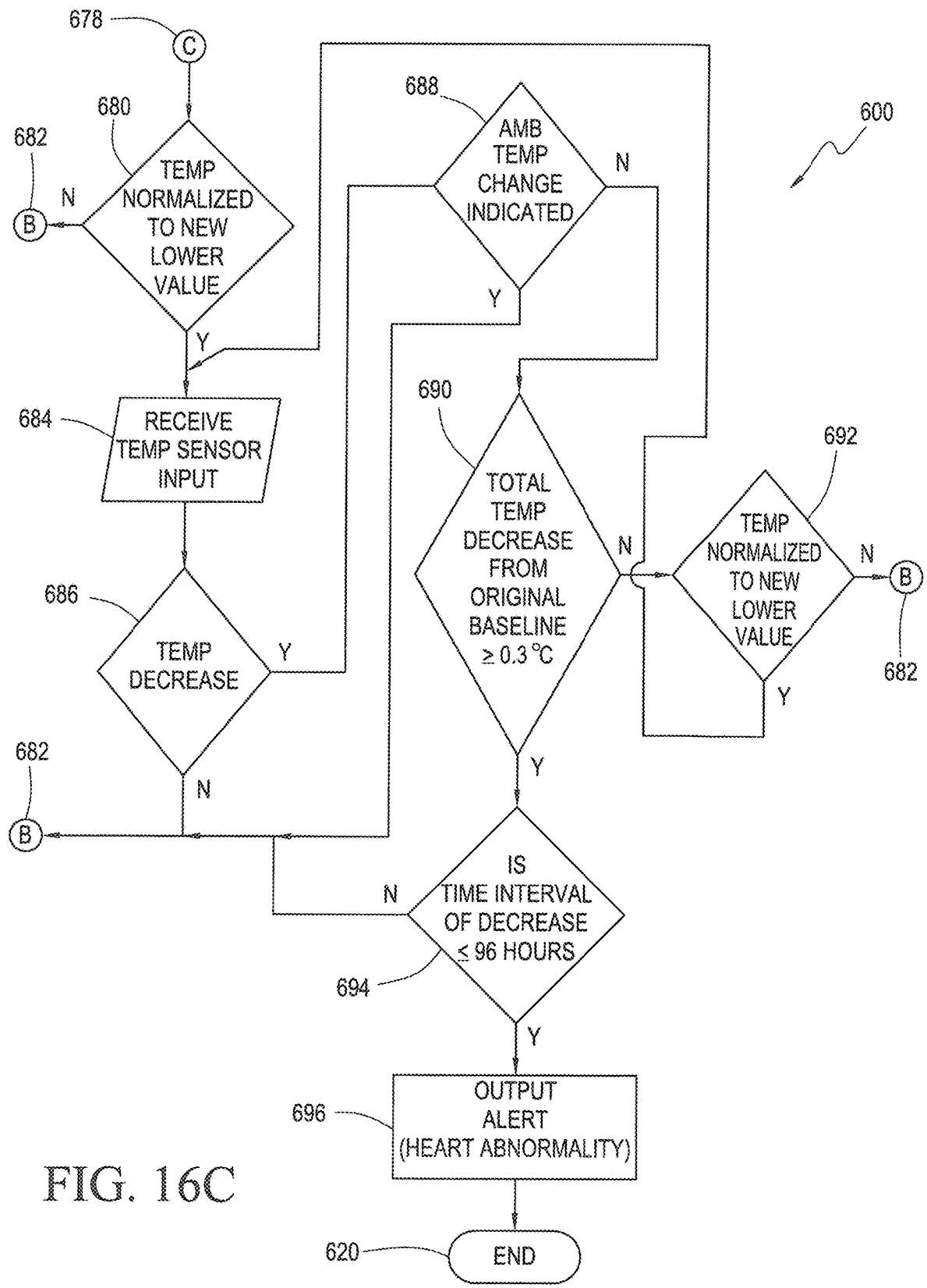

Returning to connector 648, connector 648 connects to a connector 650 in FIG. 16B, which further connects to a temperature decrease on both sides decision process 652. In decision process 652, it is determined whether a temperature increase in both ABTT terminuses 10 is greater than or equal to a predetermined temperature value of 0.2 degrees Celsius. If this condition is met, control passes from decision process 652 to an ambient temperature decision process 654. Otherwise, control passes to another temperature decrease on both sides decision process 658.

In ambient temperature decision process 654, it is determined whether the ambient temperature has affected the temperature of ABTT terminuses 10. If the ambient temperature has affected the temperature of ABTT terminuses 10, control passes from ambient temperature decision process 654 to temperature decrease on both sides decision process 658. Otherwise, control passes to a decision process 656.

In decision process 656, it is determined whether the elapsed time in which the temperature decrease was measured is less than 120 minutes, and whether the temperature measurement occurred in a time period before normal sleep time. If the elapsed time is greater than or equal to 120 minutes or the temperature decrease occurred outside normal sleep hours, control passes from decision process 656 to a temperature decrease decision process 670. If the elapsed time is less than 120 minutes and the temperature decrease occurred outside normal sleep hours, control passes from elapsed time decision process 656 to an output alert process 664.

In output alert process 664, an alert is output, such as via display 74, audibly, or by vibration, warning that a heart attack is imminent or presently occurring. Control then passes from output alert process 664 to end process 620, previously described herein.

Returning to temperature decrease on both sides decision process 658, it is determined whether the temperature of both ABTT terminuses 10 decreased by an amount greater than or equal to 0.4 degrees Celsius. If the decrease on both sides is less than 0.4 degrees Celsius, control passes to connector 666 to connector 668 in FIG. 16A, returning to receive temperature sensor input process 604, which operates as described hereinabove. If the decrease on both side is greater than or equal to 0.4 degrees Celsius, control passes to an ambient temperature decision process 660.

In ambient temperature decision process 660, it is determined whether the ambient temperature has affected the temperature of ABTT terminuses 10. If the ambient temperature has affected the temperature of ABTT terminuses 10, control passes from ambient temperature decision process 660 to connector 666. Otherwise, control passes to an elapsed time decision process 662.

In elapsed time decision process 662, it is determined whether the elapsed time in which the temperature decrease was measured is less than or equal to 96 hours. If the decrease occurred in an interval greater than 96 hours, control passes from elapsed time decision process 662 to connector 666, described hereinabove. If the decrease occurred in an interval that is less than or equal to 96 hours, control passes from elapsed time decision process 662 to output alert process 664, which functions as described hereinabove.

Returning to temperature decrease decision process 670, it is determined whether the temperature decrease of both ABTT terminuses 10 is greater than or equal to 0.4 degrees Celsius on both sides. If the decrease is greater than or equal to 0.4 degrees Celsius, control passes from temperature decrease decision process 670 to an output alert process 672. Otherwise, control passes from temperature decrease decision process 670 to connector 676, which connects to connector 678 in FIG. 16C.

In output alert process 672, an alert is output via display 74, audibly, or by vibration to provide an indication that a heart attack is imminent or is currently in progress. A medical practitioner can use such an indication to warrant further testing and analysis. Control then passes from output alert process 672 to end process 620.

Returning to connector 678, connector 678 connects to a normalized temperature decision process 680, where it is determined whether the temperature of ABTT terminuses 10 has normalized, or established a new, lower baseline level. If a new, lower baseline has not been established, control passes to connector 682, which connects to connector 668 in FIG. 16A, and then receive temperature sensor input process 604, described hereinabove. If a new, lower baseline temperature has been established, control passes to a receive temperature sensor input process 684.

In receive temperature sensor input process 684, temperature signals are received from a temperature sensor, such as temperature sensor 62. Control then passes to a temperature decrease decision process 686.

In temperature decrease decision process 686, it is determined whether the temperature of one or more ABTT terminuses 10 has decreased further. If a decrease has occurred, control passes to an ambient temperature decision process 688. If a decrease has not occurred, control passes to connector 682, described hereinabove.

In ambient temperature decision process 688, it is determined whether the ambient temperature has affected the temperature of ABTT terminuses 10. If the ambient temperature has affected the temperature of ABTT terminuses 10, control passes from ambient temperature decision process 660 to connector 682. Otherwise, control passes to a total temperature decrease decision process 690.

In total temperature decrease decision process 690, it is determined whether the total temperature decrease from the original baseline is greater than or equal to 0.3 degrees Celsius. If the total decrease is less than 0.3 degrees Celsius, control passes from total temperature decrease decision process 690 to elapsed time decision process 694. If the total decrease is greater than or equal to 0.3 degrees Celsius, control passes from total temperature decrease decision process 690 to a normalized temperature decision process 692.

In normalized temperature decision process 692, it is determined whether the temperature of ABTT terminuses 10 has normalized to a new, lower baseline value. If the temperature of ABTT terminuses 10 has normalized to a new, lower baseline value, control passes from normalized temperature decision process 692 to receive temperature sensor input process 684, which functions as described hereinabove. Otherwise, control passes from normalized temperature decision process 692 to connector 682, which functions as described hereinabove.

Returning to elapsed time decision process 694, it is determined whether the elapsed time of temperature decreases has occurred in an interval that is less than or equal to 96 hours. If the interval is greater than the predetermined interval of 96 hours, control passes from elapsed time decision process 694 to connector 682, which functions as described hereinabove. If the elapsed interval is less than or equal to 96 hours, control passes from elapsed time decision process 694 to an output alert process 696.

In output alert process 696, an alert is output via display 74, audibly, or by vibration to indicate an indication that a heart abnormality is imminent or is currently in progress. A medical practitioner can use such an indication to warrant further testing and analysis. Control then passes from output alert process 696 to end process 620.

Figure 16D:
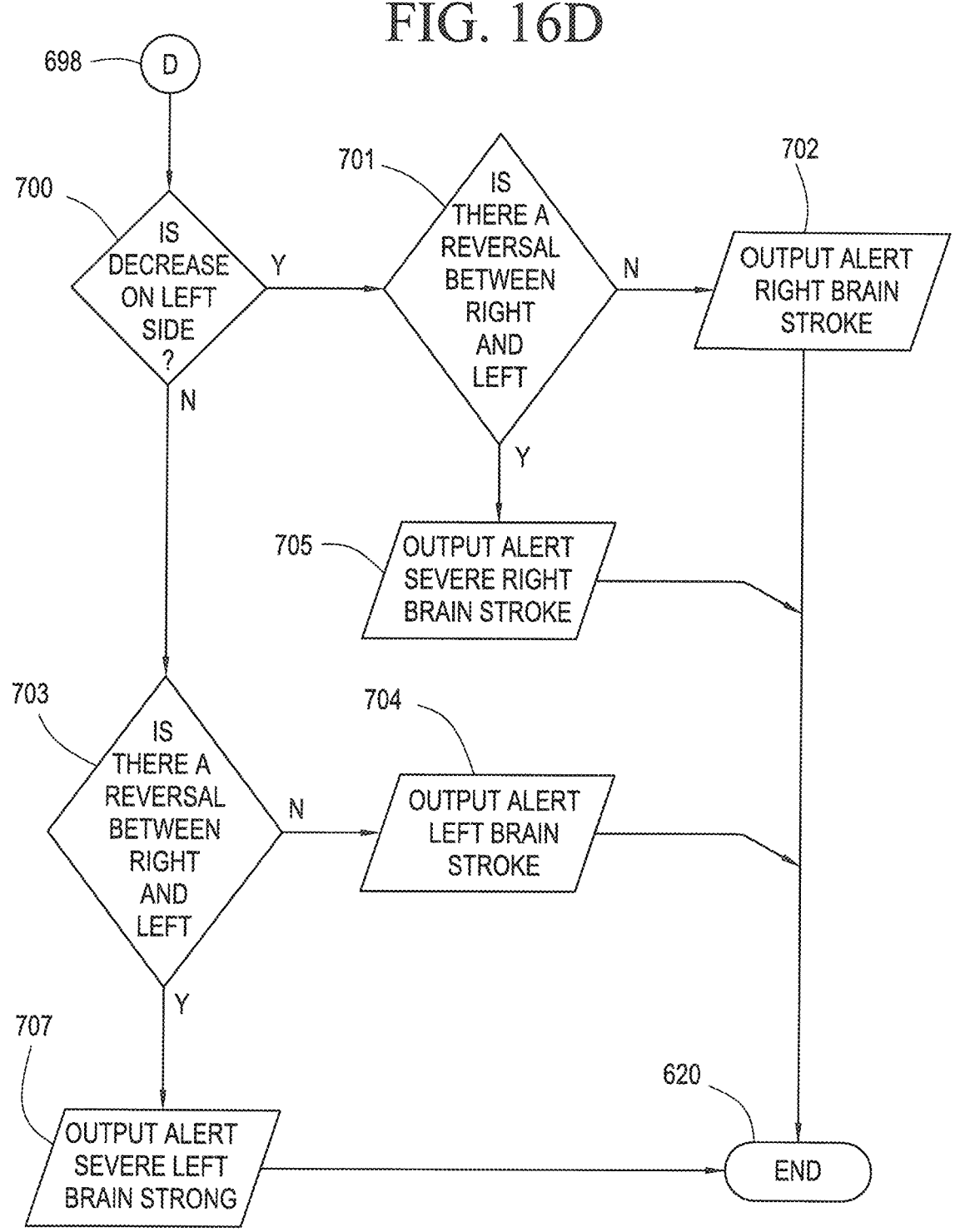

Returning to connector 638 in FIG. 16A, connector 638 is connected to a connector 698 in FIG. 16D, which then connects to a left side decrease decision process 700. In left side decrease decision process 700, a determination of whether the temperature decrease is at the left ABTT terminus 10 is made. If the decrease is at the left ABTT terminus, control passes from left side decrease decision process 700 to a reversal decision process 701. Otherwise, control passes from left side decrease decision process 700 to a reversal decision process 703.

In reversal decision process 701, a determination of whether there is a temperature reversal between left ABTT terminus 10 and right ABTT terminus 10 is made. If there is a temperature reversal, control passes from reversal decision process 701 to an output alert process 705. Otherwise, control passes from reversal decision process 701 to an output alert process 702.

In output alert process 702, an alert is sent to, for example, a display 74 or other output device, which can be audible or vibratory. The output alert indicates a right brain stroke, which can be imminent, i.e., predictive, or in progress. Control then passes from output alert process 702 to end process 620.

In output alert process 705, an alert is sent to, for example, a display 74 or other output device, which can be audible or vibratory. The output alert indicates a severe right brain stroke, which can be imminent, i.e., predictive, or in progress. Control then passes from output alert process 705 to end process 620.

Returning to reversal decision process 703, a determination of whether there is a temperature reversal between left ABTT terminus 10 and right ABTT terminus 10 is made. If there is a temperature reversal, control passes from reversal decision process 703 to an output alert process 707. Otherwise, control passes from reversal decision process 703 to an output alert process 704.

In output alert process 704, an alert is sent to, for example, a display 74 or other output device, which can be audible or vibratory. The output alert indicates a right brain stroke, which can be imminent, i.e., predictive, or in progress. Control then passes from output alert process 704 to end process 620.

In output alert process 707, an alert is sent to, for example, a display 74 or other output device, which can be audible or vibratory. The output alert indicates a severe left brain stroke, which can be imminent, i.e., predictive, or in progress. Control then passes from output alert process 707 to end process 620.

Figure 16E:
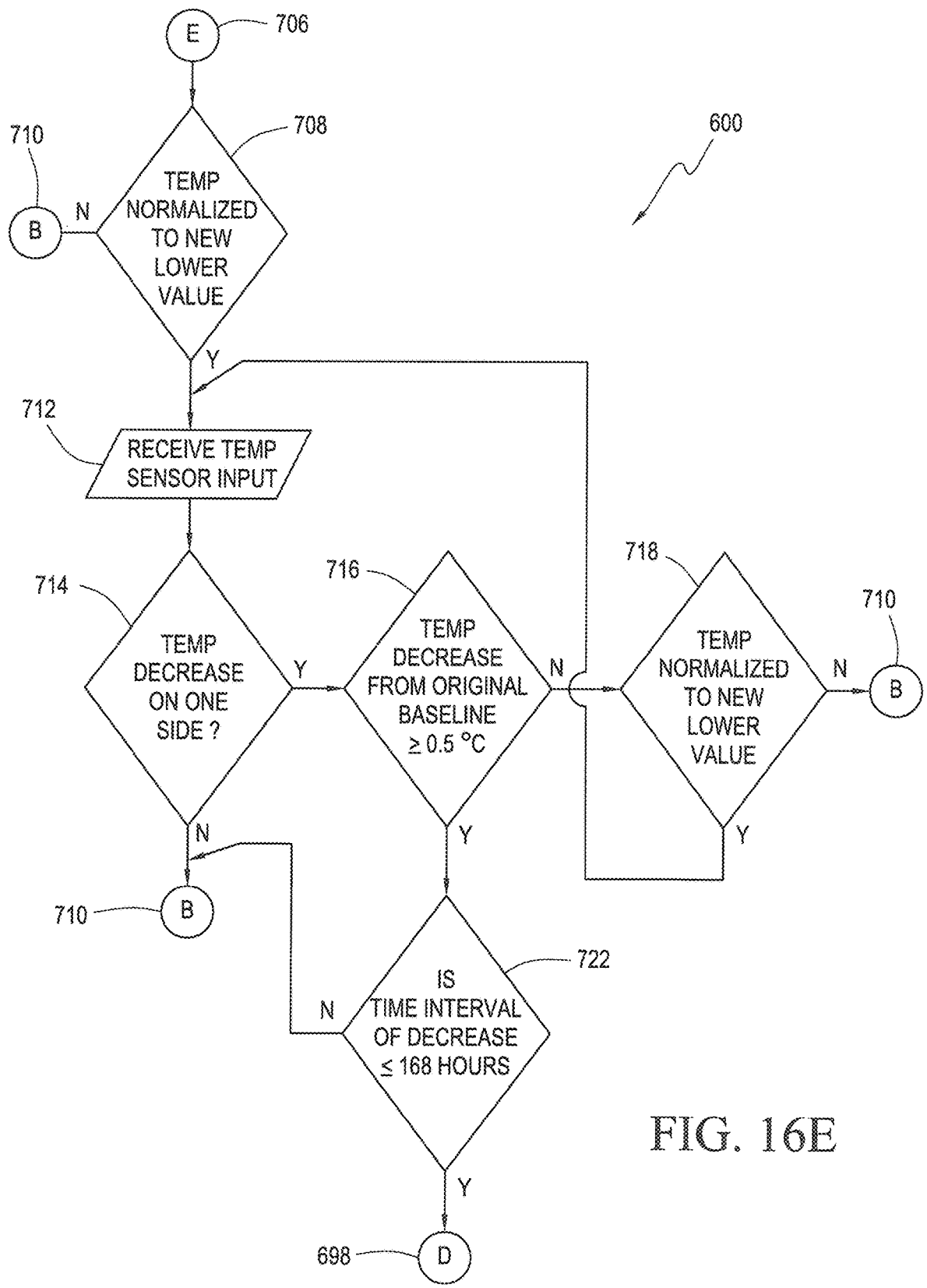

Returning to 642 in FIG. 16A, connection is to a connector 706 in FIG. 16E, which connects to a normalized temperature decision process 708, where it is determined whether the temperature of ABTT terminuses 10 has normalized, or established a new, lower baseline level. If a new, lower baseline has not been established, control passes to connector 710, which connects to connector 668 in FIG. 16A, followed by receive temperature sensor input process 604, described hereinabove. If a new, lower baseline temperature has been established, control passes to a receive temperature sensor input process 712.

In receive temperature sensor input process 712, temperature signals are received from a temperature sensor, such as temperature sensor 62. Control then passes to a temperature decrease decision process 714.

In temperature decrease decision process 714, it is determined whether the temperature of one or more ABTT terminuses 10 has decreased further. If a decrease has occurred at only one ABTT terminus 10, control passes to a total temperature decrease decision process 716. If a decrease has not occurred at only one ABTT terminus 10, control passes from temperature decrease decision process 714 to connector 710, which functions as described hereinabove.

In total temperature decrease decision process 716, it is determined whether the total temperature decrease from the original baseline is greater than or equal to 0.5 degrees Celsius. If the total ABTT terminus 10 temperature decrease is greater than or equal to 0.5 degrees Celsius, control passes from total temperature decrease decision process 716 to elapsed time decision process 722. If the total decrease is less than 0.5 degrees Celsius from the original baseline, control passes from total temperature decrease decision process 716 to a normalized temperature decision process 718.

In normalized temperature decision process 718, it is determined whether the temperature of ABTT terminuses 10 has normalized to a new, lower baseline value. If the temperature of ABTT terminuses 10 has normalized to a new, lower baseline value, control passes from normalized temperature decision process 718 to receive temperature sensor input process 712, which functions as described hereinabove. Otherwise, control passes from normalized temperature decision process 718 to connector 710, which functions as described hereinabove.

Returning to elapsed time decision process 722, it is determined whether the elapsed time of temperature decreases has occurred in an interval that is less than or equal to 168 hours. If the interval is greater than the predetermined interval of 168 hours, control passes from elapsed time decision process 722 to connector 710, which functions as described hereinabove. If the elapsed interval is less than or equal to 168 hours, control passes from elapsed time decision process 722 to connector 698, which connects to connector 698 in FIG. 16D, which functions as described hereinabove.

Figure 16F:
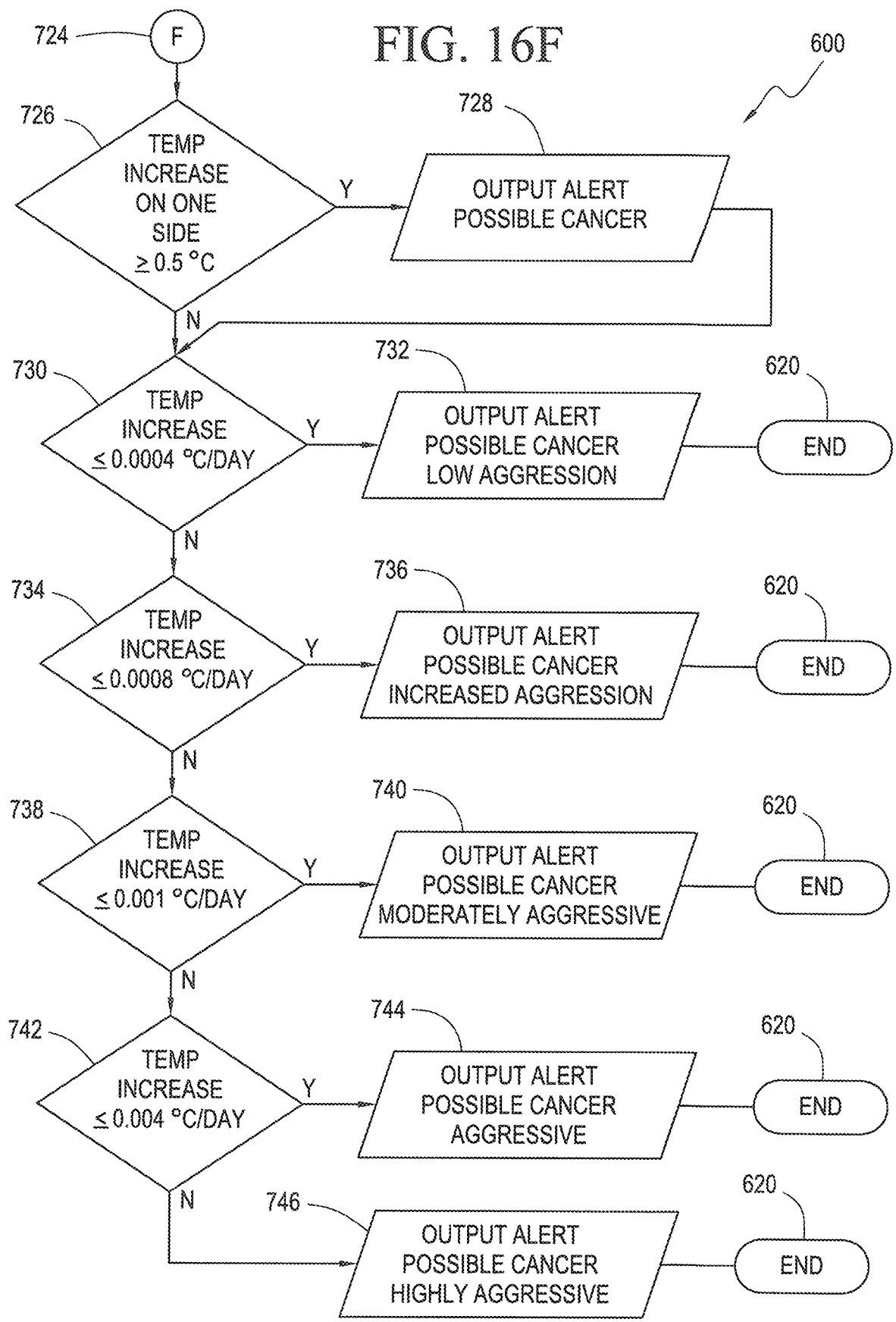

Returning to connector 628 in FIG. 16A, connector 628 connects to a connector 724 in FIG. 16F, which connect to a one side temperature increase decision process 726. In one side temperature increase decision process 726, it is determined whether a temperature increase of one ABTT terminus 10 is greater than or equal to 0.5 degrees Celsius. If such a temperature increase has been measured, control passes from one side temperature increase decision process 726 to an output alert process 728. If such a temperature increase has not been measured, control passes from one side temperature increase decision process 726 to a temperature increase decision process 730.

In output alert process 728, an alert is sent to, for example, a display 74 or other output device, which can be audible or vibratory. The output alert indicates a possible cancer condition. Control then passes from output alert process 728 to temperature increase decision process 730.

In temperature increase decision process 730, it is determined whether a temperature increase is less than or equal to 0.0004 degrees Celsius per day. If such an increase has been measured, control passes from temperature increase decision process 730 to an output alert process 732. If such an increase has not been measured, control passes from temperature increase decision process 730 to a temperature increase decision process 734.

In output alert process 732, an alert is sent to, for example, a display 74 or other output device, which can be audible or vibratory. The output alert indicates a possible low aggression cancer condition, which should indicate to a medical practitioner that additional diagnosis is likely advisable. Control then passes from output alert process 732 to end process 620.

In temperature increase decision process 734, it is determined whether a temperature increase is less than or equal to 0.0008 degrees Celsius per day. If such an increase has been measured, control passes from temperature increase decision process 734 to an output alert process 736. If such an increase has not been measured, control passes from temperature increase decision process 734 to a temperature increase decision process 738.

In output alert process 736, an alert is sent to, for example, a display 74 or other output device, which can be audible or vibratory. The output alert indicates a possible increased aggression cancer condition, which should indicate to a medical practitioner that additional diagnosis is likely advisable. Control then passes from output alert process 736 to end process 620.

In temperature increase decision process 738, it is determined whether a temperature increase is less than or equal to 0.001 degrees Celsius per day. If such an increase has been measured, control passes from temperature increase decision process 738 to an output alert process 740. If such an increase has not been measured, control passes from temperature increase decision process 738 to a temperature increase decision process 742.

In output alert process 740, an alert is sent to, for example, a display 74 or other output device, which can be audible or vibratory. The output alert indicates a possible moderately aggressive cancer condition, which should indicate to a medical practitioner that additional diagnosis is advisable. Control then passes from output alert process 740 to end process 620.

In temperature increase decision process 742, it is determined whether a temperature increase is less than or equal to 0.004 degrees Celsius per day. If such an increase has been measured, control passes from temperature increase decision process 742 to an output alert process 744. If such an increase has not been measured, control passes from temperature increase decision process 743 to an output alert process 746.

In output alert process 744, an alert is sent to, for example, a display 74 or other output device, which can be audible or vibratory. The output alert indicates a possible aggressive cancer condition, which should indicate to a medical practitioner that additional diagnosis is advisable. Control then passes from output alert process 744 to end process 620.

In output alert process 746, an alert is sent to, for example, a display 74 or other output device, which can be audible or vibratory. The output alert indicates a possible highly aggressive cancer condition, which should indicate to a medical practitioner that additional diagnosis is advisable. Control then passes from output alert process 746 to end process 620.

Figure 16G:
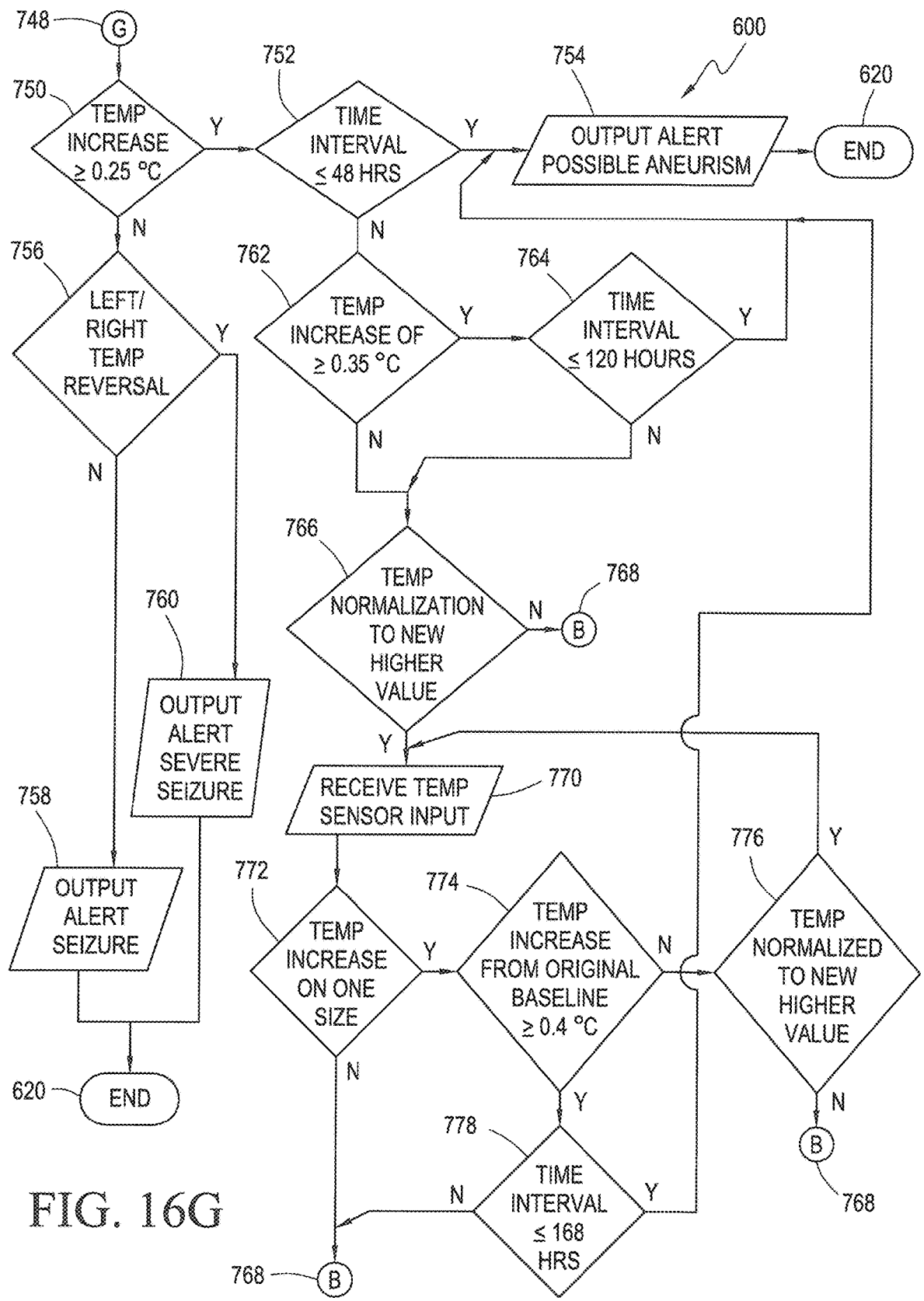

Returning to connector 630 in FIG. 16A, connector 630 connects to a connector 748 in FIG. 16G, which connects to a temperature increase decision process 750. In temperature increase decision process 750, it is determined whether the temperature increase in one ABTT terminus 10 is greater than or equal to 0.25 degrees Celsius. If the temperature increase in one ABTT terminus 10 is greater than or equal to 0.25 degrees Celsius, control passes from temperature increase decision process 750 to a time elapsed decision process 752. If the temperature increase in one ABTT terminus 10 is less than 0.25 degrees Celsius, control passes from temperature increase decision process 750 to a temperature reversal decision process 756.

In time elapsed decision process 752, it is determined whether the elapsed time of the temperature increase is less than or equal to 48 hours. If the elapsed time is less than or equal to 48 hours, control passes from time elapsed decision process 752 to an output alert process 754. If the elapsed time is greater than 48 hours, control passes from time elapsed decision process 752 to a temperature increase decision process 762.

In output alert process 754, an alert is sent to, for example, a display 74 or other output device, which can be audible or vibratory. The output alert indicates a possible aneurism is imminent or in progress, which should indicate to a medical practitioner that additional diagnosis is advisable. Control then passes from output alert process 754 to end process 620.

Returning to temperature reversal decision process 756, it is determined whether a temperature reversal between the left and right ABTT terminus 10 has occurred. In other words, the temperature of the previously lower ABTT terminus 10 is now the higher temperature ABTT terminus 10. If a temperature reversal is not indicated, control passes from temperature reversal decision process 756 to an output alert process 758. If a temperature reversal is indicated, control passes from temperature reversal decision process 756 to an output alert process 760.

In output alert process 758, an alert is sent to, for example, a display 74 or other output device, which can be audible or vibratory. The output alert indicates a possible seizure is imminent or in progress, which should indicate to a medical practitioner that treatment and possibly additional diagnosis is advisable. Control then passes from output alert process 758 to end process 620.

In output alert process 760, an alert is sent to, for example, a display 74 or other output device, which can be audible or vibratory. The output alert indicates a possible severe seizure is imminent or in progress, which should indicate to a medical practitioner that treatment and possibly additional diagnosis is advisable. Control then passes from output alert process 760 to end process 620.

Returning to temperature increase decision process 762, a determination is made as to whether the temperature increase on one side is greater than or equal to 0.35 degrees Celsius. If the temperature increase on one side is greater than or equal to 0.35 degrees Celsius, control passes to a time elapsed decision process 764. If the temperature increase on one side is less than 0.35 degrees Celsius, control passes from temperature increase decision process 762 to a normalized temperature decision process 766.

In time elapsed decision process 764, it is determined whether the elapsed time of the temperature increases is less than or equal to 120 hours. If the elapsed time of the temperature increases is less than or equal to 120 hours, control passes from time elapsed decision process 764 to output alert process 754, which functions as described hereinabove. If the elapsed time of the temperature increases is greater than 120 hours, control passes from time elapsed decision process 764 to normalized temperature decision process 766.

In normalized temperature decision process 766, it is determined whether the ABTT terminuses 10 have normalized to a new, higher temperature value. If ABTT terminuses 10 have not normalized to a new, higher temperature value, control is passed from normalized temperature decision process 766 to connector 768, which connects to connector 668 in FIG. 16A, which connects to receive temperature sensor input process 604, which functions as described hereinabove. If the temperature of ABTT terminuses 10 has normalized to a new, higher temperature value, control is passed from normalized temperature decision process 766 to a receiving temperature sensor input process 770.

In receive temperature sensor input process 770, temperature signals are received from a temperature sensor such as sensor 62. Once temperature data has been received, control passes from receive temperature input process 770 to a one side decision process 772.

In one side decision process 772, it is determined whether the temperature increase of one ABTT terminus 10 only has increased. If the temperature of both ABTT terminuses have increased or decreased, control passes from one side decision process 772 to connector 768, which functions as described hereinabove. If the temperature of only one ABTT terminus 10 has increased, control passes from one side decision process 772 to a total temperature decision process 774.

In total temperature decision process 774, it is determined whether the total temperature increase of one ABTT terminus 10 is greater than or equal to 0.4 degrees Celsius. If the total temperature increase of one ABTT terminus 10 is greater than or equal to 0.4 degrees Celsius, control passes from total temperature decision process 774 to a time elapsed decision process 778. If the total temperature increase of one ABTT terminus 10 is less than 0.4 degrees Celsius, control passes from total temperature decision process 774 to a normalized temperature decision process 776.

In normalized temperature decision process 766, it is determined whether the temperature of ABTT terminuses 10 has normalized to a new, higher value. If the temperature has normalized to a new higher value, control passes from normalized temperature decision process 766 to receive temperature sensor input 770, which functions as described hereinabove. If the temperature has not normalize to a new higher value, control passes from normalized temperature decision process 766 to connector 768, which functions as described hereinabove.

In time elapsed decision process 778, it is determined whether the elapsed time of the temperature increase in one ABTT terminus 10 is less than or equal to 168 hours. If the temperature increase has occurred in less than or equal to 168 hours, control passes from time elapsed decision process 778 to output alert process 754. If the temperature increase in one ABTT terminus 10 has increases in a period that is greater than 168 hours, control passes from time elapsed decision process 778 to connector 768, which functions as described hereinabove.

Figure 16H:
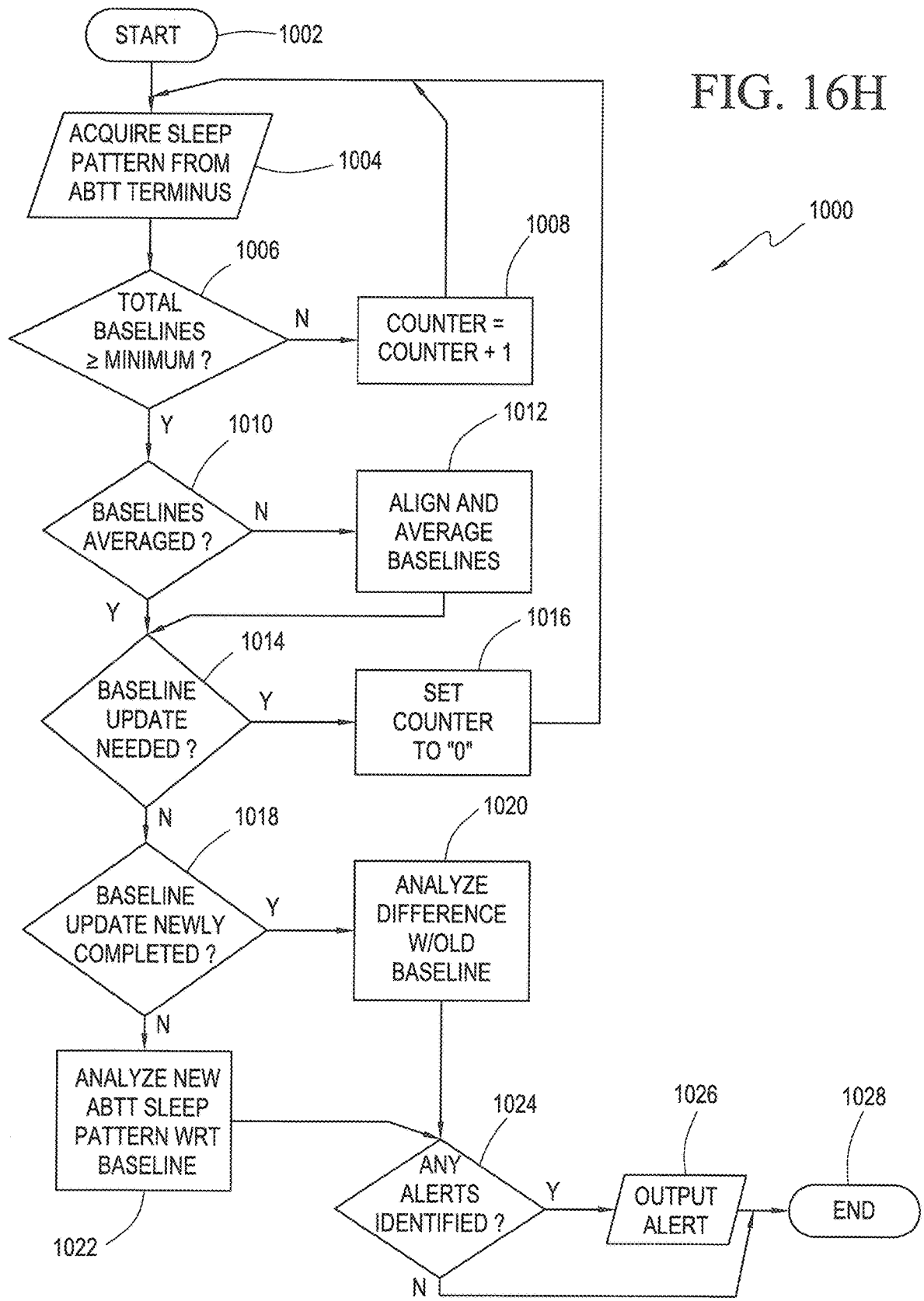
FIG. 16H shows a diagnostic process in accordance with another exemplary embodiment of the present disclosure.

FIG. 16H shows a diagnostic process in accordance with an exemplary embodiment of the present disclosure, indicated generally at 1000. Process 1000 is a process configured to acquire emitted signals from ABTT terminus 10 during a sleep cycle, with sleep cycle defined as the interval from pre-sleep, to sleep, through REM sleep, etc., until a the moment that awakening is defined. Applicant has identified that the emitted signals from ABTT terminus 10 are consistent during each sleep cycle in a healthy individual, and thus such sleep cycles can be analyzed for long term changes. It should be apparent that such changes can be, for example, those changes in temperature from a comparison baseline that are indicative of conditions such as cancer, stroke, etc.

For example, when a temperature decrease of greater than or equal to 0.1 degrees Celsius from a comparison baseline is identified over a sleep cycle, it can be indicative of the condition(s) described elsewhere herein when a temperature decrease of 0.1 degrees Celsius is observed. Indeed, a sleep cycle can be a convenient location to measure the temperature deviations described elsewhere herein and can decrease the risk of transients that might affect an analysis.

Process 1000 begins with a start process 1002, which can include initializing a control device, temperature sensors, and other electronic elements of a system, loading a program and predetermined values for comparison from non-transitory memory, and the like. Once start process 1002 is completed, control passes from start process 1002 to an acquire sleep pattern process 1004.

In acquire sleep pattern process 1004, signals emitted from ABTT terminus 10 during an entire sleep cycle are acquired and stored in non-transitory memory. One sleep pattern process 1004 is complete, control passes from sleep pattern process 1004 to a total baselines decision process 1006.

In total baselines decision process 1006, it is determined whether the number of baselines acquired has reached a predetermined minimum number. Such determination is made by comparing the value of a counter to the predetermined minimum number. A minimum number of baselines is needed to average or statistically compensate for minor variations during a sleep cycle. In an exemplary embodiment, a minimum of seven sleep cycles is acquired for a comparison baseline. In another exemplary embodiment a minimum of 10 sleep cycles is acquired for a comparison baseline. In yet another exemplary embodiment, a minimum of 15 sleep cycles is acquired for a comparison baseline. Applicant has determined that because sleep cycles in a healthy individual tend to be consistent, the number of sleep cycles for a comparison baseline need not be greater than 15, though more can be used if analysis of initially acquired sleep cycle determines identifies greater than expected variation in ABTT emission data over the initial baseline period.

If the number of baselines acquired is less than the predetermined minimum number, control passes from total baselines decision process 1006 to counter process 1008, where the counter, which may be set to zero the very first time process 1000 is implemented, is incremented by one and saved as the new counter, since the counter determines the number of sleep patterns acquired. Control then passes from counter process to acquire sleep pattern process 1004, which functions as previously described.

Returning to total baselines decision process 1006, if the total number of baseline sleep patterns has reach the predetermined minimum, control passes from total baselines decision process 1006 to a baselines averaged decision process 1010, where it is determined whether the baseline sleep patterns have been analyzed and statistically combined to form a comparison baseline. If the baselines have yet to be analyzed, control passes to align and analyze, which can include averaging, baseline process 1012. In process 1012, the acquired baseline sleep patterns are analyzed to develop the comparison baseline. Once the comparison baseline is created, control passes from process 1012 to a baseline update needed decision process 1014. Furthermore, if the baselines were previously analyzed, control passes from baselines averaged decision process 1010 to process 1014.

In baseline updated needed decision process 1014, it is determined whether the existing comparison baseline needs to be replaced. While comparison baselines can be stable for weeks or even months, with slow changes in physical condition, such as changes in exercise regimen, weight gain or loss, aging, etc., the signals emitted by ABTT terminus 10 can change. Accordingly, a new comparison baseline can be acquired at periodic intervals, such as, for example, once every three months. If a new comparison baseline needs acquired, control passes from baseline updated needed decision process 1014 to a set counter to zero process 1016, where the counter is reset to zero, which initiates acquisition of a new set of baseline data during the following cycle. Otherwise, control passes from baseline updated needed decision process 1014 to a baseline update newly completed decision process 1018.

In baseline update newly completed decision process 1018, it is determined whether a comparison baseline update was recently completed. If such an update was recently completed, control passes from process 1018 to an analyze baselines process 1020. In analyze baselines process 1020, the newly updated comparison baseline is compared with the previous comparison baseline to determine whether any variation exceeds a predetermined limit Control then passes to an alerts identified process 1024.

Returning to baseline update newly completed decision process 1018, if a baseline update was not recently completed, control passes from process 1018 to an analyze new ABBT pattern process 1022, where the newly acquired ABTT sleep pattern is compared with the existing comparison baseline. Control then passes to an alerts identified decision process 1024.

If any condition is identified in process 1020 or process 1022 by determining that a predetermined change, deviation, or difference with the comparison baseline has occurred, then alerts identified decision process 1024 will pass control to an output alert process 1026. Otherwise, control will pass to an end process 1028.

In alerts identified decision process 1026, an alert is displayed or transmitted to an electronic device to be displayed. Such an alert can be a suggestion to perform additional diagnostics, along with an indication of a possible or active condition. Such alert can warn of imminent or active conditions require immediate medical attention. Such alert can include a visual display, an audible output, vibrations, lights, etc. Such alert can be transmitted wirelessly or by wire to a central location, such as a nurses' station (not shown). Once output alert process 1026 is complete, control passes to end process 1028.

It should be understood that end process 1028 is an end of a complete cycle of process 1000, which can continue for a period of years. Such complete cycle is acquisition of baseline data to develop a comparison baseline, and acquisition of at least one sleep cycle of signal data from ABTT terminus 10. However, cycle 1000 will continue to function for subsequent sleep cycles, and subsequent updates of the comparison baseline. Accordingly, process 1000 could be described as a periodic process that should typically occur at least once daily.

Figure 17:
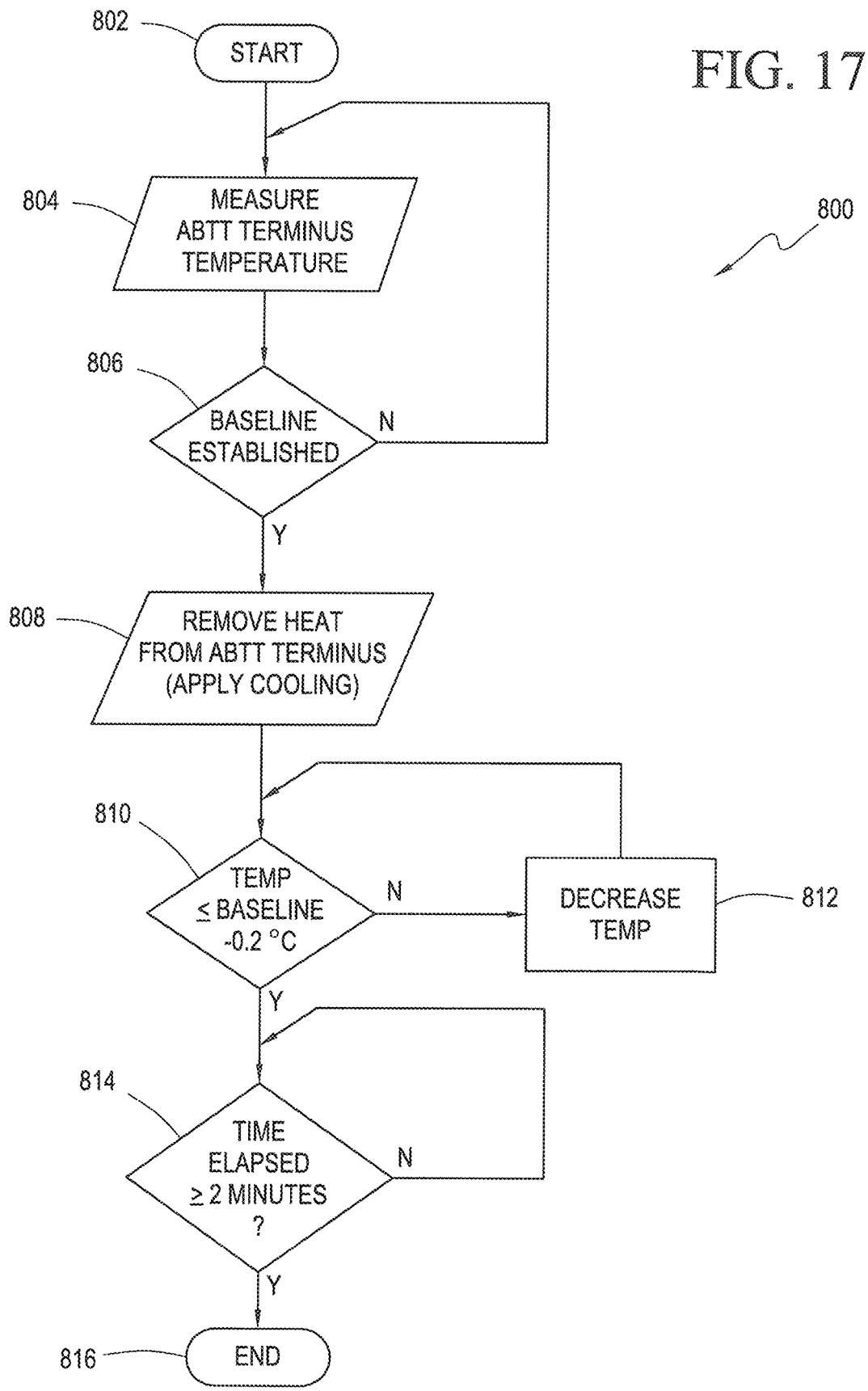
FIG. 17 shows an eighth treatment process for thyroid and other disorders in accordance with an exemplary embodiment of the present disclosure.

FIG. 17 shows a seventh treatment process for thyroid and other disorders in accordance with an exemplary embodiment of the present disclosure, indicated generally at 800. This embodiment for increasing production of thyroid hormones includes a device that can remove heat from ABTT terminus 10, such as a thermoelectric or Peltier device, as described herein.

The embodiment of FIG. 17 is configured to prevent or treat multiple sclerosis, epilepsy, ischemic stroke, headaches, and migraine, by decreasing the temperature at ABTT terminus 10 by an amount that is lower than a baseline temperature by an amount that is greater than or equal to 0.2 degrees Celsius.

Process 800 begins with a start process 802, which can include initializing a control device, temperature sensors, and other electronic elements of a system, loading a program and predetermined values for comparison from non-transitory memory, and the like. Once start process 802 is completed, control passes from start process 802 to a receive temperature input process 804.

In temperature input process 804, temperature signals from one or more temperature sensors, such as temperature sensors 62, is received. As described herein, such signals can be from one ABTT terminus 10 or from two ABTT terminuses 10. Once temperature signals have been received, control passes from temperature input process 804 to an establish baseline decision process 806.

In establish baseline decision process 806, a processor, such as processor 68, determines whether sufficient temperature information has been received to establish a baseline temperature. If sufficient information has yet to be received, control passes from establish baseline decision process 806 to receiving temperature input process 804. If sufficient temperature information has been received to establish a baseline temperature, which should be considered an average temperature over an interval, such as at least two minutes, control passes from establish baseline decision process 806 to remove heat process 808.

In remove heat process 808, the temperature modification device is actuated to remove heat from ABTT terminus 10 to increase hormone production. The initial temperature of the temperature modification device can be the baseline temperature, or the baseline temperature minus 0.3 degrees Celsius, or another value. Once remove heat process 808 is complete, control passes to a temperature decision process 810.

In temperature decision process 810, it is determined whether the temperature of each ABTT terminus 10 is less than or equal to the baseline temperature minus 0.3 degrees Celsius. If the temperature is greater than this value, control passes to a decrease temperature process 812. If the temperature is less than or equal to this value, control passes from decision process 810 to a time elapsed decision process 814.

In time elapsed decision process 814, it is determined whether the elapsed time of heat removal has reached greater than or equal to a predetermined period, such as 2 minutes. If the predetermined elapsed time has been reached, control passes to an end process 816, which terminates process 800. If the elapsed time is less than the predetermined period, control loops back to time elapsed decision process 814 until the predetermined interval is reached.

Returning to decrease temperature process 812, the temperature of the temperature modification device is decreased by a predetermined amount, such as 0.1 degrees Celsius. Control then passes from decrease temperature process 812 to temperature decision process 810, which functions as previously described hereinabove.

Figure 18:
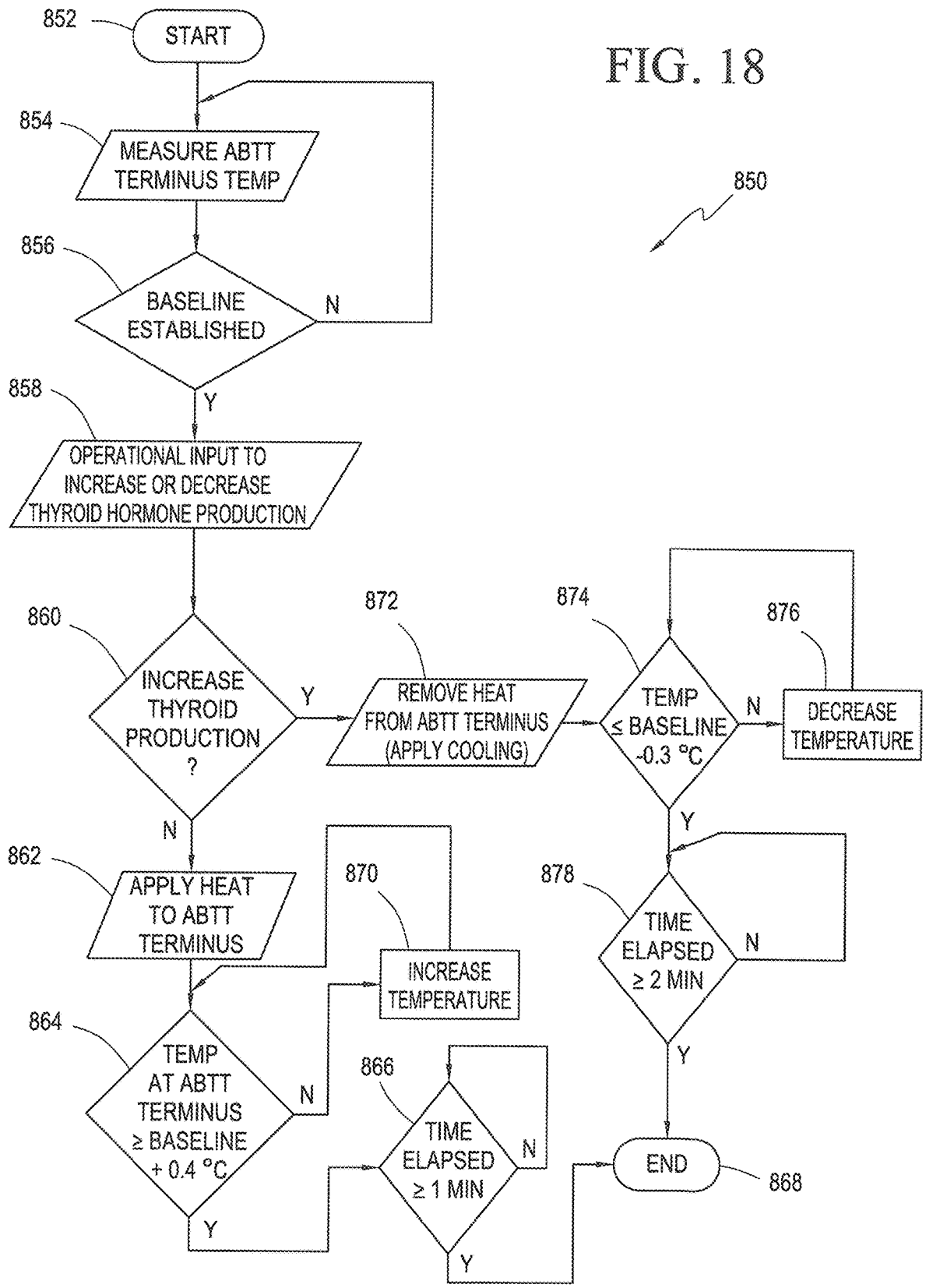
FIG. 18 shows a ninth treatment process for thyroid and other disorders in accordance with an exemplary embodiment of the present disclosure.

FIG. 18 shows a ninth treatment process for thyroid and other disorders in accordance with an exemplary embodiment of the present disclosure, indicated generally at 850, which is similar to the embodiment of FIG. 135. This embodiment for increasing or decreasing production of thyroid hormones includes a device that can add or remove heat from ABTT terminus 10, such as a thermoelectric or Peltier device, that is able to add or remove heat from ABTT terminus 10, as described herein.

The embodiment of FIG. 18 is configured to prevent or treat hypothermia and sleep disorders, by decreasing the temperature at ABTT terminus 10 by an amount that is lower than a baseline temperature by an amount that is greater than or equal to 0.4 degrees Celsius.

Further, the embodiment of FIG. 18 is configured to prevent or treat hypothermia by increasing the temperature at ABTT terminus 10 by an amount that is greater than a baseline temperature by an amount that is greater than or equal to 0.4 degrees Celsius.

Process 850 begins with a start process 852, which can include initializing a control device, temperature sensors, and other electronic elements of a system, loading a program and predetermined values for comparison from non-transitory memory, and the like. Once start process 852 is completed, control passes from start process 852 to a receive temperature input process 854.

In temperature input process 854, temperature signals from one or more temperature sensors, such as temperature sensors 62, is received. As described herein, such signals can be from one ABTT terminus 10 or from two ABTT terminuses 10. Once temperature signals have been received, control passes from temperature input process 854 to an establish baseline decision process 856.

In establish baseline decision process 856, a processor, such as processor 68, determines whether sufficient temperature information has been received to establish a baseline temperature. If sufficient information has yet to be received, control passes from establish baseline decision process 856 to receiving temperature input process 854. If sufficient temperature information has been received to establish a baseline temperature, which should be considered an average temperature over an interval, such as at least two minutes, control passes from establish baseline decision process 856 to an operator input process 858.

In operator input process 858, an operator or other user inputs whether a system needs to increase or decrease hormone production. Once operator input process 858 is complete, control passes from operator input process 858 to an increase thyroid production decision process 860.

In increase thyroid product decision process 860, if hormone production is to be increased, control passes to remove heat process 872. If hormone production is to be decreased, control passes from decision process 860 to an apply heat process 862.

In apply heat process 862, the temperature of one or more temperature modification devices, such as devices 64, is increased to apply heat to one or more ABTT terminuses 10. Control then passes from apply heat process 862 to a temperature decision process 864.

In temperature decision process 864, it is determined whether the temperature of each ABTT terminus 10 is greater than or equal to the baseline temperature plus 0.3 degrees Celsius. If the temperature is less than this value, control passes to an increase temperature process 870. If the temperature is greater than or equal to this value, control passes from decision process 864 to a time elapsed decision process 866.

In time elapsed decision process 866, it is determined whether the elapsed time of heat application has reached greater than or equal to a predetermined period, such as 1 minute. If the predetermined elapsed time has been reached, control passes to an end process 868, where process 850 is terminated. If the elapsed time is less than the predetermined period, control loops back to time elapsed decision process 866 until the predetermined interval is reached.

Returning to increase temperature process 870, the temperature of the temperature modification device is increased by a predetermined amount, such as 0.1 degrees Celsius. Control then passes from increase temperature process 870 to temperature decision process 864, which functions as previously described hereinabove.

Returning now to remove heat process 872, the temperature modification device is actuated to remove heat from ABTT terminus 10 to increase hormone production. The initial temperature of the temperature modification device can be the baseline temperature, or the baseline temperature minus 0.3 degrees Celsius, or another value. Once remove heat process 872 is complete, control passes to a temperature decision process 874.

In temperature decision process 874, it is determined whether the temperature of each ABTT terminus 10 is less than or equal to the baseline temperature minus 0.3 degrees Celsius. If the temperature is greater than this value, control passes to a decrease temperature process 876. If the temperature is less than or equal to this value, control passes from decision process 874 to a time elapsed decision process 878.

In time elapsed decision process 878, it is determined whether the elapsed time of heat removal has reached greater than or equal to a predetermined period, such as 2 minutes. If the predetermined elapsed time has been reached, control passes to end process 868, described hereinabove. If the elapsed time is less than the predetermined period, control loops back to time elapsed decision process 878 until the predetermined interval is reached.

Returning to decrease temperature process 876, the temperature of the temperature modification device is decreased by a predetermined amount, such as 0.1 degrees Celsius. Control then passes from decrease temperature process 876 to temperature decision process 874, which functions as previously described hereinabove.

Figure 19:
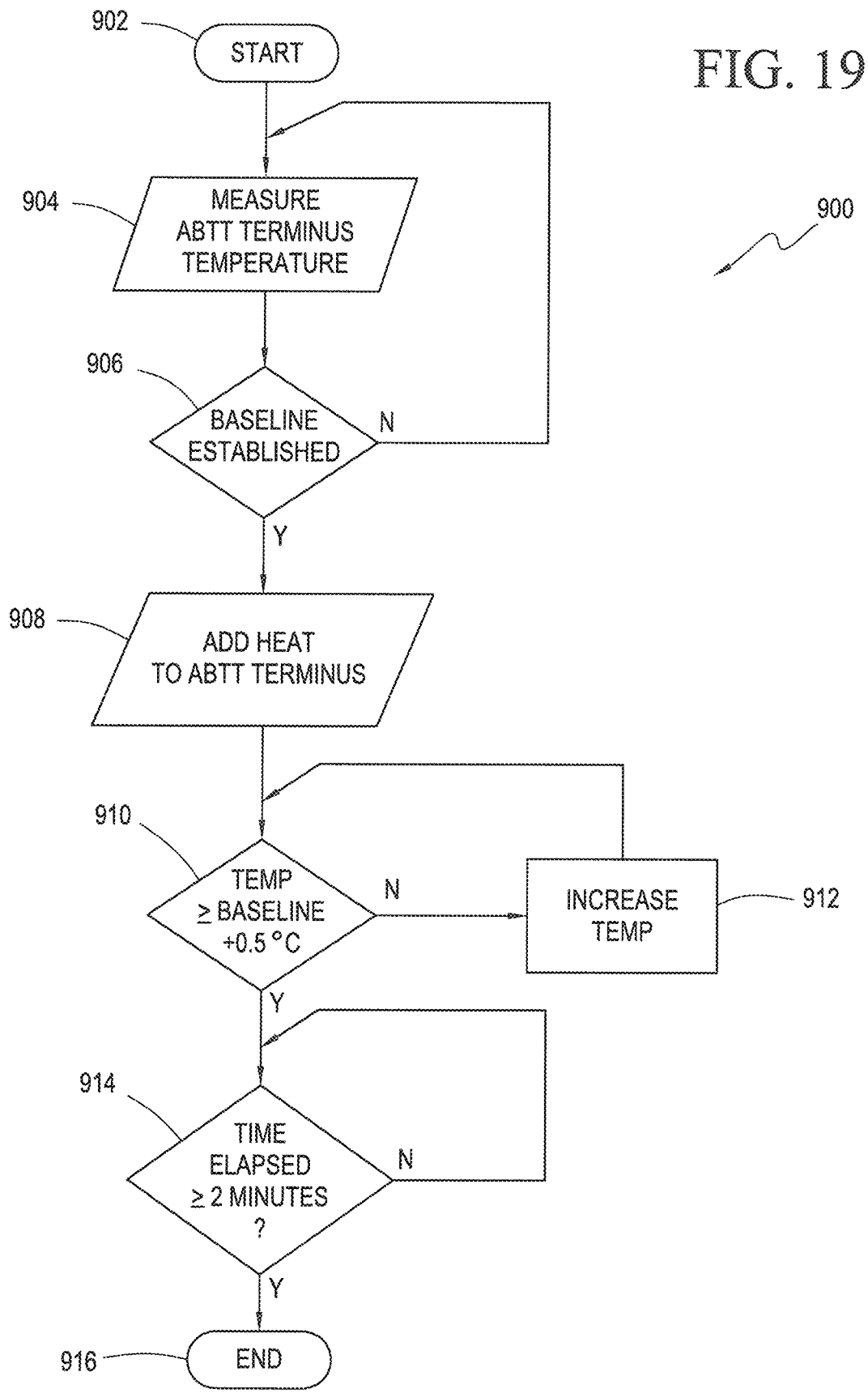
FIG. 19 shows a tenth treatment process for thyroid and other disorders in accordance with an exemplary embodiment of the present disclosure.

FIG. 19 shows a tenth treatment process for thyroid and other disorders in accordance with an exemplary embodiment of the present disclosure, indicated generally at 900. This embodiment for decreasing production of thyroid hormones includes a device that can add heat from ABTT terminus 10, such as a thermoelectric or Peltier device, thermally retentive materials, resistive heater, IR heaters, and the like.

The embodiment of FIG. 19 is configured to prevent or treat cancer, by increasing the temperature at ABTT terminus 10 by an amount that is higher than a baseline temperature by an amount that is greater than or equal to 0.5 degrees Celsius.

Process 900 begins with a start process 902, which can include initializing a control device, temperature sensors, and other electronic elements of a system, loading a program and predetermined values for comparison from non-transitory memory, and the like. Once start process 902 is completed, control passes from start process 902 to a receive temperature input process 904.

In temperature input process 904, temperature signals from one or more temperature sensors, such as temperature sensors 62, is received. As described herein, such signals can be from one ABTT terminus 10 or from two ABTT terminuses 10. Once temperature signals have been received, control passes from temperature input process 904 to an establish baseline decision process 906.

In establish baseline decision process 906, a processor, such as processor 68, determines whether sufficient temperature information has been received to establish a baseline temperature. If sufficient information has yet to be received, control passes from establish baseline decision process 906 to receiving temperature input process 904. If sufficient temperature information has been received to establish a baseline temperature, which should be considered an average temperature over an interval, such as at least two minutes, control passes from establish baseline decision process 906 to add heat process 908.

In add heat process 908, the temperature modification device is actuated to add heat to ABTT terminus 10 to decrease hormone production. The initial temperature of the temperature modification device can be the baseline temperature, or the baseline temperature plus 0.5 degrees Celsius, or another value. Once add heat process 908 is complete, control passes to a temperature decision process 910.

In temperature decision process 910, it is determined whether the temperature of each ABTT terminus 10 is greater than or equal to the baseline temperature plus 0.5 degrees Celsius. If the temperature is greater than this value, control passes to a time elapsed decision process 914. If the temperature is less than or equal to this value, control passes from decision process 910 to an increase temperature process 912.

In time elapsed decision process 914, it is determined whether the elapsed time of heat removal has reached greater than or equal to a predetermined period, such as 2 minutes. If the predetermined elapsed time has been reached, control passes to an end process 916, which terminates process 900. If the elapsed time is less than the predetermined period, control loops back to time elapsed decision process 914 until the predetermined interval is reached.

Returning to increase temperature process 912, the temperature of the temperature modification device is decreased by a predetermined amount, such as 0.1 degrees Celsius. Control then passes from increase temperature process 912 to temperature decision process 910, which functions as previously described hereinabove.

Figure 21:
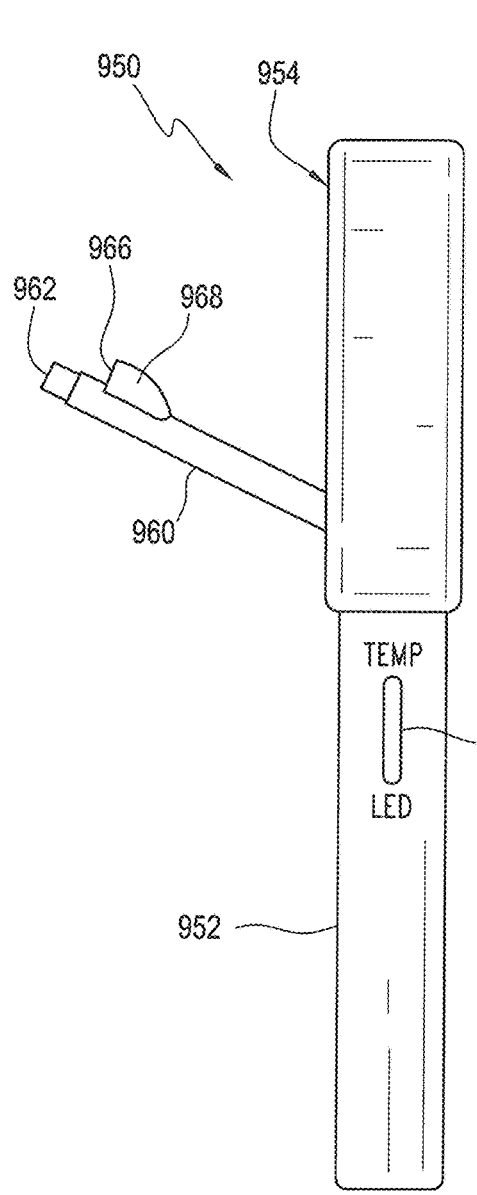
FIG. 21 shows a side view of a device configured to assist in locating an ABTT terminus and then measure the temperature at the ABTT terminus in accordance with an exemplary embodiment of the present disclosure.
Figure 22:
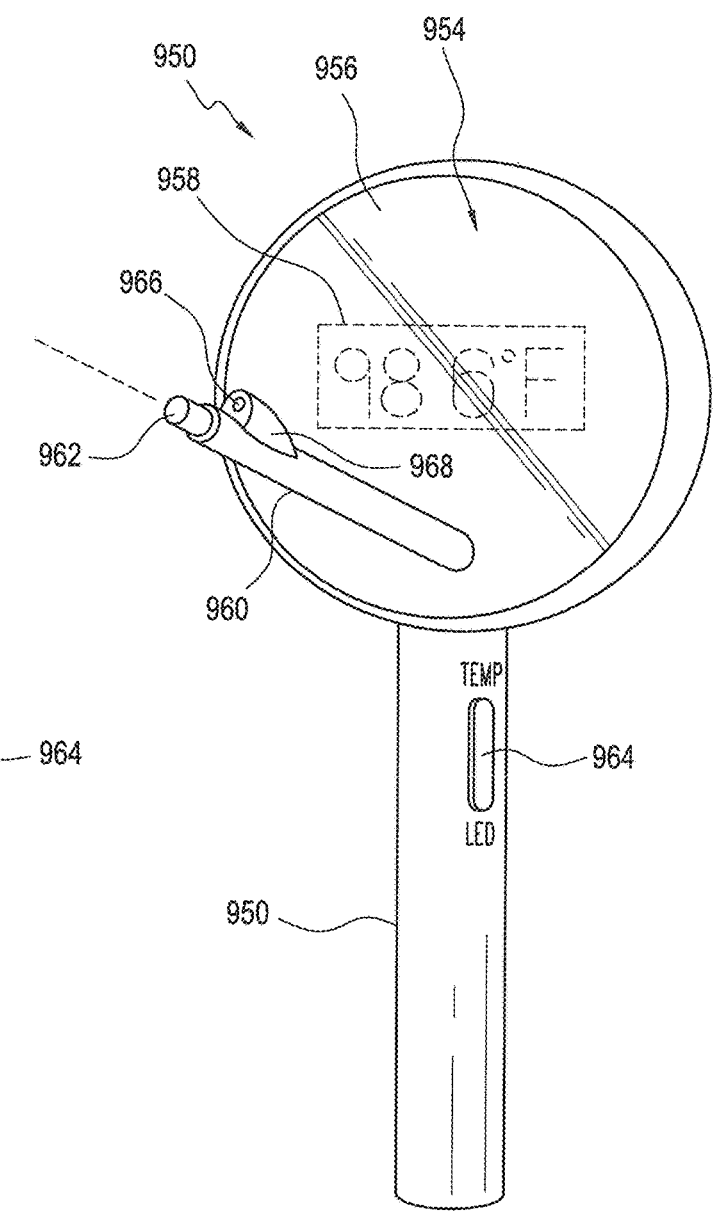
FIG. 22 shows a perspective view of the device of FIG. 21.

Referring to FIGS. 21 and 22, an ABTT temperature measurement device in accordance with an exemplary embodiment of the present disclosure is shown and indicated generally at 950. Device 950 includes a handle 952 that is configured to support a mirror 954, which includes a partially reflecting mirrored or reflective surface 956. Device 950 is further configured to include a display 958, which can be positioned behind reflective surface 956, which is partially reflecting to permit light to travel through reflective surface 956 to enable display 958 to be seen by a user, when display 958 is illuminated.

Device 950 is also configured to include an arm 960 that extends in a direction that is away from mirrored or reflective surface 956, and is preferably at an angle with respect to surface 956 that matches an angle of ABTT terminus 10. While arm 960 is shown extending from surface 956 in FIGS. 21 and 22, in another exemplary embodiment arm 960 is configured to extend from handle 952. Arm 960 is configured to include a temperature sensor 962 at an end thereof, and the size and dimension of arm 960 is such that temperature sensor 962 is positioned near a center of mirrored surface 956 to enable the user to more easily use mirrored surface 956 to assist in positioning temperature sensor 962 at, near, on, adjacent, close, or alongside ABTT terminus 10. Device 950 further includes a switch 964, which can be located on handle 952. Switch 964 is configured to operate temperature sensor 962, with a resulting temperature measurement being presented on display 958. It should be understood that other sensors besides temperature can be used including infrared detector coupled to an emitter.

Device 950 can also be configured to include a light source such as a collimated LED 966 configured to emit visible light; i.e., a visible output. LED 966 is located in an LED housing 968, which can be positioned on arm 960. Switch 964 can be configured as a rocker-type switch that operates LED 966 in a first position, and operates LED 966 and temperature sensor 962 in a second position. Display 958 is operated automatically as a result of the operation of LED 966 and temperature sensor 962.

In operation, a user grasps handle 952, and by using mirror 954, positions temperature sensor 962 in an area that is adjacent to, meaning over or next to, ABTT terminus 10. In an exemplary embodiment, temperature sensor 962 can be a non-contact sensor, such as an infrared sensor, or can be a contact sensor, such as a thermocouple or thermopile, or an optical sensor or a dielectric sensor. If optional LED 966 is available, the user can press switch 964 to activate LED 966, which is boresighted or aligned with arm 960 such that light output from LED 966, as seen via mirror 954, can serve as a guide for positioning temperature sensor 962. Once temperature sensor 962 is properly placed, switch 964 may be moved to actuate temperature sensor 962. LED 966 can remain on during temperature measurement to assist in maintaining the position of temperature sensor 962. Device 950 may be configured to permit "scanning" of temperature sensor 962 to find the location of ABTT terminus 10. If device 950 includes this capability, once device 50 locates ABTT terminus 10, display 958 can be configured to display an appropriate indication, such as "ON TARGET." Once device 950 acquires a temperature measurement from ABTT terminus 10, the temperature result is presented on display 958, and the temperature result can remain on display 958 for a predetermined period, or can shutoff with release of switch 964.

Figure 23:
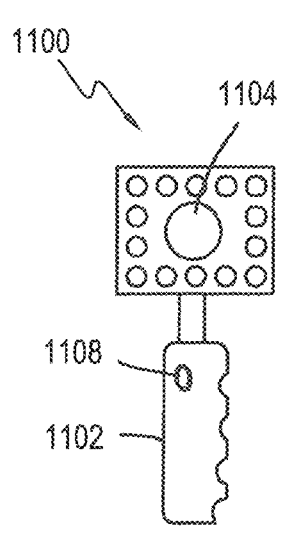
FIG. 23 shows a front view of another device configured to assist in locating an ABTT terminus and then to measure the temperature of the ABTT terminus in accordance with an exemplary embodiment of the present disclosure.
Figure 24:
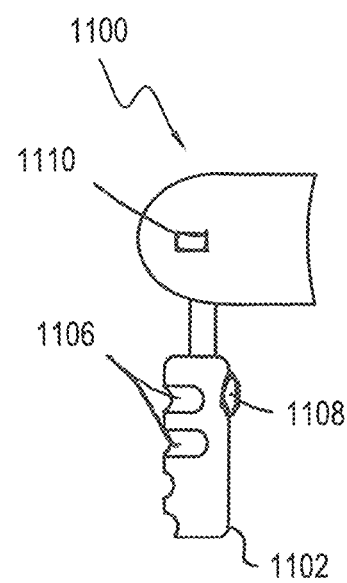
FIG. 24 shows a side view of the device of FIG. 23.

Other devices to capture temperature from ABTT terminus 10 can include an infrared (IR) array configured to capture and analyze a face, and to automatically identify ABTT terminus 10 as well as provide the temperature at ABTT terminus 10. Such a temperature measurement device configured in accordance with an exemplary embodiment of the present disclosure is shown in FIGS. 23 and 24 and indicated generally at 1100.

Device 1100 is configured to include a handle 1102 that is configured to support an IR imaging camera 1104. Handle 1102 can be configured to include a fingerprint recognition apparatus 1106 as well as an operating switch 1108. Device 1100 can further be configured with an integral display (not shown), or can include a connector 1110 that is configured to provide communication with an external electronic device, such as a laptop, cell phone, tablet, etc. (not shown). Device 1100 can also include a transceiver, transmitter, or receiver to transmit information to an external electronic device. In an exemplary embodiment, infrared sensor array or IR imaging camera 1104 can be configured to detect infrared light in the wavelength range of 8,200 to 11,200 nanometers.

Device 1100 is operated by first grasping handle 1102. If fingerprint recognition apparatus 1106 is active, device 1100 identifies the user to associate measured temperature data with a particular patient, and may also identify an authorized user. Once device 1100 has provided the proper recognition, which may be indicated audibly, by display on a separate electronic device, or by illumination of an indicator (not shown) on device 1100, acquisition of IR signals by camera 1104 is available. Infrared light emitted from the ABTT carries brain diagnostic information within certain wavelengths, and IR imaging camera of the present disclosure is configured to preferably detect infrared light in the wavelength between 6,000 nanometers and 14,000 nanometers, and most preferably in the wavelength between 8,000 nanometers and 12,000 nanometers, and yet most preferably in the wavelength between 8,500 nanometers and 11,500 nanometers, and further yet most preferably between 8,200 nanometers and 11,200.

A user holds device 1100 to aim at the area of the face that includes ABTT terminus 10, and presses operating switch 1108. Because IR camera 1104 has a relatively large field of view (FOV), camera 1104 is able to image ABTT terminus 10 in addition to surrounding areas of the face. The image received by IR camera 1104 may be transmitted to and processed within device 1100 by a processor or controller (not shown), or the image may be transmitted as signals by a cable (not shown) attached to connector 1110 to a separate electronic device, where the image data is processed to determine the temperature of ABTT terminus 10, as well as time varying temperature data. Additionally, the separate electronic device, which can be, for example, a laptop, tablet, cell phone, etc., can be configured to display the image, which can be useful for optimizing the position of device 1100 as well as analyzing the image for thermal abnormalities, such as infection, poor blood flow, etc.

Figure 24A:
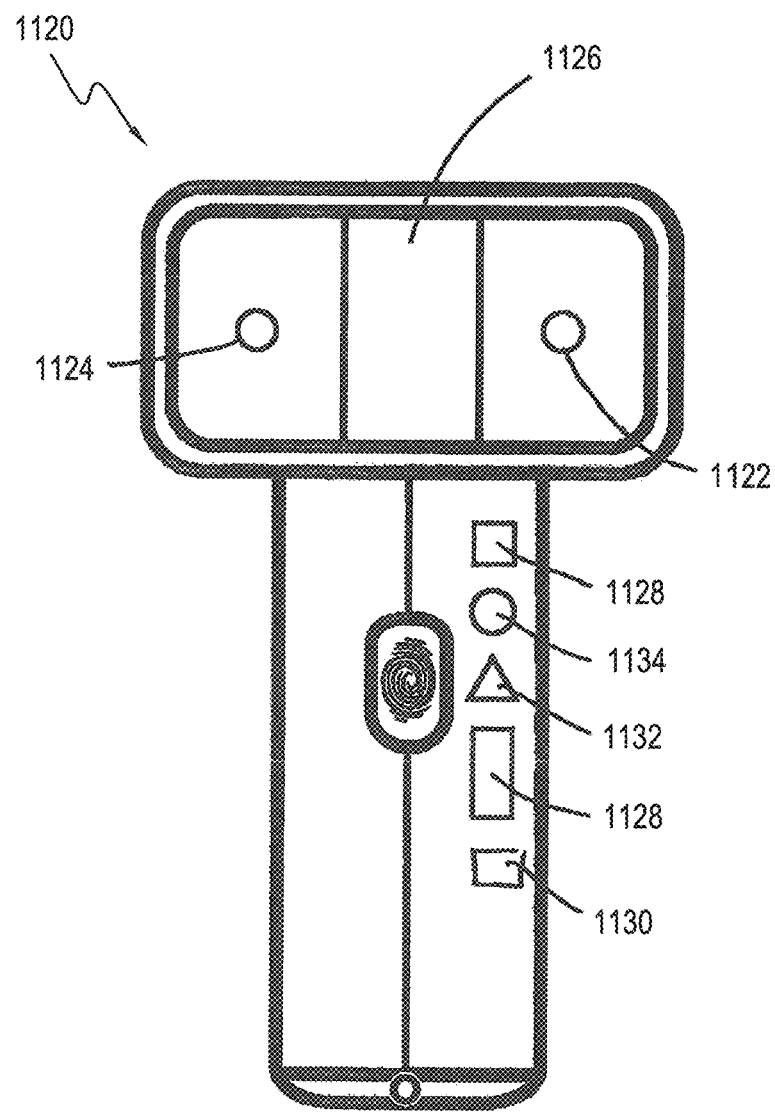
FIG. 24A shows a view of yet another device configured to assist in locating the ABTT terminus and then to measure the temperature of the ABTT terminus in accordance with an exemplary embodiment of the present disclosure.
Figure 24B:
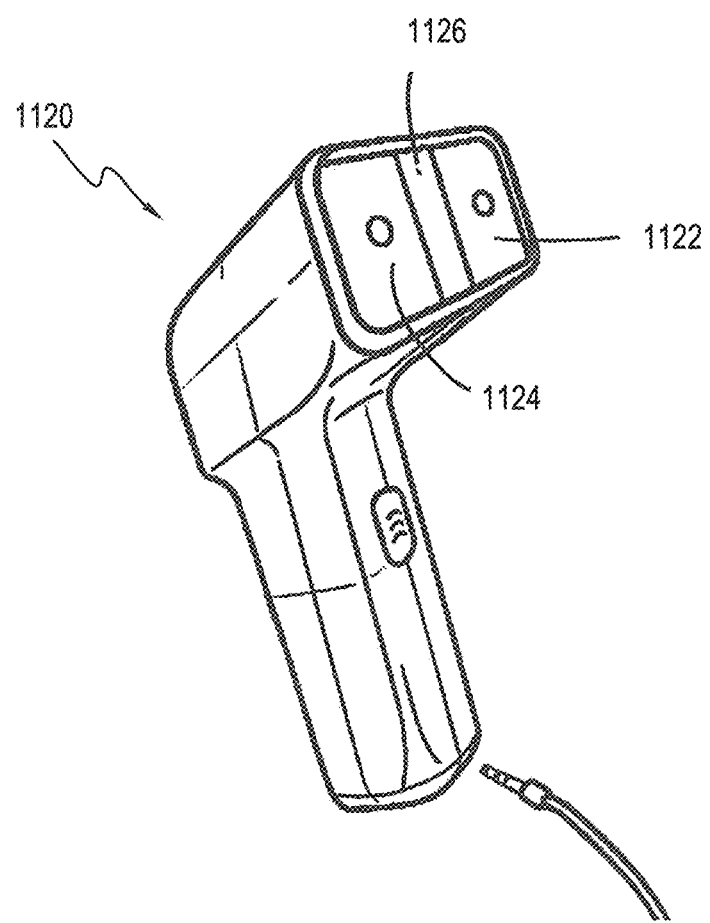
FIG. 24B shows another view of the device of FIG. 24A.
Figure 24C:
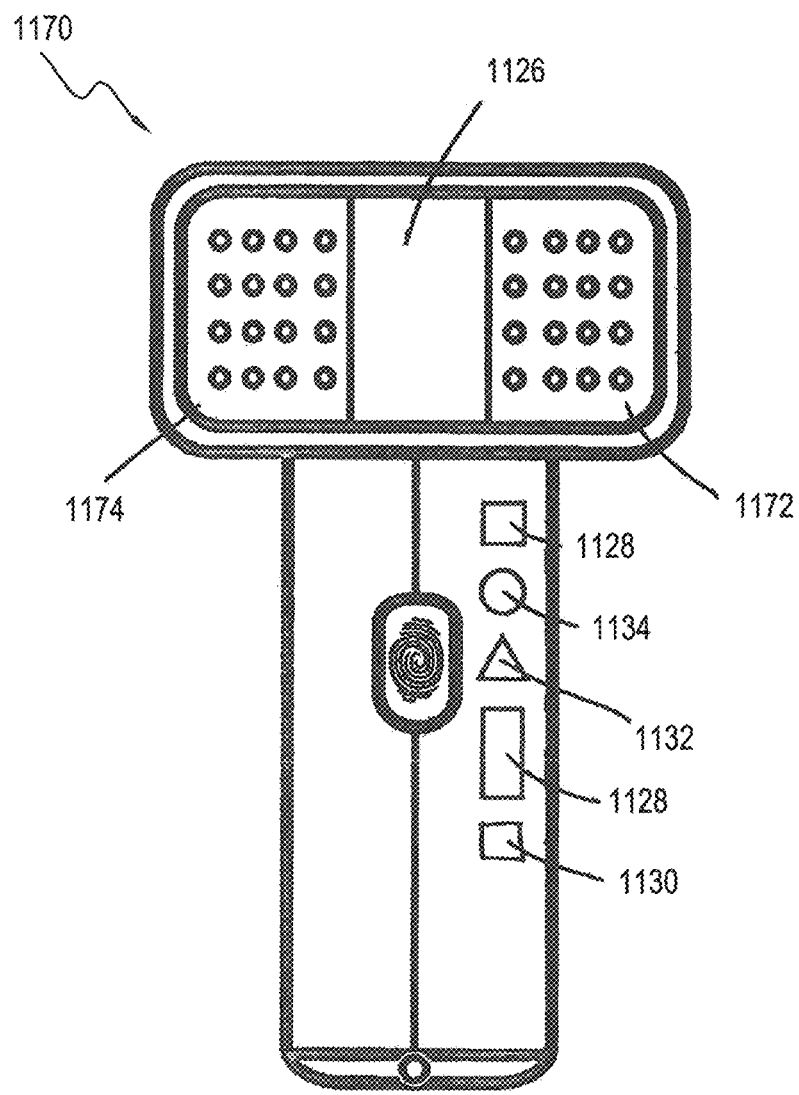
FIG. 24C shows a view of still yet another device configured to assist in locating the ABTT terminus and then to measure the temperature of the ABTT terminus in accordance with an exemplary embodiment of the present disclosure.
Figure 24D:
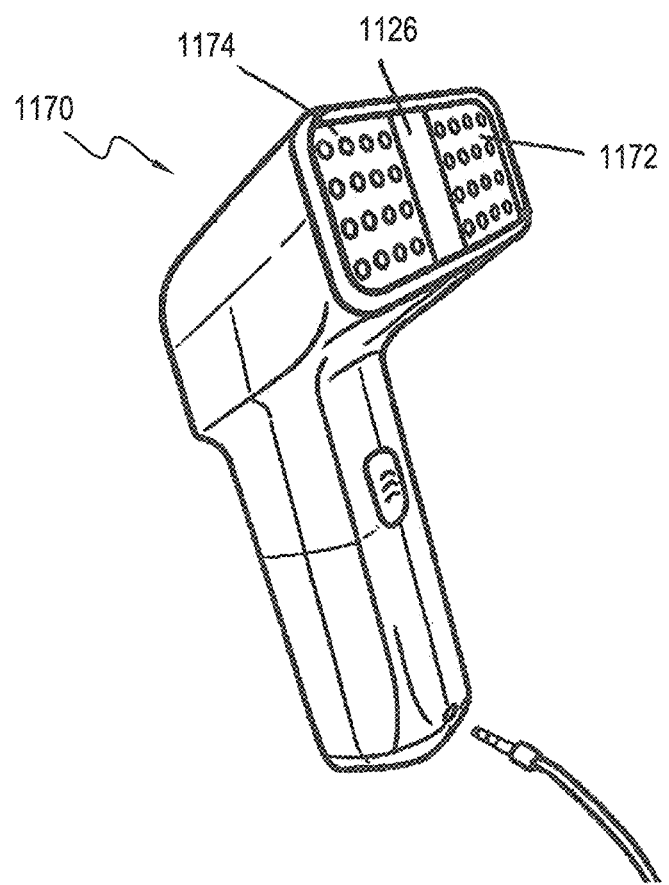
FIG. 24D shows another view of the device of FIG. 24C.
Figure 24E:
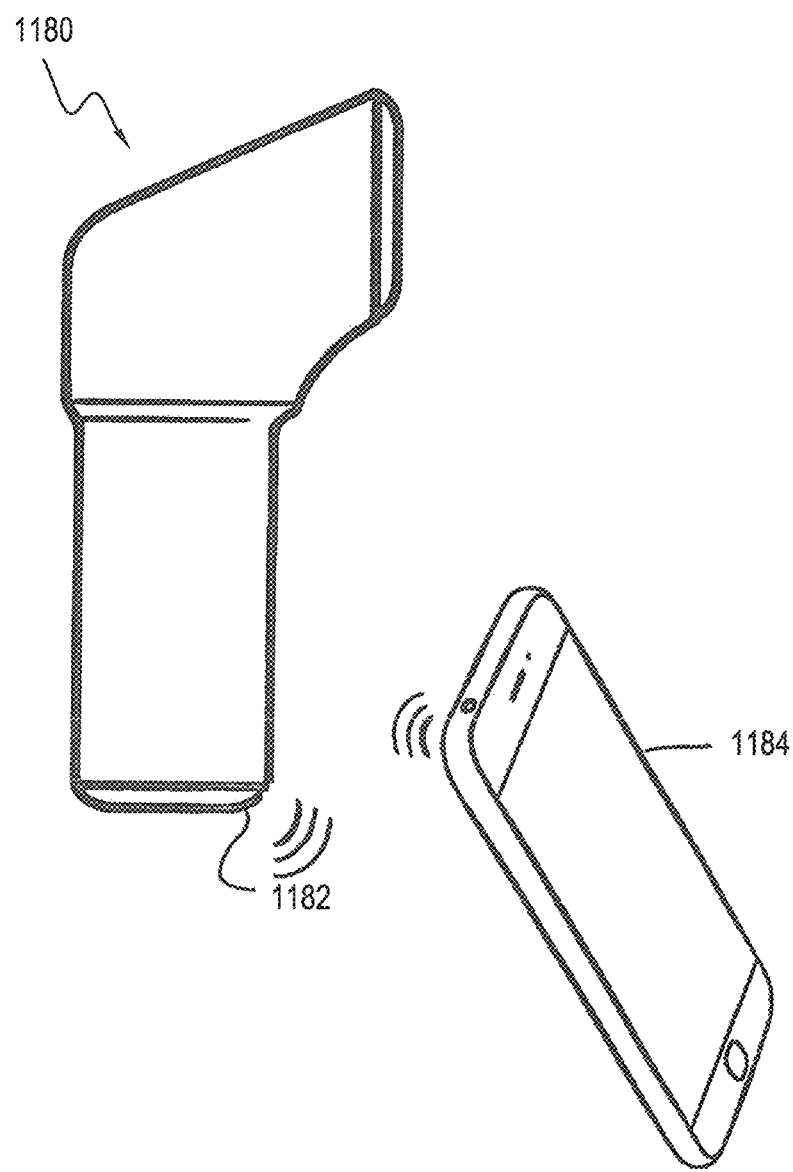
FIG. 24E shows a view of an even further device configured to assist in locating the ABTT terminus and then to measure the temperature of the ABTT terminus in accordance with an exemplary embodiment of the present disclosure.
Figure 24F:
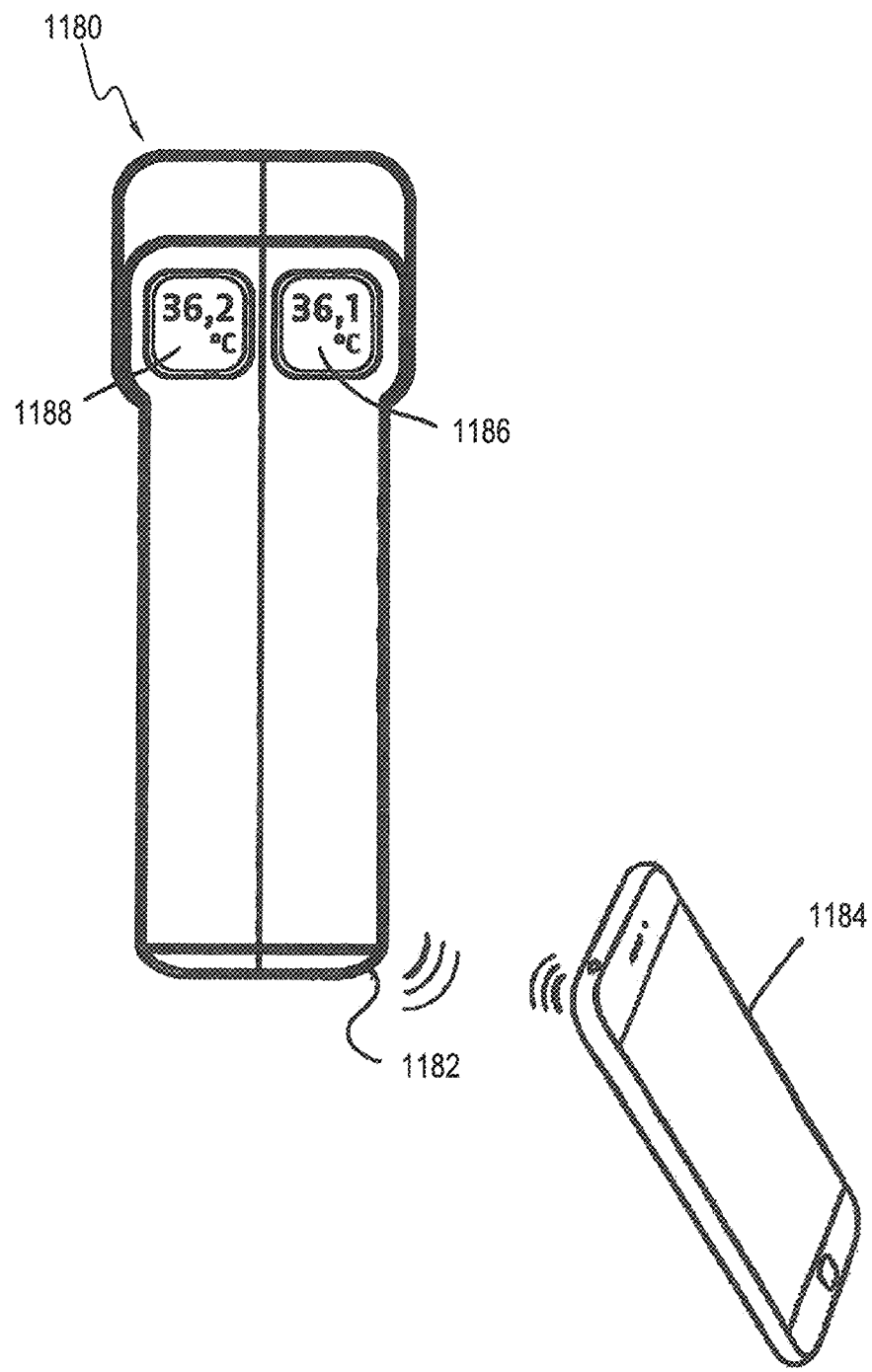
FIG. 24F shows another view of the device of FIG. 24E.
Figure 24G:
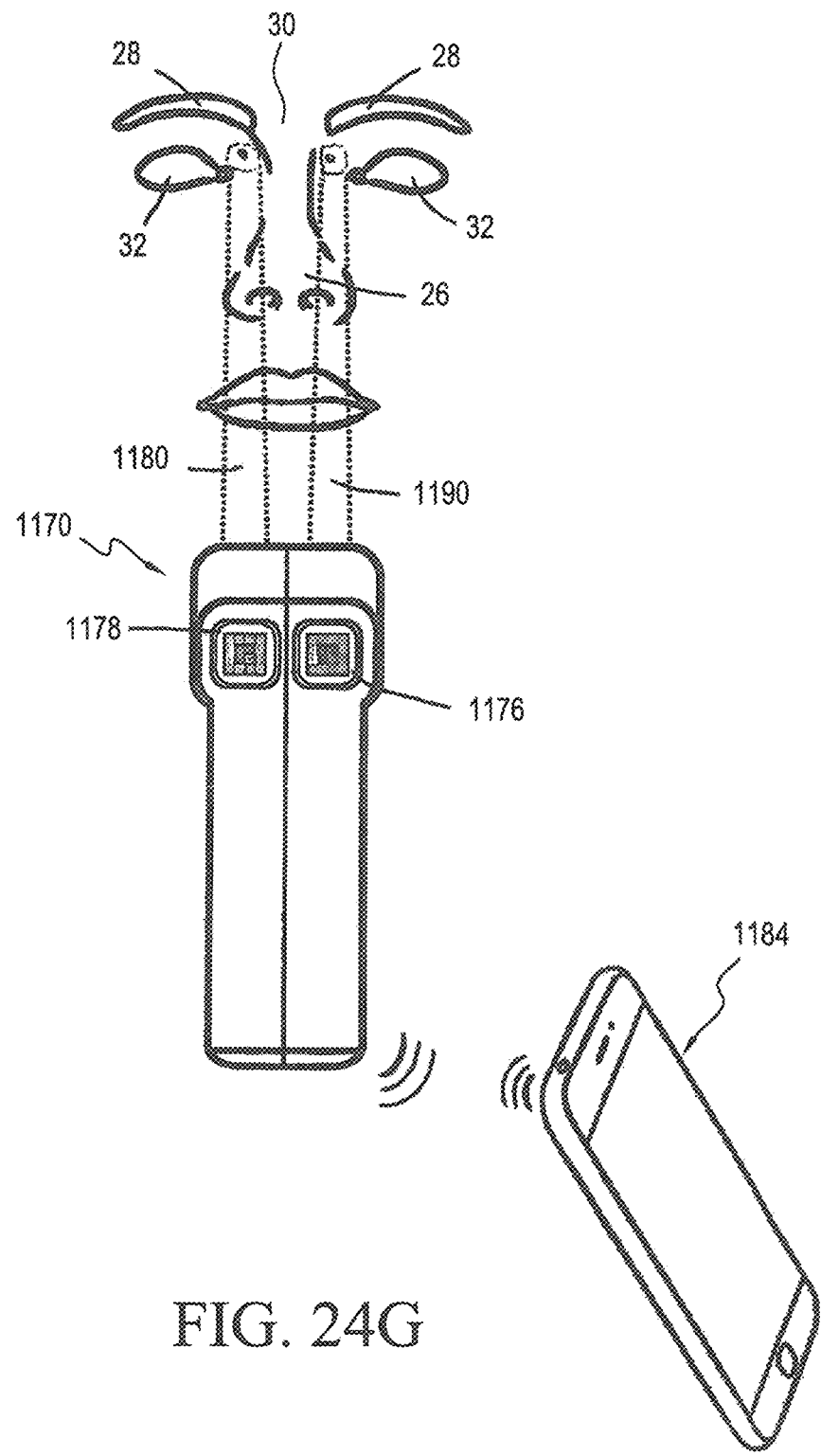
FIG. 24G shows another view of the device of FIG. 24C.
Figure 24H:
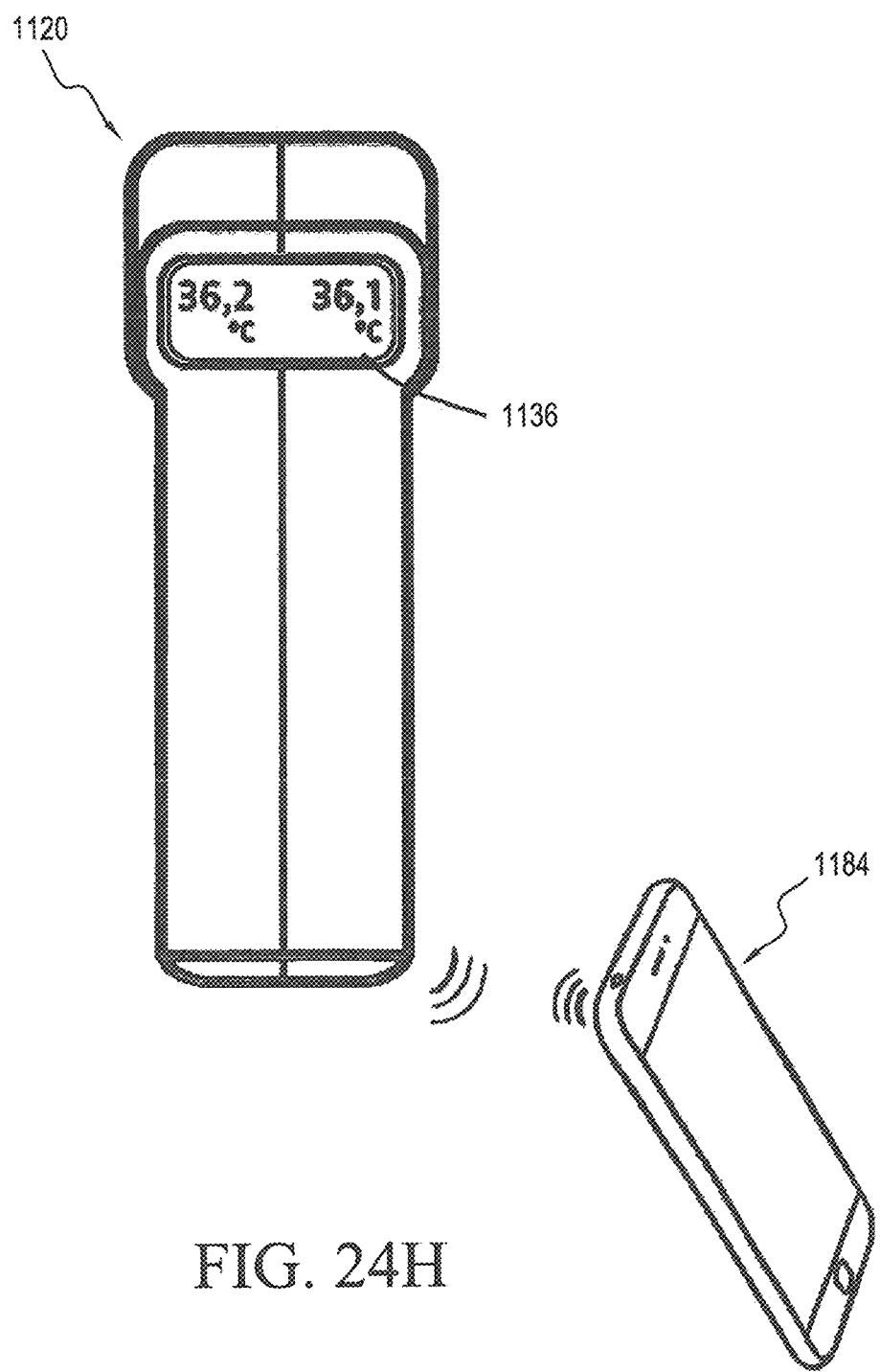
FIG. 24H shows another view of the device of FIG. 24A.

FIGS. 24A, 24B, and 24H show views of yet another device, indicated generally at 1120, configured to assist in locating ABTT terminus 10 and then to measure the temperature of ABTT terminus 10 in accordance with an exemplary embodiment of the present disclosure. Device 1120 includes a right sensor 1120 and a left sensor 1122 separated by an extendable connecting portion 1126 to adjust for different nose sizes. Temperature measurement device 1120 also includes a processor 1128, a transmitter (or transceiver) 1130, a non-transitory memory 1132, a power source 1134, such as a battery, and a display 1136. Display 1136 is positioned on an opposite side of device 1120 from right sensor 1120 and left sensor 1122. FIG. 24B shows device 1120 with connecting portion 1126 retracted to exemplarily adjust to a smaller nose size (or interpupillary distance). FIG. 24H shows simple display 1136 displaying the temperature of right ABTT terminus 10 and of left ABTT terminus 10.

FIGS. 24C, 24D, and 24G show views of still yet another device, indicated generally at 1170, configured to assist in locating ABTT terminus 10 and then to measure the temperature of ABTT terminus 10 in accordance with an exemplary embodiment of the present disclosure. Temperature measurement device 1170 also includes processor 1128 (which can be incorporated into any of the devices, apparatus, systems, etc., described herein), transmitter (or transceiver) 1130, non-transitory memory 1132, power source 1134, such as a battery, a right display 1176, and a left display 1178. Right display 1176 and left display 1178 are positioned on an opposite side of device 1170 from the sensors of device 1170. FIG. 24D shows device 1170 with connecting portion 1126 retracted to exemplarily adjust to a smaller nose size (or interpupillary distance). FIG. 24G shows right display 1176 and left display 1178 on the back of device 1170 capturing emissions from ABTT terminus 10, after device 1170 has been adjusted and positioned to place sensor fields of view 1190 on ABTT terminus 10. Right display 1176 and left display 1178 depict multiple pixels with stylized temperatures in the region of ABTT terminus 10, which includes a maximal temperature at ABTT terminus 10. It should be understood that a single display can be used in accordance to the principles of the present disclosure.

FIGS. 24E and 24F show views of an even further device, indicated generally at 1180, configured to assist in locating ABTT terminus 10 and then to measure the temperature of ABTT terminus 10 in accordance with an exemplary embodiment of the present disclosure. Temperature measurement device 1180 includes a transceiver 1182 for communication with separate electronic device 1184 (such as a cell phone), a right display 1186, and a left array 1188 positioned on an opposite side of device 1180 from the sensors of device 1180.

FIGS. 25-28 (excluding FIGS. 25A and 25B) show a temperature measurement device in accordance with an exemplary embodiment of the present disclosure, indicated generally at 1150. Device 1150 is configured with a device support 1152, which rotatably supports a first device member 1154 and a second device member 1156. Device 1150 is configured with at least one switch 1158 to actuate a temperature measurement process by actuating temperature sensors (not shown) located within first device member 1154 and second device member 1156. Each device member 1154 and 1156 includes optics 1160 such as lenses that are configured to gather a large FOV to make it easier to include ABTT terminus 10 as part of the FOV; i.e., when device 1150 is held to a face, the diameter of optics 1160 is such that when eyes 32 are centered on optics 1160, optics 1160 can also see ABTT terminus 10. Because first device member 1154 and second device member 1156 are configured to swivel or rotate, first device member 1154 and second device member 1156 can be adjusted to accommodate the variation in spacing of eyes 32 from each other. Device 1150 may further include a connector 1162 that is configured to permit connection of signals from device 1150 to a separate electronic device (not shown), such as a laptop, tablet, cell phone, or the like. The separate electronic device can be configured to analyze the signals from device 1150 and to display the results of the analysis, including display of temperature maps or images acquired by temperature sensors located within device 1150.

Figure 25A:
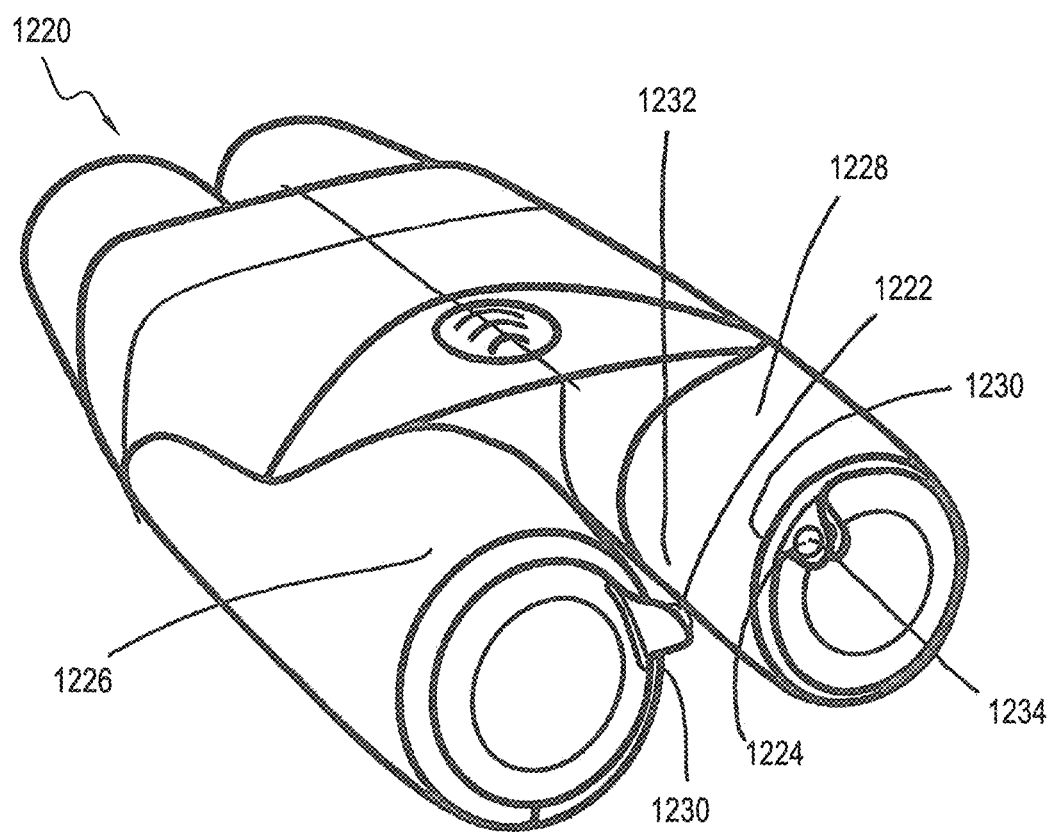
FIG. 25A shows a view of yet an even further device configured to locate at least one ABTT terminus and then to measure the temperature of the at least one ABTT terminus in accordance with an exemplary embodiment of the present disclosure.

FIG. 25A shows a view of yet an even further device, indicated generally at 1220, configured to locate at least one ABTT terminus 10 and then to measure the temperature of the at least one ABTT terminus 10 in accordance with an exemplary embodiment of the present disclosure. Temperature measurement device 1220 includes left sensor 1222 and right sensor 1224, each rotatably mounted on a front portion of device 1220. Device 1220 further includes a first optical member 1226 and a second optical member 1228, each having an outer periphery or edge 1230. First optical member 1226 and second optical member 1228 are configured such that an open space or volume 1232 is formed between first optical member 1226 and second optical member 1228. Each of first sensor 1222 and second sensor 1224 extend or protrude past outer periphery or edge 1230 into space or volume 2132 so as to be positioned to view ABTT terminus 10 when device 1220 is placed on the face of a subject. Each of right sensor 1222 and left sensor 1224 include a sensor surface 1234 that is adapted to view ABTT terminus 10, allowing eyes of user to see an image, hologram, virtual reality, and/or augmented reality displayed by way of first optical member 1226 and second optical member 1228, thereby allowing capturing a signal from ABTT terminus 10 while viewing an image provided by first optical member 1226 and second optical member 1228.

Figure 25B:
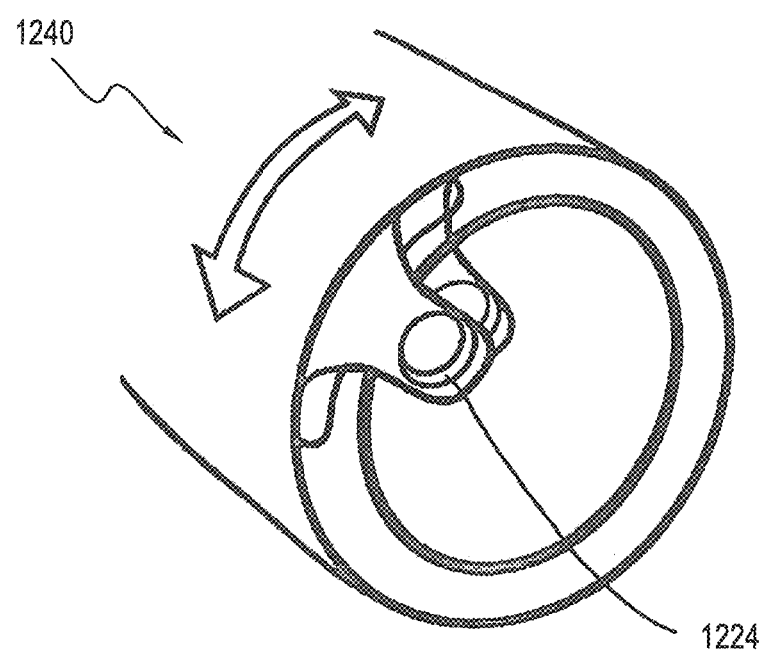
FIG. 25B shows a view of still an even further device configured to locate at least one ABTT terminus and then to measure the temperature of the at least one ABTT terminus in accordance with an exemplary embodiment of the present disclosure.

FIG. 25B shows a view of a portion of still an even further device, indicated generally at 1240, configured to locate at least one ABTT terminus and then to measure the temperature of the at least one ABTT terminus in accordance with an exemplary embodiment of the present disclosure. Device 1240 includes a single sensor, such as right sensor 1224. In addition, device 1240 indicates two of the plurality of optional positions available for right sensor 1224 by way of the rotational mounting of right sensor 1224. It should be understood that a variety of mechanisms including sliding and rotating can be used to align right sensor 1224 with ABTT terminus 10.

FIGS. 29-32 show another temperature measurement device in accordance with an exemplary embodiment of the present disclosure, indicated generally at 1200. Device 1200 is configured with a first device member 1202 and a second device member 1204, which are rotatably connected to each other. First device member 1202 includes a first arm 1206 and second device member 1204 includes a second arm 1208. Each of first arm 1206 and second arm 1208 include a temperature sensor 1210 positioned at an end thereof. Each temperature sensor 1210 is oriented to face the same direction. Temperature sensors 1210 are oriented to be parallel to each other. In addition, the outermost surface of temperature sensors 1210 that measure the thermal output of ABTT terminus 10 is approximately co-planar. Each temperature sensor 1210 is a spaced distance away from respective first device member 1202 and second device member 1204 to permit each temperature sensor 1210 to be positioned adjacent to an ABTT terminus 10 without interference of first device member 1202 and second device member 1204 with an associated face. Device 1200 is configured with at least one switch 1212 to actuate a temperature measurement process by actuating temperature sensors 1210. Because first device member 1202 and second device member 1204 are configured to swivel or rotate with respect to each other, first device member 1202 and second device member 1204 can be adjusted to accommodate the variation in spacing of eyes 32 from each other. Device 1200 may further include a connector 1214 that is configured to permit connection of signals from device 1200 that originate from temperature sensors 1210 to a separate electronic device (not shown), such as a laptop, tablet, cell phone, or the like. The separate electronic device can be configured to analyze the signals from device 1200 and to display the results of the analysis.

Figure 33:
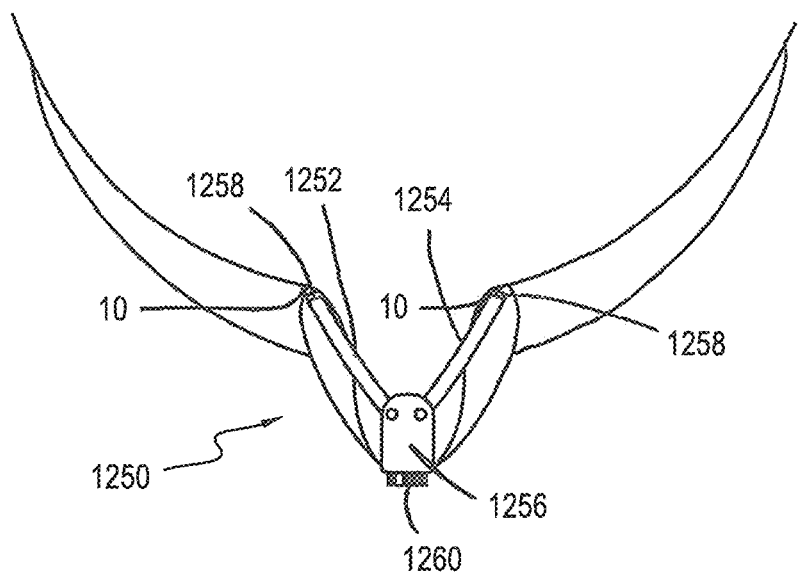
FIG. 33 shows a top view of another device configured to measure the temperature of at least one ABTT terminus, with the device positioned adjacent to a user's face, in accordance with an exemplary embodiment of the present disclosure.
Figure 34:
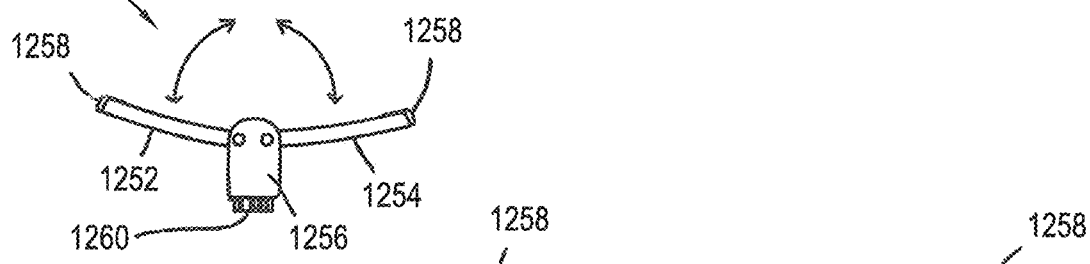
FIG. 34 shows another view of the device of FIG. 33, showing a range of motion for portions of the device.
Figure 35:
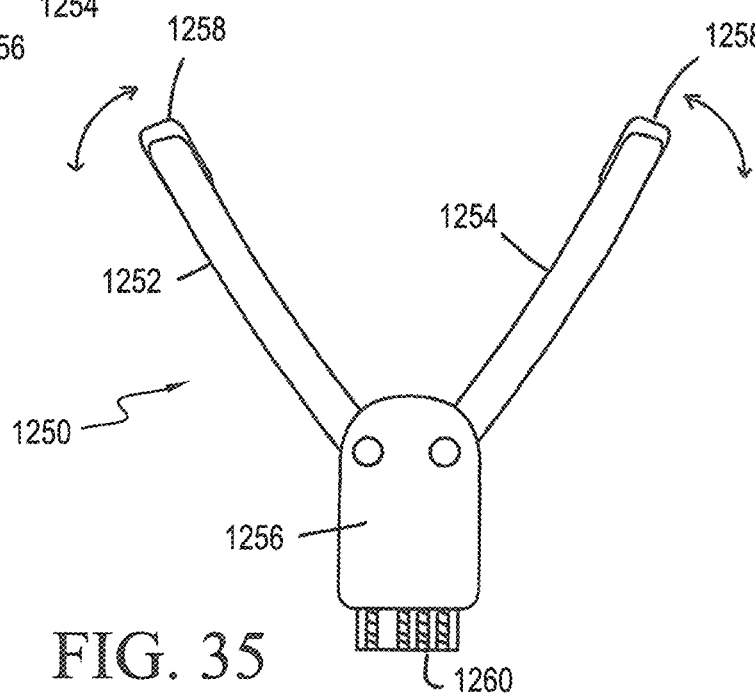
FIG. 35 shows a back view of the device of FIG. 33.
Figure 36:
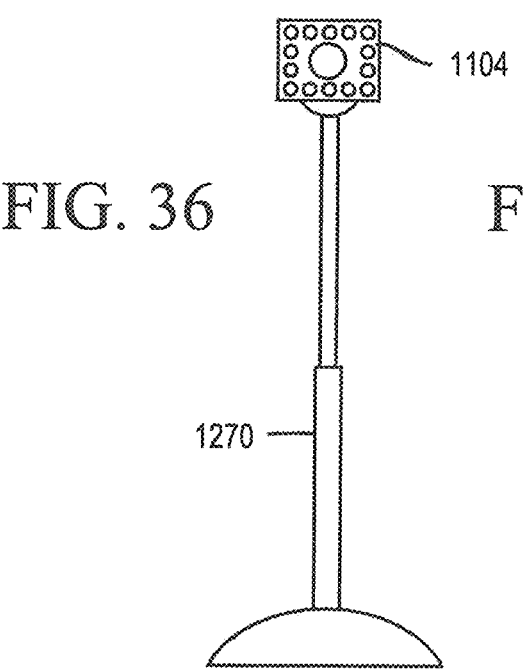
FIG. 36 shows a view of an apparatus configured to locate an ABTT terminus and then to measure the temperature of the ABTT terminus, in accordance with an exemplary embodiment of the present disclosure.
Figure 37:
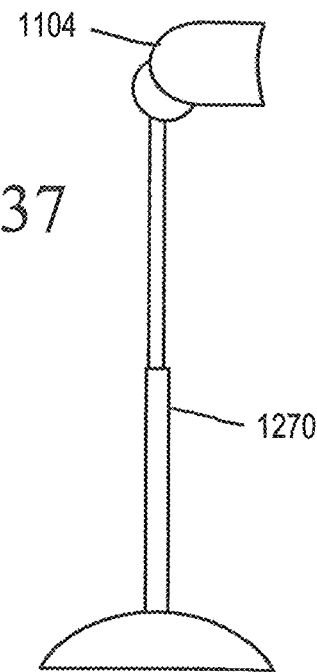
FIG. 37 shows a side view of the apparatus of FIG. 36.

FIGS. 33-35 show another temperature measurement device in accordance with an exemplary embodiment of the present disclosure, indicated generally at 1250. Device 1250 is configured with a first device member 1252 and a second device member 1254, both of which are rotatably supported on a device support 1256. As with devices 1150 and 1200, first device member 1252 and second device member 1254 are configured to swivel or rotate with respect to each other, such that first device member 1252 and second device member 1254 can be adjusted to accommodate the variation in spacing of eyes 32 from each other. First device member 1252 and second device member 1254 are each configured to support a temperature sensor 1258. In the exemplary embodiment of FIGS. 33-35, first device member 1252 and second device member 1254 are configured to move independently with respect to each other. In another embodiment, first device member 1252 and second device member 1254 can be configured to move each other through a frictional or gear arrangement. In yet another embodiment, first device member 1252 and second device member can be configured to slide laterally or transversely to change the spacing between first device member 1252 and second device member 1254. Device 1250 is further configured to include a connector 1260 that is configured to permit connection of signals from device 1250 that originate from temperature sensors 1258 to a separate electronic device (not shown), such as a laptop, tablet, cell phone, or the like. The separate electronic device can be configured to analyze the signals from device 1250 and to display the results of the analysis.

Figure 38:
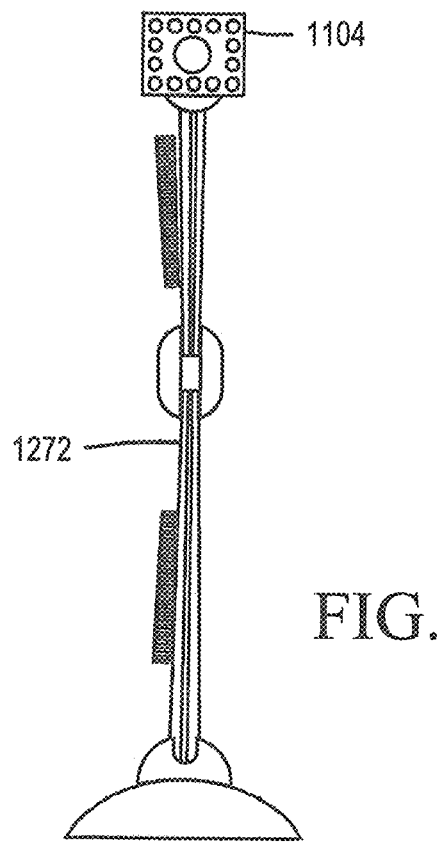
FIG. 38 shows a view of another apparatus configured to locate an ABTT terminus and then to measure the temperature of the ABTT terminus, in accordance with an exemplary embodiment of the present disclosure.
Figure 39:
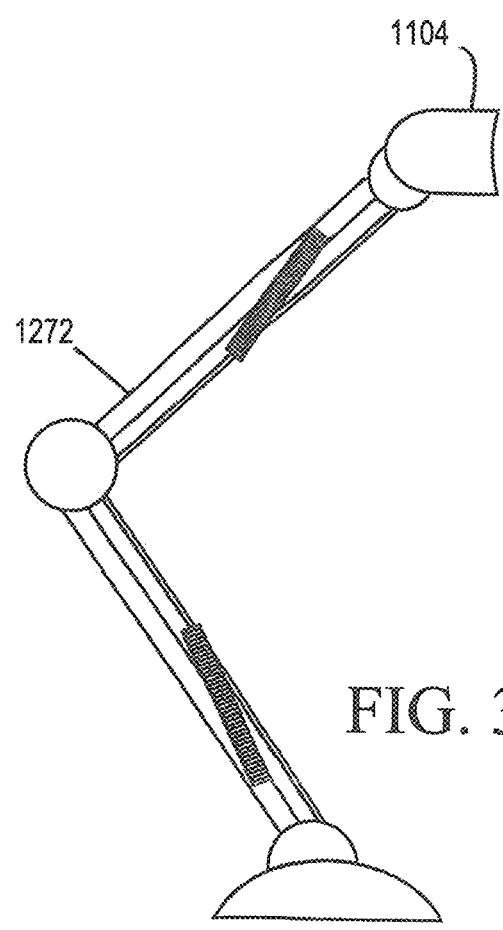
FIG. 39 shows a side view of the apparatus of FIG. 38.
Figure 40:
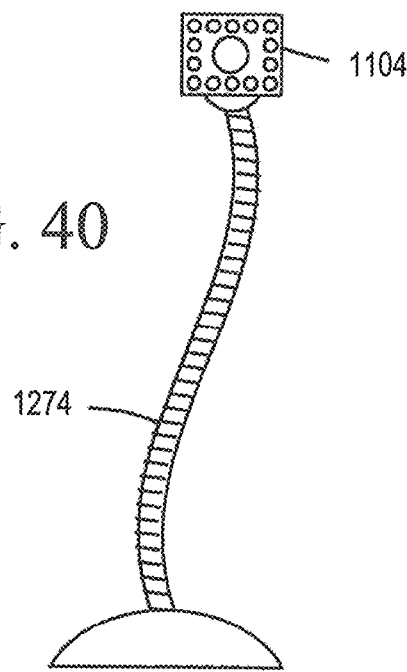
FIG. 40 shows a front view of yet another apparatus configured to locate an ABTT terminus and then to measure the temperature of the ABTT terminus, in accordance with an exemplary embodiment of the present disclosure.
Figure 41:
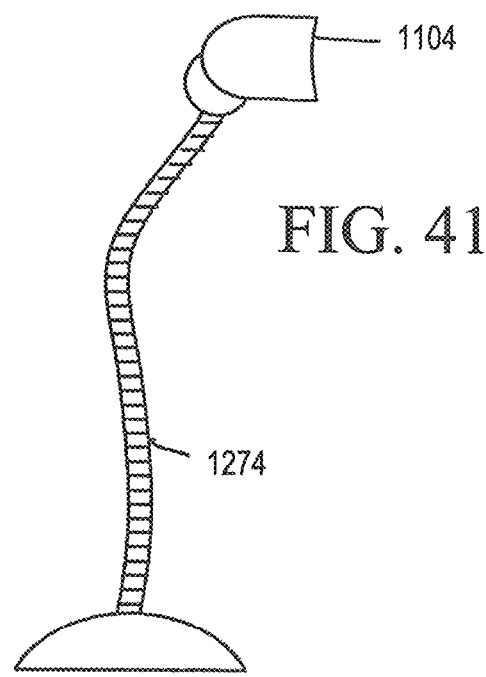
FIG. 41 shows a side view of the apparatus of FIG. 40.
Figure 42:
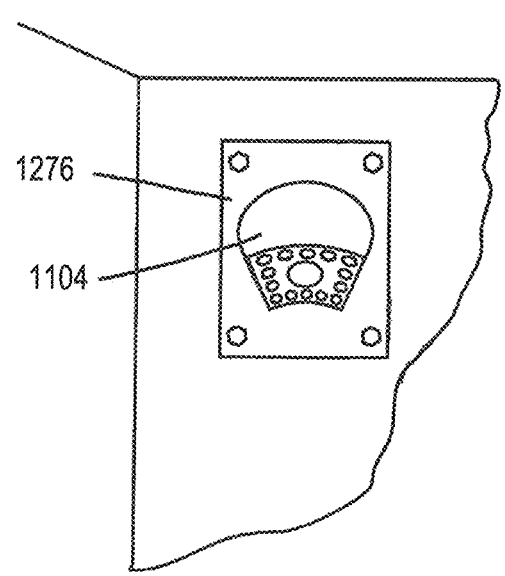
FIG. 42 shows a front view of a further apparatus configured to locate an ABTT terminus and then to measure the temperature of the ABTT terminus, in accordance with an exemplary embodiment of the present disclosure.
Figure 43:
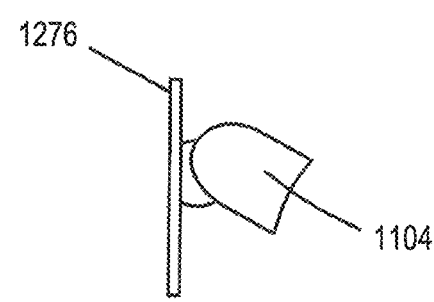
FIG. 43 shows a side view of the apparatus of FIG. 42.
Figure 44:
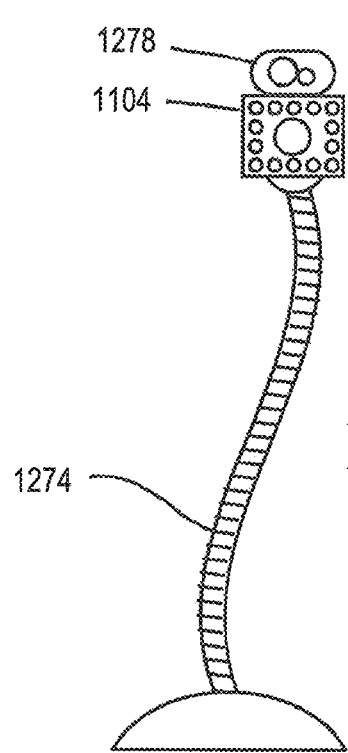
FIG. 44 shows a front view of a still further apparatus configured to locate an ABTT terminus and then to measure the temperature of the ABTT terminus, in accordance with an exemplary embodiment of the present disclosure.
Figure 45:
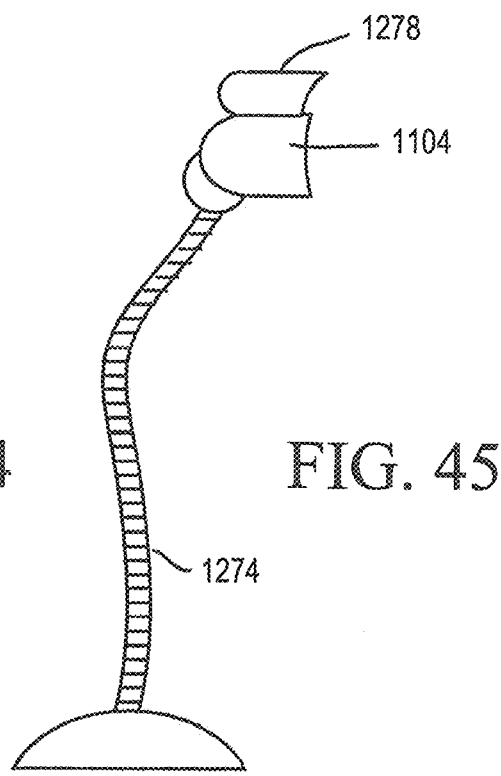
FIG. 45 shows a side view of the apparatus of FIG. 44.
Figure 46:
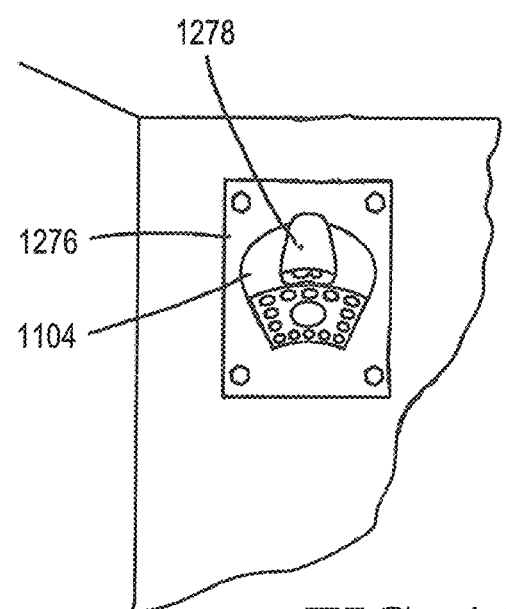
FIG. 46 shows a front view of an even further apparatus configured to locate an ABTT terminus and then to measure the temperature of the ABTT terminus, in accordance with an exemplary embodiment of the present disclosure.

IR camera imaging camera 1104, shown positioned on a handle in FIGS. 23 and 24, can be mounted in other ways, such as are shown in FIGS. 36-43. FIGS. 19 and 20 show camera 1104 positioned or located on a telescoping support 1270 suitable to be positioned on a desk or table. FIGS. 38 and 39 show camera 1104 positioned or located on a swing arm support 1272. FIGS. 40 and 41 show camera 1104 positioned or located on a goose neck support 1274. FIGS. 42 and 43 show camera 1104 positioned or located on a wall mount support 1276.

Other devices may be collocated with camera 1104. For example, FIGS. 44-47 show a configuration of camera 1104 that includes a transceiver, transmitter, or receiver 1278 configured to communicate with a separate electronic device, e.g., a laptop, cell phone, tablet, non-transitory storage medium, etc.

Figure 47:
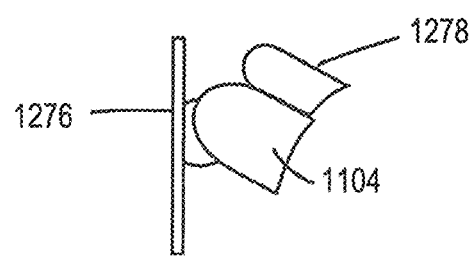
FIG. 47 shows a side view of the apparatus of FIG. 46.
Figure 47A:
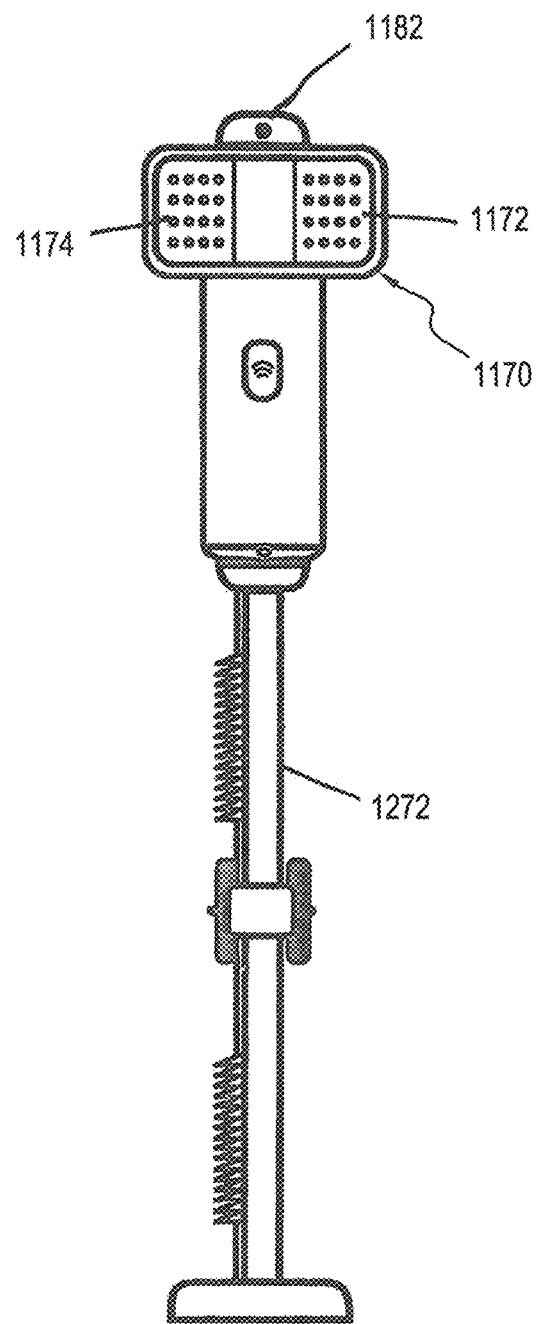
FIG. 47A shows a view of the device of FIGS. 24C and 24D positioned on a swing arm support apparatus.
Figure 47B:
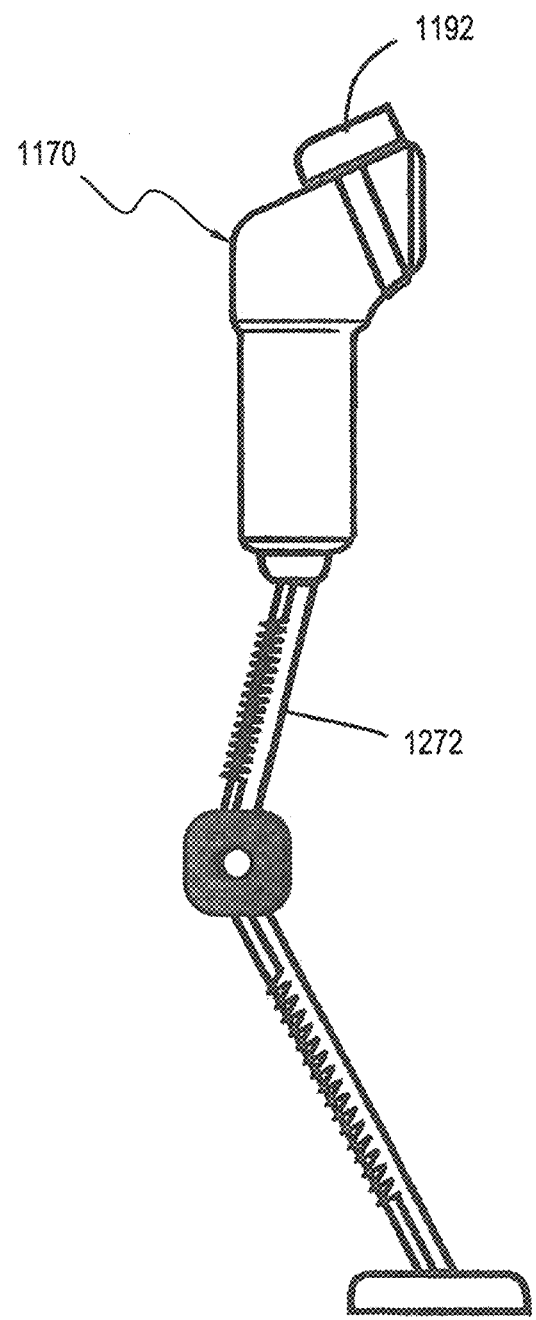
FIG. 47B shows another view of the device of FIG. 47A.

FIGS. 47A and 47B show device 1170 of FIGS. 24C and 24D positioned on swing arm support 1272 for adjustment to different heights of subjects being measured. In the embodiment of FIG. 47A, a digital camera 1192 is positioned above right sensor array 1172 and left sensor array 1174, and said camera is adapted to superimpose a digital image on top of an infrared image to allow identification of certain anatomic landmarks in relation to the amount of thermal emission of said anatomic landmarks. FIG. 47B is a side view of the elements shown in FIG. 47A and shows shortening.

Figure 47C:
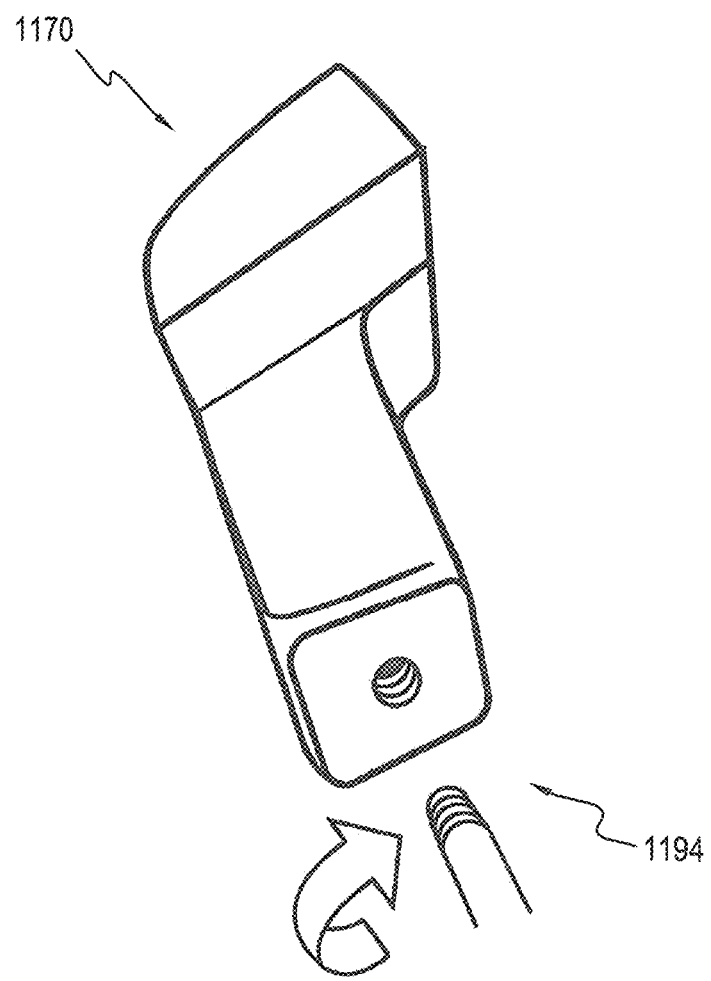
FIG. 47C shows a view of a screw-based mounting mechanism for the apparatus of FIG. 47A.
Figure 47D:
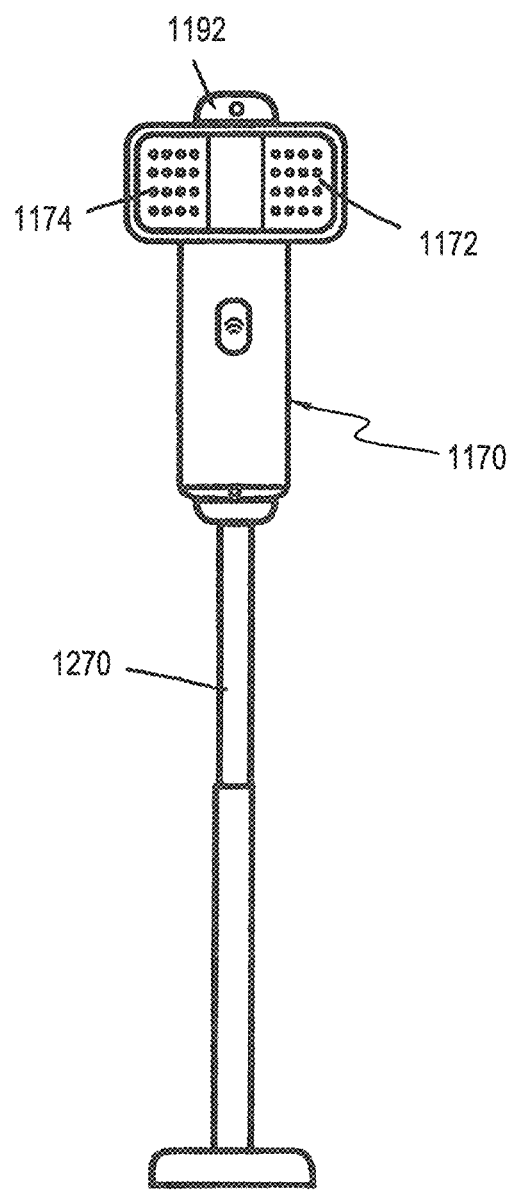
FIG. 47D shows a view of the device of FIGS. 21C and 21D positioned on a telescoping support.
Figure 47E:
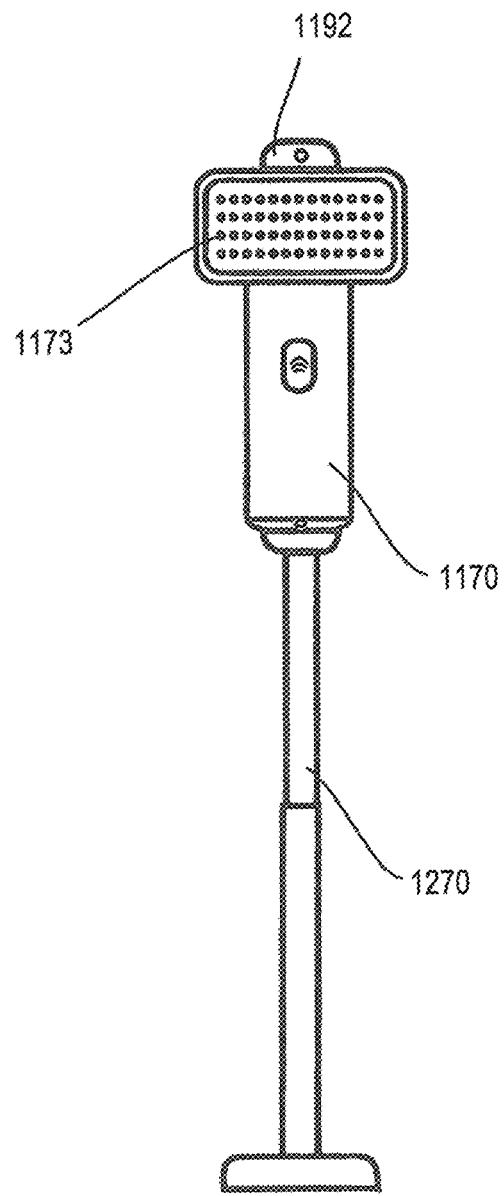
FIG. 47E shows a view of another device positioned on the telescoping support in accordance with an exemplary embodiment of the present disclosure.

FIGS. 47C and 47D show a screw-based mounting mechanism 1194 for device 1170. FIG. 47D shows device 1170 positioned on telescoping support 1270 for adjustment to different height of subjects being measured. Device 1170 is configured similar to the arrangement of FIGS. 47A and 47B and includes digital camera 1192 positioned above right sensor array 1172 and left sensor array 1174. Although infrared detector was shown as a dual detector or dual sensor array, right and left sensor arrays, it should be understood that one single array adapted to detect signal from both the right ABTT and the left ABTT can be used, and are shown in FIG. 47E as one single sensor array 1173. It should also be understood that a single sensor array can be used in any embodiment of the present invention.

Figure 48:
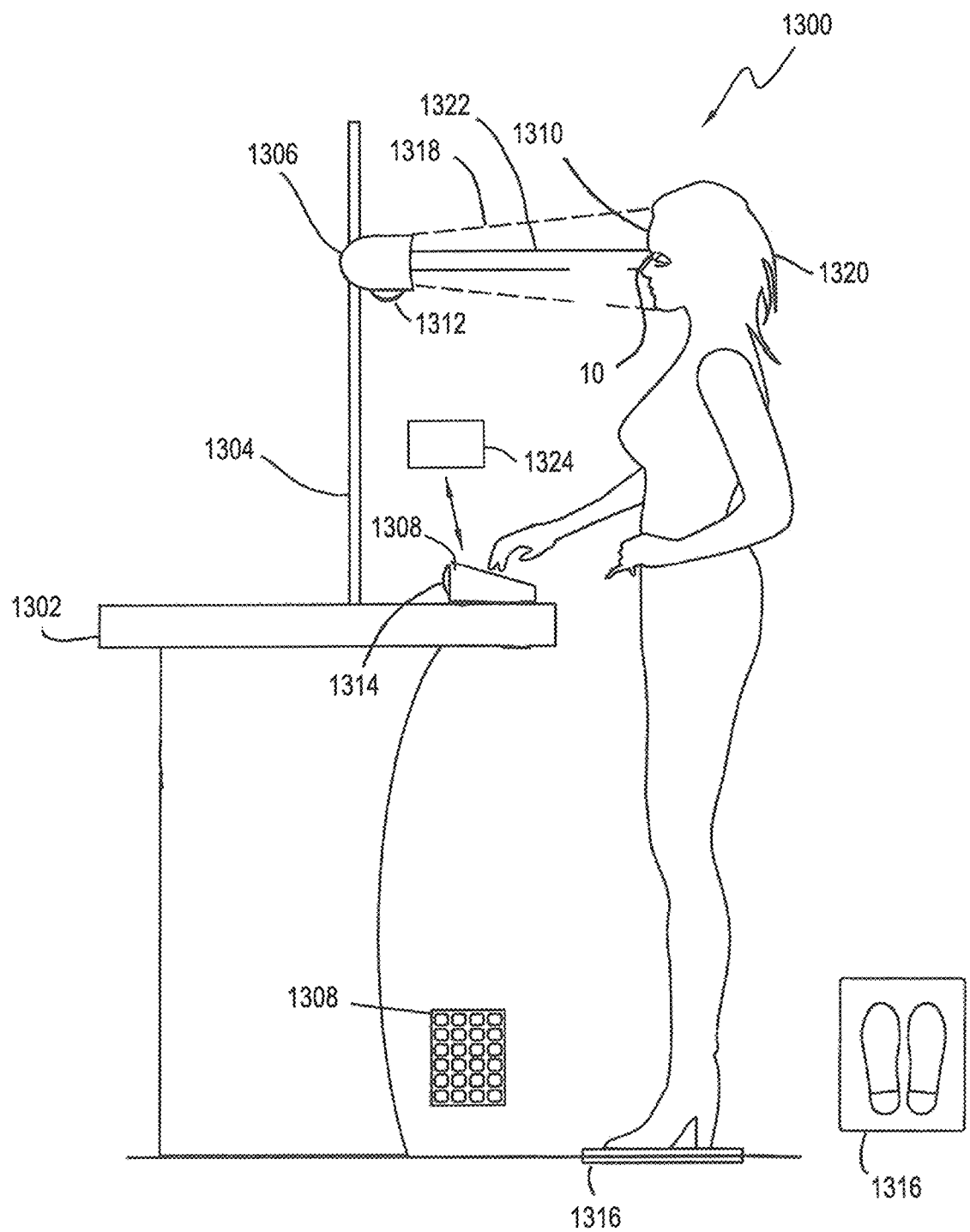
FIG. 48 shows a view of a system configured to locate an ABTT terminus and then to measure the temperature of the ABTT terminus, in accordance with an exemplary embodiment of the present disclosure.
Figure 49:
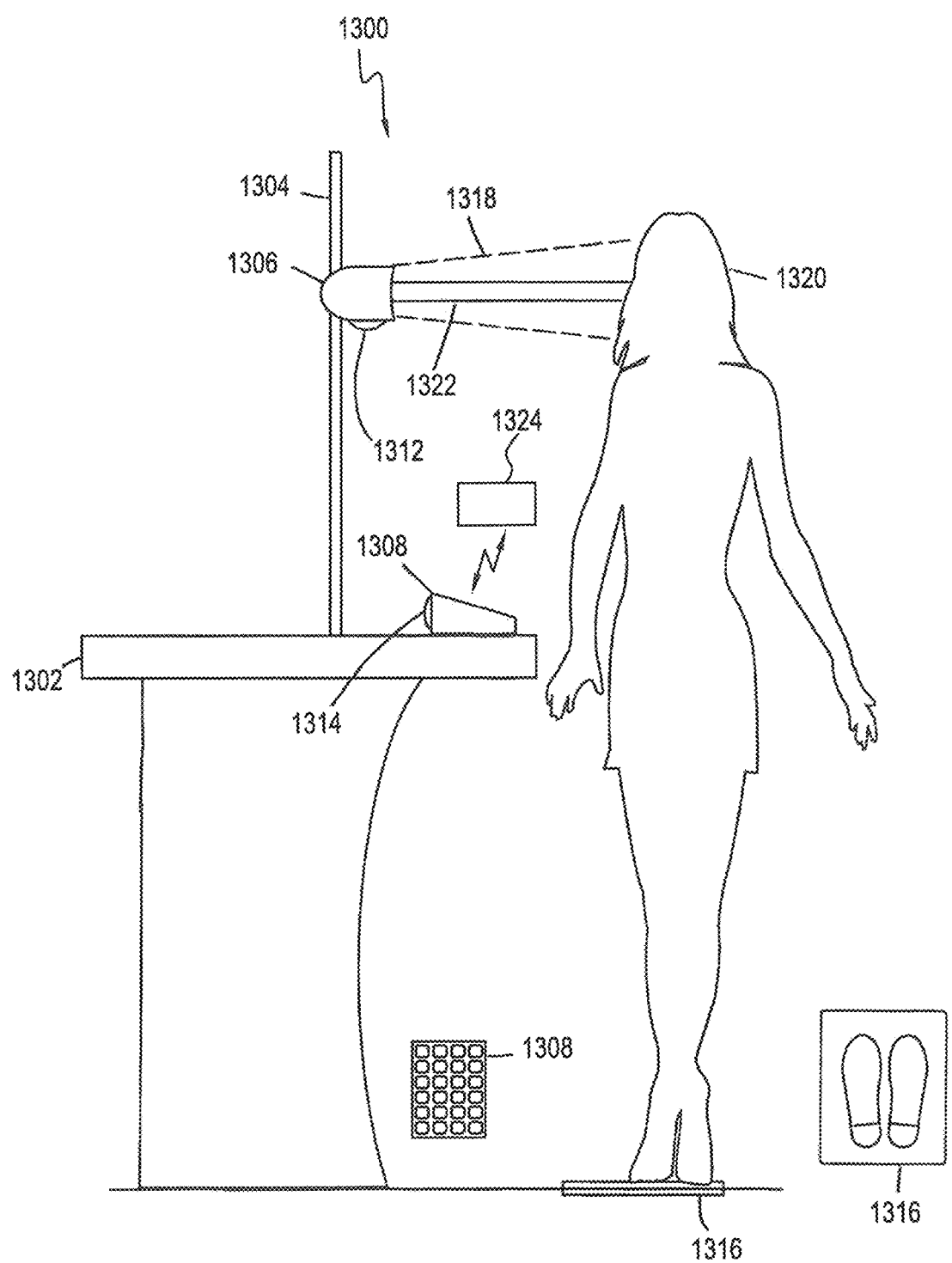
FIG. 49 shows another view of the system of FIG. 48.
Figure 50:
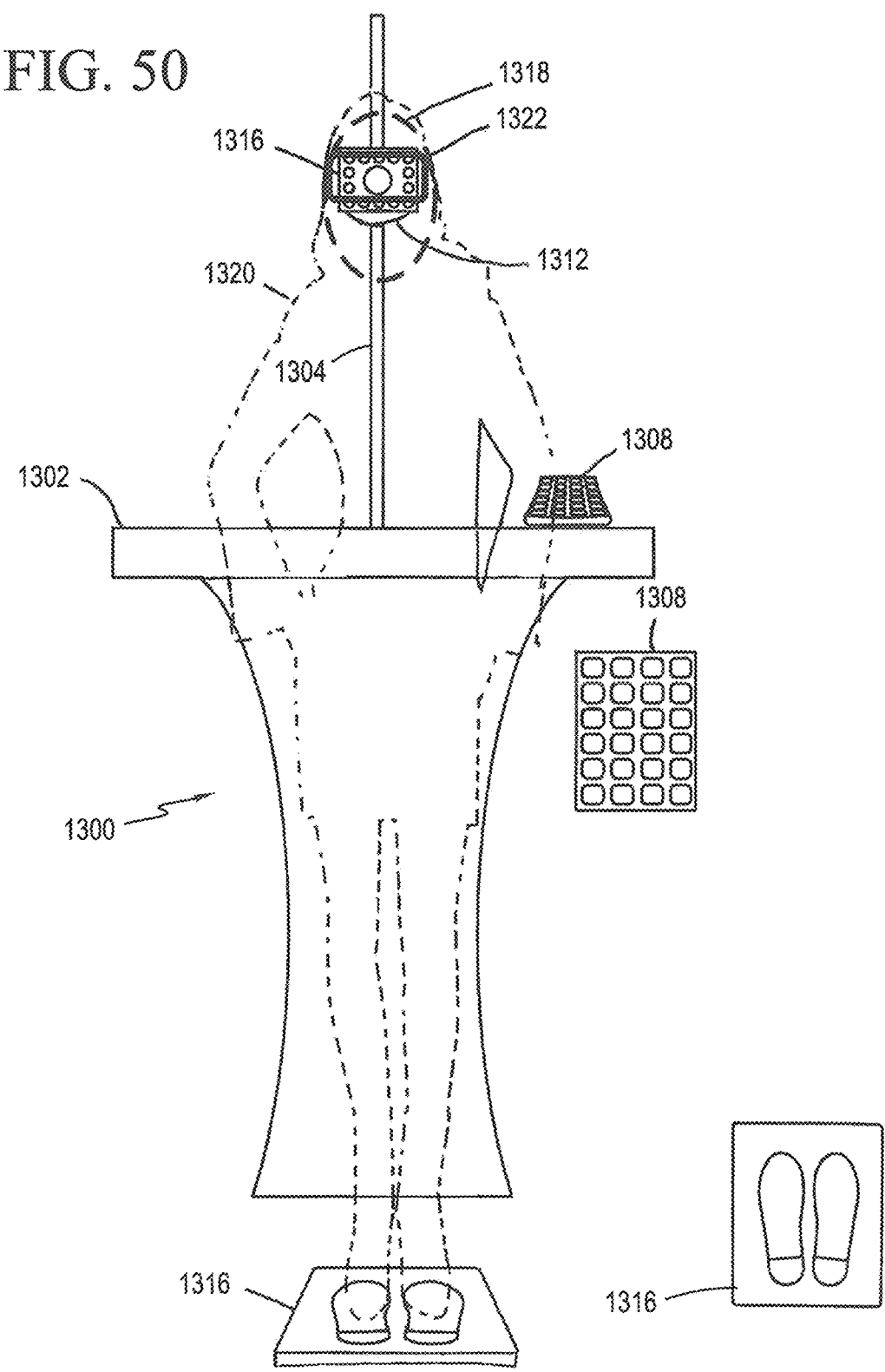
FIG. 50 shows a further view of the system of FIG. 48.

FIGS. 48-50 show a system configured to locate ABTT terminus 10 and then to measure the temperature of ABTT terminus 10, in accordance with an exemplary embodiment of the present disclosure, indicated generally at 1300. System 1300 is configured to include a desk, table, or platform 1302 that is further configured to support element of system 1300. System 1300 is further configured to include a support system 1304 configured to support a movable IR camera 1306. Support system 1304 is configured to allow camera 1306 to be movable or adjustable to a plurality of vertical positions to be able to locate at least one ABTT terminus 10. In an exemplary embodiment, camera 1306 is moved manually. In another exemplary embodiment, camera 1306 is moved by way of a controller, described in more detail herein. In a further exemplary embodiment, camera 306 is automatically moveable to locate a face and at least one ABTT terminus 10.

System 1300 is further configured to include a control device 1308 that can be configured to include a keypad, microphone, USB or other port, card scanner, or other device to provide various control functions for system 1300. Such control functions can include movement of IR camera 1306 along support system 1304 to align IR camera 1306 with a face 1310. IR camera 1306 can be configured to include a connector (not shown), a transceiver 1312, or both. Similarly, control device 1308 can be configured to include a connector (not shown), a transceiver 1314, or both. Thus, control device 1308 can communicate with IR camera 1306 by way of a cable (not shown) or by way of transceivers 1312 and 1314. System 1300 can further be configured to include a pressure or presence detection device 1316 that includes a pressure or presence sensor and is configured to communicate with control device 1308 either through a cable (not shown) or wirelessly.

It should be understood that IR camera 1306 includes a FOV 1318 of a certain angle. In an exemplary embodiment, the configuration and position of IR camera 1306 is such that FOV 1318 is sufficiently large to include most or all of a subject or patient's face 1310 when a subject 1320 is standing at a location of pressure or presence detection device 1316. It should be understood that within FOV 1318 is a smaller two-dimensional area 1322 that corresponds to the area of ABTT terminus 10 and an area directly adjacent or next to ABTT terminus 10.

To operate system 1300, subject 1320 stands on pressure or presence detection device 1316, which initiates or actuates system 1300. Pressure or presence detection device 1316 can immediately provide the weight of subject 1320. In an exemplary embodiment, subject 1320 can begin a temperature measurement operation by pressing a key on control device 1308. Alternatively, the presence of subject 1320 on pressure detection device 1316 can initiate a temperature measurement operation. As yet another alternative, a separate electronic device 1324, such as a cell phone, laptop, tablet, etc., can be configured to communicate with system 1300 and to initiate system 1300 operation as well as control the functions of system 1300.

In an exemplary embodiment, subject 1320 either manually moves IR camera 1306 to be at an eye level, or uses controls on control device 1308 to position IR camera 1306 vertically along support system 1304. In another exemplary embodiment, IR camera 1306 moves along support system 1304, scanning for a hot spot represented by ABTT terminus 10. In this latter embodiment, once IR camera 1306 identifies the hot spot represented by ABTT terminus 10, IR camera 1306 positions itself to acquire temperature signals from ABTT terminus 10. It should be noted that the movement of IR camera 1306 also provides system 1300 with the ability to measure the height of subject 1320, since IR camera 1306 can determine the location of the top of a head of subject 1320 through its thermal imaging capability. Alternatively, once IR camera 1306 has located ABTT terminus 10, system 1300 can estimate the height of subject 1320 given that the average distance from ABTT terminus 10 to the top of a typical person's head is a previously measured distance.

Once IR camera 1306 is positioned to measure the temperature of ABTT terminus 10, acquisition and analysis of temperature data begins, which may be accomplished in control device 1308 or in separate electronic device 1324. The data acquisition process can be configured to include a plurality of time intervals, depending on the type of data analysis required. For simple temperature measurements, the length of data acquisition is typically seconds, e.g., 10 to 20 seconds. For complex measurements, the length of data acquisition can be minutes. Some data acquisition intervals may be very lengthy and it can be beneficial to provide a chair for subject 1320.

Figure 50A:
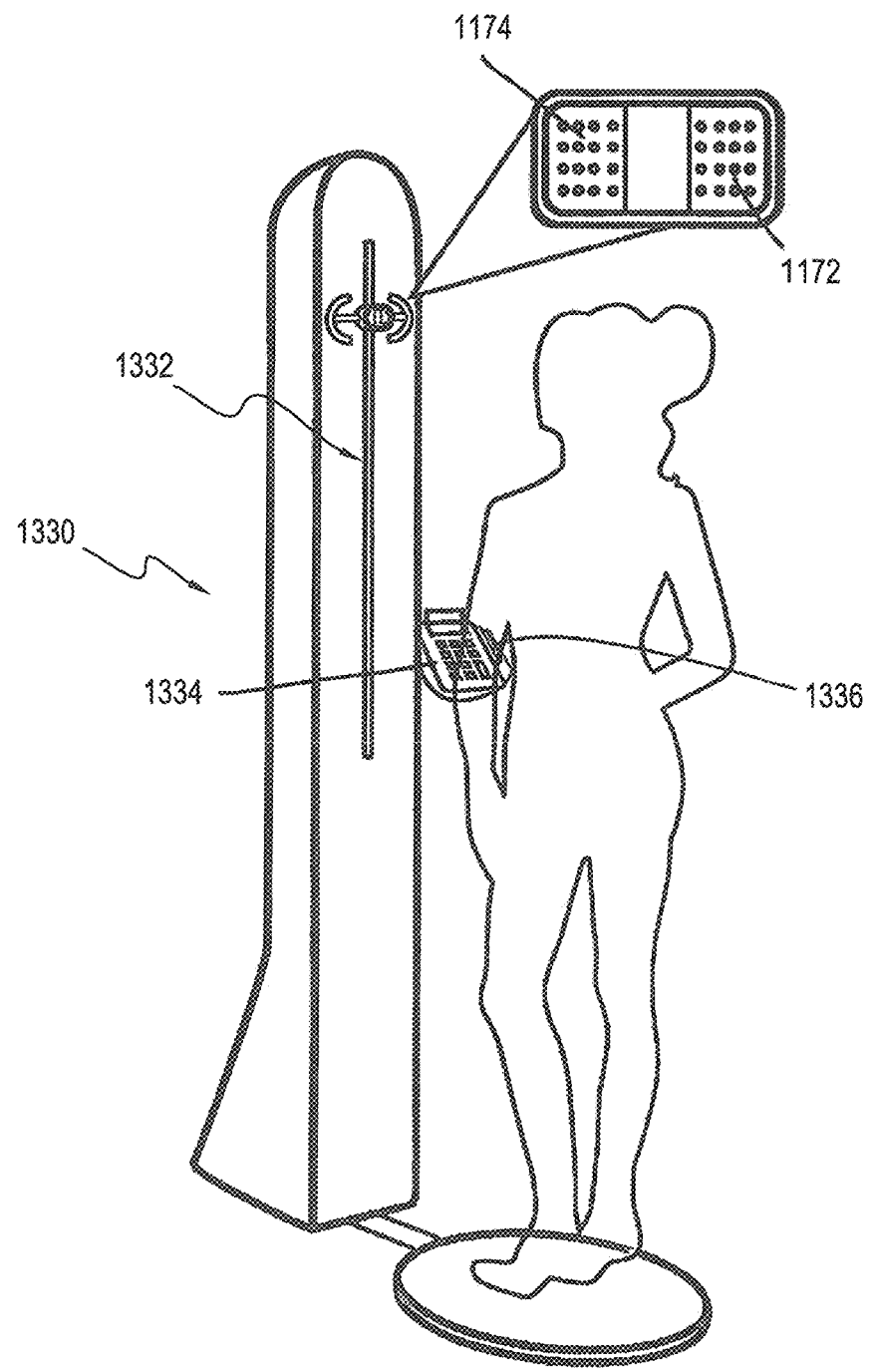
FIG. 50A shows a view of another system configured to locate an ABTT terminus and then to measure the temperature of the ABTT terminus, in accordance with an exemplary embodiment of the present disclosure.
Figure 50B:
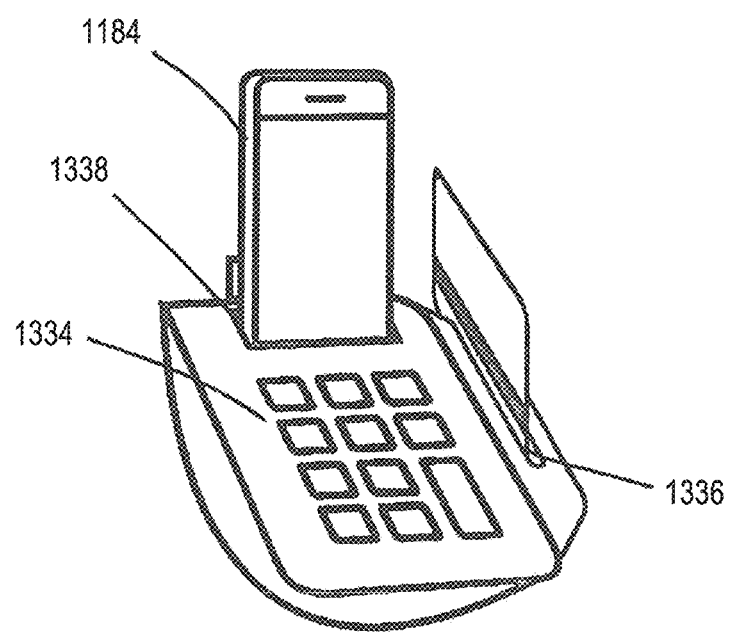
FIG. 50B shows a view of a card reader of the system of FIG. 50A.

FIGS. 50A and 50B show views of another system, indicated generally at 1330, configured to locate ABTT terminus 10 and then to measure the temperature of ABTT terminus 10, in accordance with an exemplary embodiment of the present disclosure. ABTT temperature measurement system includes right sensor array 1172, left sensor array 1174, a sliding mechanism 1332 to change the position of right sensor array 1172 and left sensor array 1174, and a combination keypad and card reader 1334 having a card slot 1336. In this embodiment there is no display, such as might be used for advertisements, and measurement is done by inserting an ID card in card slot 1336 or inserting a credit card in card slot 1336 for payment. As shown in FIG. 50B, keypad and card reader 1334 includes a second slot 1338 for connecting with electronic device 1184 being operatively coupled with system 1330 during measurement, in which electronic device 1184, for example a cell phone, when placed in electronic device slot 1338 provides height information to system 1330 allowing thereby automatic height adjustment by sliding mechanism 1332. Keypad and card reader 1334 can include a reader for a credit card in the event a user is purchasing measurement, an identification card, and the like.

Figures 51, 52:
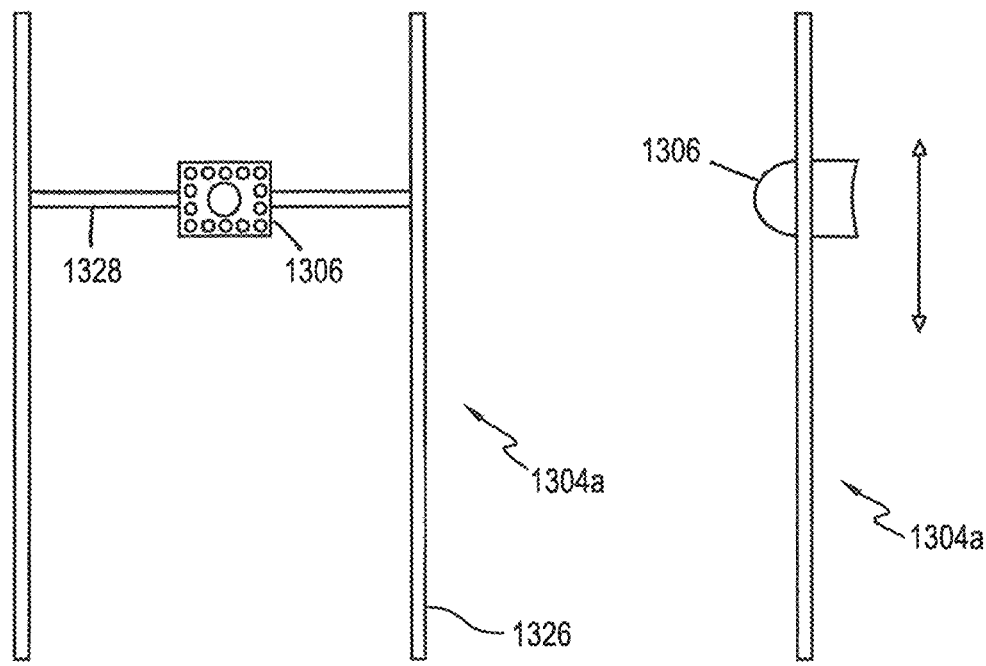
FIG. 51 shows a view of a support structure for the system of FIG. 48, in accordance with an exemplary embodiment of the present disclosure.
FIG. 52 shows a side view of the support structure of FIG. 51.
Figures 53, 54:
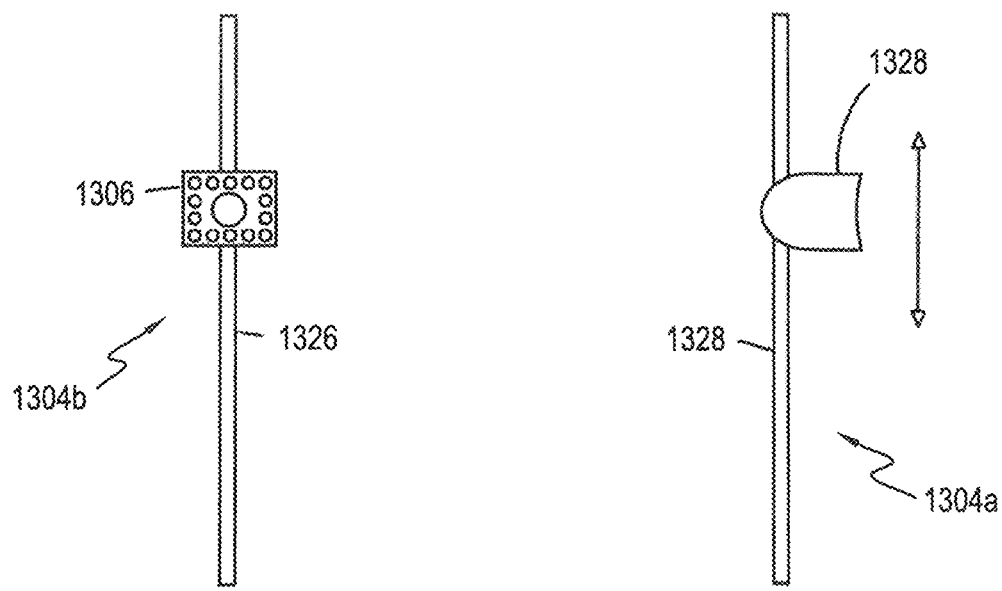
FIG. 53 shows a view of an alternative embodiment support structure for the system of FIG. 48, in accordance with an exemplary embodiment of the present disclosure.
FIG. 54 shows a side view of the support structure of FIG. 53.
Figure 55:
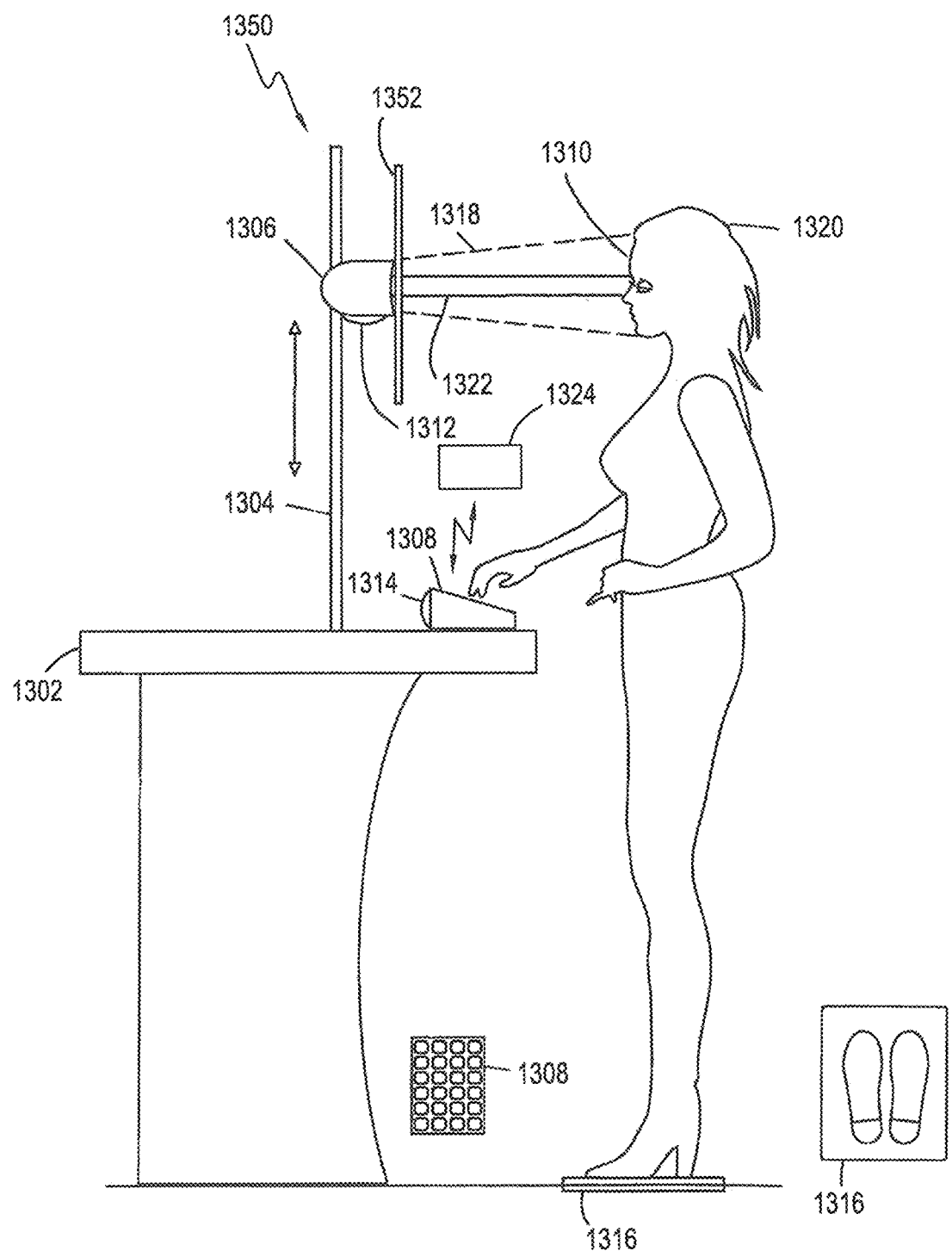
FIG. 55 shows a view of another system configured to locate an ABTT terminus and then to measure the temperature of the ABTT terminus, in accordance with an exemplary embodiment of the present disclosure.
Figure 56:
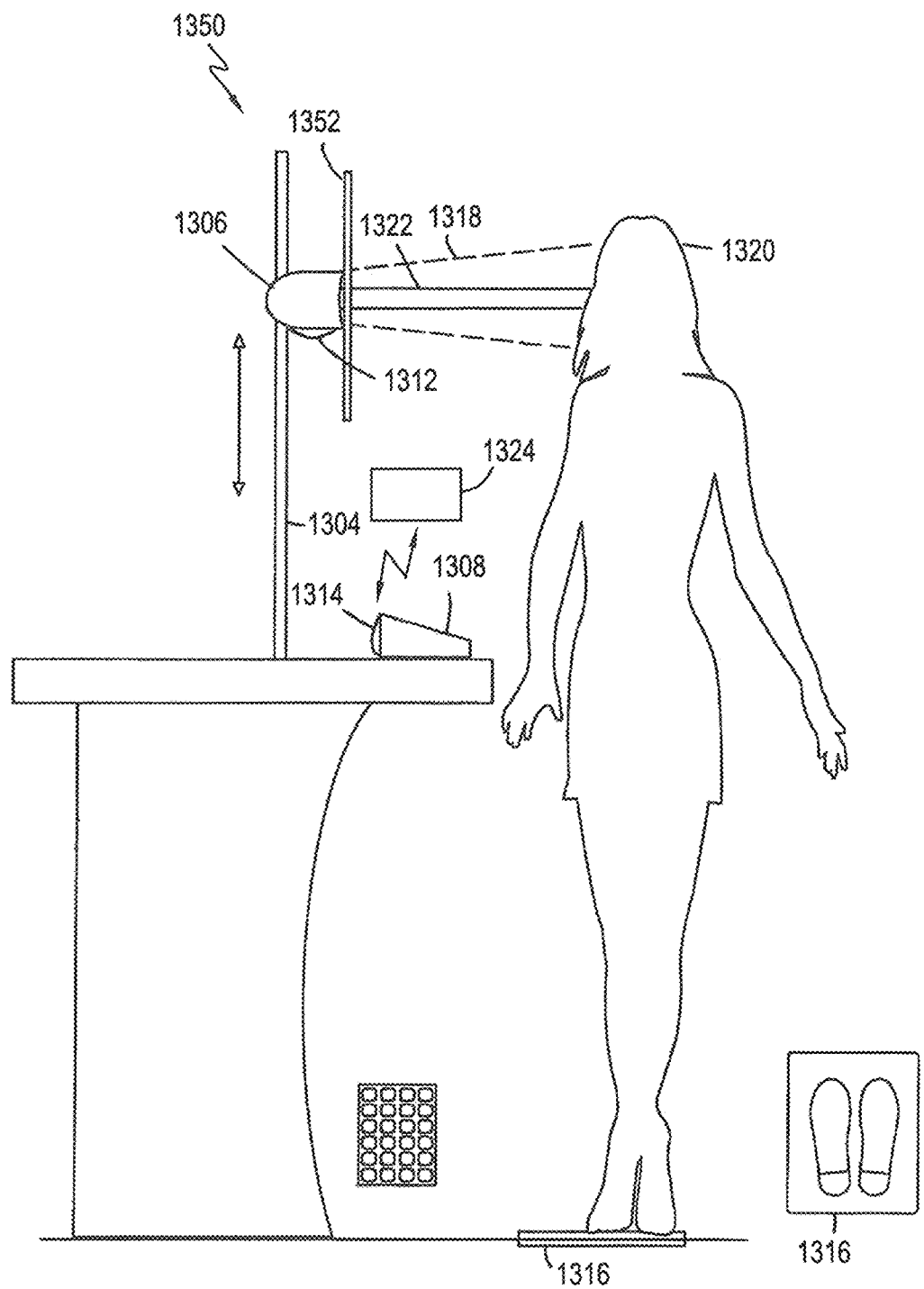
FIG. 56 shows another view of the system of FIG. 55.
Figure 60:
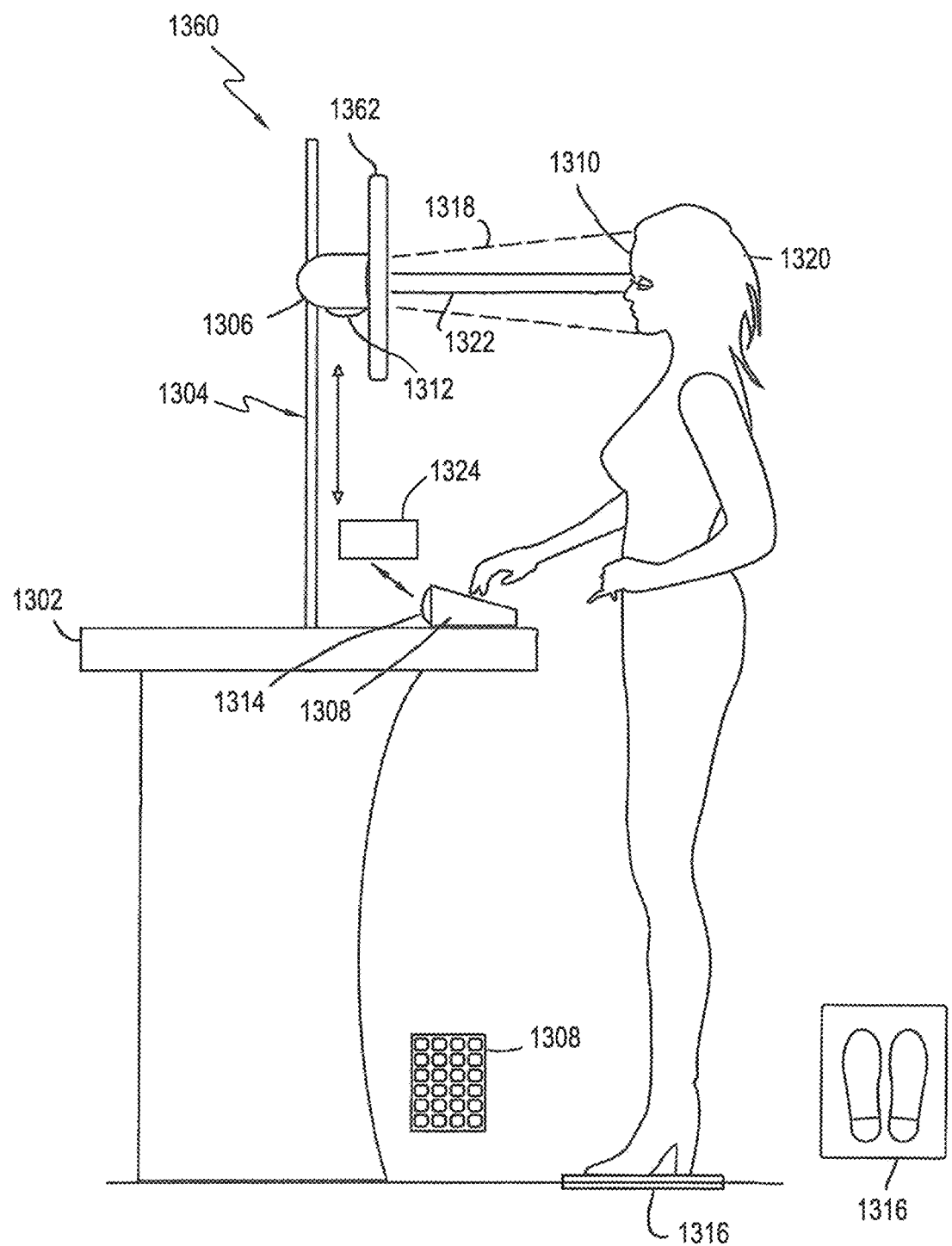
FIG. 60 shows a view of a further system configured to locate an ABTT terminus and then to measure the temperature of the ABTT terminus, in accordance with an exemplary embodiment of the present disclosure.
Figure 61:
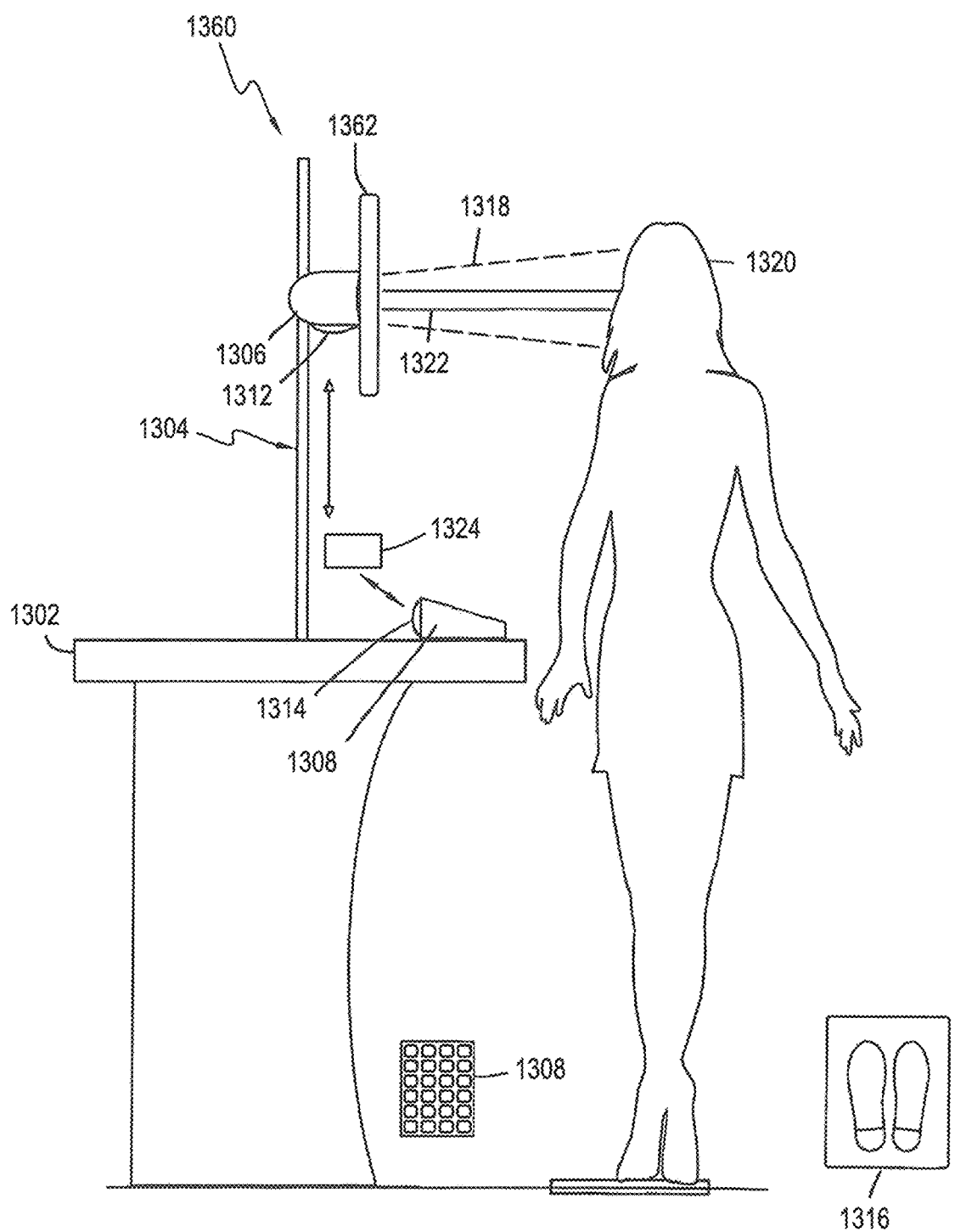
FIG. 61 shows another view of the system of FIG. 60.
Figure 62:
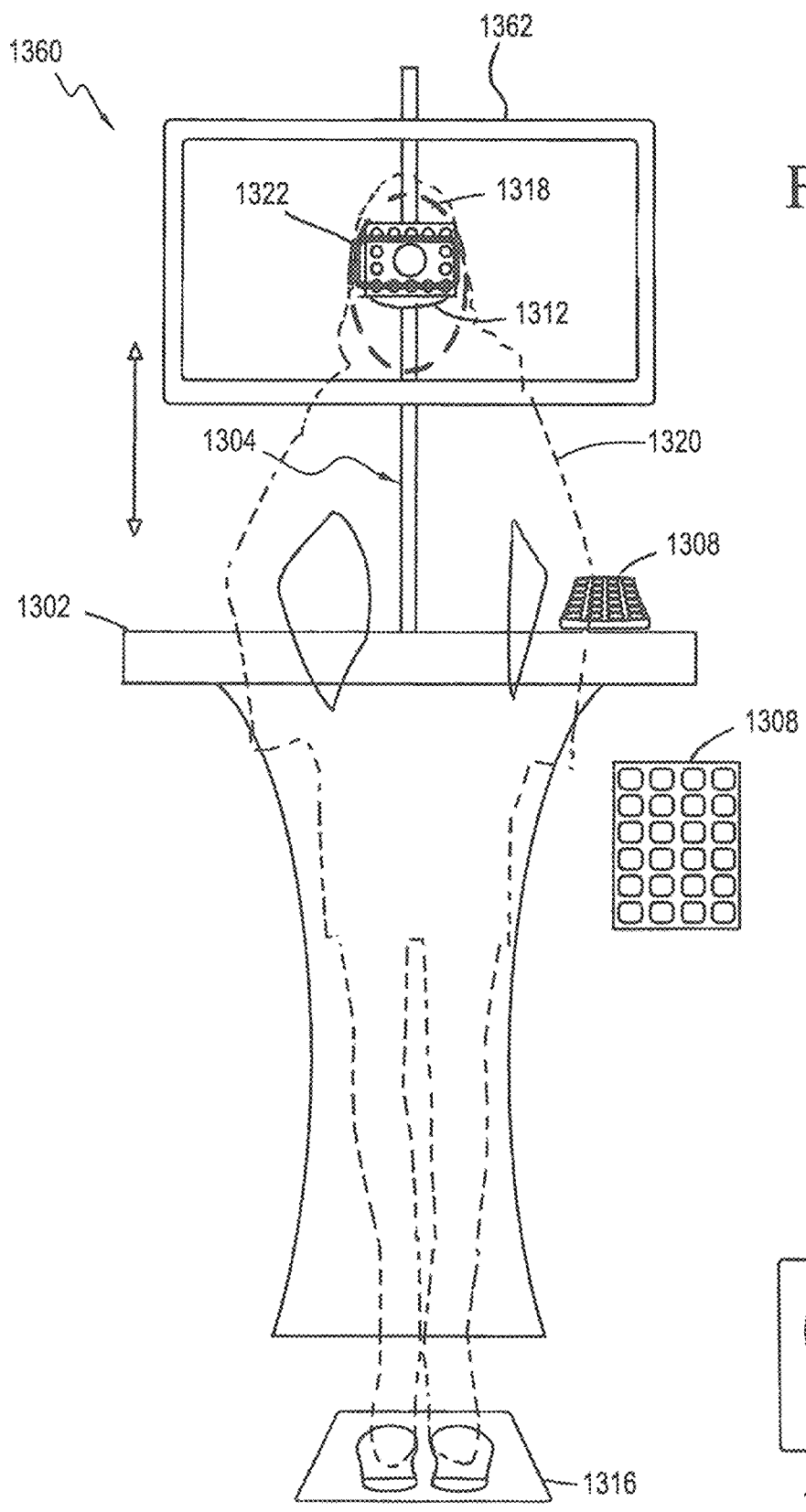
FIG. 62 shows a further view of the system of FIG. 60.
Figure 66:
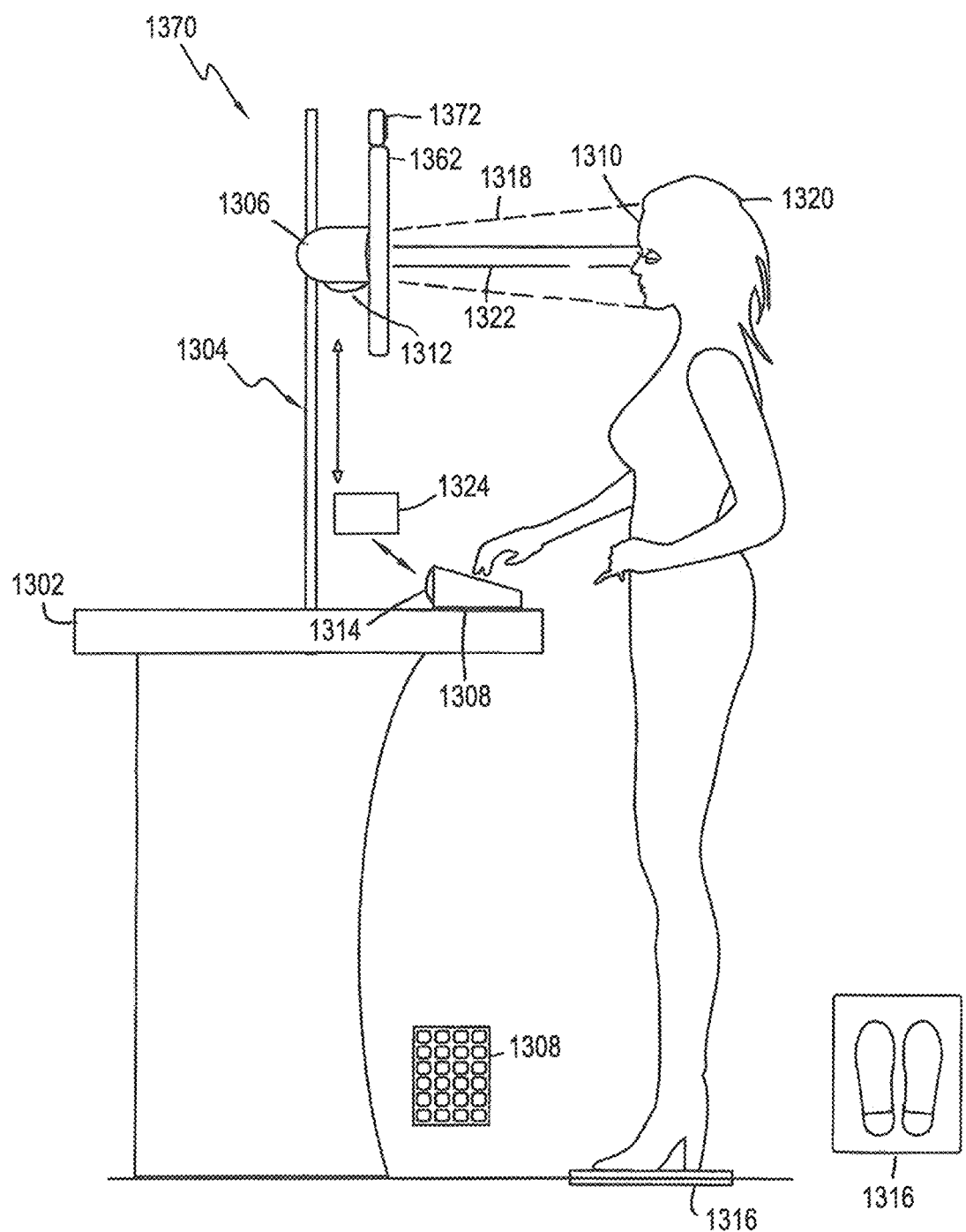
FIG. 66 shows a view of an even further system configured to locate an ABTT terminus and then to measure the temperature of the ABTT terminus, in accordance with an exemplary embodiment of the present disclosure.
Figure 67:
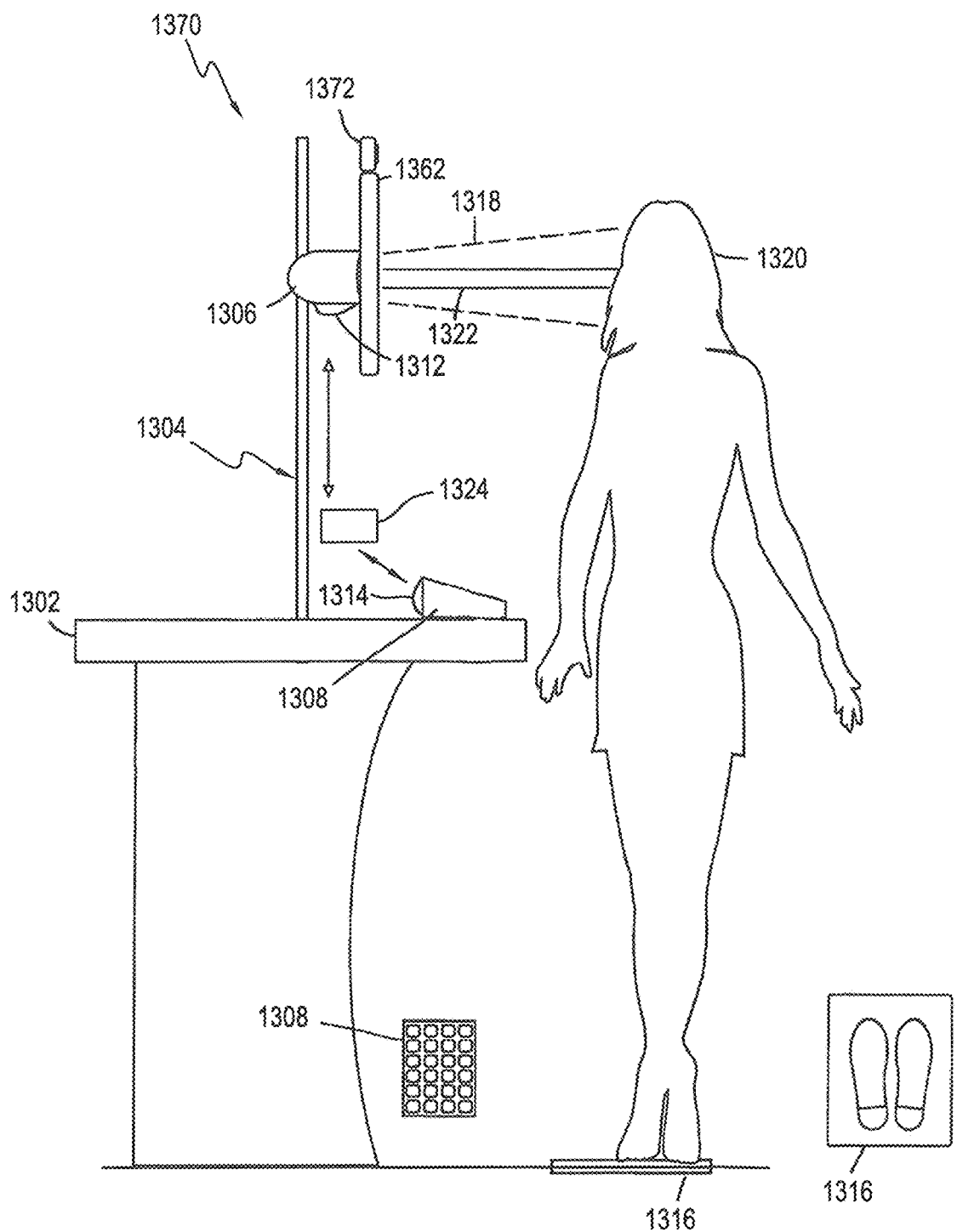
FIG. 67 shows another view of the system of FIG. 66.
Figure 68:
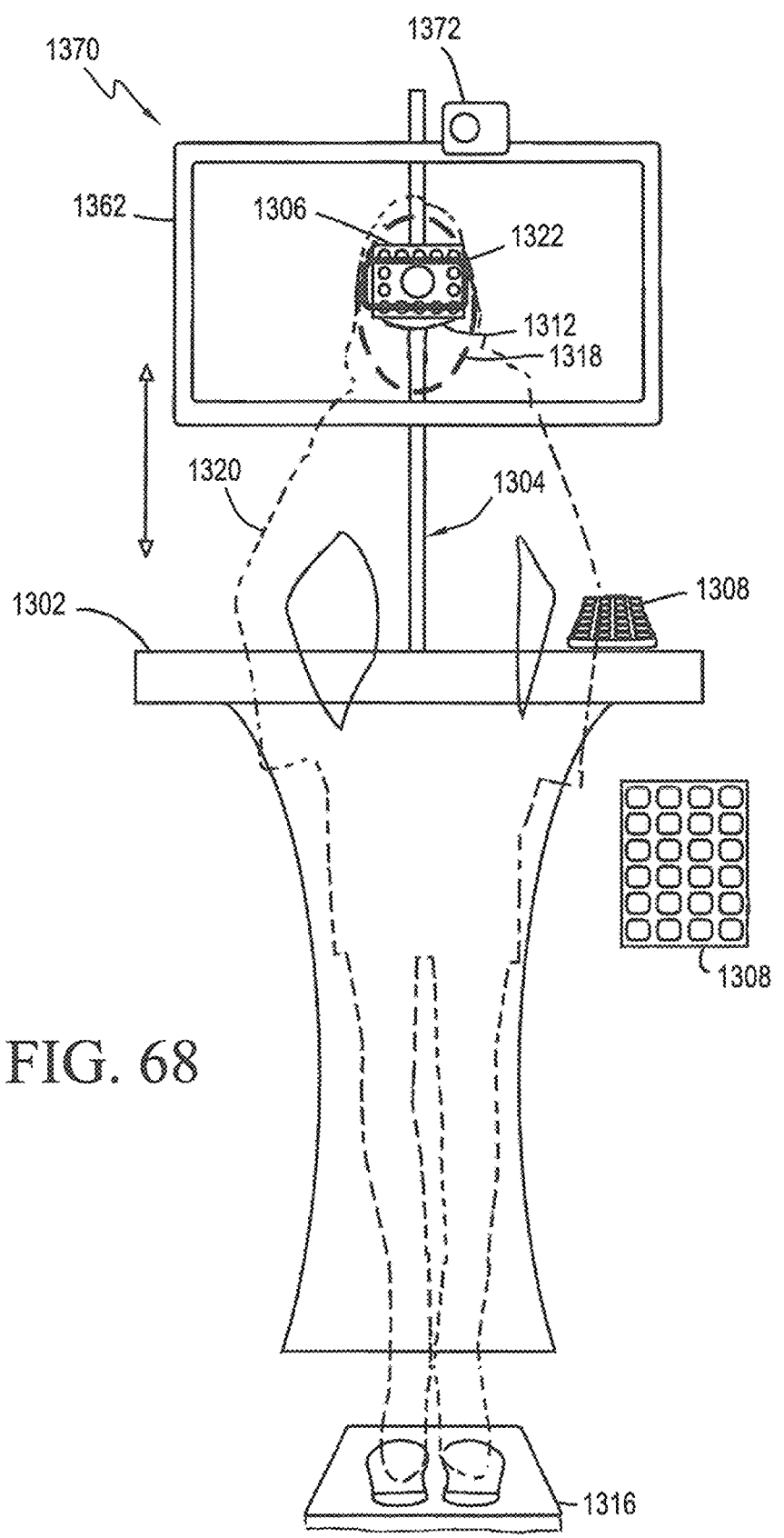
FIG. 68 shows a further view of the system of FIG. 66.
Figure 69:
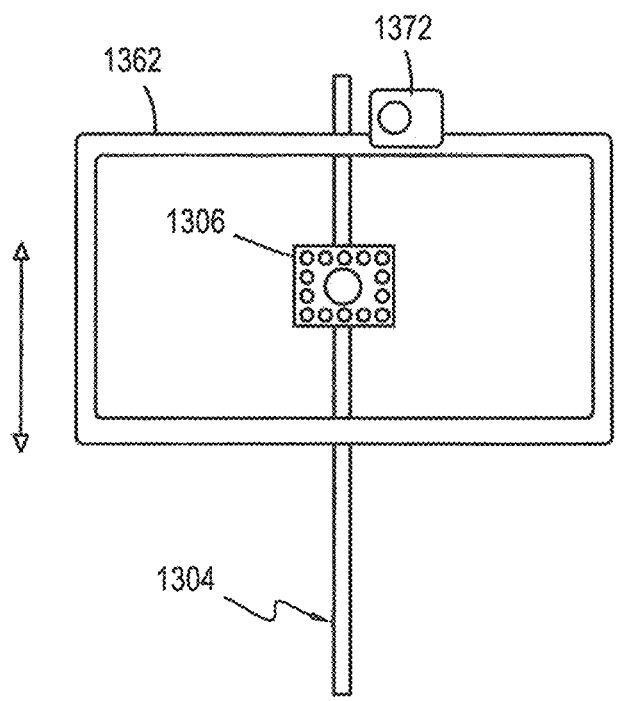
FIG. 69 shows a view of a support structure for the system of FIG. 66, in accordance with an exemplary embodiment of the present disclosure.
Figure 70:
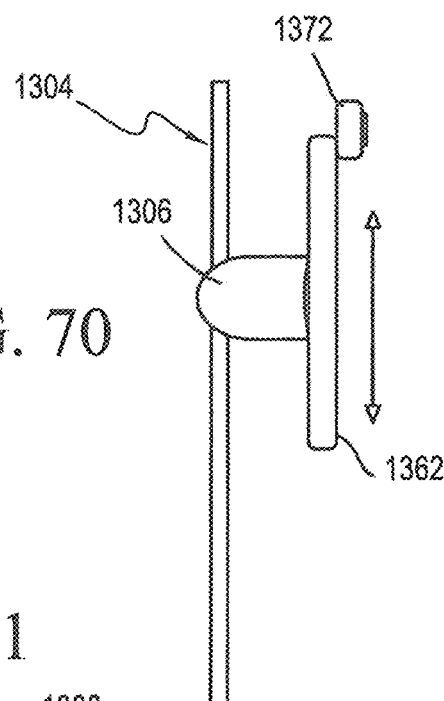
FIG. 70 shows a side view of the support structure of FIG. 52.
Figure 71:
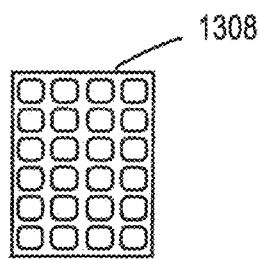
FIG. 71 shows a view of a device to control a camera position of the system of FIG. 66.
Figure 72:
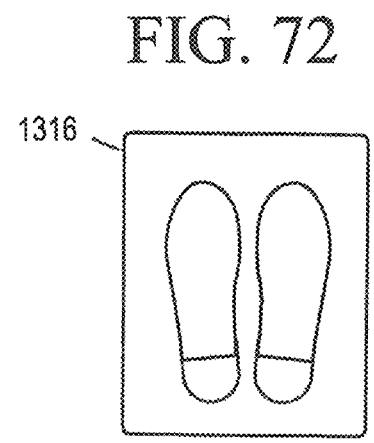
FIG. 72 shows a view of an activation device of the system of FIG. 66.
Figure 73:
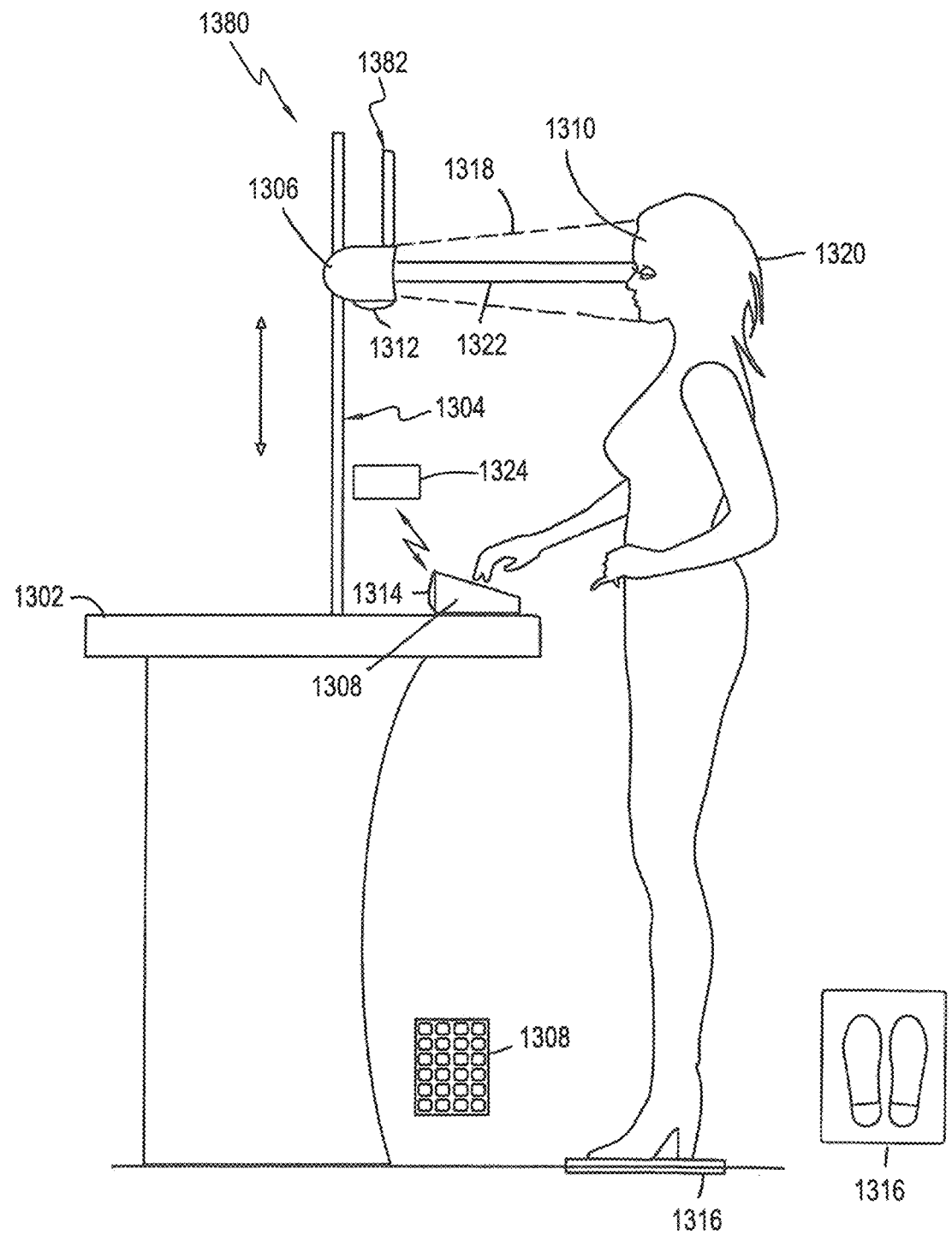
FIG. 73 shows a view of a still further system configured to locate an ABTT terminus and then to measure the temperature of the ABTT terminus, in accordance with an exemplary embodiment of the present disclosure.
Figure 74:
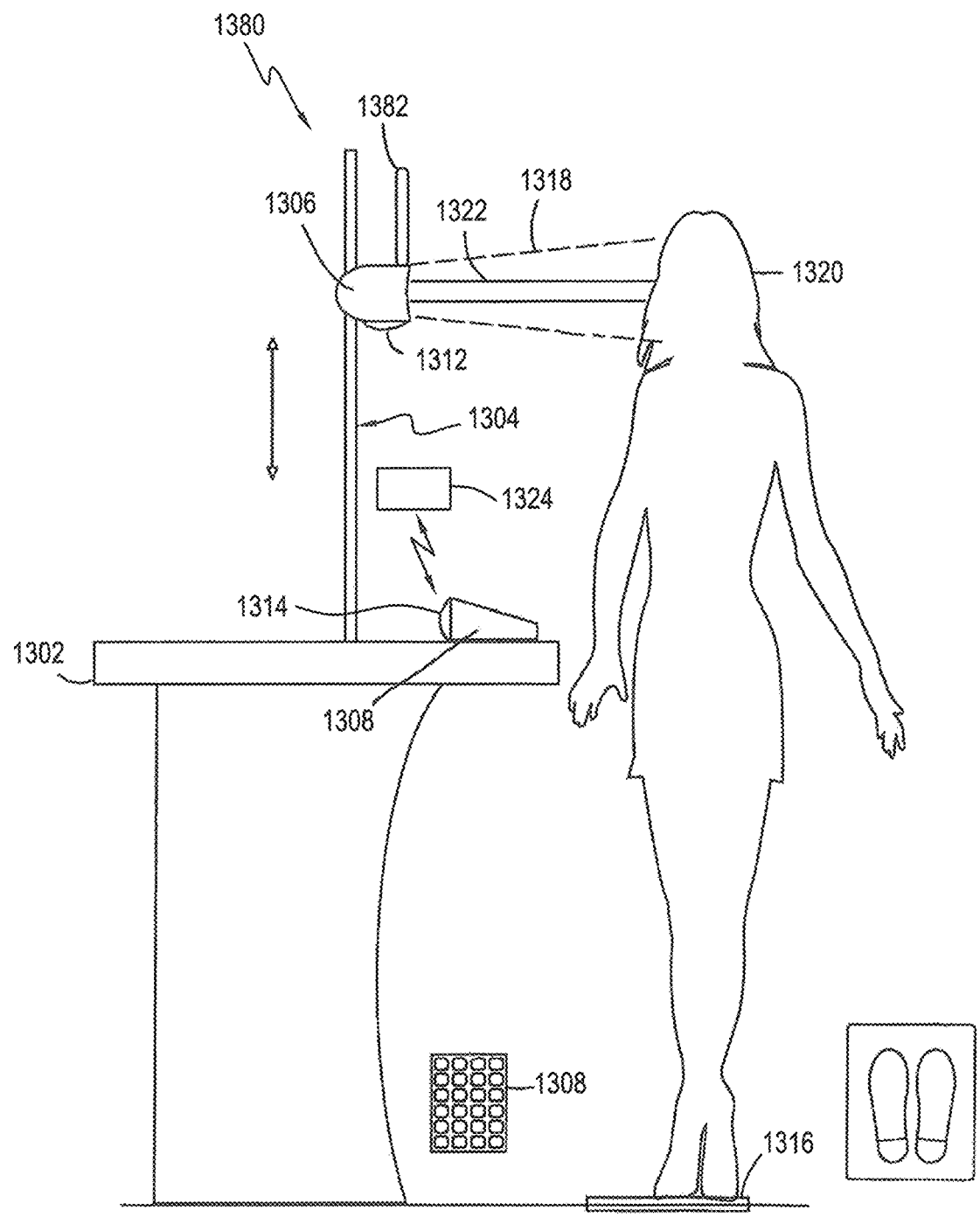
FIG. 74 shows another view of the system of FIG. 73.
Figure 75:
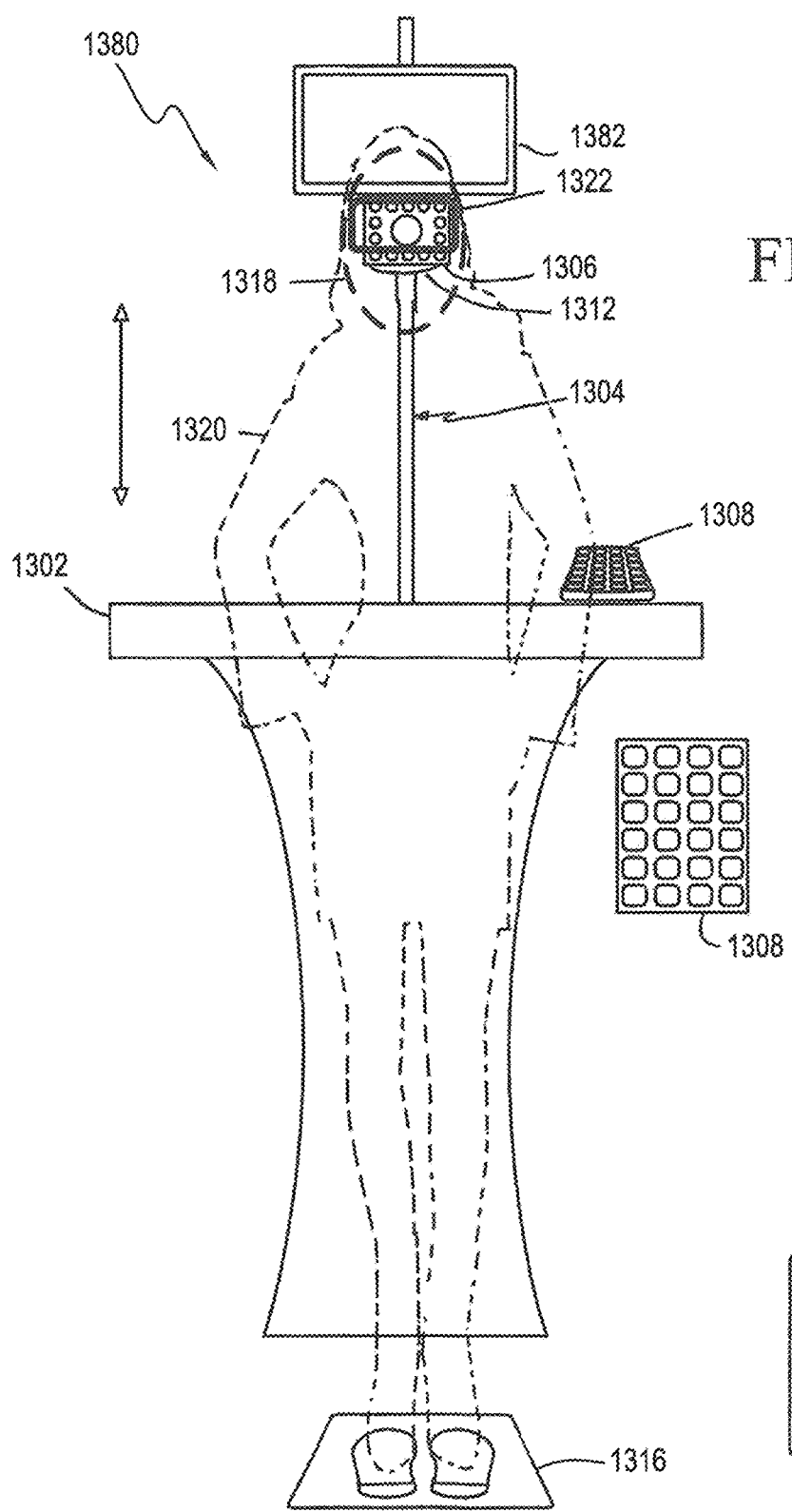
FIG. 75 shows a further view of the system of FIG. 73.
Figure 80:
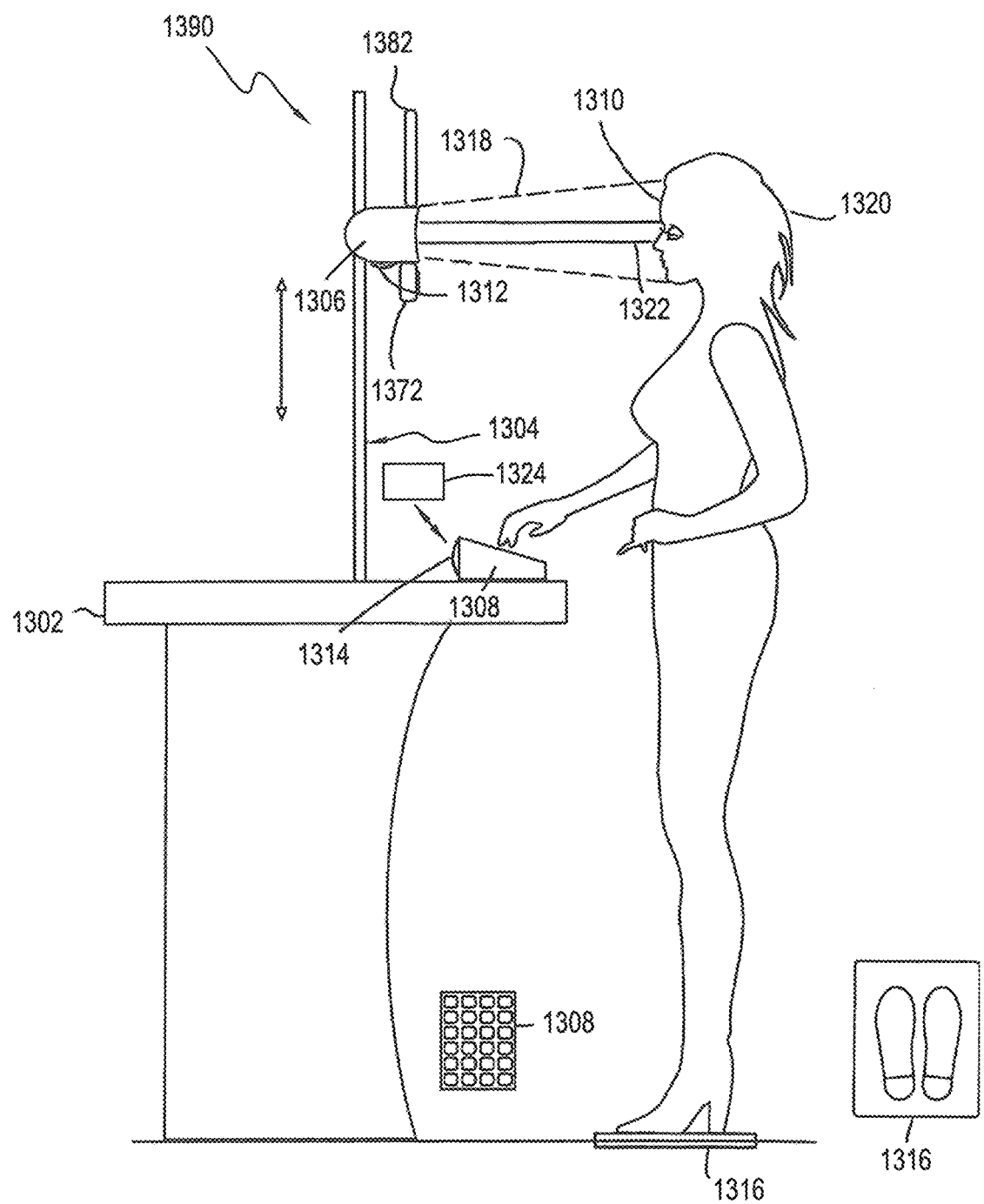
FIG. 80 shows a view of yet an even further system configured to locate an ABTT terminus and then to measure the temperature of the ABTT terminus, in accordance with an exemplary embodiment of the present disclosure.
Figure 81:
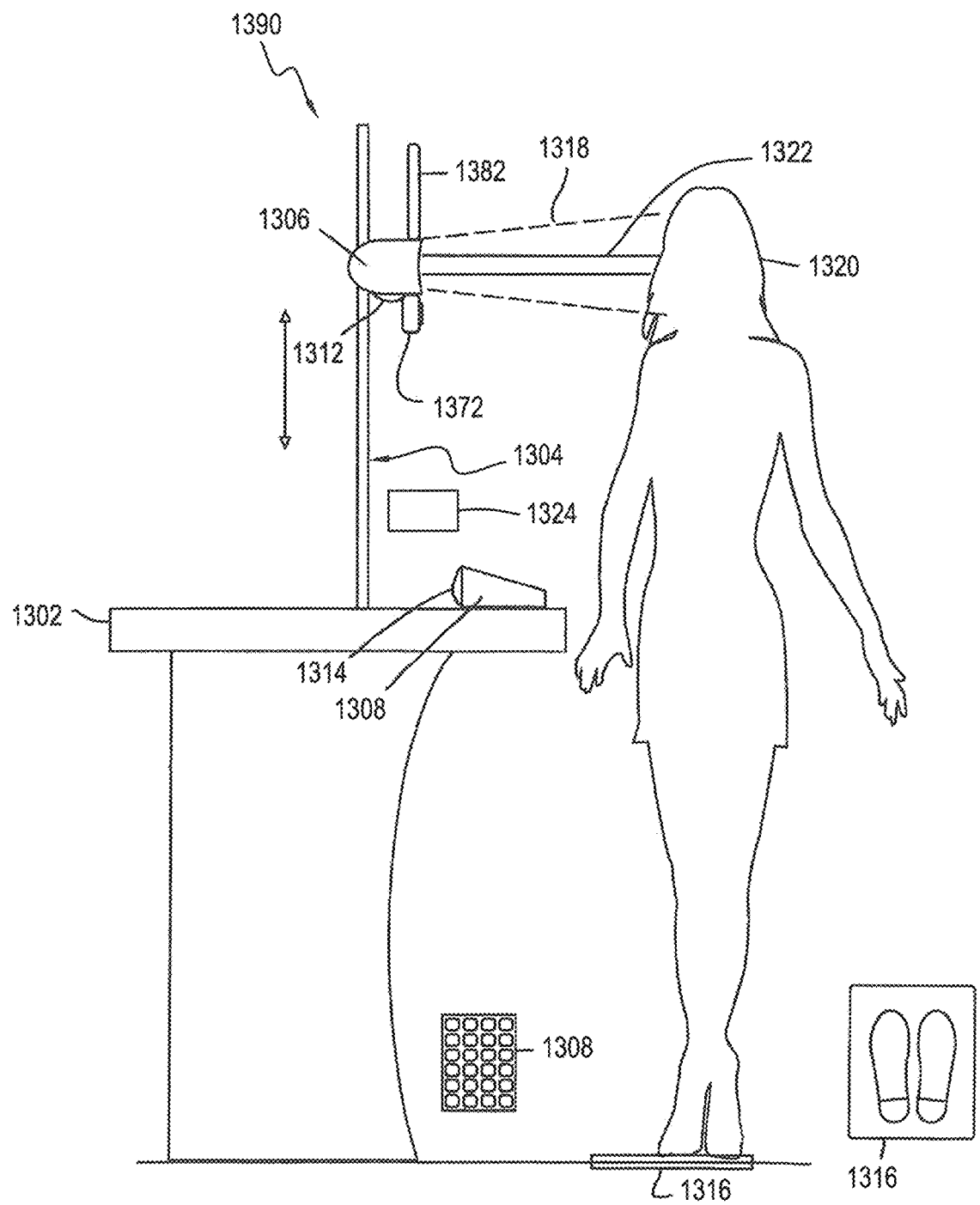
FIG. 81 shows another view of the system of FIG. 80.
Figure 82:
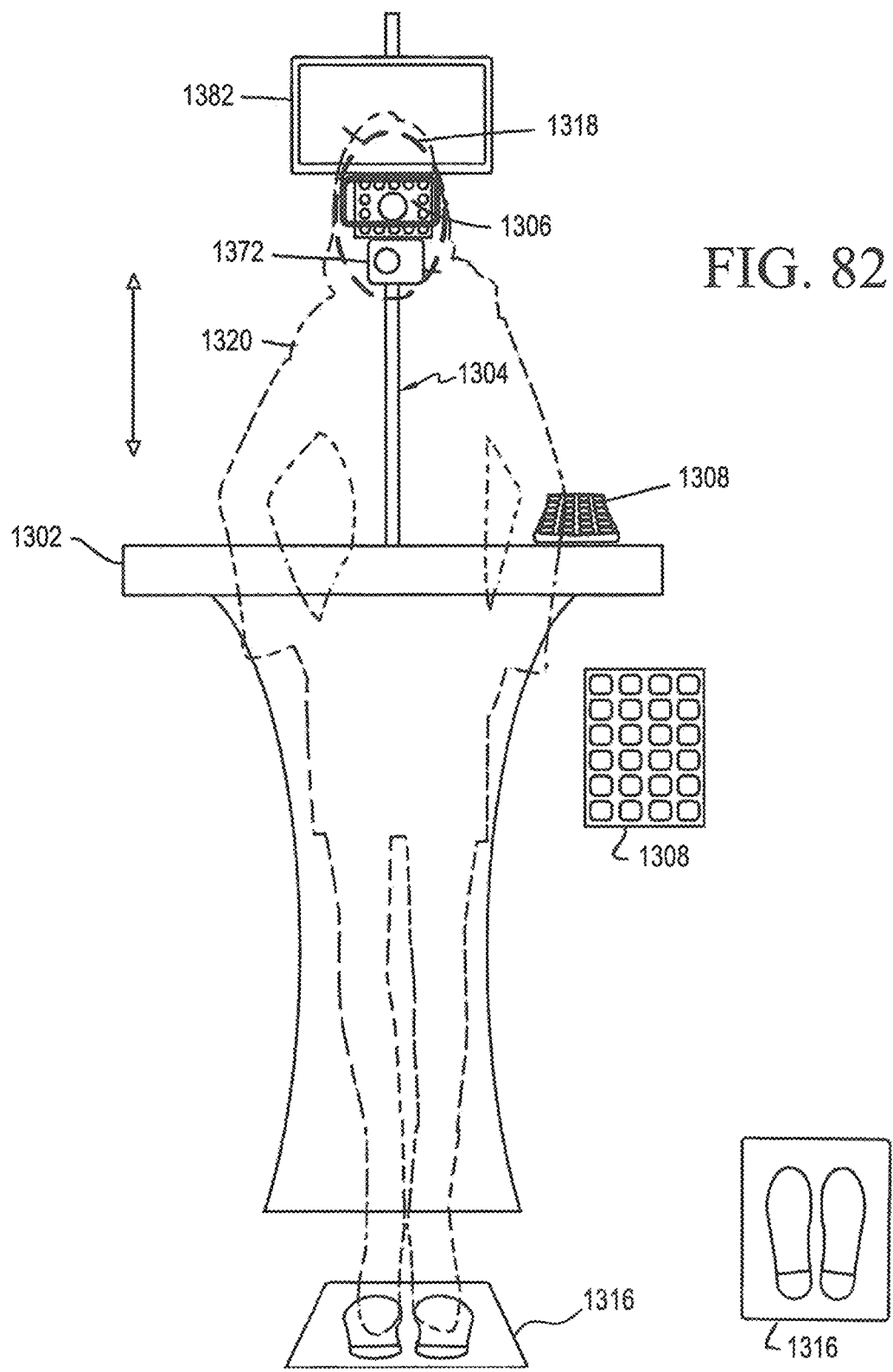
FIG. 82 shows a further view of the system of FIG. 80.

Support system 1304 can be configured in a variety of arrangements. FIGS. 51 and 52 show an exemplary support system 1304a that includes an "H" configuration, including two vertically extending poles 1326 and a cross bar 1328. IR camera 1306 is configured to move left and right along cross bar 328, and cross bar 1328 is configured to move vertically along poles 1326, with both movements permitting movement of IR camera 1306 to align with a subject or patient's face. FIGS. 53 and 54 show another exemplary support system 1304b that includes a single pole 1326 configured to permit movement of IR camera 1306 vertically along pole 1326. To achieve left-right or horizontal positioning, a patient or subject would move left or right.

FIGS. 55-59 show another ABTT temperature measurement system in accordance with an exemplary embodiment of the present disclosure, indicated generally at 1350. System 1350 is similar to system 1300 in many respects, but system 1350 further includes a mirror 1352.

FIGS. 60-65 show another ABTT temperature measurement system in accordance with an exemplary embodiment of the present disclosure, indicated generally at 1360. System 1360 is similar to systems 1300 and 1350 in many respects, but system 1360 further includes a display 1362 configured to present the output of IR camera 1306 to subject 1320. Display 1362 is transparent to IR energy, so camera 1306 receives IR energy transmitted through display 1362.

FIGS. 66-72 show another ABTT temperature measurement system in accordance with an exemplary embodiment of the present disclosure, indicated generally at 1370. System 1370 is similar to system 1360 in many respects, but system 1370 further includes a digital camera 1372 configured to capture an image of face 1310 at visible optical wavelengths and to present face 1310 on display 1362 to aid in aligning IR camera 1306.

FIGS. 73-79 show another ABTT temperature measurement system in accordance with an exemplary embodiment of the present disclosure, indicated generally at 1380. System 1380 is similar to systems 1360 and 1370 in many respects, but system 1380 further includes a display device 1382 positioned adjacent to IR camera 1306. Display device 1382 can be configured to include a digital camera, the output of which is presented on display device 1382 to aid in aligning IR camera 1306 with respect to face 1310.

FIGS. 80-86 show another ABTT temperature measurement system in accordance with an exemplary embodiment of the present disclosure, indicated generally at 1390. System 1390 includes selective features from systems 1370 and 1380. Display device 1382 is configured to present visual data provided by digital camera 1372 to aid in aligning IR camera 1306 with respect to face 1310.

FIG. 87 shows another system configured to locate ABTT terminus 10 and then to measure the temperature of ABTT terminus 10, in accordance with an exemplary embodiment of the present disclosure, indicated generally at 1400. System 1400 is configured to include a support system 1402 configured to support a movable IR camera 1404. Support system 1402 is configured to allow IR camera 1404 to be movable or adjustable to a plurality of vertical positions to be able to locate at least one ABTT terminus 10. In an exemplary embodiment, camera 1404 is moved manually. In another exemplary embodiment, camera 1404 is moved by way of a controller. In a further exemplary embodiment, camera 1404 is automatically moveable to locate a face 1406 and at least one ABTT terminus 10.

Figure 87A:
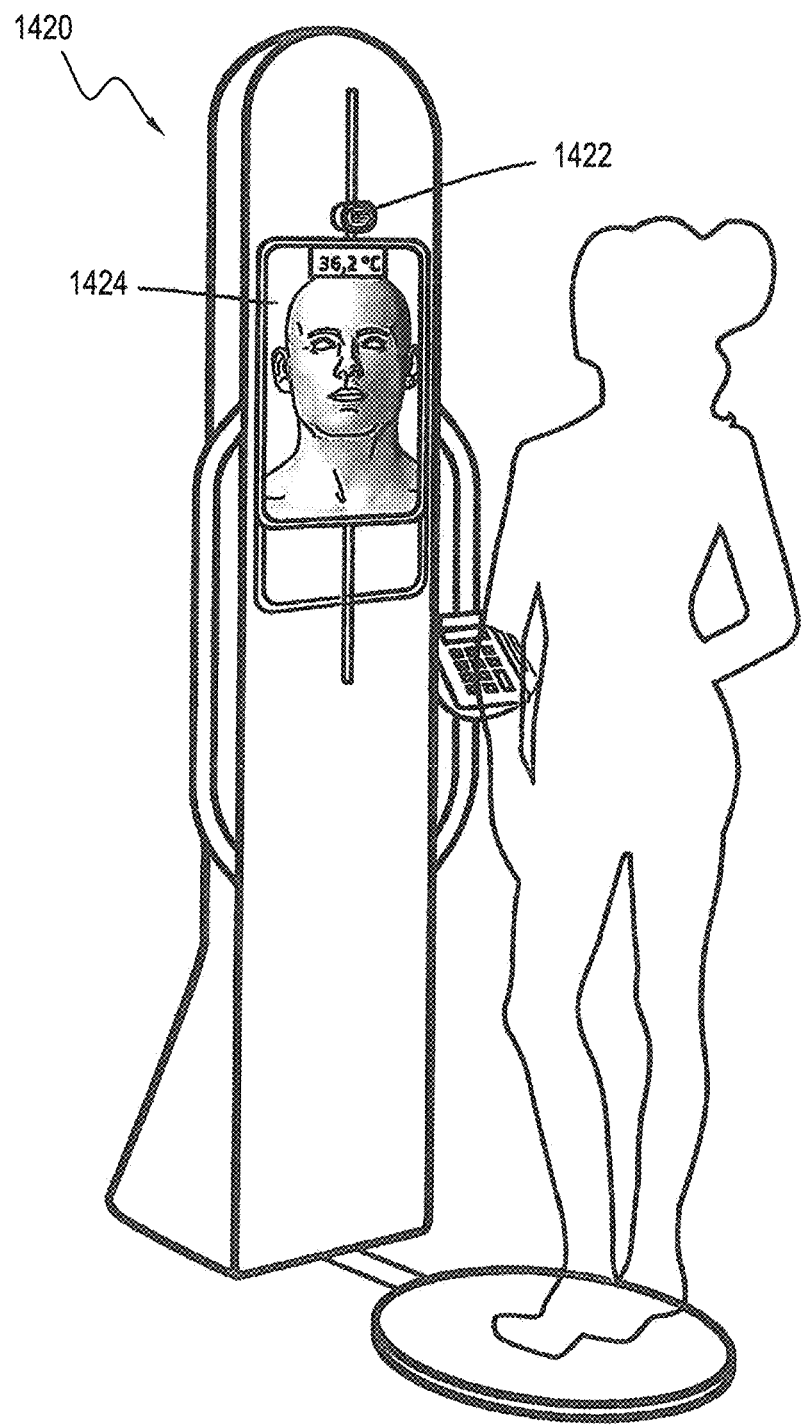
FIG. 87A shows a view of yet another system configured to locate an ABTT terminus and then to measure the temperature of the ABTT terminus, in accordance with an exemplary embodiment of the present disclosure.
Figure 87B:
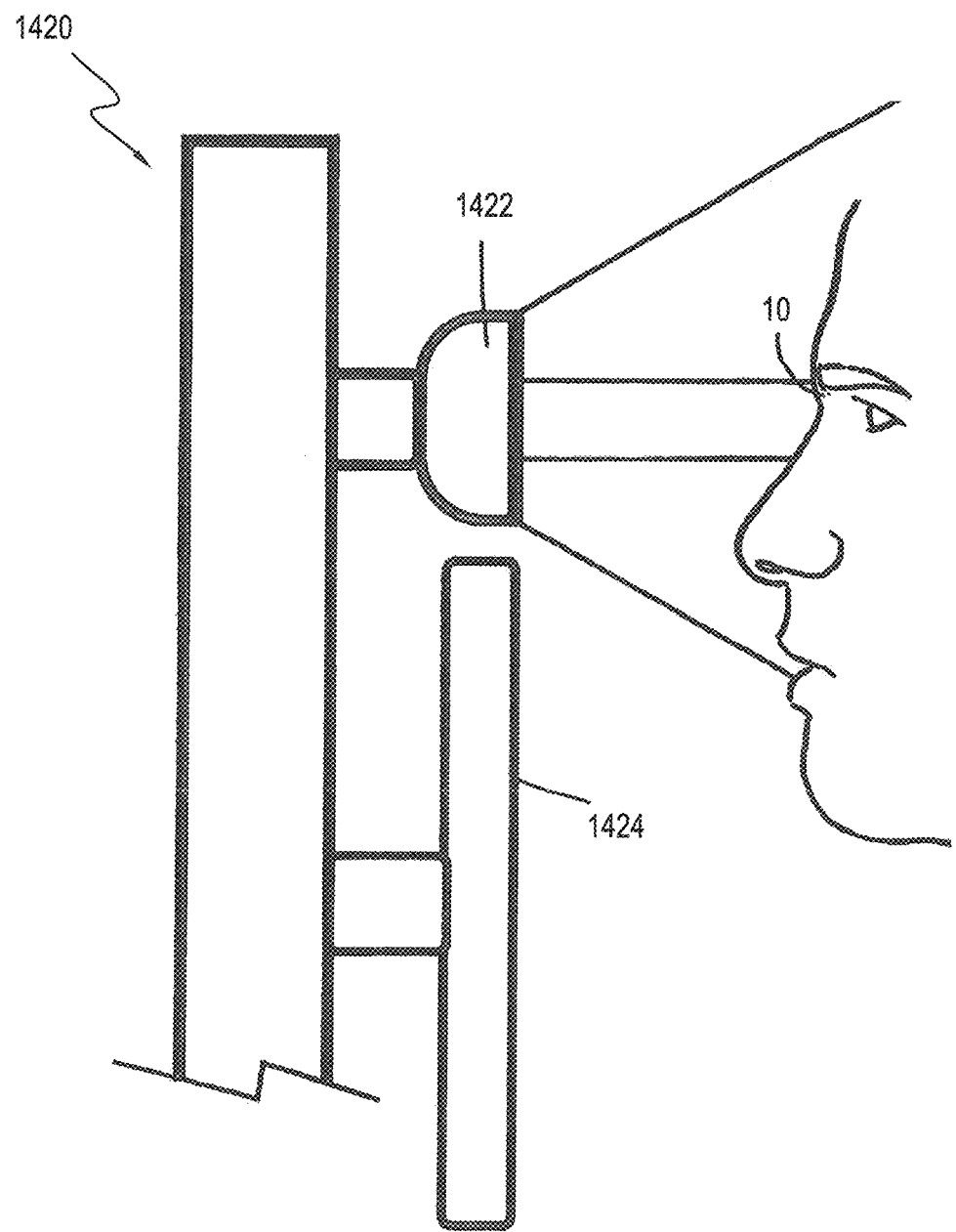
FIG. 87B shows a view of a portion of the system of FIG. 87A.

FIGS. 87A and 87B show views of yet another system, indicated generally at 1420, configured to locate ABTT terminus 10 and then to measure the temperature of the ABTT terminus 10, in accordance with an exemplary embodiment of the present disclosure. System 1420 includes an infrared sensor array 1422, which may include a thermopile array, positioned above a display 1424 and being operatively coupled with display 1424. Display 1424 can be configured to display an advertisement during measurement of emissions from ABTT terminus 10, and measurement results can be configured to appear on display 1424 at random times during the advertisement. FIG. 87B shows view of a portion of system 1420 during measurement of a subject, with sensor array 1422 capturing thermal signals from ABTT terminus 10 of the subject.

Figure 87C:
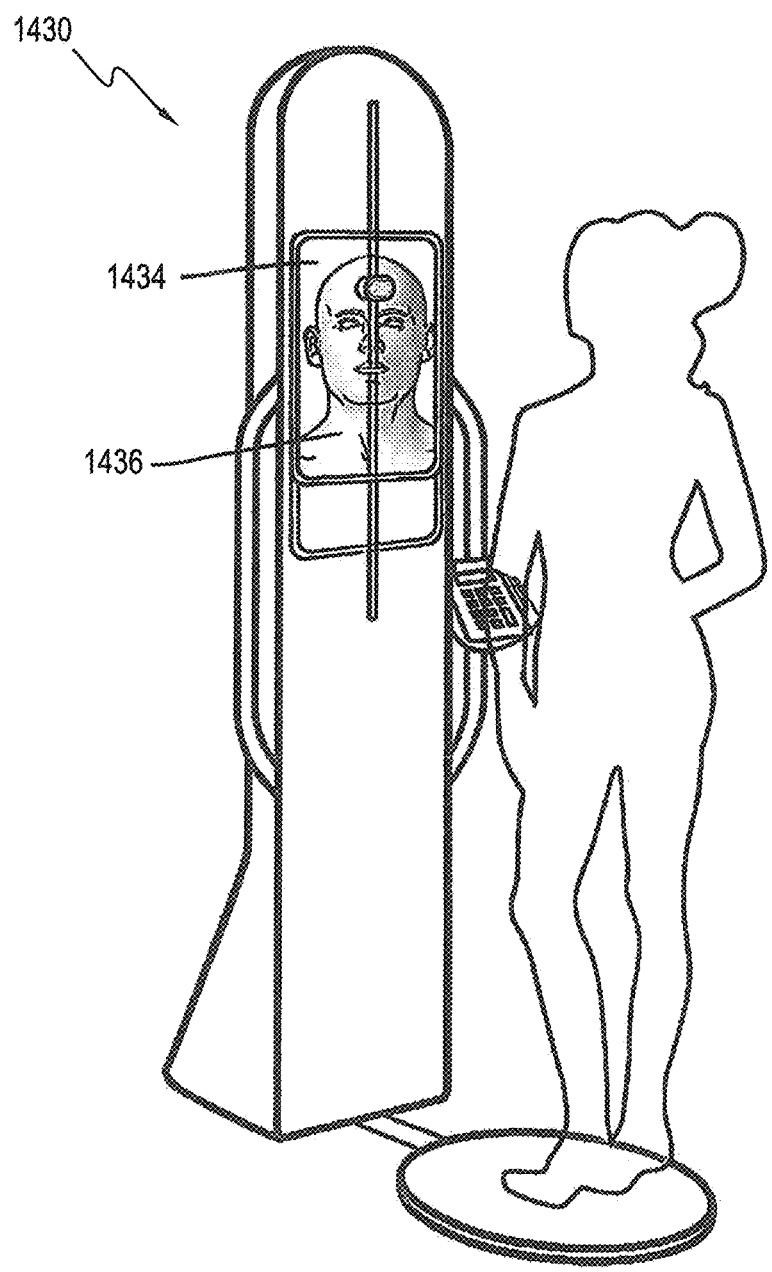
FIG. 87C shows a view of still yet another system configured to locate an ABTT terminus and then to measure the temperature of the ABTT terminus, in accordance with an exemplary embodiment of the present disclosure.
Figure 87D:
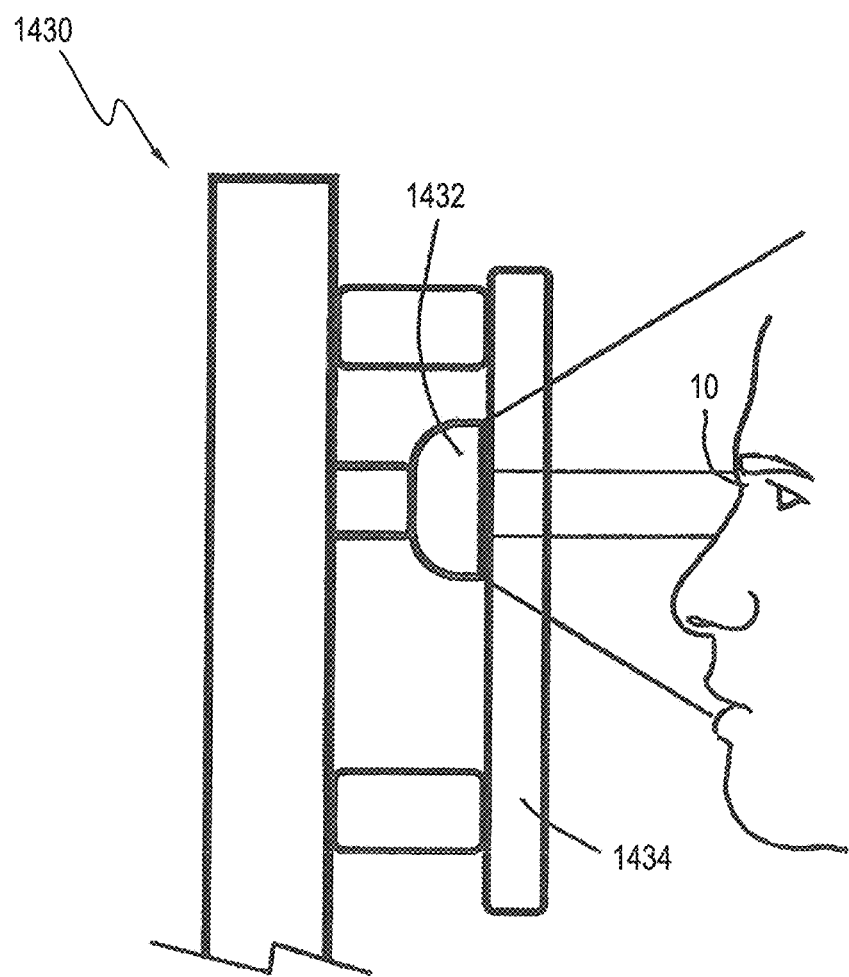
FIG. 87D shows a view of a portion of the system of FIG. 87C.

FIGS. 87C and 87D show views of still yet another system, indicated generally at 1430, configured to locate ABTT terminus 10 and then to measure the temperature of ABTT terminus 10, in accordance with an exemplary embodiment of the present disclosure. ABTT temperature measurement system 1430 includes thermal sensors 1432 positioned behind a screen 1434, thermal sensors 1432 include at least one of infrared sensors and a thermal imaging device, and screen 1434 being preferably an LED display to facilitate calculating thermal energy generated by screen 1434, since LED's have a rather stable temperature, and the temperature of LED screen 1434 can be used to adjust or correct the temperature measured by sensors 1432 to determine the temperature of ABTT terminus 10. Screen 1434 can also be transparent to IR energy, so infrared sensors 1432 receive IR energy transmitted through screen 1434. System 1430 is configured to measure thermal signals from ABTT terminus 10 while an image 1436, such as an advertisement, is being shown on screen 1434, and the subject must look at screen 1434 to be measured. In addition, the measurement results are shown on screen 1434. FIG. 87D shows system 1430 during measurement of the subject, with sensor array 432 capturing thermal signals from ABTT terminus 10 of the subject.

Figure 87E:
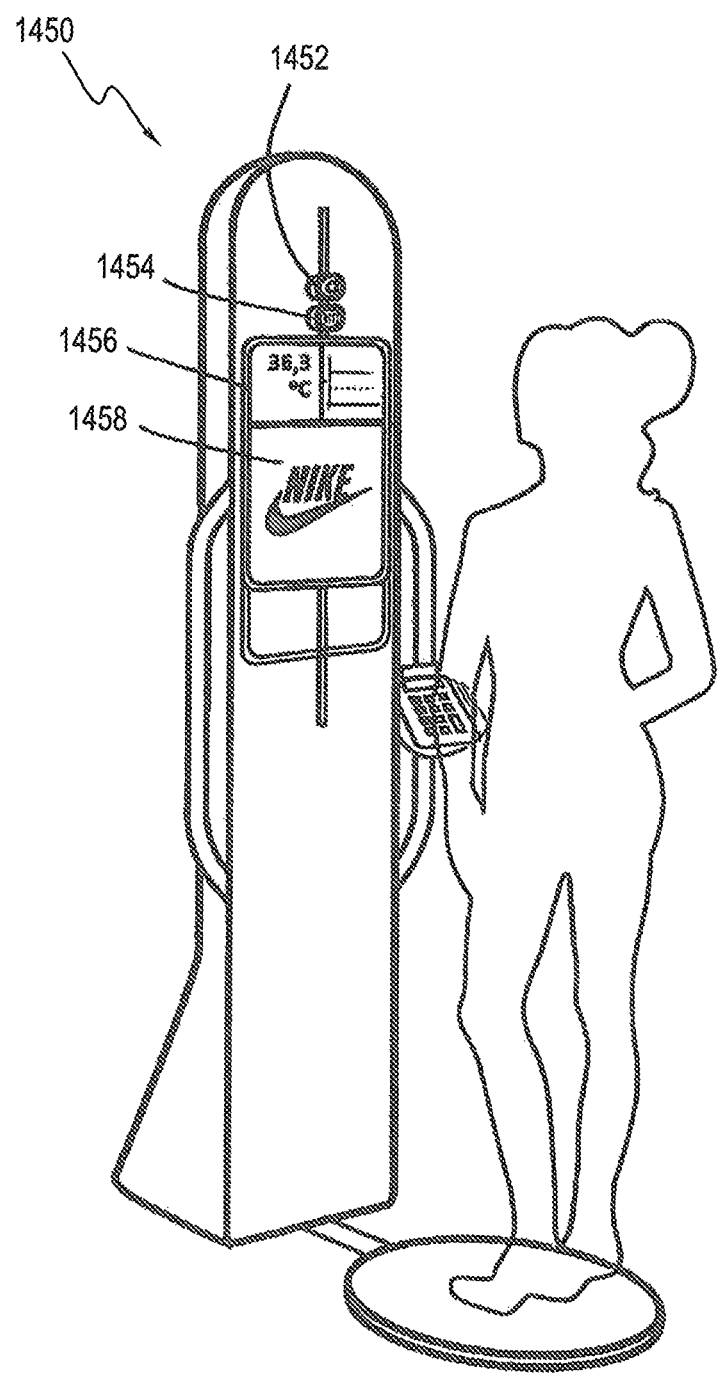
FIG. 87E shows a view of an even further system configured to locate an ABTT terminus and then to measure the temperature of the ABTT terminus, in accordance with an exemplary embodiment of the present disclosure.
Figure 87F:
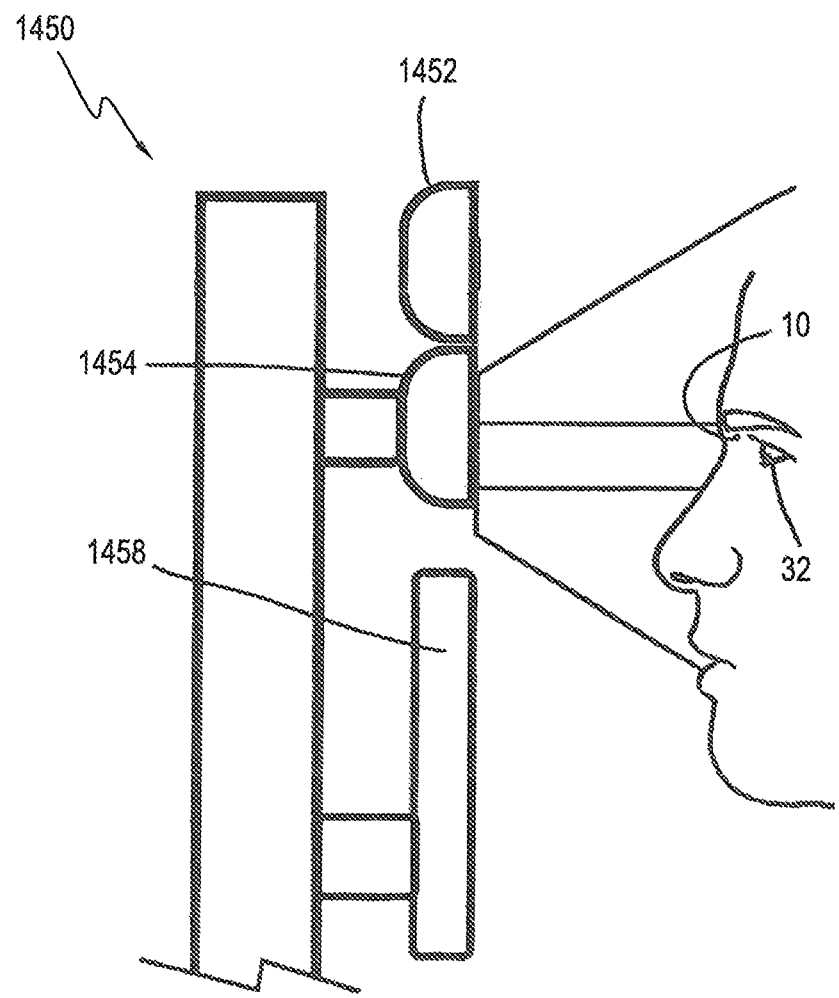
FIG. 87F shows a view of a portion of the system of FIG. 87E.

FIGS. 87E and 87F show views of an even further system, indicated generally at 1450, configured to locate ABTT terminus 10 and then to measure the temperature of ABTT terminus 10, in accordance with an exemplary embodiment of the present disclosure. ABTT temperature measurement system 1450 includes a digital camera 1452, an infrared sensor array 1454, and a screen 1456 showing advertisement 1458 or other information while measurement of emissions from ABTT terminus 10 is conducted. FIG. 87F shows system 1450 during measurement of the subject, with sensor array capturing thermal signal from ABTT of a subject. Digital camera 1452 captures an image of ABTT terminus 10 and eyes 32, and uses this image information to align infrared sensor array 1454 with ABTT terminus 10. Then the digital image is superimposed on the displayed thermal image.

Figure 87G:
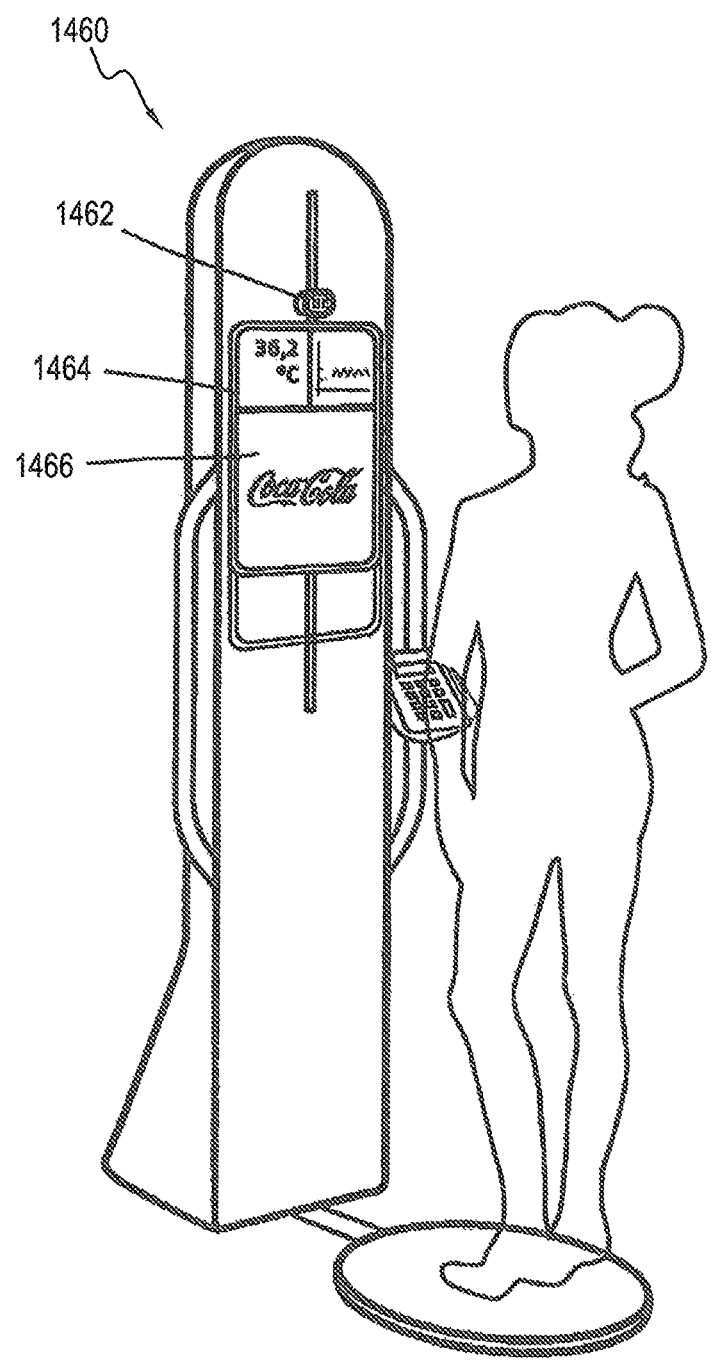
FIG. 87G shows a view of an even further system configured to locate an ABTT terminus and then to measure the temperature of the ABTT terminus, in accordance with an exemplary embodiment of the present disclosure.
Figure 87H:
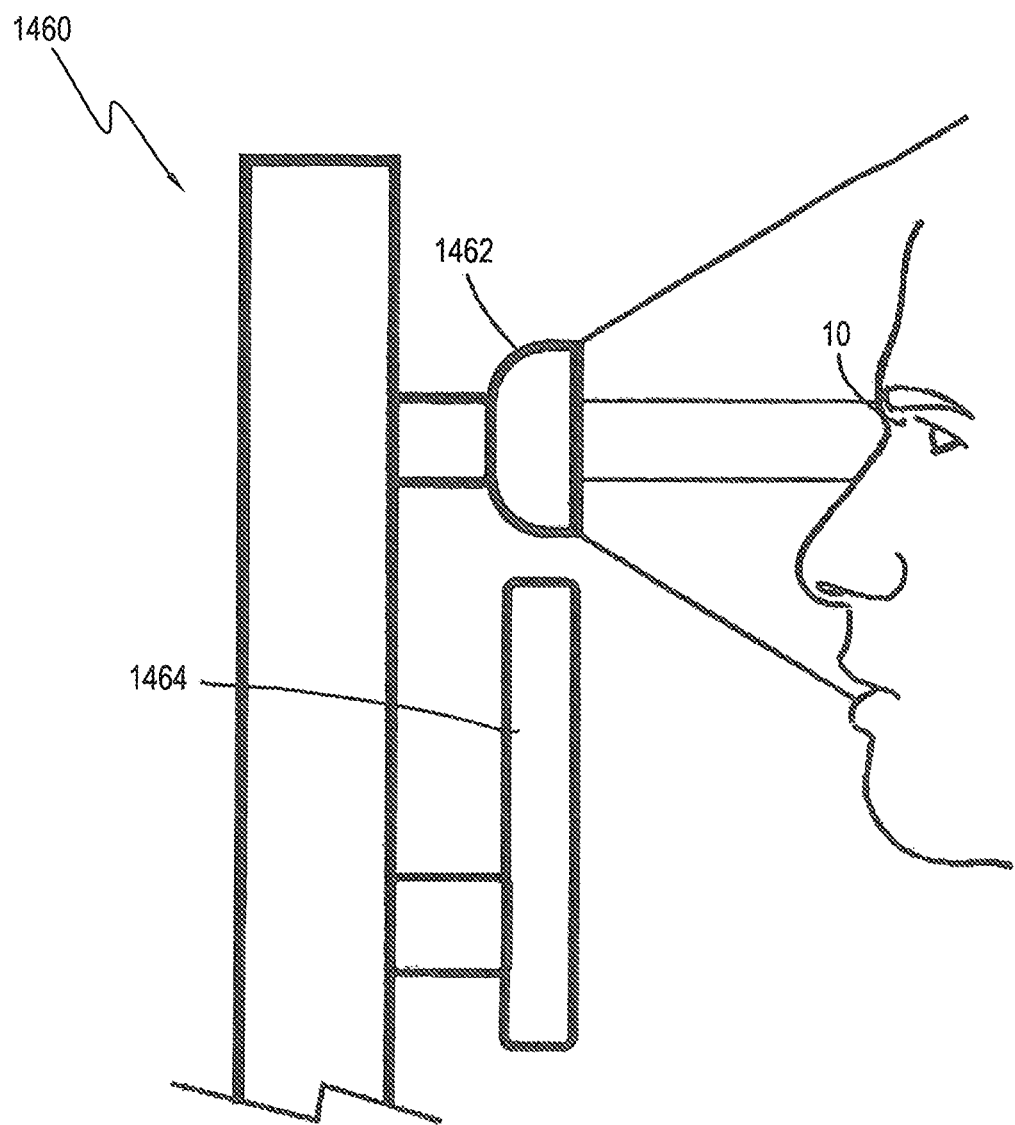
FIG. 87H shows a view of a portion of the system of FIG. 87G.

FIGS. 87G and 70H show views of an even further system, indicated generally at 1460, configured to locate ABTT terminus 10 and then to measure the temperature of ABTT terminus 10, in accordance with an exemplary embodiment of the present disclosure. ABTT temperature measurement system 1460 includes a thermal image camera 1462 and a screen 1464 showing advertisement 1466 or other information while measurements are is being taken of thermal emissions of ABTT terminus 10. FIG. 87H shows a view of system 1460 during measurement of the subject, with sensor array 1462 capturing thermal signals from ABTT terminus 10 of the subject.

Figure 87I:
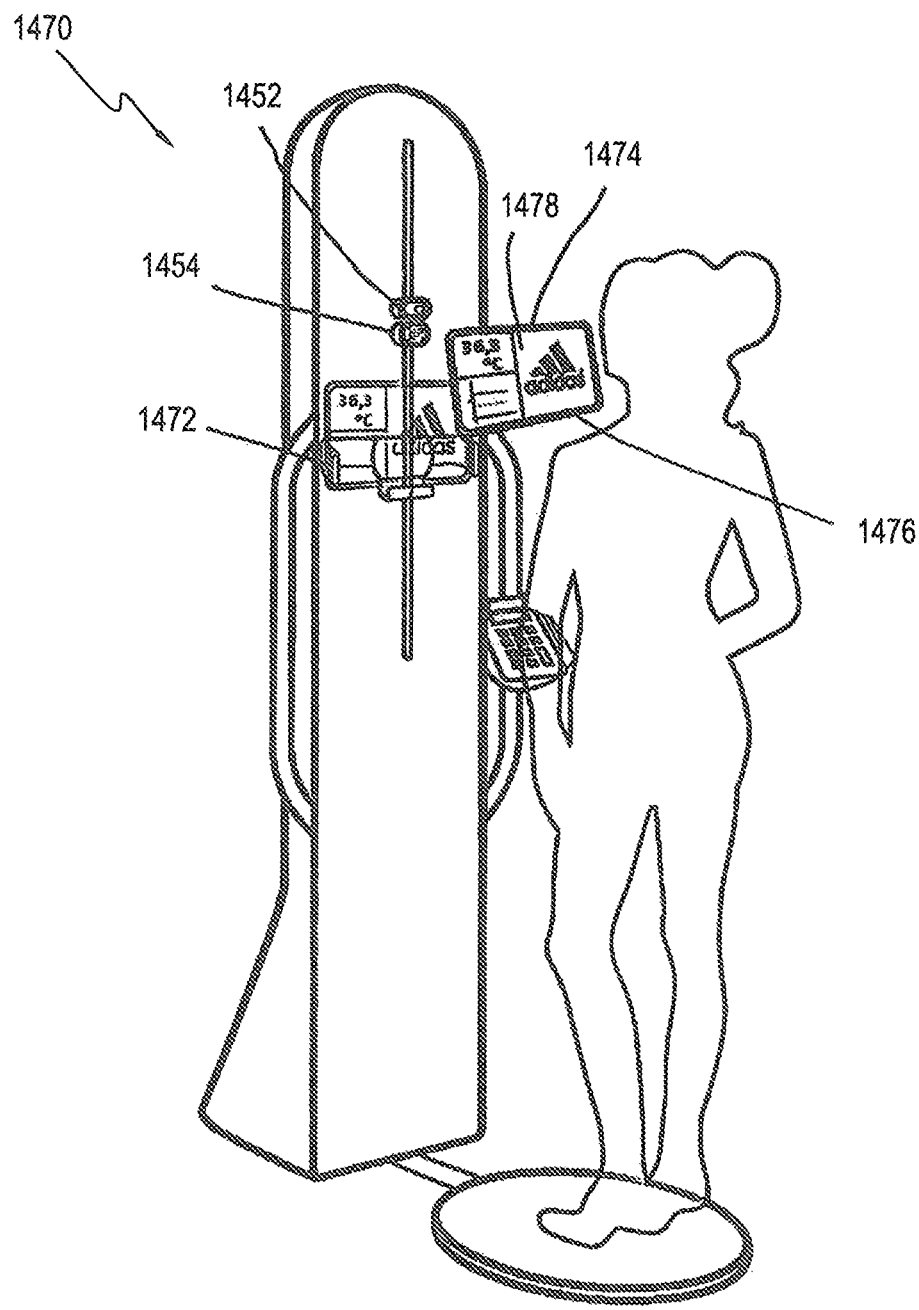
FIG. 87I shows a view of an even further system configured to locate an ABTT terminus and then to measure the temperature of the ABTT terminus, in accordance with an exemplary embodiment of the present disclosure.
Figure 87J:
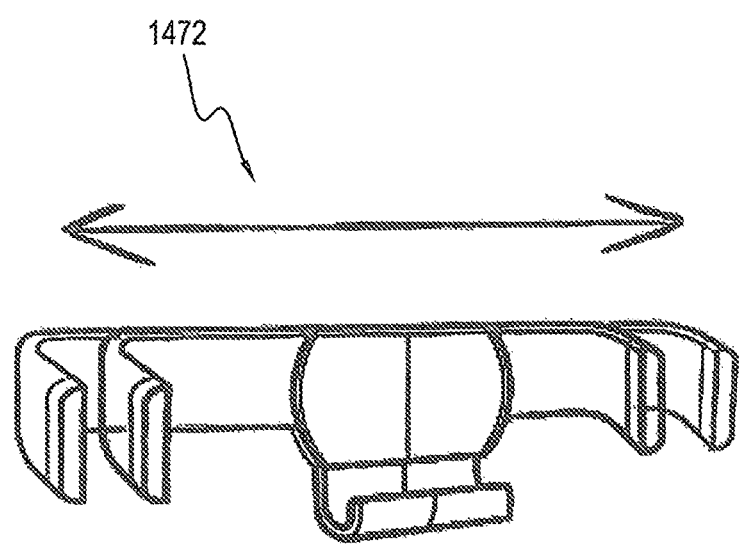
FIG. 87J shows a view of a clamp of FIG. 87I.
Figure 87K:
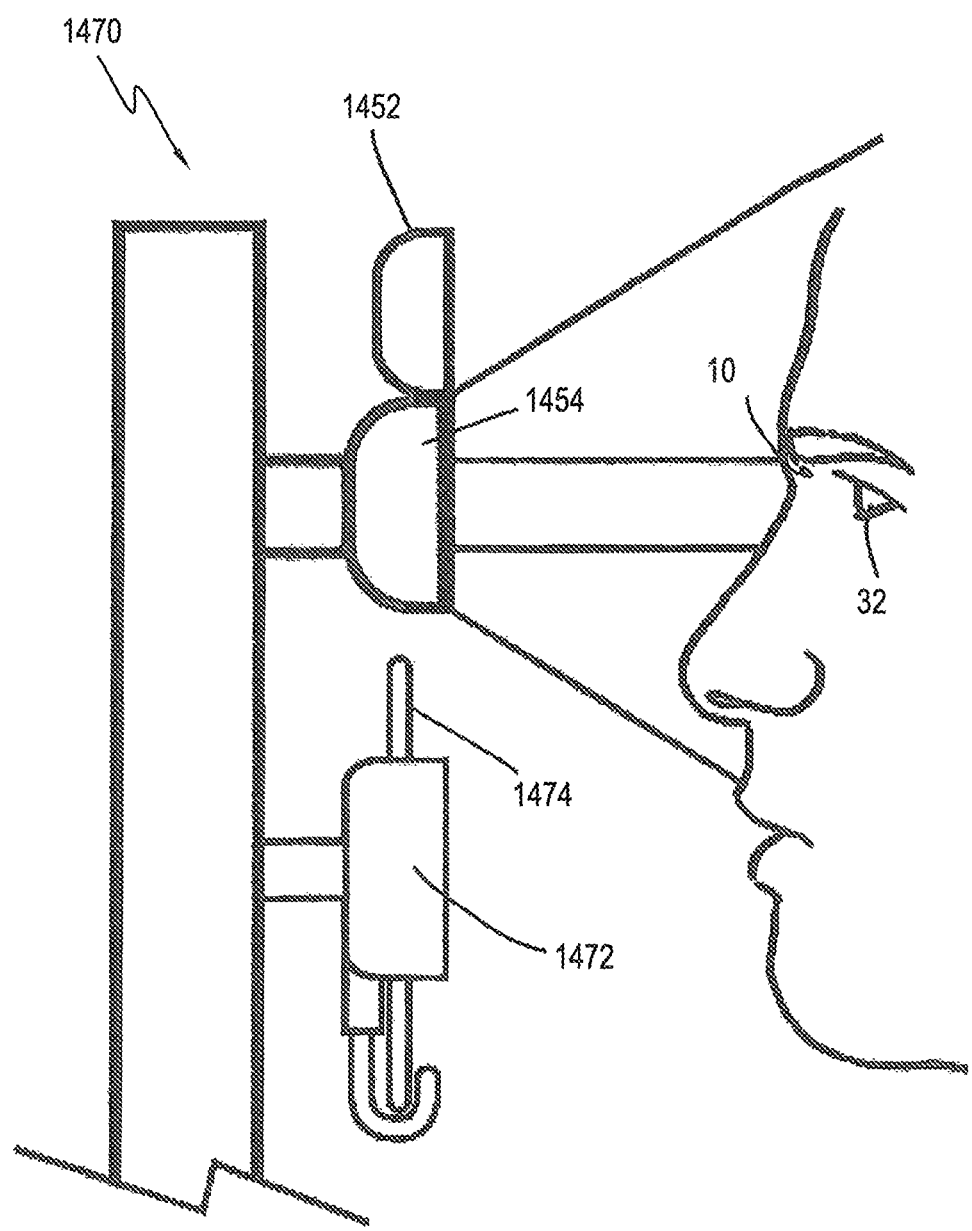
FIG. 87K shows a view of a portion of the system of FIG. 87I.

FIGS. 87I-K show views of an even further system, indicated generally at 1470, configured to locate ABTT terminus 10 and then to measure the temperature of ABTT terminus 10, in accordance with an exemplary embodiment of the present disclosure. ABTT temperature measurement system 1470 includes digital camera 1452, infrared sensor array 454, and a clamp mechanism 1472 being configured to secure an electronic device 1474, electronic device 1474 including a display 1476 and showing on its display 476 an advertisement 1478 or other information while measurement is being taken. FIG. 87J shows details of clamp mechanism 1472 for securing electronic device 1474, such as a cell phone, tablet, computer, and the like. FIG. 87I shows a view of system 1470 during measurement of the subject, with sensor array 1454 capturing thermal signals from ABTT terminus 10 of the subject. Digital camera 1452 captures an image of ABTT terminus 10 and eyes 32, and uses this image information to align infrared sensor 1454 with ABTT terminus 10. The digital image is then superimposed on the thermal image.

Figure 87L:
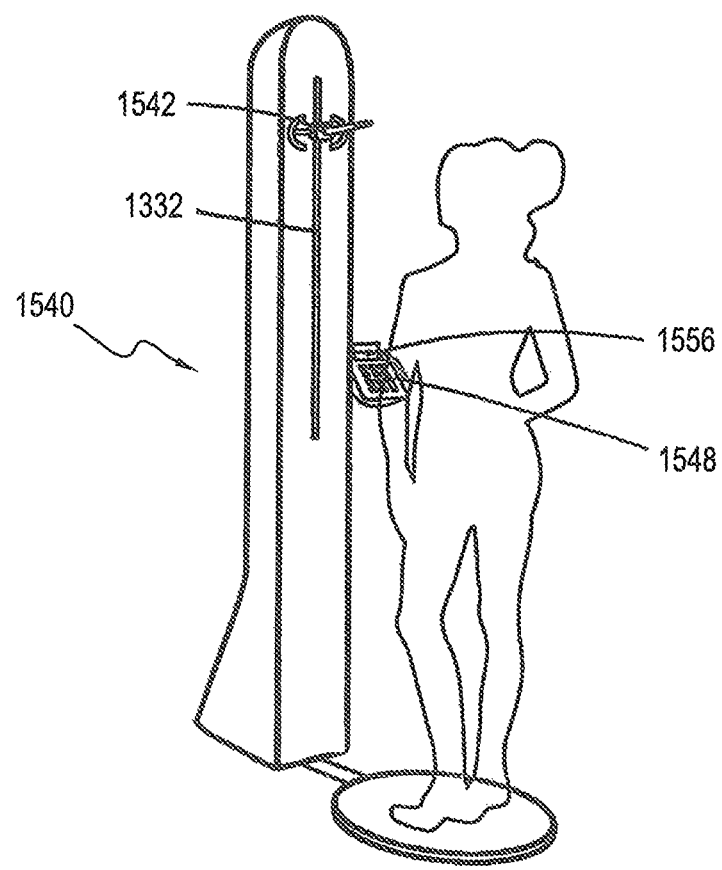
FIG. 87L shows a view of a system configured to locate an ABTT terminus and then to measure the temperature of the ABTT terminus, in accordance with an exemplary embodiment of the present disclosure.
Figure 87M:
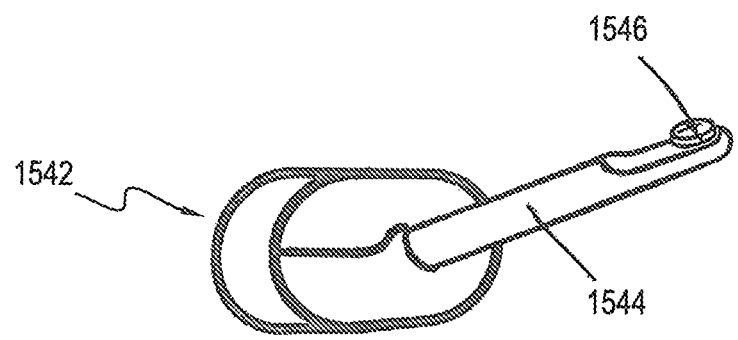
FIG. 87M shows a view of a sensor device of the system of FIG. 87L.

FIGS. 87L-87M show views of an even further system, indicated generally at 1540, configured to locate ABTT terminus 10 and then to measure the temperature of ABTT terminus 10, in accordance with an exemplary embodiment of the present disclosure. System 1540, and other systems of the present disclosure, can alternatively be described as being measuring stations. ABTT temperature measurement system 1540 includes sensor device 1542, which includes a rod 1544 having a contact sensor 1546 at its free end, such as a thermistor, a keypad 1548, and a display 1550 adjacent to keypad 1548, display 1550 reporting the value measured by sensor device 1542. Display 1550 is operatively coupled with electronics of sensor device 1542, display 1550 displaying an advertisement after the measurement is done, and display 1550 displaying simultaneously the measurement results. Pen-like sensor device 1542 is connected to sliding mechanism 1332 of system 1540 for alignment of sensor 1546 with ABTT terminus 10 of people with different height. In this embodiment, the results are calculated and reported after the measurement is done, and there is no movable display, as it was shown in FIGS. 87A to 87H. FIG. 87M shows one single sensor device 1542, which includes a mechanical connector (not shown) for connecting with sliding mechanism 1332 of system 1540 and includes a rotating mechanism for alignment of contact sensor 1546 with ABTT terminus 10.

Figure 87N:
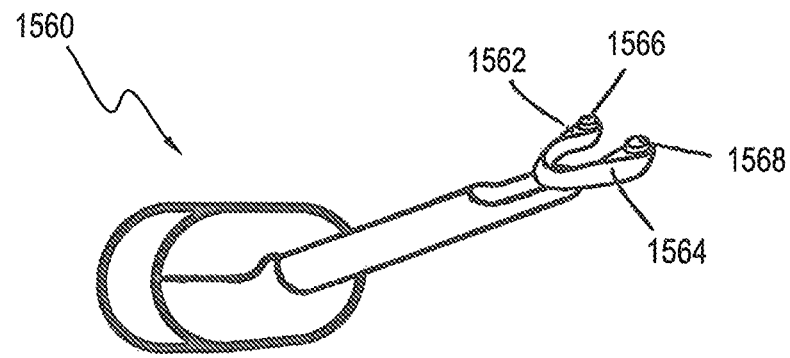
FIG. 87N shows a view of another sensor device in accordance with an exemplary embodiment of the present disclosure.

FIG. 87N shows a dual sensor device, indicated generally at 1560, in accordance with an exemplary embodiment of the present disclosure. Device 1560 includes a connector (not shown) for connecting with sliding mechanism 1332 of system 1540. Device 1560 includes a right arm 1562 and a left arm 1564. Right arm 1562 includes a right sensor 1566 and left arm 1564 includes a left sensor 1568.

Figure 87O:
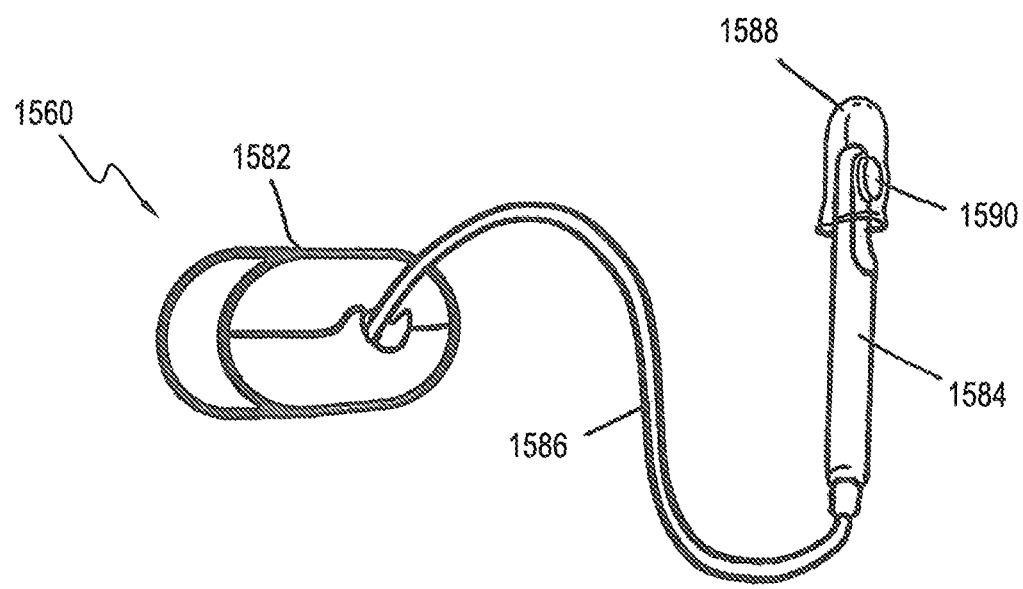
FIG. 87 shows a view of another system configured to locate an ABTT terminus and then to measure the temperature of the ABTT terminus, in accordance with an exemplary embodiment of the present disclosure.

FIG. 87O shows a sensor device, indicated generally at 1580, in accordance with an exemplary embodiment of the present disclosure. Device 1580 includes a sensor body 1582, and a sensor rod 1584 connected to sensor body 1582 by a retractable cable or wire 1586. Sensor body 1582 is configured to mount on and interface with sliding mechanism 1332 of system 1540. Device 580 further includes sensor 1590 positioned on sensor rod 1584 at a distal end thereof and a cover 1588 to protect sensor 1590 to avoid cross-contamination during measurement.

Figure 87P:
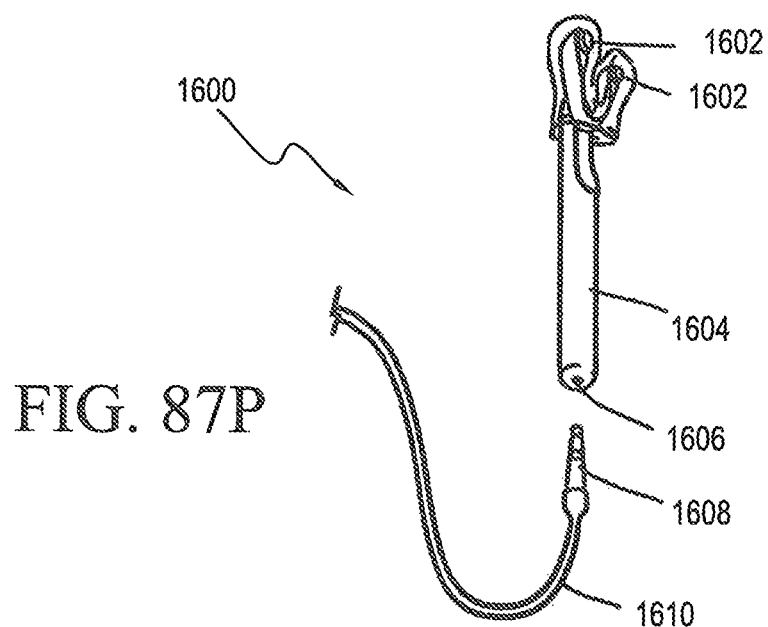

FIG. 87P shows a sensor device, indicated generally at 1600, in accordance with an exemplary embodiment of the present disclosure. Device 1600 includes dual sensors 1602 and a sensor rod 1604 on which sensors 1602 are positioned. Sensor rod 1604 includes a connector 1606 for mating with a connector or jack 1608 of a retractable cable or wire 1610 of, for example, system 1540. Sensor device 1600 further includes a cover 1612 for sensors 1602 to avoid cross-contamination during measurement.

Figure 87Q:
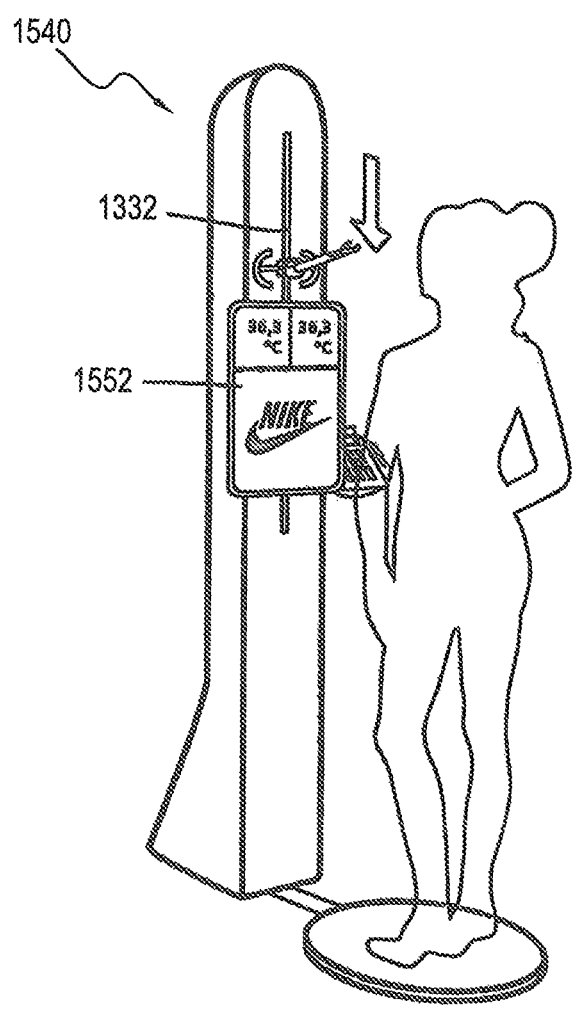

FIG. 87Q shows system 1540 with the addition of a display 1552 connected to sliding mechanism 1332, with display 1553 the temperature of right ABTT terminus 10 and left ABTT terminus 10.

Clinical experiments by Applicant, who is a medical doctor, showed that measuring right ABTT terminus 10 and left ABTT terminus, preferably simultaneously, provides key clinical information on the risk of several diseases and the diagnosis of several diseases. The measurements can include the absolute number (for instance, 36.6 degrees Celsius on the right and 36.0 Celsius on the left) and differences between the left and right side, or variations of temperature with time. The following graphs, which plot temperature vs. time for right ABTT terminus 10 ("R") and left ABTT terminus 10 ("L"), describe hitherto unrecognized characteristics of diseases and conditions based on analysis of the output of ABTT terminuses 10.

Figure 89:
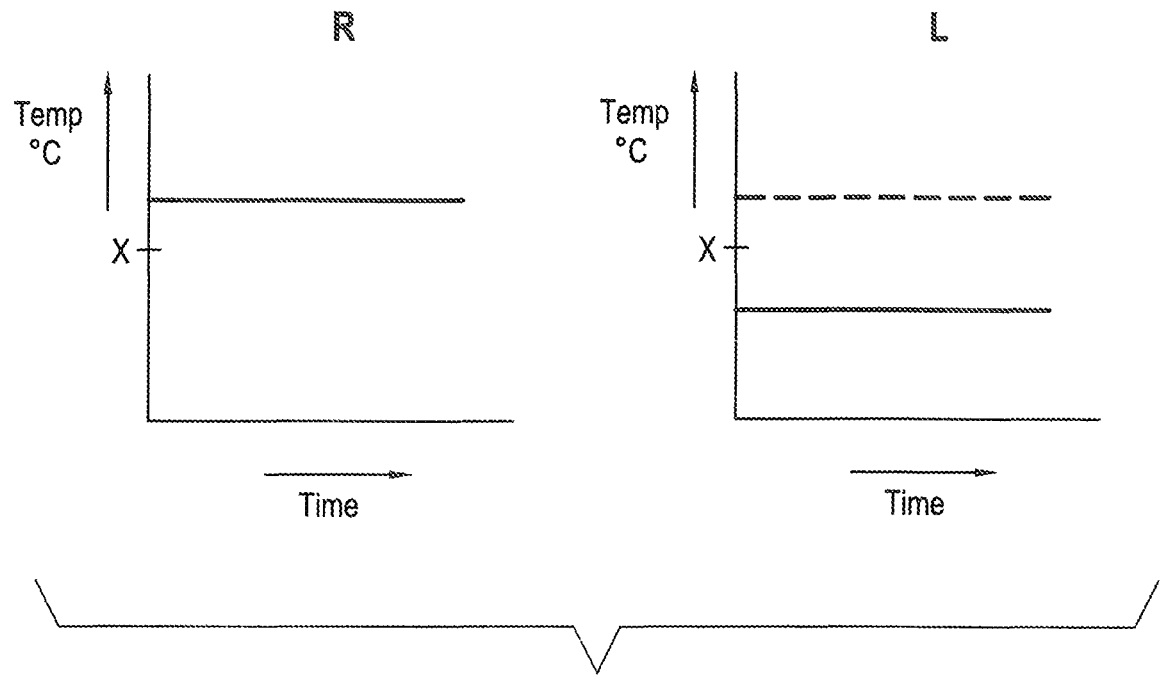

FIG. 89 shows right ABTT terminus 10 having a higher temperature than left ABTT terminus 10, indicating risk of aneurysm rupture on the right side.

Figure 90:
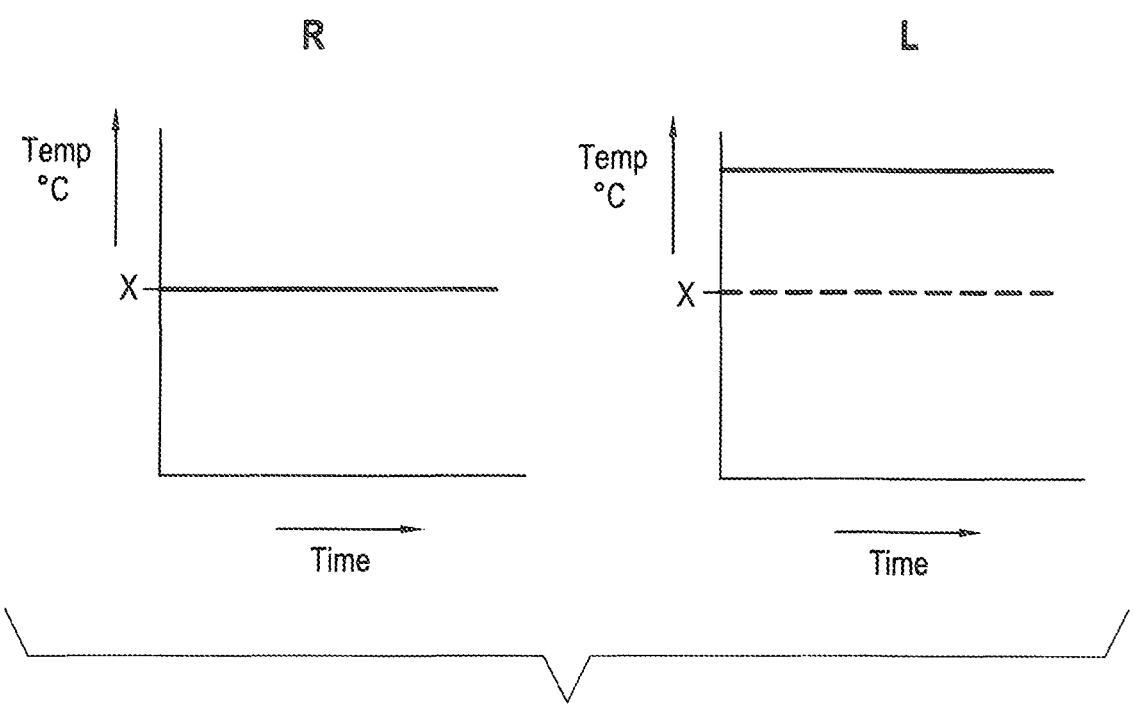

FIG. 90 shows normal temperature in right ABTT terminus 10 and higher temperature in left ABTT terminus 10 indicating risk of brain cancer in the left side.

Figure 91:
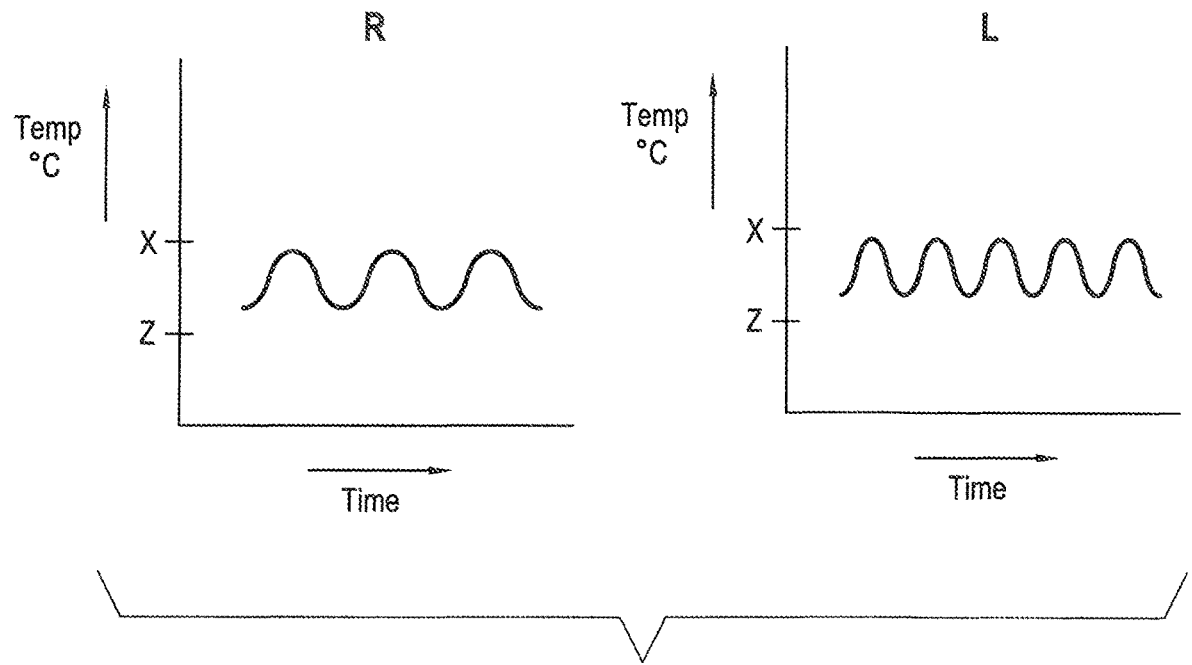

FIG. 91 shows an oscillatory pattern with higher frequency on left ABTT terminus 10 and lower frequency on right ABTT terminus 10 indicating risk of seizures on the left side.

Figure 92:
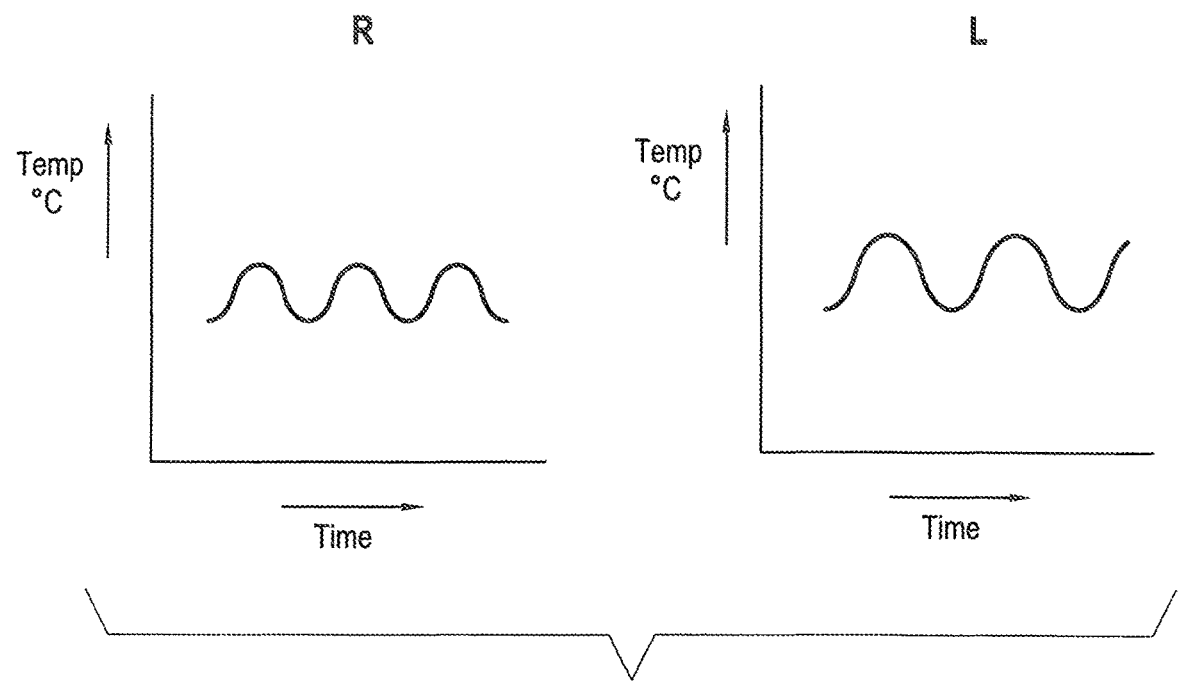

FIG. 92 shows an oscillatory pattern with frequency lower than normal in both sides, but higher frequency in right ABTT terminus 10, indicating progression of infection on the left side of the brain or nervous system.

Figure 93:
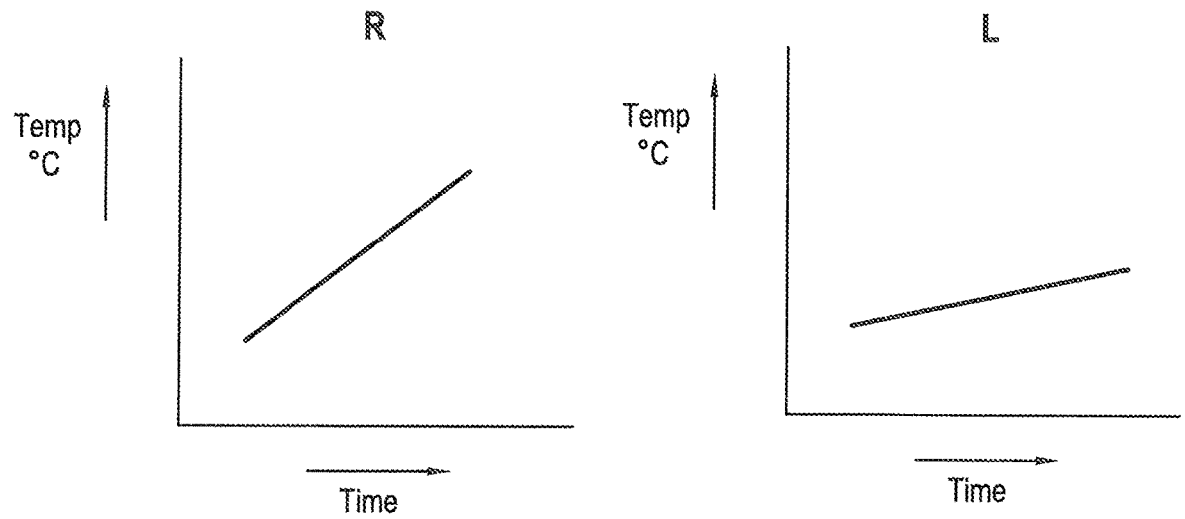

FIG. 93 shows a higher velocity of temperature change in right ABTT terminus 10 as compared to the lower ABTT indicating risk of abscess in the right side.

Figure 94:
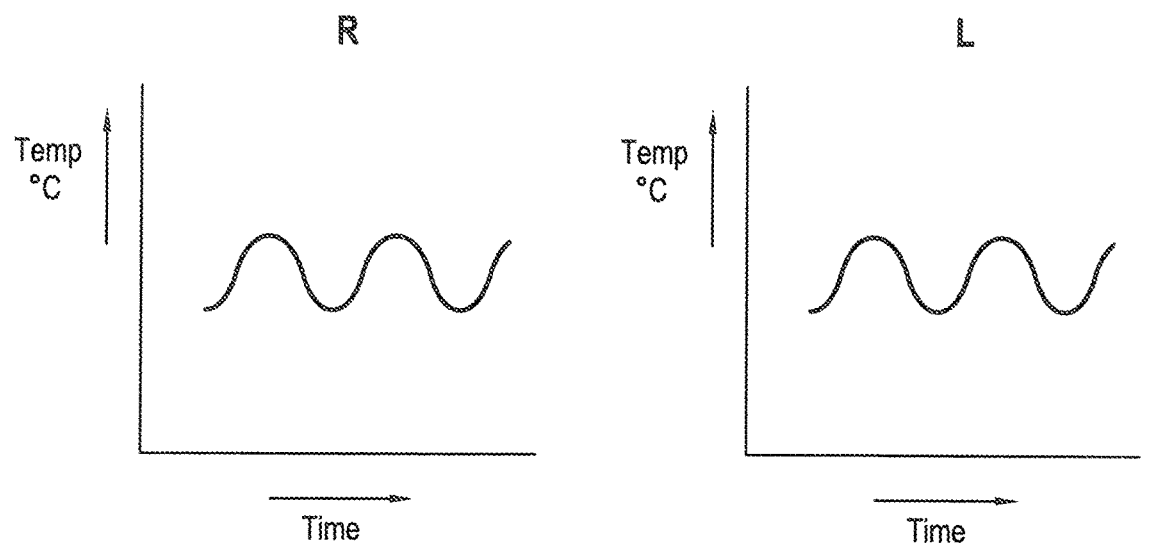

FIG. 94 shows an oscillatory pattern with lower frequency on both, right ABTT terminus 10 and left ABTT terminus 10, indicating Alzheimer's disease or spread of Alzheimer's disease beyond the hippocampus.

Figure 95:
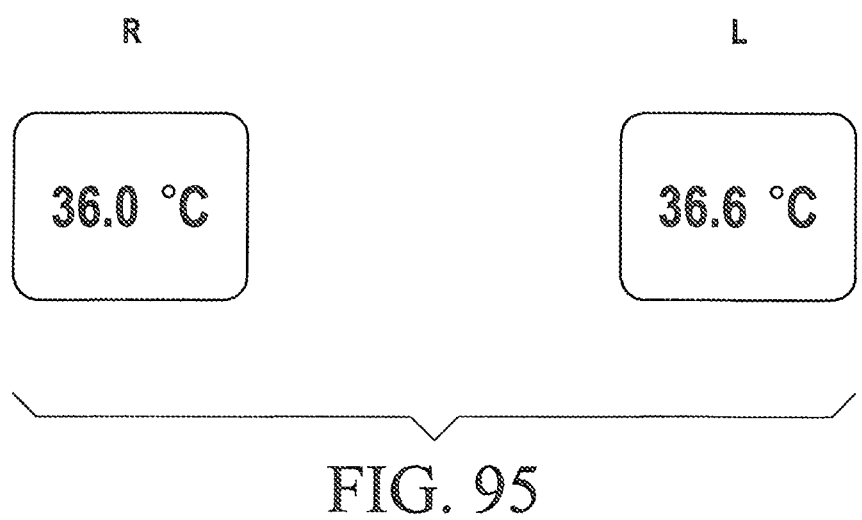

FIG. 95 shows a display indicating numerical absolute value with lower temperature in right ABTT terminus 10 (36.0 degrees Celsius) and normal temperature in left ABTT terminus 10 (36.7 degrees Celsius) indicating risk of stroke in the right side.

System 1400 is further configured to include a control device 1408 that can be configured to include a keypad, microphone, USB or other port, card scanner, or other device to provide various control functions for system 1400. Such control functions can include movement of IR camera 1404 along support system 1402 to align IR camera 1404 with face 1406. IR camera 1404 can be configured to include a connector (not shown), a transceiver (not shown), or both. Similarly, control device 1408 can be configured to include a connector (not shown), a transceiver (not shown), or both. Thus, control device 1408 can communicate with IR camera 1404 by way of a cable (not shown) or wirelessly. System 1400 can further be configured to include pressure or presence detection device 1316 that includes a pressure or presence sensor and is configured to communicate with control device 1408 either through a cable (not shown) or wirelessly.

It should be understood that IR camera 1404 includes a FOV 1410 of a certain angle. In an exemplary embodiment, the configuration and position of IR camera 1404 is such that FOV 1410 is sufficiently large to include most or all of face 1406 when a subject 1412 is standing at a location of pressure or presence detection device 1316. It should be understood that within FOV 1410 is a smaller two-dimensional area 1414 that corresponds to the area of ABTT terminus 10 and an area directly adjacent or next to ABTT terminus 10.

To operate system 1400, subject 1412 stands on pressure or presence detection device 1316, which initiates or actuates system 1400. Pressure or presence detection device 1316 can immediately provide the weight of subject 1412. In an exemplary embodiment, subject 1412 can begin a temperature measurement operation by pressing a key on control device 1408. Alternatively, the presence of subject 1412 on pressure detection device 1316 can initiate a temperature measurement operation. As yet another alternative, a separate electronic device (not shown), such as a cell phone, laptop, tablet, etc., can be configured to communicate with system 1400 and to initiate system 1400 operation as well as control the functions of system 1400.

In an exemplary embodiment, subject 1412 either manually moves IR camera 1404 to aim toward an eye of subject 1412, or uses controls on control device 1408 to position IR camera 1404 vertically along support system 1402. In another exemplary embodiment, IR camera 1404 moves along support system 1402, scanning for the hot spot represented by ABTT terminus 10. In this latter embodiment, once IR camera 1404 identifies the hot spot represented by ABTT terminus 10, IR camera 1404 positions itself to acquire temperature signals from ABTT terminus 10. It should be noted that the movement of IR camera 1404 also provides system 1400 with the ability to measure the height of subject 1412, since IR camera 1404 can determine the location of the top of a head of subject 1412 through its thermal imaging capability. Alternatively, once IR camera 1404 has located ABTT terminus 10, system 1400 can estimate the height of subject 1412 given that the average distance from ABTT terminus 10 to the top of a typical person's head is a previously measured distance.

Once IR camera 1404 is positioned to measure the temperature of ABTT terminus 10, acquisition and analysis of temperature data begins, which may be accomplished in control device 1408 or in separate electronic device (not shown). The data acquisition process can be configured to include a plurality of time intervals, depending on the type of data analysis required. For simple temperature measurements, the length of data acquisition is typically seconds, e.g., 10 to 20 seconds. For complex measurements, the length of data acquisition can be minutes. Some data acquisition intervals may be very lengthy and it can be beneficial to provide a chair for subject 1412.

Figure 88:
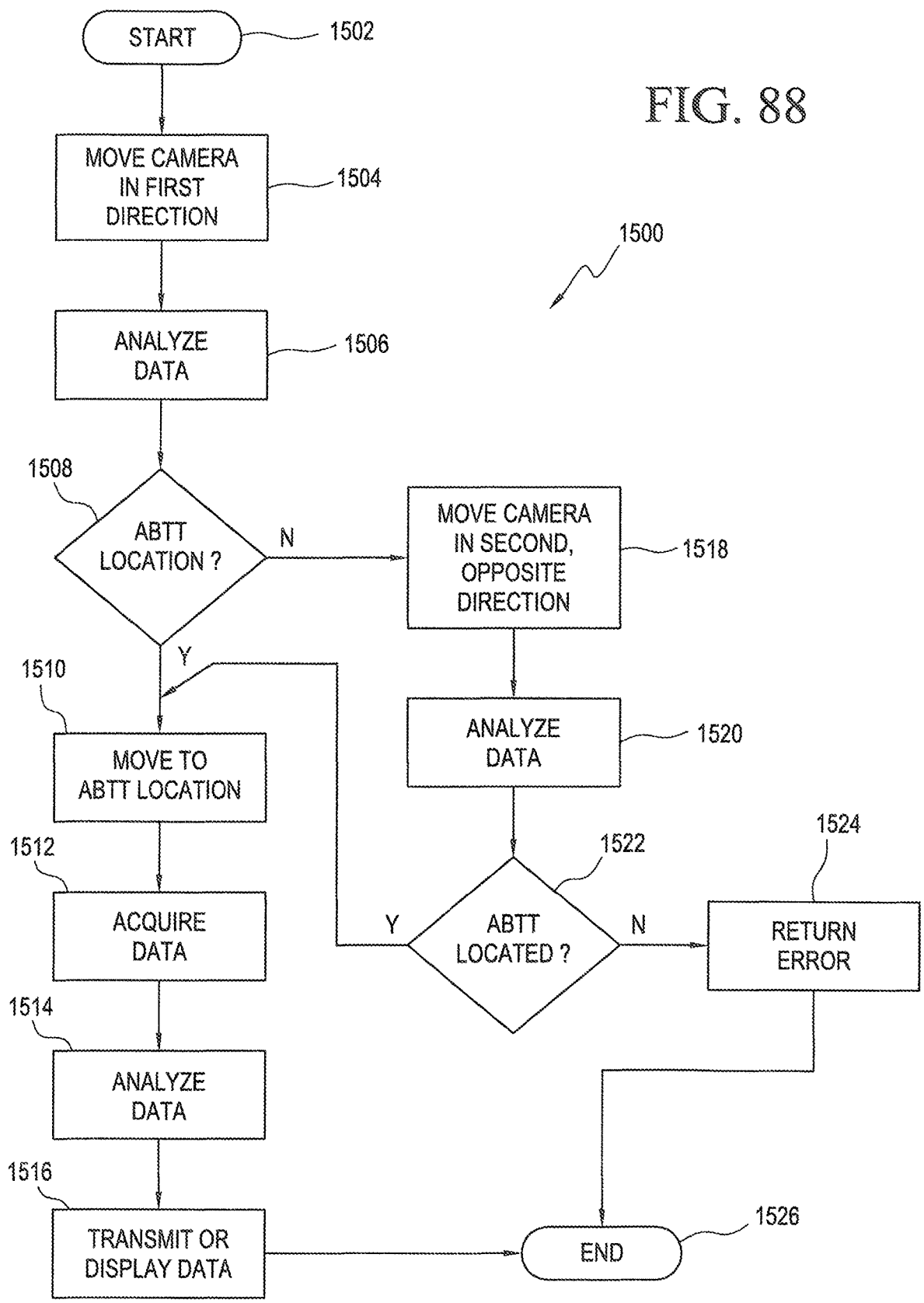

FIG. 88 shows an ABTT acquisition process in accordance with an exemplary embodiment of the present disclosure, indicated generally at 1500. The function of process 1500 is to drive an IR camera, such as IR camera 1306, to a location where the temperature output of ABTT terminus 10 can be measured. Process 5100 begins with a start process 1502, during which various elements of an ABTT temperature measurement system are powered and initialized. Once the ABTT temperature measurement system is initialized, control passes from start process 1502 to a first direction movement process 1504.

In first direction movement process 1504, the IR camera is moved vertically along a support system. While the IR camera is moving, it is acquiring IR imagery. In an exemplary embodiment, the data from the IR camera is being analyzed, for example at an analyze data process 1506, as the data is acquired. In another exemplary embodiment, the data is analyzed after the IR camera reaches a first limit of travel. If the data is analyzed in near real time, as the data is acquired, control moves to an ABTT terminus located decision process 1508 once a location of ABTT terminus 10 has been identified. Otherwise, the IR camera is permitted to reach the first limit before control is passed to ABTT terminus located decision process 1508.

At ABTT terminus located decision process 1508, a decision as to whether ABTT terminus 10 has been located is made. Such a decision may be made if a predetermined temperature of a face is identified, such as a temperature in a range of 97.5 to 106 degrees Fahrenheit. In certain circumstances, skin surrounding ABTT terminus 10 may be hotter than ABTT terminus 10. The ABTT temperature measurement systems of the present disclosure are able to handle this situation by recognizing that all temperatures surrounding ABTT terminus 10 are hotter than ABTT terminus 10, thus recognizing that ABTT terminus 10 is cooler than skin surrounding ABTT terminus 10. In a very rare circumstance, the temperature of surrounding skin is approximately the same temperature of ABTT terminus 10, which may require additional measures to cool the surrounding skin to gain valid temperature measurements. If ABTT terminus 10 can be identified, control passes to a move to an ABTT terminus location process 1510. If ABTT terminus 10 cannot be identified, control passes to a second direction movement process 1518.

In move to ABTT terminus location process 1510, the IR camera is driven to the height or location at which ABTT terminus 10 was identified. Once the IR camera reaches the determined location, control passes from ABTT terminus location process 1510 to an acquire data process 1512.

In acquire data process 1512, temperature data from ABTT terminus 10 is acquired for a predetermined period. Such data acquisition can be for seconds to many minutes. A typical range of data acquisition for temperature readings only is approximately 10 to 20 seconds. For more detailed data acquisition to diagnose medical conditions, data acquisition can be from 30 seconds to 20 minutes or even more. Once the predetermined period for data acquisition has been reached, control passes from acquire data process 1512 to an analyze data process 1514.

The data received in acquire data process 1512 is analyzed in analyze data process 1514. Once analysis is complete, control moves from analyze data process 1514 to a transmit or display data process 1516, where the analyzed data is transmitted to an electronic device, such as a laptop, tablet, cell phone, etc., or the data is displayed on a system display, or both. Control then passes to an end process 1526, which can place all hardware into a standby mode or an off mode after a predetermined period to permit review of the analyzed data.

Returning to second direction movement process 1518, the IR camera is moved vertically along the support system in a second direction that is opposite to the first direction. While the IR camera is moving, it is acquiring IR imagery. In an exemplary embodiment, the data from the IR camera is being analyzed, for example at an analyze data process 1520, as the data is acquired. In another exemplary embodiment, the data is analyzed after the IR camera reaches a second limit of travel. If the data is analyzed in near real time, as the data is acquired, control moves to an ABTT terminus located decision process 1522 once a location of ABTT terminus 10 has been identified. Otherwise, the IR camera is permitted to reach the first limit before control is passed to ABTT terminus located decision process 1522.

At ABTT terminus located decision process 1522, a decision as to whether ABTT terminus 10 has been located is made. Such a decision may be made if a predetermined temperature of a face is identified, such as a temperature in a range of 97.5 to 1106 degrees Fahrenheit. In certain circumstances, skin surrounding ABTT terminus 10 may be hotter than ABTT terminus 10. The ABTT temperature measurement systems of the present disclosure are able to handle this situation by recognizing that all temperatures surrounding ABTT terminus 10 are hotter than ABTT terminus 10, thus recognizing that ABTT terminus 10 is cooler than skin surrounding ABTT terminus 10. In a very rare circumstance, the temperature of surrounding skin is approximately the same temperature of ABTT terminus 10, which may require additional measures to cool the surrounding skin to gain valid temperature measurements. If ABTT terminus 10 can be identified, control passes to a move to ABTT terminus location process 1510, which operates as previously described herein. If ABTT terminus 10 cannot be identified, control passes to a return error process 1524.

In return error process 1524, a notification is provided to the subject, patient, or other individual that ABTT terminus 10 was not located. Control then passes from return error process 1524 to end process 1526, which functions as previously described.

While some embodiments herein describe thermal imaging such that an entirety of a face is acquired, it should be apparent that full face imaging is not required to locate and identify a horn-shaped region between the eye and the nose where ABTT terminus 10 is located. Thus, in some embodiments the thermal imaging camera may only need a field of view sufficient to identify the unique location on the face where ABTT terminus 10 is located rather than an entire face.

Referring to FIGS. 96-99, an electronic apparatus configured with a measurement device in accordance with an exemplary embodiment of the present disclosure is shown, indicated generally at 2040. Electronic apparatus 2040 may be configured as a cell phone, tablet, or other similarly sized electronic device. Electronic apparatus 2040 is configured to include a camera 2042, a display 2044, a first sensor 2046, and a second sensor 2048 positioned a spaced distance from first sensor 2046 to permit simultaneous acquisition of temperature from a left ABTT terminus 10 and a right ABTT terminus 10.

Figure 3:
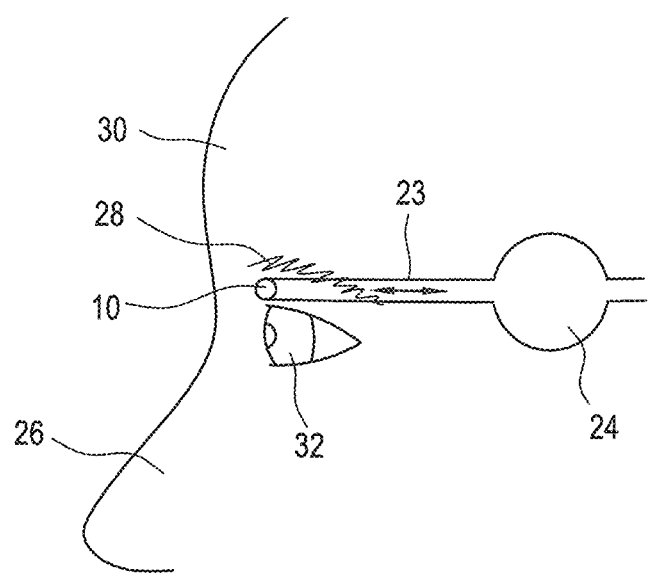
FIG. 3 shows a stylized representation of the flow of blood into a brain core.

Electronic apparatus 2040 may be configured to acquire the temperature of one or both ABTT terminuses 10 by first activating camera 2042 and displaying a face, such as that shown in FIGS. 2 and 3, on display 2044. In an exemplary embodiment, in addition to displaying a face, a complementary display of temperature may be displayed to enable a user to guide electronic apparatus to the location of left ABTT terminus 10 and right ABTT terminus 10. Once first sensor 2046 and second sensor 2048 are positioned to measure the temperature of left ABTT terminus 10 and right ABTT terminus 10, which takes seconds, electronic apparatus 2040 acquires and provides the temperature of each ABTT terminus 10 on display 2044, rapidly, accurately, and precisely providing a non-contact measurement of the temperature of brain core 2024. All functions of electronic apparatus 2040 may be activated through display 2044, which may be configured as an interactive touch screen, or through one or more physical buttons, switches, or other controls located on electronic apparatus 2040. It should be understood that sensors 2046 and 2048 may be configured as thermopiles, infrared sensors, or other suitable sensors configured to measure body parameters without direct contact, though either sensor 2046 or sensor 2048 may be placed into direct contact with one ABTT terminus 10 at a time.

Referring to FIGS. 100 and 101, another electronic apparatus configured with a temperature measurement device in accordance with an exemplary embodiment of the present disclosure is shown and indicated generally at 2050. Electronic apparatus 2050 is configured as a wrist-mounted device, e.g., a wrist watch, including a strap 2052, and an apparatus body 54. Electronic apparatus 50 further includes a display 2056 and a sensor 2058, which can be similar in function and construction to first sensor 2046 and second sensor 2048. A user of electronic apparatus 2050 can acquire the temperature at ABTT terminus 10 by pressing one or more controls (not shown), or using display 2056, which can be configured as a touch screen, as an input to electronic apparatus 2050, and then holding their wrist in a location that places sensor 2058 near ABTT terminus 10. Electronic apparatus 2050 may be configured with a first audible output to indicate that ABTT terminus has been located, which may be accomplished by receiving a temperature in a predetermined range, or by mapping the temperature in the region around ABTT terminus 10. Such mapping can be accomplished by, for example, a scanning type of motion of electronic apparatus 2050 so that sensor 2058 can find the peak temperature at ABTT terminus 10, or, in those rare circumstances where the temperature at ABTT terminus 10 is lower than the temperature of surrounding skin, which can occur in very hot ambient conditions, the minimum temperature at ABTT terminus 10. Such scanning in described in more detail in co-pending U.S. patent application Ser. No. 14/593,848, incorporated herein by reference in its entirety. Once ABTT terminus 10 has been located, a second audible output, which can be different from the first audible output, can indicate that temperature at ABTT terminus 10 has been measured. Once the temperature of ABTT terminus 10 has been measured, a user will move display 2056 to a location where it can be viewed, seeing a displayed temperature, or an audible output can present the temperature of ABTT terminus 10.

FIG. 102 is a view of yet another electronic apparatus configured with a temperature measurement device in accordance with an exemplary embodiment of the present disclosure, indicated generally at 2060. Electronic apparatus 2060 is configured to include a display 2062, a temperature sensing device 2064, and an electrical connector 2066. Temperature sensing device 2064 is configured to attach to electronic apparatus 2060, and to interface with connector 2066. Temperature sensing device 2064 is configured to include a probe 2068, a sensor body 2070 configured to attach to a housing 2070 of electronic apparatus 2060, and an electrical sensor connector 2072 configured to mate with connector 2066. Probe 2068 is configured to include a sensor 2074 located at a distal end of a sensor arm 2076. Sensing device 2064 is configured as a plug-in device, which can be by way of sensor connector 2072.

Sensor 2074 may be positioned to be in contact with ABTT terminus 10. To find ABTT terminus 10, the area of ABTT terminus 10 may be scanned by sensor 2074, with electronic apparatus 2060 providing an audible, visual, such as on display 2062 or a flashing light, or vibratory, also described as tactile feedback, output. A first indication from electronic apparatus 2060 can be indicative of locating ABTT terminus 10, and a second indication from electronic apparatus 2060 can be indicative of a temperature measurement of ABTT terminus 10. Electronic apparatus 2060 can be configured to transmit temperature data wirelessly or by wire to other electronic devices.

Referring to FIG. 103, another electronic apparatus configured with a temperature measurement device in accordance with an exemplary embodiment of the present disclosure is shown and indicated generally at 2080. Electronic apparatus 80 can be configured as a cell phone (or alternatively a tablet, a computer device, and the like) and includes an apparatus body 2082 including a front face 2084, a back face 2086, a display 2088, and a temperature sensor 2090. Apparatus body 2082 further includes a top side face 2092, a right side face 2094, a bottom side face 2096, and a left side face 2098, in addition to a left top corner 2100, a right top corner 2102, a right bottom corner 2104, and a left bottom corner 2106. Temperature sensor 2090 can be similar in function and construction to first sensor 2046 and second sensor 2048.

Considering that the ABTT is located in a rather confined and hidden area at a junction of the nose with eyebrow, and in an orbital roof area, the position of temperature sensor 2090 in apparatus body 2082 is configured to mate with this area in a specific and defined way, otherwise measurements will be difficult and the nose may hinder proper measurement. If a sensor, for instance, is positioned in a mid-portion of apparatus body 2082 exemplified as a cell phone, the orbital bone would prevent temperature sensor 2090 from reaching ABTT terminus 10 at a roof of the orbit. In order to reach ABTT terminus 10, which is positioned at the roof of the orbit and in the junction of the eyebrow and nose, temperature sensor 2090 in apparatus body 2082 is preferably located adjacent to one of corners 2100, 2102, 2104, or 2106, temperature sensor 2090 being also preferably located in one of side faces 2092, 2094, 2096, and 2098. The preferred distance from temperature sensor 2090 to one of corners 2100, 2102, 2104, or 2106 is equal to or less than 30 mm, is more preferably equal to or less than 20 mm, is even more preferably equal to or less than 15 mm, is still more preferably equal to or less than 10 mm, and is most preferably equal to or less than 5 mm.

Temperature sensor 2090 is preferably located adjacent to one of top corners 2094 and 2096, and bottom corners 2098 and 2100. By way of example but not of limitation, in FIG. 103 temperature sensor 2090 is located on top side face 2092 and adjacent, alongside, near, or close to corner 2102.

FIG. 104 shows a perspective view of yet a further electronic apparatus, indicated generally at 2110, configured with a measurement device in accordance with an exemplary embodiment of the present disclosure. While electronic apparatus 110 includes differences from electronic apparatus 2080 shown in FIG. 103, the features are sufficiently similar that the same element numbers are used for the sake of brevity. In FIG. 104, temperature sensor 2090 is positioned on or in left side face 98 in a location that is adjacent, near, alongside, or close to corner 2106.

Electronic apparatus 2080 and electronic apparatus 2110 can be configured to include a nose piece 2112, which can be permanently or integrally fixed or detachably connected to temperature sensor 2090, to assist positioning apparatus body 2082 to align temperature sensor 2090 with ABTT terminus 10, as shown in FIGS. 105 and 106.

A user of electronic apparatus 2080 can acquire the temperature at ABTT terminus 10 by pressing one or more controls (not shown), or using display 2088, which can be configured as a touch screen, as an input to electronic apparatus 2080, and then holding apparatus body 2082 next to, alongside, near, or close to nose 2026 with display 2088 essentially parallel to nose 2026, and in a location that places temperature sensor 2090 near, adjacent to, alongside, close to, at, or on ABTT terminus 10, as shown in FIG. 107, with sensor 2090 of FIG. 104 exemplarily showing as the measurement sensor (performing a contact or a non-contact measurement) and receiving a thermal signal from ABTT terminus 10. FIG. 108 shows electronic apparatus 2080 with nose piece 112 positioned on nose 2026 of the user's face for measurement.

It should be understood that although sensor 2090 is primarily described as a temperature sensor, sensor 2090, as well as other sensors described herein for interfacing with ABTT terminus 10, can include a variety of sensors including, and by way of example, a glucose sensor, a chemical sensor, an oxygen sensor, a pulse sensor, an oximetry sensor, blood pressure sensor, an optical sensor, a fluorescent sensor, and any sensor capable of measuring any biological variable or biological signal including the various biological signals and parameters described by Applicant in various patents and applications under the title "Apparatus and Method for Measuring Biologic Parameters," including U.S. Pat. No. 7,187,960, issued Mar. 6, 2007, U.S. Pat. No. 8,172,459, issued May 8, 2012, U.S. Pat. No. 8,328,420, issued Dec. 11, 2012, U.S. Pat. No. 8,721,562, issued May 13, 2014, U.S. Pat. No. 8,849,379, issued Sep. 30, 2014, U.S. Pat. No. 9,011,349, issued Apr. 21, 2015, U.S. Pat. No. 9,119,530, issued Sep. 1, 2015, pending U.S. patent application Ser. No. 14/500,362, filed Sep. 29, 2014, pending U.S. patent application Ser. No. 14/500,550, filed Sep. 29, 2014, pending U.S. patent application Ser. No. 14/622,284, filed Feb. 13, 2015, and pending U.S. patent application Ser. No. 14/687, 106, filed Apr. 15, 2015, the contents of which are incorporated by reference in their entirety herein.

Sensor 2090 can include contact and non-contact sensors and detectors, including infrared detectors. Other sensors such as proximity sensors, optical sensors, and the like can be included as part of sensor 2090 and can be used alone or in combination with other sensors. Any of the sensors described in this disclosure can include the plurality of sensors mentioned herein, as a single sensor or a combination of sensors.

FIG. 109 shows a view of an electronic apparatus, indicated generally at 130, configured with a measurement device, indicated generally at 2132, in accordance with an exemplary embodiment of the present disclosure. Measurement device 2132 includes a pair of sensors 2134 positioned on one of side faces 2092, 2094, 2096, or 2098 of apparatus body 2082. By way of example, sensors 2134 can each include an array of infrared sensors configured to read infrared emission from at least one ABTT terminus 10 on the user's face. Emission from ABTT terminus 10 is captured by sensors 2134, and can be displayed on display 2088. The captured image can be analyzed by electronic apparatus 2120 to determine a temperature of ABTT terminus 10. It should be understood that chemical measurements and measurement of analytes including glucose can be accomplished by capturing emissions from ABTT terminus 10, and the processor (not shown) located in apparatus body 2082 execute operations to calculate and report concentration and amount of the chemical substances and the analytes.

FIG. 110 shows a view of an electronic apparatus, indicated generally at 2140, in accordance with an exemplary embodiment of the present disclosure. Electronic apparatus 2140 is similar to electronic apparatus 2120 of FIG. 110, but each array 2134 is replaced by a single sensor 2136, meaning a single thermal sensor rather than an array of thermal sensors. It should be understood that although two sensors 2142 are described, in an alternative embodiment electronic apparatus 2140 includes only one sensor 2140.

FIG. 111 shows a view of an electronic apparatus, indicated generally at 2150, configured to include a measurement device, indicated generally at 2152, in accordance with yet another exemplary embodiment of the present disclosure. Measurement device 2152 includes a thermal sensor array in the exemplary embodiment of FIG. 111. Each ABTT terminus 10 can be measured by measuring a first side, such as the right side, and then measuring the second opposite side, such as the left side. Measurement device 2152 is removably attached connected to the body of electronic apparatus by an electrical jack or connector, described elsewhere herein, configured to fit in a connector positioned the body of electronic apparatus 2150.

Anatomy of ABTT terminus 10 is associated with anatomy and dimensions of nose 2026. FIGS. 112-115 show views of an electronic apparatus, indicated generally at 2160, in accordance with an exemplary embodiment of the present disclosure. Electronic apparatus 2160 includes a pair of rotatable sensors 2162 disposed near an end of electronic apparatus 2160, each rotatable sensor 2162 positionable or adjustable to a particular nose 2026 for each individual of a population. Each sensor 2162 is positioned on a corner, such as a top left corner 2164 and/or a top right corner 2166 of an apparatus body 2168 of electronic apparatus 2160. Each sensor 2162 of the pair or the dual sensors is rotatable about a longitudinal axis of electronic apparatus 2160 that extends along the longest length of electronic apparatus 2160 to enable a user to align each sensor 2162 with a respective ABTT terminus 10. Electronic apparatus 2160 further includes a pair of sensors 2170 on a side face of electronic apparatus, such as right side face 2172. Each sensor 2170 is individually slidable in a slot or groove 2174 to modify the spacing between sensors 2170, with such spacing having a minimum predetermined spacing 2176 and a maximum predetermined spacing 2178 to adjust the spacing of sensors 2170 for alignment with respect ABTT terminuses 10. Although rotatable sensors 2162 and slidable or sliding sensors 2170 are shown permanently affixed to apparatus body 2168, it should be understood that a removably attached sensor assembly with a rotatable or sliding mechanism are within the scope of the disclosure.

FIGS. 116 and 120 show views of a separable sensor device, indicated generally at 2180, in accordance with an exemplary embodiment of the present disclosure. It should be understood that separable sensor device 2180 can also be described as a sensor assembly, as can other separable sensor devices disclosed herein. Separable sensor device 2180 includes an electrical jack or connector 2182 configured to connect to a mating electrical connector positioned in an electronic apparatus. Separable sensor device 2180 includes two flexible arms 2184, which can be approximately parallel in the relaxed condition shown in FIG. 116, and can be moved away from each other in as shown in FIG. 120 to configure a first spaced distance 2204 between sensors 2186 up to a second spaced distance 2206 between sensors 2186. First spaced distance 2204 and second spaced distance 2206 permit a range of adaptability for the nose and facial anatomy, e.g., nose widths, of individuals. Each flexible arm extends in a longitudinal direction and includes a sensor 2186 at a terminus or distal end 2188, each sensor 2186 with an axis that is disposed essentially perpendicular to the longitudinal direction of arm 184 and having a measuring surface 2190. Measuring surface 2190 is configured to measure an emitted signal of ABTT terminus 10.

FIG. 117 shows separable sensor device 2180 positioned on an apparatus body 2194 of an electronic apparatus 2192, secured by jack 2182. In an alternative embodiment, a separable sensor device 2196 includes a wire or cable 2198 terminating in a jack 2200, as shown in FIG. 118. Jack 2200 is configured to mate with an electrical connector 2202 positioned in apparatus body 2194 to form a system.

FIG. 119 shows a sensor system, indicated generally at 2210, in accordance with an exemplary embodiment of the present disclosure. Sensor system 2210 includes a separable sensor device 2212 including a near field wireless transmitter operatively coupled to a remote electronic apparatus 2214, which includes at least a complementary wireless receiver. Thus, separable sensor device 2212 can be physically entirely separate from a corresponding electronic apparatus 2214 and still communication with electronic apparatus 2214 for the purpose of acquiring emissions from ABTT terminus 10.

Application of energy, including thermal energy to ABTT terminus 10, has been shown by Applicant to treat a variety of disorders, including Alzheimer's disease, Parkinson's disease, multiple sclerosis, cancer, and hyperthermia and hypothermia conditions. The present disclosure discloses temperature modification devices and systems connecting temperature modification devices operatively coupled with electronic apparatus, configured to remove and apply heat to ABTT terminus 10. Temperature modification elements located in temperature modification devices can be bi-directional thermoelectric devices that are configured to provide heating and cooling, resistive heaters, fluid systems, infrared lights, infrared LEDs, or other devices configured to change modify temperature.

FIG. 121 shows a temperature modification device, indicated generally at 2220, and an electronic apparatus, indicated generally at 2222. When temperature modification device 2220 is positioned on, attached to, or connected to electronic apparatus 2222, a temperature sensing and modification system 224 is formed. Temperature modification device 2220 can connect or attach to an apparatus body 2226 of electronic apparatus 2222 via an electrical connector or jack 228, which mates with an electrical connector 2238 positioned in apparatus body 2226. Temperature modification device 2220 includes two flexible arms 2230 that can be similar or identical to flexible arms 184 described elsewhere herein, and which can be approximately parallel or parallel. Each of flexible parallel arms 2230 includes at least one temperature modification element 2231 and a sensor 2232 positioned at a distal terminus 2234. Each sensor 2232 includes a measuring surface 2236 disposed essentially perpendicular to the longest dimension of arm and configured to measure a signal at ABTT terminus 10.

FIG. 122 shows a view of a temperature modification device, indicated generally at 2240, in accordance with another exemplary embodiment of the present disclosure. Temperature modification device 2240 includes some features either similar to or identical to the features of temperature modification device 2220. Accordingly, similar or identical elements in FIG. 30 to those of FIG. 121 are labelled with the same element numbers. Temperature modification device 240 includes a wire or cable 2242 terminating in a jack 2244. Jack 2244 is configured to mate with an electrical connector 2238 positioned in apparatus body 2226 to form a system.

FIG. 123 shows a view of a temperature modification device, indicated generally at 2250, in accordance with yet another exemplary embodiment of the present disclosure. Temperature modification device 2250 is similar in some ways to temperature modification device 2220 shown in FIG. 121, and is accordingly similarly labelled for brevity. Temperature modification device 2250 includes a transmitter 2252 for communication with a separate or remote electronic apparatus, such as electronic apparatus 222 shown in FIG. 121.

Considering the anatomy of ABTT terminus and morphology of a bridge of the nose, an arm that forms part of a separable sensor device or a temperature modification device includes a specialized dimension for fitting on or around the ABTT area. The preferred length of an arm, such as arm 2184, is equal to or less than 100 mm, is more preferably equal to or less than 50 mm, is even more preferably equal to or less than 30 mm, is even yet more preferably equal to or less than 20 mm, and is most preferably equal to or less than 10 mm. The preferred diameter (or width) of each arm is equal to or less than 40 mm, is more preferably equal to or less than 20 mm, is even more preferably equal to or less than 15 mm, is even yet more preferably equal to or less than 10 mm, and is most preferably equal to or less than 5 mm.

FIG. 124 shows a view of a temperature modification device, indicated generally at 2260, in accordance with still yet another exemplary embodiment of the present disclosure. Elements that are functionally similar to previously described temperature modification device 2220 are similarly labelled. Temperature modification device 2220 includes a processor 2262, a transmitter 2264, a power source 2268, and two longitudinally extending, flexible, parallel arms 2268. Each flexible parallel arm includes a heat transfer device 2270 at a distal end or terminus 2272, each heat transfer device 2270 includes a heat transfer surface 2274. Each heat transfer device 2270 extends in a direction that is approximately perpendicular to the longitudinal direction of a respective arm 2268. Heat transfer surface 2274 and heat transfer device 2270 are configured to apply to or remove heat from ABTT terminus 10. Arms 2268 are connected by a spring mechanism 2276 for securing temperature modification device 2260 on the user's nose applying pressure against the nose. It should be understood that any mechanism and compression mechanism, adhesive mechanisms and the like to support the assembly on the nose can be used and are within the scope of the disclosure. It should further be understood that any embodiment for temperature modification can used in any separable sensor device and in conjunction with any sensor of the present disclosure, and any embodiment for a sensor can be used with any temperature modification device of the present disclosure.

FIG. 125 shows a view of a separable sensor device, indicated generally at 2280, in accordance with an exemplary embodiment of the present disclosure. Separable sensor device 2280 is configured to include a sensor head 2282 and a rotating mechanism 2284 that rotates sensor head 2282. Sensor head 2282 includes a sensor 2286 positioned thereon. Rotating mechanism 2284 is configured to positioned sensor 2286 at a 45 degree angle in relation to the ground, which allows alignment with ABTT terminus 10, since the skin entrance of ABTT 12 is located adjacent to the corner made by the eyebrow and bridge of the nose, and underneath the eyebrow.

FIGS. 126 and 128 show views of a separable sensor device, indicated generally at 2290, in accordance with another exemplary embodiment of the present disclosure. Separable sensor device 2290 includes an electrical connector or jack 2292 that extends in a direction that is approximately perpendicular to a longitudinal axis 2294 that extends along a longitudinal body 2296 of separable sensor device 290. Separable sensor device 2290 includes a sensor surface 2298 that extends in a direction that is away connector 2292. FIG. 128 shows a view of separable sensor device 2290 connected to an electronic apparatus 2304 and positioned to acquire emissions from ABTT terminus 10.

FIG. 127 shows a perspective view of another separable sensor device, indicated generally at 2300, in accordance with an exemplary embodiment of the present disclosure. Separable sensor device 2300 includes a plurality of sensor measuring surfaces 2302 that are approximately parallel to the longitudinal extent of connector 2292 of separable sensor device 2300. Both sensor measuring surface 2302 are oriented to be approximately parallel to each other and to be oriented to face in a front or forward direction.

It should be understood that a sensor measuring surface can be disposed in any orientation on a measuring arm, including facing forward, as shown in FIG. 127, diagonally, as shown in FIG. 125, and upwardly, as shown in FIG. 126. It should also be understood that all embodiments of sensor assemblies can be used in embodiments of temperature modification devices, and the embodiments of temperature modification devices can have heat transfer surface disposed at angles and in similar orientations as manner as measuring surfaces of various separable sensor devices and sensor.

FIG. 129-131 show views of an electronic apparatus, indicated generally at 2310, configured with a measurement device in accordance with an exemplary embodiment of the present disclosure. Electronic apparatus 2310 includes an apparatus body 2312, and apparatus body 2312 includes a movable, rotatable, or flippable arm 2314. Flippable arm 2314 includes a sensor 2316 positioned at a distal or far end of arm 2314 from a pivot or rotation axis 2318 of arm 2314. Sensor 2316 is oriented with a sensor surface 2320 that is approximately perpendicular to a longitudinal extent of arm 2314. As shown in FIG. 131, arm 2314 rotates in the direction of arrow 3222 shown in FIG. 130 and in the direction of arrow 2324 in FIG. 131 to position sensor 2316 at a spaced distance from electronic apparatus 2310 in a location to acquire an emission from ABTT terminus 10 of the user, with sensor 2316 resting on or adjacent to ABTT terminus 10. It should be understood that sensor can be replaced by a temperature modification device, in similar manner as shown in previous sensor embodiments, and said temperature modification device embodiments are within the scope of the present disclosure.

FIGS. 132 to 139 show alternative embodiment separable sensor devices in accordance with exemplary embodiments of the present disclosure. The separable sensor devices shown in FIGS. 132-139 are similar to the separable sensor devices shown in FIGS. 116 to 120, however, the embodiments of FIGS. 132-139 include only a single sensor and a single arm to support the sensor, and an end of each separable sensor device opposite the end with the sensor terminates in a c-shape nose support. When features between the embodiments are common or similar, the same element number is used for the sake of brevity.

FIG. 132 shows a separable sensor device, indicated generally at 2330, in accordance with an exemplary embodiment of the present disclosure and which includes a sensor support arm 2332, a sensor 2334 positioned on sensor support arm 2332, a "C"-shaped support portion 2336, and a transmitter 2338. C-shaped support portion 2336 is configured to conform to the shape of the user's nose, thus providing the ability to support separable sensor device 2330 while ABTT terminus 10 emissions are measured. FIG. 133 shows a separable sensor device, indicated generally at 2340, in accordance with an exemplary embodiment of the present disclosure. In this embodiment, transmitter 338 is replaced by an electrical connector or jack 2342 configured to mate with an electrical connector positioned on an electronic apparatus, as described elsewhere herein. FIGS. 134 and 135 show separable sensor device 2340 positioned on an electronic apparatus 2344, supported by the connection of connector 2342 with electronic apparatus 2344. FIG. 136 shows a separable sensor device, indicated generally at 2346, in accordance with an exemplary embodiment of the present disclosure. In this embodiment, connector or jack 2342 is replaced by an electrical connector or jack 2348 connected to a device body 2350 of separable sensor device 2346 by a wire or cable 2352. Furthermore, in place of C-shaped support portion 2336 is a short, straight arm 2354 that is approximately perpendicular to a sensor support arm 2356 of separable sensor device 2346. FIGS. 137-139 shows a separable sensor device, indicated generally at 2360, in accordance with an exemplary embodiment of the present disclosure. Separable sensor device 2360 includes features of separable sensor device 2336 shown in FIG. 133 and separable sensor device 2346 shown in FIG. 136, and is labelled accordingly. FIG. 137 shows double axis rotation movement of separable sensor device 2360, one first rotation to position at 45 degrees angle in relation to the main axis of apparatus body, and a second rotation of the sensor head to a 45 degrees angle in relation to the axis of the arm, for alignment with ABTT terminus 10. FIG. 138 shows separable sensor 2360 being positioned on nose 2026 and aligned with ABTT terminus 10. FIG. 139 shows an angle of sensor 2334 for preferred alignment with ABTT terminus 10.

FIG. 140 shows a perspective view of another separable sensor device, indicated generally at 2370, in accordance with an exemplary embodiment of the present disclosure. Separable sensor device 2370 includes a first, right arm 2372, a second, left arm 2374, each of which are essentially flat or planar for apposition to the skin of nose 2026, and a connecting portion 2376 positioned between and connected to right arm 2372 and left arm 2374. Connecting portion 2376 includes an adhesive surface 2378 to anchor separable sensor device 2370 to the skin of nose 26. At least one of right arm 2372 and left arm 2274 includes a sensor 2380 positioned at a distal or free end thereof. Separable sensor device 2370 further includes a transmitter 2382 for wireless communication, which can be, for example, Wi-Fi or Blue Tooth, a processor 2384, and a power source 2386, such as one or more batteries.

FIG. 141 shows a view of yet another separable sensor device, indicated generally at 2390, in accordance with an exemplary embodiment of the present disclosure. Separable sensor device 2390 includes a first, right arm 2392, a second, left arm 2394, each of which are essentially flat or planar for apposition to the skin of nose 2026, and a connecting portion 2396 positioned between and connected to right arm 2392 and left arm 2394. Connecting portion 2396 includes an adhesive surface 2398 to anchor separable sensor device 2390 to the skin of nose 26. Adhesive surface 2398 is covered by a peelable protective cover or layer 2400. Each of right arm 2392 and left arm 2394 includes a sensor 2402 positioned at a distal or free end thereof. Separable sensor device 2390 further includes, for balance between right arm 2392 and left arm 2394, a power source 2404 positioned on right arm 2392 and an integrated circuit 2406 that includes a processor and a transmitter (i.e., a wireless device). The electronic elements of right arm 2392 and left arm 2394 are connected by wires or preferably a flexible circuit (not shown).

FIG. 142 shows a perspective view of a further separable sensor device, indicated generally at 2410, and an electronic apparatus, indicated generally at 2412, in accordance with an exemplary embodiment of the present disclosure. Separable sensor device 2410 and electronic apparatus 2412 form a sensor system 2414. Separable sensor device 2410 includes a left arm 2416, a right arm 2418, and a spring 420 or other compressible material with spring capabilities, including plastic with memory, configured to force left arm 2416 and right arm 418 toward each other, which means that left arm 2416 and right arm 2418 will be pressed against the sides of nose 226 when separable sensor device 2410 is placed on a nose. Each of left arm 2416 and right arm 2418 includes sensor 2402 positioned at a free or distal of each arm for balance. Sensor system 2414 also includes a wire or cable 2422 for connecting separable sensor device 2410 to electronic apparatus 2412. Electronic device 2412 is configured to include a power source 2424, a processor 2426, a transmitter 2428, and a display 2430.

FIG. 143 shows a perspective view of a still further separable sensor device, indicated generally at 2440, in accordance with an exemplary embodiment of the present disclosure. Separable sensor device 2440 includes a left arm 2442, a right arm 2444. Separable sensor device 2440 further includes sensor 2402 located at a free or distal end of right arm 2444, a temperature modification device 2446 located at a free end of left arm 2442, an integrated circuit 448 having a processor and wireless device positioned on left arm 2442, and a power source 2450 positioned on right arm 2444.

FIG. 144 shows a perspective view of a separable temperature modification device, indicated generally at 2460, and an electronic apparatus, indicated generally at 2462, in accordance with an exemplary embodiment of the present disclosure. Device 2460 includes a left arm 2464 and a right arm 2466. Device 2460 further includes a heat transfer device 2468 positioned on a free or distal end of right arm 2466, an integrated circuit 2470 having a processor and wireless device positioned on left arm 2464 wirelessly connected to electronic apparatus 2462, which can be a cell phone, a tablet, a computer device, and the like, and a power source 2472.

FIG. 145 shows a view of separable sensor device 2370 shown in FIG. 140 positioned on nose 2026 of the user. FIG. 146 shows a view of separable sensor device 2410 and electronic apparatus 412 shown in FIG. 142 positioned on a helmet 2432 and being used by the subject. FIG. 147 shows a view of temperature modification device 2460 and electronic apparatus 2462 positioned on helmet 2432 and being used by the subject. Temperature modification device 2460 communicates with electronic apparatus 2462 wirelessly. It should be understood that any head-mounted gear and neck-mounted gear can be used, in accordance to the principles of the present disclosure and are within the scope of the disclosure.

FIG. 148 shows a perspective view of a separable sensor device, indicated generally at 2480, in accordance with an exemplary embodiment of the present disclosure. Separable sensor device 2480 includes a longitudinally extending rod-like body 2482. Device 480 further includes a sensor 2484 positioned at a distal end of body 2482, an electrical connector positioned at a proximate end of body 2482 and extending approximately perpendicular to a longitudinal axis through body 2482, and a pair of expandable grasping arms 2486. Grasping arms 2486 are configured to grasp an apparatus body.

FIG. 149 shows a perspective view of another separable sensor device, indicated generally at 2490, in accordance with an exemplary embodiment of the present disclosure. Device 2490 is similar to device 2480 in certain aspects. Accordingly, similar elements are similarly numbered. Device 2490 includes a rod-like body 492. Device 490 further includes an electrical connector or jack 2494 and a cable or wire 496 that connects jack 2494 to body 2492.

FIG. 150 shows a perspective view of a separable sensor device, indicated generally at 2500, attached to an electronic apparatus, indicated generally at 2502, in accordance with an exemplary embodiment of the present disclosure. Separable sensor device 2500 includes a rod-like body 2504. Grasping arms 2488 grasp a front face of electronic apparatus 2502 and a back face of electronic apparatus 2502 and are connected to body 2504 by a rotating mechanism 2506 configured to position rod-like body 2504 alongside electronic apparatus 2502 in a first position or orientation and to position rod-like body 2504 approximately perpendicular to electronic apparatus 2502. Separable sensor device 2500 also includes a wireless device, such as a transmitter, for communication with electronic apparatus 2502 (e.g., operatively coupled).

FIG. 151 shows grasping arms 2488 in a first, un-extended position 2508 and in a second, extended position 2510. When grasping arms 2488 are in first position 2508, grasping arms 2508 are positioned a first spaced distance 2512 apart. When grasping arms 2488 are in second position 2510, grasping arms 2488 are positioned a second spaced distance 2514, which is greater than first spaced distance 2512, apart. The ability to extend or expand grasping arms 488 permits anchoring an equipped separable sensor device to different thicknesses of an apparatus body. Separable sensor device 2500 is configured to position sensor 484 at a diagonal position or angle 2516 in relation to a main longitudinal axis 2518 of body 2504.

FIGS. 153 to 156 show embodiments of a sensor case configured to mate with an apparatus body of an electronic apparatus. Each sensor case includes a sensor.

FIG. 153 shows a view of yet another separable sensor device, indicated generally at 2530, positioned on an electronic apparatus, indicated generally at 2532, in accordance with an exemplary embodiment of the present disclosure. Separable sensor case 2530 includes a case body 2534 configured to receive an apparatus body 2536 of electronic apparatus 2532, an electrical connector 2538 configured to mate with an electrical connector 2540 of electronic apparatus 2532, which are shown in a cutaway portion of device 530 and electronic apparatus 2532, and a sensor device 2542 connected to case body 2534 by rotating mechanism 2506. Sensor device 2542 includes a rod-like body 2544 on which is positioned sensor 2484. A sensor surface 2544 of sensor 2484 is disposed diagonally in relation to a main axis of sensor device 2542. Sensor 2484 generates signals proportional to emissions received by sensor 2484. The signals are transmitted to connector 2538.

FIG. 154 shows a view of still yet another separable sensor device, indicated generally at 2550, positioned on an electronic apparatus, indicated generally at 2552, in accordance with an exemplary embodiment of the present disclosure. Separable sensor device 2550 includes a rod-like body 2554 in which is positioned a transmitter 2556 that is communicatively coupled with a receiver 2558 of electronic apparatus 2550. Rod-like body 554 also includes a processor 2560, and power source 562.

FIGS. 155-157 show views of separable sensor device 2530 with rod-like body 2544 rotated to be approximately perpendicular to a planar front face 2546 of electronic apparatus 2532 to position and align sensor 2484 with ABTT terminus 10.

FIGS. 158 to 166 show views of sensorial watches in accordance with exemplary embodiments of the present disclosure. Each sensorial watch includes a front face, a display positioned on the front fact, a back face, and a plurality of side faces extending from the front face to the back face.

FIG. 158 shows a view of a sensorial watch, indicated generally at 2570, including a measurement device in accordance with an exemplary embodiment of the present disclosure. Sensorial watch 2570 includes front face 2572, on which is positioned a display 2574, a pair of side-by-side dual sensors or detectors 2576 adjacent to display 2574, a camera 2578 disposed between sensors 2576, and a cross-hair light source 2580 for helping aligning sensors 2576 with ABTT terminus 10. When elements similar or identical to the elements of FIG. 158 are used in subsequent figures, such similar or identical elements are labelled with the same item number as the elements of FIG. 158.

FIG. 159 shows a view of a sensorial watch, indicated generally at 2590, including a measurement device in accordance with another exemplary embodiment of the present disclosure. Sensorial watch 2570 includes front face 2592, on which is positioned a display 2594, one sensor 2576, camera 578 disposed adjacent to sensor 2576, cross-hair light source 2580, and a wireless device, i.e., a transmitter or transceiver, communicatively or operatively coupled with an external or separate electronic device 2598, including a cell phone, computer, tablet, or other electronic device.

FIG. 160 depicts sensorial watch 2570 being used by the subject to align a field of view of sensors 2576 with ABTT terminus 10 and to then acquire signals from ABTT terminus 10.

FIG. 161 shows a view a sensorial watch, indicated generally at 2600, including a measurement device in accordance with yet another exemplary embodiment of the present disclosure. Sensorial watch 2600 includes a front face 2602, a back face 2604, and a plurality of side faces 2606 extending from front face 2602 to back face 2604. Sensorial watch 2600 includes sensor 2576, camera 2578 disposed adjacent to sensor 2576, and cross-hair light source 2580 positioned on one of side faces 2606.

FIG. 162 shows a view of a sensorial watch, indicated generally at 2610, including a measurement device in accordance with still another exemplary embodiment of the present disclosure. Sensorial watch 2610 includes a front face 2612, a back face 2614, and a plurality of side faces 2616 extending from front face 2612 to back face 2614. Sensorial watch 2610 includes duel dual sensors or detectors 2576 positioned on one of side faces 2616, each sensor 2576 is configured to be slidingly supported on sensorial watch 2610 by a sliding mechanism 2618. Sliding mechanism 2618 is configured to adjusting a spaced distance between sensors 576 for alignment of sensors 2576 with ABTT terminus 10. The space distance is configured to be in a range from a first, minimum spaced distance 2620 to a maximum spaced distance 2622. The actual dimensions of spaced distance 2620 and spaced distance 2622 depend on the longest dimension of side face 2616 on which sensors 2576 are positioned. FIG. 163 shows a view of the user operating sensorial watch 2610 to position a field of view 2624 of each sensor 2576 to acquire signals from ABTT terminus 10, with measurement results being displayed on a display 2626 positioned on front face 2612.

FIGS. 164 to 166 show sensorial wrist-bands having sensor assemblies and connected to a display and electronics. As with other embodiments herein, when similar or identical elements exist between embodiments, the same item number is used.

FIG. 164 shows a view of a watch, indicated generally at 2630, including a measurement device in accordance with an even further exemplary embodiment of the present disclosure. Watch 2630 includes a display 2634 and a sensorial wrist-band 2632 extending away from display 634 in two, generally opposite directions. Sensorial wrist-band 2632 includes a strap 2636, a first, right arm 2638, and a second, left arm 2640. Each of right arm 2638 and left arm 2640 include a sensor 2642 disposed along a free end of right arm 2638, and along a free end of left arm 2640. Right arm 2638 and left arm 2640 are disposed adjacent to an edge of strap 2636, beginning at a location that is adjacent to display 2634. Right arm 2638 and left arm 2640 include a flexible and adjustable mechanism for adjusting right arm 2638 and left arm 2640 to different sizes of noses and for alignment with ABTT terminus 10. FIG. 166 shows watch 2630 being operated by the user and positioned next to nose 2026 of the face with sensors aligned with the ABTT. Although in FIG. 166 contact sensors are being used and are contacting the skin, it should be understood that non-contact sensors can be used in accordance to the principles of the disclosure in any of the embodiments showing contact sensors. It should be understood that contact sensors can be used in accordance to the principles of the disclosure in any of the embodiments using non-contact sensors. It should be understood that temperature modification devices can be used in accordance to the principles of the disclosure in any of the embodiments showing sensors.

FIG. 165 shows a view of a watch, indicated generally at 2650, including a measurement device in accordance with an even yet further exemplary embodiment of the present disclosure. Watch 2650 is similar to watch 2630, though with only a single sensor 2642. Further, the adjustability of first, right arm 2638 and second, left arm 2640 are shown by arrows 2652. Right arm 2640 is void of sensors and is used for positioning sensorial wrist-band 2632 on nose 2026.

FIG. 167 shows a view of a sensor device, indicated generally at 2660, in accordance with an exemplary embodiment of the present disclosure. Sensor device 2660 includes a pen-shaped or essentially cylindrical-shaped body 2662 including a proximate end 2664 and a distal end 2666. Distal end 2666 includes a sensor head 2668, which includes a sensor 2670 disposed thereon. Proximate end 2664 includes an electrical connector 2672, which is configured to mate with a jack 2674, which is connected to an electronic apparatus 2678 by a cable or wire 2676.

FIG. 168 shows a view of another sensor device, indicated generally at 2680, in accordance with an exemplary embodiment of the present disclosure. Sensor device 2680 includes a cylindrical or rod-like sensor body 2682 on which is positioned a sensor head 2684 at a distal end thereof. Sensor head 2684 includes a two prong support 2686 that includes a right arm 2690 and a left arm 2688, with each arm including a sensor 2692 positioned on a free end thereof. Sensor body 2682 also includes an electrical connector 2694 configured to accept a jack or connector 2696, which is connected to an electronic apparatus 2698 by way of a cable or wire 2700. Electronic apparatus 2698 includes a display 2702 and a trigger button 2704 for actuating sensor device 2680. It should be understood that sensor body 2682 can be connected to any electronic device or thermometer configured to read the signals from sensors 2692 and to report the signals sensors 2692.

FIG. 169 shows a view of yet another sensor device, indicated generally at 2710, in accordance with an exemplary embodiment of the present disclosure. Sensor device 2710 is similar in some respects to the embodiment of FIG. 168, and such similar elements are labelled with the same element number. Sensor device 2710 includes a cylindrical, rod-like, tubular, or pen-shaped sensor body 2712 and an electronic apparatus 2714, for example a cell phone, or a specialized electronic apparatus 2716. Sensor body 2712 includes a sensor head 2718 at a distal end on which is positioned a sensor 2720 at a free end thereof. Sensor body 2712 also includes an electrical connector 2722 positioned at a proximate end. Connector 2722 is configured to connect to electronic apparatus 2714 and to electronic apparatus 2716.

FIG. 170 shows a view of a further sensor device, indicated generally at 730, in accordance with an exemplary embodiment of the present disclosure. Sensor device 2730 is similar to the embodiments of FIGS. 168 and 169, but communication with electronic apparatus 2714 and electronic apparatus 2716 is by way of a transmitter.

FIG. 171 shows sensor device 2730 connected to an electronic apparatus, indicated at 2740, in accordance with an exemplary embodiment of the present disclosure. Electronic apparatus 2740 includes display 2702 and is configured to read signal from sensor device 2730. Electronic apparatus 2740 includes an electrical connector 2742 configured with an up and down rotating mechanism to align sensor 2720 with ABTT terminus 10. Display 2702 is also rotatable about an axis 744, as shown by arrow 2746. FIG. 172 shows display 2702 rotated by 180 degrees about axis 2744 allowing thereby another person, such as doctor, to see the result on display 2702. FIGS. 173 to 176 show a plurality of exemplary orientations of sensor device 730 as it rotates about its own axis while positioned in connector 2742.

FIG. 177 shows a view of a rotating mechanism, indicated at 2752, of a sensor device, indicated generally at 2750, in accordance with an exemplary embodiment of the present disclosure. Sensor device 750 includes a sensor body 754 and a sensor head 2756 supporting a sensor 2758. Sensor head 2756 is connected to sensor body 2754 by rotating mechanism 2752, which permits sensor head 2756 to rotate about an axis 2760 that is perpendicular to a longitudinal axis 762 of sensor body 2754 to permit sensor head 2756 to be oriented in a plurality of positions, as exemplified by the positions shown in FIG. 177. Rotating mechanism 2752 is configured to adjust the position of sensor head 2756 to provide an optimal position of sensor 2758 for measurement of ABTT terminus 10.

FIGS. 178 and 179 show view of a support structure, indicated generally at 2770, in accordance with an exemplary embodiment of the present disclosure. Support structure 2770 includes a housing 2772 that further includes three portions. One portion includes a handle 2774 that includes an operation or actuation button 2776, and a cable 2778 including an electrical connector or jack 2778 configured to fit a mating connector of an electronic apparatus. Another portion is a mid-portion 2786 that includes an electrical connector 2788 configured to receive a distal end of sensor device, such as sensor device 2730. Yet another portion is an upper portion 2790 that includes a clamp mechanism 2792 configured to secure an electronic apparatus body. Clamp mechanism 2792 is configured to extend in the direction of arrows 2794 to receive a plurality of dimensions of an electronic apparatus 2796. Although for illustration purposes cable 2778 for connection with the electronic apparatus is shown, it should be understood that an internal electrical connection can be disposed along a bottom of clamp mechanism 2792 and configured to receive a complementary electrical connection of an electronic apparatus, and such embodiment is within the scope of the disclosure. FIG. 181 shows sensor device 2730 positioned to align sensor 2670 with ABTT terminus 10.

FIG. 180 shows a view of another support structure, indicated generally at 2800, in accordance with an exemplary embodiment of the present disclosure. Support structure 2800 includes a housing 2802 that includes a handle 2804, an actuation button 2806, an upper portion 2810 including a clamp mechanism 2812, and a mid-portion 2816. Mid-portion 816 includes an extendable/retractable wire or cable 808 for connection to a sensor device, such as sensor device 2660.

FIG. 182 shows a view of a sensor clip assembly, indicated generally at 2830, in accordance with an exemplary embodiment of the present disclosure. Sensor clip assembly 2830 includes a rotatable right arm 2832, a rotatable left arm 2834, a housing 2836 in which is positioned a spring mechanism 2838 that biases or pushes right arm 2832 and said left arm 2834 toward or against each other, and a lever or handle 2840 that is connected to right arm 2832 and which moves right arm 2832 away from left arm 2834 when pressed or pushed. Sensor clip assembly 2830 also includes an electrical connector 2842, and a cable 2844 that extends from electrical connector 2842 and which terminates at an electrical connector 2846. Each of right arm 2832 and left arm 2834 includes a sensor 2848 disposed at a free end of the respective right arm 2832 and left arm 2834.

FIG. 183 shows a view of a sensor head, indicated generally at 2850, in accordance with an exemplary embodiment of the present disclosure. Sensor head 2850 includes a sensor body 2852, a connection portion 2854, and a contact sensor portion 2856. Contact sensor portion 856 includes a contact sensor 2858 and a spring mechanism 2860 disposed along an axis 2862 that is approximately perpendicular to a main longitudinal axis 2864 of sensor body 2852. Sensor head 2850 further includes wires 2866 extending along sensor body 2852 to connect contact sensor 2858 to connection portion 2854.

FIG. 183 shows a view of sensor head, indicated generally at 2870, in accordance with another exemplary embodiment of the present disclosure. Sensor head 2870 includes a sensor body 2872, a connection portion 2874, and a non-contact sensor portion 2876. Non-contact sensor portion 2876 includes a non-contact sensor 2878 position within a sensor housing 2880 that is disposed along an axis 2882 that is approximately perpendicular to a main longitudinal axis 2884 of sensor body 2872. Sensor head 2870 further includes wires 2886 extending along sensor body 2872 to connect non-contact sensor 2878 to connection portion 2874. Sensor housing 2880 protects non-contact sensor 2878, such as an infrared sensor, against interference by surrounding ambient temperature and sweat.

FIGS. 185 and 186 show views of a thermometer, indicated generally at 2890, in accordance with an exemplary embodiment of the present disclosure. Thermometer 2890 includes a handle 2892 and a sensor head 2894. Sensor head 894 includes a sensor 896 positioned thereon. Handle 2892 is positioned or disposed at an angle 898 that is optimally 45 degrees in relation to handle axis 2900. Angle 2898 is preferably in the range from 10 degrees to 80 degrees, is more in the range of 15 degrees to 75 degrees, is even more preferably in the range of 30 degrees to 60 degrees, and is most preferably in the range of 40 degrees to 50 degrees. The optimal 45 degree angle allows sensor 2896 to be aligned with ABTT terminus 10 when handle 2892 is parallel to a plane 2902 of the face or when handle 892 is positioned perpendicular to facial plane 2902, as shown in FIG. 186, which shows thermometer 2890 being used by the subject.

FIGS. 187 and 188 show views of a sensor head, indicated generally at 2910, in accordance with an exemplary embodiment of the present disclosure. Sensor head 2910 includes a sensor 2912 and a housing 2914 that surrounds sensor 2912 and includes an open end 2916 surrounding sensor 2912, and a connecting arm 2918. FIG. 188 shows sensor head 2910 positioned on skin 2920 and receiving radiation from skin 2920. Housing 2914 with open end 2916 creates a confined and protected environment (volume 922) for radiation 2924 from skin 2920. FIGS. 189 and 190 show sensor head 2910 being used by the subject and aligned in a diagonal angle of approximately 45 degrees with ABTT terminus 10. It should be understood that embodiments of FIGS. 183-190 can be used with any of the sensor devices and temperature modification devices described in the present disclosure.

FIG. 191 shows a sensor device, indicated generally at 2930, in accordance with an exemplary embodiment of the present disclosure. Sensor device 2930 includes a right arm 2932, a right sensor 2934 positioned at a free end of right arm 2932, a left arm 2936, a left sensor 2938 positioned at a free end of left arm 2936, and a vertical support arm 2940. Vertical support arm 2940 is preferably rigid and is configured to connect to right arm 2932 and left arm 2936 at a first end of vertical support arm 2940. A second end of vertical support arm 2940 terminates at a magnet or ferrous material 2942 that is configured to interact and anchor to a complementary magnet or ferrous material 2944 supported by a helmet arm 2946 supported by and connected to a helmet 2948. Helmet 2948 is configured to include a wireless device, a processor, and a power source (not shown) for transmitting signals from right sensor 2934 and left sensor 2938 to a remote electronic device.

FIG. 192 shows a view of yet another sensor device, indicated generally at 3000, in accordance with an exemplary embodiment of the present disclosure. Sensor device 3000 is similar in some respects to the embodiment of FIG. 168 and FIG. 169, and such similar elements are labeled with the same element number. Sensor device 3000 includes a cylindrical, rod-like, tubular, or pen-shaped sensor body 3002 and an electronic apparatus 2714, for example a cell phone, or a specialized thermometer 3004. Specialized thermometer 3004 can be configured as, for example, an ear thermometer, an axillary thermometer, an oral thermometer, etc. Thus, specialized thermometer 3004 includes an integral temperature sensor. Sensor body 3002 includes a sensor head 3006 at a distal end and surface facing forward, on which is positioned a sensor 3008 at a free end thereof. Sensor body 3002 also includes an electrical connector 3010 positioned at a proximate end, said electrical connector adapted to connect to jack 3014 of a non-thermometric electronic apparatus 2714 and jack 3016 of a specialized thermometer. Connector 3010 is configured to connect to electronic apparatus 2714 and to thermometer 3004. Connector 3010 is also configured to connect to connector of cable 3012. When sensor device 3000 is connected to specialized thermometer 3004, the output from sensor device 3000 takes priority over the integral thermometer of specialized thermometer 3004. In another embodiment, a switch positioned on specialized thermometer 3004 can be positioned to select input from the integral thermometer or from sensor device 3000. When sensor device 3000 is connected to specialized thermometer 3004, the output signal from specialized thermometer 3004 is presented as a value on a display of specialized thermometer 3004.

Referring to FIG. 193, another electronic apparatus configured with a sensor or a temperature measurement device in accordance with an exemplary embodiment of the present disclosure is shown and indicated generally at 3220. Electronic apparatus 3222 can be configured as an eyewear and includes a frame 3224. Frame 3224 includes a left lens rim 3226, a right lens rim 3228, a right temple 3230, a left temple 3232, a nose pad 3250, and a connecting portion 3234. Connecting portion 3234 includes a sensor assembly 3248, which connects right lens rim 3228 to left lens rim 3226. Right temple 3230 includes a battery 3236 and an entry port 3238. Left temple 3232 includes a transmitter 3240, a non-transitory memory 3242, and a processor 3244. Transmitter 3240 is configured to communicate with and transmit signals to an external device 3252. Right temple 3230 electrically connects with left temple 3232 via wires 3246, preferably as a flexible circuit. FIG. 194 shows in detail sensor assembly 3248, which includes a supporting plate 3256, a bendable junction 3254, and a sensor 3258. Sensor 3258 faces upwardly and includes a field of view that is perpendicular to a plane of supporting plate 3256. Any part of any embodiment can be used in combination to create a single embodiment, and any part of any embodiment can be used as a replacement or addition to another embodiment, and all resultant embodiments are within the scope of the present disclosure.

Referring to FIGS. 195 and 196, another apparatus configured with a sensor or a temperature measurement device in accordance with an exemplary embodiment of the present disclosure is shown and indicated generally at 3260. Sensing apparatus 3262 can be configured with an adhesive 3264 to support sensing apparatus 3262 on a human body part and includes a main body 3266, an arm 3268, a cable 3270, a measuring head 3274, and a connector 3272 adapted to connect with a reading device and display (not shown). Measuring head 3274 includes a sensor 3276. FIG. 196 shows in detail measuring head 3274, which includes an insulating material or foam 3278. Foam 3278 also secures sensor 3276.

FIG. 197 shows an alternative embodiment of the apparatus of FIG. 195, indicated generally at 3292. Apparatus 3292 includes a wireless device 3280, a processor 3282, a non-transitory memory 3284, a power source 3286, and a display 3288. Wireless device 3280 is configured to communicate with a remote device 3290, such as a cell phone, watch, eyeglasses, tablet, radio, computer, and the like. Such communication can include transfer of control and/or data signals.

While various embodiments of the disclosure have been shown and described, it is understood that these embodiments are not limited thereto. The embodiments can be changed, modified, and further applied by those skilled in the art. Therefore, these embodiments are not limited to the detail shown and described previously, but also include all such changes and modifications.

I claim:

1. A thermal diagnosis and treatment apparatus, comprising:
   a first temperature sensor configured to output a first temperature signal corresponding to a temperature of a first Abreu brain thermal tunnel (ABTT) terminus of a subject;
   a first temperature modification device positioned adjacent to the first temperature sensor, the first temperature modification device being one of a heater, a cooler, and a combination heater and cooler;
   a second temperature sensor configured to output a second temperature signal to a temperature of a second ABTT terminus of the subject, the second temperature sensor being positioned a spaced distance from the first temperature sensor, the spaced distance being equal to a distance between the first ABTT terminus and the second ABTT terminus;
   a second temperature modification device positioned adjacent to the second temperature sensor the second temperature modification device being one of a heater, a cooler, and a combination heater and cooler; and
   a processor configured to:
     receive the first temperature signal and the second temperature signal from the subject,
     determine a left-right side dominance of the subject from the first temperature signal and the second temperature signal to determine a dominant side of the subject,
     determine that the dominant side has a temperature greater than 36 degrees Celsius,
     control one of the first temperature modification device and the second temperature modification device that is positioned on the dominant side to reduce the temperature of one of the first temperature modification device and the second temperature modification device that is positioned on the dominant side until the temperature on the dominant side is less than or equal to 36 degrees Celsius, and maintain the temperature on the dominant side for a predetermined interval that is greater than or equal to 1 minute, and
     output a notification to an output device after the predetermined interval is reached.

2. The thermal diagnosis and treatment apparatus of claim 1, wherein the processor determines the left-right side dominance from a baseline temperature of the subject, and the processor determines the baseline temperature from the first temperature signal and the second temperature signal.

3. The thermal diagnosis and treatment apparatus of claim 1, wherein the processor determines that a non-dominant side has a temperature greater than the temperature of the dominant side minus 0.2 degrees, and the processor controls one of the first temperature modification device and the second temperature modification device that is positioned on the non-dominant side to reduce the temperature of one of the first temperature modification device and the second temperature modification device that is positioned on the non-dominant side until the temperature on the non-dominant side is less than or equal to the temperature on the dominant side minus 0.2 degrees Celsius, and the processor maintains the temperature on the non-dominant side for the predetermined interval.

4. The thermal diagnosis and treatment apparatus of claim 1, wherein at least the first temperature sensor and the first temperature modification device are configured to be rotatable about a vertical axis.

5. The thermal diagnosis and treatment apparatus of claim 1, wherein at least the first temperature sensor and the first temperature modification device are configured to be movable vertically with respect to a support base.

6. The thermal diagnosis and treatment apparatus of claim 1, wherein the first temperature sensor and the first temperature modification device are configured to be rotatable about a vertical axis, and the second temperature sensor and the second temperature modification device are configured to be rotatable about the vertical axis.

7. The thermal diagnosis and treatment apparatus of claim 1, wherein the first temperature sensor and the first temperature modification device are configured to be movable vertically with respect to a support base, and the second temperature sensor and the second temperature modification device are configured to be separately movable vertically with respect to the support base.

8. The thermal diagnosis and treatment apparatus of claim 1, wherein the output device is one or more of a cell phone, a watch, a television, a laptop, a display, and a tablet.

9. The thermal diagnosis and treatment apparatus of claim 1, wherein the first temperature sensor, the first temperature modification device, the second temperature sensor, and the second temperature modification device are commonly supported on a wearable support.

10. The thermal diagnosis and treatment apparatus of claim 9, wherein the wearable support is one of a nose clip, a hat, a cap, a headband, a head appliance, and a support frame.

11. The thermal diagnosis and treatment apparatus of claim 9, wherein the processor is positioned on the wearable support.

12. The thermal diagnosis and treatment apparatus of claim 1, wherein the first temperature sensor and the first temperature modification device are movably positioned on a first post.

13. The thermal diagnosis and treatment apparatus of claim 12, wherein the first temperature sensor and the first temperature modification device are rotationally movable about the first post and movable along the first post.

14. The thermal diagnosis and treatment apparatus of claim 12, wherein the first post is supported on a base.

15. The thermal diagnosis and treatment apparatus of claim 12, wherein the second temperature sensor and the second temperature modification device are movably positioned on a second post.

16. The thermal diagnosis and treatment apparatus of claim 15, wherein the second temperature sensor and the second temperature modification device are rotationally movable about the second post and movable along the second post.

17. The thermal diagnosis and treatment apparatus of claim 15, wherein the first post and the second post are supported on a base.

18. The thermal diagnosis and treatment apparatus of claim 17, wherein the base is mounted on a one of a floor, a table, a bed, or a rack.

19. The thermal diagnosis and treatment apparatus of claim 12, wherein the first temperature modification device terminates in a first interface surface that is oriented at an angle that matches an angle of the first ABTT terminus when the subject is in an upright position.

20. The thermal diagnosis and treatment apparatus of claim 19, wherein the second temperature modification device terminates in a second interface surface that is oriented at an angle that matches an angle of the second ABTT terminus when the subject is in the upright position.

* * * * *